US007888069B2

(12) United States Patent
Smith et al.

(10) Patent No.: US 7,888,069 B2
(45) Date of Patent: Feb. 15, 2011

(54) PLANT-MADE WEST NILE VIRUS (WNV) VACCINES, VECTORS AND PLANT CODON OPTIMIZED SEQUENCES

(75) Inventors: Kelley A. Smith, Lebanon, IN (US); Steven R. Webb, Westfield, IN (US); Steven L. Evans, Zionsville, IN (US); Charles A. Mihaliak, Apex, NC (US); Donald J. Merlo, Carmel, IN (US); Geoffrey J. Letchworth, Laramie, WY (US)

(73) Assignees: Dow Agrosciences LLC, Indianapolis, IN (US); The United States of America as represented by the Secretary of Argriculture, Washington, DC (US)

( * ) Notice: Subject to any disclaimer, the term of this patent is extended or adjusted under 35 U.S.C. 154(b) by 424 days.

(21) Appl. No.: 11/962,924

(22) Filed: Dec. 21, 2007

(65) Prior Publication Data

US 2009/0069229 A1 Mar. 12, 2009

Related U.S. Application Data

(60) Provisional application No. 60/871,518, filed on Dec. 22, 2006.

(51) Int. Cl.

| | |
|---|---|
| *C12N 15/40* | (2006.01) |
| *C12N 15/62* | (2006.01) |
| *C12N 5/10* | (2006.01) |
| *A01H 5/00* | (2006.01) |

(52) U.S. Cl. .................. 435/69.3; 435/69.7; 435/320.1; 435/410; 536/23.72; 536/23.4; 800/295

(58) Field of Classification Search ....................... None
See application file for complete search history.

(56) References Cited

U.S. PATENT DOCUMENTS

| | | | |
|---|---|---|---|
| 4,816,567 | A | 3/1989 | Cabilly et al. |
| 5,073,627 | A | 12/1991 | Curtis et al. |
| 5,183,740 | A | 2/1993 | Ligler et al. |
| 5,273,894 | A | 12/1993 | Strauch et al. |
| 5,276,268 | A | 1/1994 | Strauch et al. |
| 5,380,831 | A | 1/1995 | Adang et al. |
| 5,384,253 | A | 1/1995 | Krzyzek et al. |
| 5,428,147 | A | 6/1995 | Barker et al. |
| 5,436,391 | A | 7/1995 | Fujimoto et al. |
| 5,478,925 | A | 12/1995 | Wallach et al. |
| 5,561,071 | A | 10/1996 | Hollenberg et al. |
| 5,565,335 | A | 10/1996 | Capon et al. |
| 5,637,489 | A | 6/1997 | Strauch et al. |
| 5,643,570 | A | 7/1997 | Theofan et al. |
| 5,712,170 | A | 1/1998 | Kouvonen et al. |
| 5,750,352 | A | 5/1998 | Vogelstein et al. |
| 5,753,439 | A | 5/1998 | Smith et al. |
| 5,773,689 | A | 6/1998 | Thompson et al. |
| 5,773,695 | A | 6/1998 | Thompson et al. |
| 5,843,464 | A | 12/1998 | Bakaletz et al. |
| 5,879,903 | A | 3/1999 | Strauch et al. |
| 5,990,275 | A | 11/1999 | Whitlow et al. |
| 6,121,424 | A | 9/2000 | Whitlow et al. |
| 6,214,545 | B1 | 4/2001 | Dong et al. |
| 6,239,328 | B1 | 5/2001 | Thompson |
| 6,277,375 | B1 | 8/2001 | Ward |
| 6,319,691 | B1 | 11/2001 | Pang |
| 6,342,362 | B1 | 1/2002 | Mytelka |
| 6,419,931 | B1 | 7/2002 | Vitiello et al. |
| 6,524,825 | B1 | 2/2003 | Mizzen et al. |
| 2004/0268442 | A1 | 12/2004 | Miller et al. |
| 2005/0053624 | A1 * | 3/2005 | Arroyo et al. ............ 424/218.1 |

FOREIGN PATENT DOCUMENTS

| | | |
|---|---|---|
| WO | WO 91/09957 | 7/1991 |
| WO | WO 93/11161 | 6/1993 |
| WO | WO 94/07902 | 4/1994 |
| WO | WO 94/10308 | 5/1994 |
| WO | WO 97/27207 | 7/1997 |
| WO | WO 98/49305 | 11/1998 |
| WO | WO 2004/112694 | 12/2004 |
| WO | WO 2005/113775 | * 12/2005 |

OTHER PUBLICATIONS

Shirato et al (Journal of General Virology 85:3637-3645, 2004).*

Genbank locus BAD34489, Mar. 15, 2005. Dec. 2005.*

Hanna et al (Journal of Virology 79:13262-13274, 2005).*

Streatfield, S. J. "Plant-based vaccines for animal health" *Rev. Sci. Tech. Off. Int. Epiz*, 2005, pp. 189-199, vol. 24, No. 1, XP-009110074.

(Continued)

*Primary Examiner*—Mary E Mosher
(74) *Attorney, Agent, or Firm*—Saliwanchik, Lloyd & Bisenschenk

(57) ABSTRACT

The subject application provides various compositions of matter directed to West Nile virus (WNV) polypeptides and fragments thereof and polynucleotides, vectors and transformed host cells that encode, direct the expression of, or produce WNV polypeptides as set forth herein. Methods of using the polypeptides and polynucleotides for the production of immune responses in individuals or detecting the presence of WNV specific or neutralizing antibodies are also provided herein.

11 Claims, 21 Drawing Sheets

OTHER PUBLICATIONS

Schillberg, S. et al. "Opportunities for recombinant antigen and antibody expression in transgenic plants-technology assessment" *Vaccine*, 2005, pp. 1764-1769, vol. 23.

Warzecha, H. et al. "Oral Immunogenicity of Human Papillomavirus-Like Particles Expressed in Potato" *Journal of Virology*, Aug. 2003, pp. 8702-8711, vol. 77, No. 16, XP-002993767.

Chang, G. et al. "Recent advancement in flavivirus vaccine development" *Expert Rev Vaccines*, 2004, pp. 199-220, vol. 3, No. 2, XP-009061787.

Plotkin, S.A. "Vaccines, Vaccination, and Vaccinology" *Journal of Infectious Diseases*, 2003, pp. 1349-1359, vol. 187, XP-009070448.

Beasley, D. W. et al. "Identification of Neutralizing Epitopes within Structural Domain III of the West Nile Virus Envelope Protein" *Journal of Virology*, Dec. 2002, pp. 13097-13100, vol. 76, No. 24.

Blitvich, B. J. et al. "Epitope-Blocking Enzyme-Linked Immunosorbent Assays for the Detection of Serum Antibodies to West Nile Virus in Multiple Avian Species" *Journal of Clinical Microbiology*, Mar. 2003, pp. 1041-1047, vol. 41, No. 3.

Hanna, S. L. et al. "N-Linked Glycosylation of West Nile Virus Envelope Proteins Influences Particle Assembly and Infectivity" *Journal of Virology*, Nov. 2005, pp. 13262-13274, vol. 79, No. 21.

Kanai, R. et al. "Crystal Structure of West Nile Virus Envelope Glycoprotein Reveals Viral Surface Epitopes" *Journal of Virology*, Nov. 2006, pp. 11000-11008, vol. 80, No. 22.

Mukhopadhyay, S. et al. "Structure of West Nile Virus" *Science*, Oct. 10, 2003, p. 248, vol. 302.

Sanchez, M. D. et al. "Characterization of Neutralizing Antibodies to West Nile Virus" *Virology*, 2005, pp. 70-82, vol. 336.

Wengler, G. et al. "An Analysis of the Antibody Response against West Nile Virus E Protein Purified by SDS-PAGE Indicates that This Protein Does Not Contain Sequential Epitopes for Efficient Induction of Neutralizing Antibodies" *J. Gen. Virol.*, 1989, pp. 987-992, vol. 7.

Winkler, G. et al. "Characterization of a Disulphide Bridge-stabilized Antigenic Domain of Tick-borne Encephalitis Virus Structural Glycoprotein" *J. Gen. Virol.*, 1987, pp. 2239-2244, vol. 68.

Cecilia, D. et al. "Nucleotide Changes Responsible for Loss of Neuroinvasiveness in Japanese Encephalitis Virus Neutralization-Resistant Mutants", *Virology*, 1991, pp. 70-77, vol. 181.

* cited by examiner

| Ln | Sample | |
|---|---|---|
| 1 | MW | |
| 2 | NT1 negative | |
| 3 | WNV standard | |
| 4 | NT1 negative | |
| 5 | (pDAB2478)1623 | -126 |
| 6 | (pDAB2478)1623 | -205 |
| 7 | (pDAB2478)1623 | -316 |
| 8 | (pDAB2478)1623 | -016 |
| 9 | (pDAB2478)1623 | -279 |
| 10 | NT1 negative | |
| 11 | (pDAB2478)1623 | -240 |
| 12 | (pDAB2478)1623 | -203 |
| 13 | (pDAB2478)1623 | -317 |
| 14 | (pDAB2478)1623 | -209 |
| 15 | (pDAB2478)1623 | -199 |

All samples day 14 callus
(pDAB2478)1623 – prME

| Ln | Sample | |
|---|---|---|
| 1 | MW | |
| 2 | NT1 negative | |
| 3 | WNV standard | |
| 4 | NT1 negative | |
| 5 | (pDAB2481)1702 | -421 |
| 6 | (pDAB2481)1702 | -070 |
| 7 | (pDAB2481)1702 | -525 |
| 8 | (pDAB2481)1702 | -220 |
| 9 | (pDAB2481)1702 | -506 |
| 10 | NT1 negative | |
| 11 | (pDAB2481)1702 | -523 |
| 12 | (pDAB2481)1702 | -321 |
| 13 | (pDAB2481)1702 | -474 |
| 14 | (pDAB2481)1702 | -185 |
| 15 | NT1 negative | |

All samples day 14 callus
(pDAB2481)1702 –
prME w/ glycan modification

| Lane | | |
|---|---|---|
| 1 | See Blue/Magic Mark | |
| 2 | Plant Reference (15 ng) | |
| 3 | (pDAB2475) 1622 | -207 |
| 4 | (pDAB3920) 1960 | -001 |
| 5 | (pDAB3920) 1960 | -005 |
| 6 | (pDAB3920) 1960 | -013 |
| 7 | (pDAB3920) 1960 | -015 |
| 8 | (pDAB3920) 1960 | -024 |
| 9 | (pDAB2475) 1622 | -207 |
| 10 | (pDAB3922) 1961 | -001 |
| 11 | (pDAB3922) 1961 | -002 |
| 12 | (pDAB3922) 1961 | -004 |
| 13 | (pDAB3922) 1961 | -006 |
| 14 | (pDAB3922) 1961 | -017 |
| 15 | (pDAB2475) 1622 | -207 |

All samples day 14 callus
Load normalize to total soluble protein

| Lane | | |
|---|---|---|
| 1 | See Blue/Magic Mark | |
| 2 | Plant Reference (15 ng) | |
| 3 | (pDAB2475) 1622 | -207 |
| 4 | (pDAB3924) 1962 | -001 |
| 5 | (pDAB3924) 1962 | -009 |
| 6 | (pDAB3924) 1962 | -014 |
| 7 | (pDAB3924) 1962 | -018 |
| 8 | (pDAB3924) 1962 | -024 |
| 9 | (pDAB2475) 1622 | -207 |
| 10 | (pDAB3927) 1963 | -004 |
| 11 | (pDAB3927) 1963 | -009 |
| 12 | (pDAB3927) 1963 | -013 |
| 13 | (pDAB3927) 1963 | -015 |
| 14 | (pDAB3927) 1963 | -023 |
| 15 | (pDAB3927) 1622 | -207 |

All samples day 14 callus
Load normalize to total soluble protein

| Lane | | |
|---|---|---|
| 1 | See Blue/Magic Mark | |
| 2 | Plant Reference (15 ng) | |
| 3 | (pDAB2475) 1622 | -207 |
| 4 | (pDAB3929) 1964 | -001 |
| 5 | (pDAB3929) 1964 | -008 |
| 6 | (pDAB3929) 1964 | -013 |
| 7 | (pDAB3929) 1964 | -018 |
| 8 | (pDAB3929) 1964 | -024 |
| 9 | (pDAB2475) 1622 | -207 |
| 10 | (pDAB3934) 2040 | -003 |
| 11 | (pDAB3934) 2040 | -005 |
| 12 | (pDAB3934) 2040 | -007 |
| 13 | (pDAB3934) 2040 | -008 |
| 14 | (pDAB3934) 2040 | -009 |
| 15 | (pDAB2475) 1622 | -207 |

All samples day 14 callus
Load normalize to total soluble protein

20/21

PLANT-MADE WEST NILE VIRUS (WNV) VACCINES, VECTORS AND PLANT CODON OPTIMIZED SEQUENCES

CROSS-REFERENCE TO RELATED APPLICATION

This application claims the benefit of U.S. Provisional Application Ser. No. 60/871,518, filed Dec. 22, 2006, the disclosure of which is hereby incorporated by reference in its entirety, including all figures, tables and amino acid or nucleic acid sequences.

This invention was made with government support under USDA-ARS CRADA Agreement No. 58-3K95-M-1040. The government has certain rights in the invention.

BACKGROUND OF THE INVENTION

Understanding of West Nile virus (WNV) neutralization by antibodies comes from the study of WNV and its close relatives Saint Louis encephalitis virus, Murray Valley encephalitis virus (MVEV), and Japanese encephalitis virus, as well as more distant relatives such as dengue virus, yellow fever virus, and tick-borne encephalitis virus (TBEV). Strong similarities in the sequence of the flavivirus envelope proteins and the nearly identical position of the cysteines that form intramolecular bonds within the envelope proteins (Nowak et al., 1987) suggest that the envelope proteins of all flaviviruses must have very similar structures. Therefore, information about any flavivirus is generally applicable to the others.

Heinz and Kunz (1982, 1977) showed that flaviviruses contain only three proteins, the envelope protein (E), the membrane protein (M), and the capsid protein (C). Recent structural studies of dengue virus (Kuhn et al., 2002) confirmed this and showed the physical relationship of these proteins in the virion. Only the E protein is exposed on the virion surface (Kuhn et al., 2002). Thus far, the three-dimensional structures of the E proteins for WNV, TBEV, and dengue have been solved (Kuhn et al., 2002; Mukhopadhyah et al., 2003; Rey et al., 1995). These have a finger-like structure with three clearly distinct domains, domain I being in the middle between domains II and III. Individual molecules of E protein lay flat across the virion surface with pairs of molecules lying beside each other in opposite orientation and three pairs laying side-by-side.

The flavivirus E protein is synthesized as part of a genome-length polyprotein that includes all viral proteins. It is subsequently released from the polyprotein by proteolytic cleavage. Early cleavages inside the polyprotein release the E protein still attached to the pre-membrane (pr) and M proteins, the combination of the pr and M proteins being known as the “prM” protein. The resulting prM-E protein is inserted into the endoplasmic reticulum membrane where it begins to fold into its mature conformation. The virus is assembled in intracellular compartments with the prM-E on the surface. Subsequent cleavages separate the E and prM proteins and cleave the prM to yield the mature M protein. The pr fragment is not incorporated into virions. The E protein may or may not have glycosylation sequences and therefore may or may not be glycosylated (Hanna, et al., 2005).

Flaviviruses infect cells by binding to the cell membrane, probably through an interaction between the RGD sequence of E protein domain III and cell-surface integrin (Lee et al., 2000), and entering through endosomes. When the endosome acidifies, the virion envelope proteins undergo extensive and irreversible changes in their intra- and inter-molecular conformation. The 180 individual E protein molecules disassociate from their dimers, reorient their domains and join to form 60 trimeric spikes that protrude from the virion membrane, insert the tip of the spikes into the endosomal membrane, and aggregate into 12 pentameric rings of trimeric spikes that fuse the virion membrane with the endosomal membrane, thus allowing the capsid to enter the cell’s cytoplasm and begin replication (Bressanelli et al., 2004). It is clear that solubilization of the dimers from the virion surface ablates some neutralization-related epitopes (Heinz et al., 1991) but it is not clear how the rearrangement and trimerization alters E protein antigenic sites (Stiasny et al., 1996).

Since only the E protein is exposed on the virion surface, antibodies that bind to and neutralize intact, infectious virions must bind to the E protein. This has been proven by showing the development of neutralizing antibodies in animals immunized with proteins purified from virus (Heinz et al., 1990) and viral proteins produced in recombinant systems (Bray et al., 1989; Heinz et al., 1986; Heinz et al., 1982; Jan et al., 1993; Konishi et al., 1992; Mason et al., 1991; Men et al., 1991; Pincus et al., 1992; Schlesinger et al., 1992), and by passive protection experiments with monoclonal antibodies directed against the E protein (reviewed in Heinz et al., 1977, 1986; Roehrig 1986).

Antibodies that bind some areas on the E protein would be expected to neutralize the virus and antibodies that bind other areas might not. In order to discriminate between the neutralization activity of antibodies that bind the primary amino acid sequence from those that bind the secondary and tertiary structure of the properly folded E protein, Wengler and Wengler (1989) showed that reduction of disulfide bonds to destroy the protein’s secondary and tertiary structure ablated the ability of WNV E protein to engender neutralizing antibodies. This experiment strongly suggested that neutralizing antibodies bind to the E protein secondary and tertiary conformational structure rather than linear structure. To confirm this, Roehrig et al. (1989) made peptides from MVEV E protein predicted epitopes and found that only one engendered neutralizing antibodies and only at a low level. Indeed, subsequent studies have shown that monoclonal antibodies usually bind either native E protein or denatured E protein and its peptides (Guirakhoo et al., 1989; Holzmann et al., 1993; Roehrig et al., 1989). Only antibodies that bind the native structure neutralize the virus.

To show exactly which areas of the E protein are attacked by neutralizing antibodies, mutations in viruses that have escaped neutralization by monoclonal antibodies were sequenced and mapped on the E protein surface (reviewed in Heinz et al., 1983; Heinz et al., 1990; Roehrig 1986). These data enabled the generation of crude structural models (Cammack et al., 1986; Kolaskar et al., 1999; Mandl et al., 1989; Roebrig et al., 1989; Roehrig et al.; 1983) that were subsequently refined to show that mutations mapped to all three structural domains defined by x-ray crystallographic methods (Cecilia et al., 1991; Gao et al., 1994; Hasegawa et al., 1992; Holzmann et al., 1997; Holzmann et al., 1993; Jiang et al., 1993; Lin et al., 1994; Mandl et al., 1989). This strongly suggests that antibodies can neutralize flaviviruses by binding to any of the three domains. Nevertheless, most studies have focused on domain III where many neutralizing monoclonal antibody escape mutations occur (Beasley et al., 2002). Domain III is also the binding site for some non-neutralizing antibodies (Sanchez et al., 2005). Domain III can be isolated from purified virions as a trypsin-resistant fragment (Winkler et al., 1987) or generated as a recombinant protein (Mason et al. 1989) but its reactivity with neutralizing monoclonal antibodies is dependent on the maintenance of its conformational structure by its single disulfide bond. Several antibodies appear to neutralize WNV by binding a peptide that is exposed on domain I only during the membrane fusion transition (Kanai et al., 2006) or a site that interferes with conformational changes in domain III (Nybakken et al., 2005).

BRIEF SUMMARY OF THE INVENTION

The subject application provides various compositions of matter directed to West Nile virus (WNV) polypeptides and fragments thereof and polynucleotides, vectors and transformed host cells that encode, direct the expression of, or produce WNV polypeptides as set forth herein. Methods of using the polypeptides and polynucleotides for the production of immune responses in individuals or detecting the presence of WNV specific or neutralizing antibodies are also provided herein.

BRIEF DESCRIPTION OF THE SEQUENCES

Figure 1:
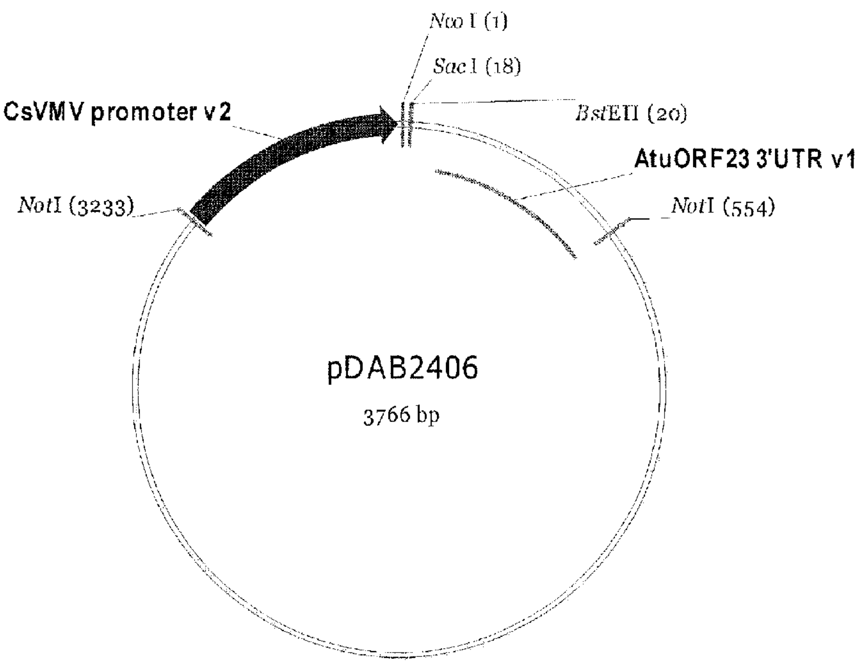
FIG. 1 depicts plasmid pDAB2406 which contains the cassava vein mosaic virus (CsVMV) promoter described in WO 97/48819 and an open reading frame 3' untranslated region, ORF23 3'UTR (GenBank accession number X00493) v1. Located between the CsVMV promoter and ORF23 3'UTR v1 are unique sites, NcoI and SacI, which were used for inserting the gene of interest.

SEQ ID NO: 1 is a native DNA sequence of flamingo isolate of West Nile Virus from GenBank Accession AF196835, encoding prM-, M-, and E-peptides (Version 1). The native WNV prM-M-E peptide coding region is 2004 bases in length and encodes the prM peptide (bases 1-276), the M-peptide (bases 277-501) and the E-Peptide (bases 502-2004).

SEQ ID NO: 2 is an amino acid sequence of native prM-, M-, and E-peptides encoded by SEQ ID NO: 1. The prM peptide is amino acids 1-92, the M-peptide is amino acids 93-167 and the E-peptide is amino acids 168-668.

SEQ ID NO: 3 is a tobacco-optimized DNA sequence for prM-, M- and E-peptides (Version 2). SEQ ID NO: 3 is 2004 bases in length and the prM-peptide is encoded by bases 1-276, the M-peptide is encoded by bases 277-501 and the E-Peptide encoded by bases 502-2004.

SEQ ID NO: 4 is a tobacco-optimized DNA sequence for prM-, M- and E-peptides with mutated N-glycosylation site (Version 4). The proline codon is at nts 967-969 and the sequence is 2004 bases in length. The prM-peptide is encoded by bases 1-276, the M-peptide encoded by bases 277-501 and the E-Peptide encoded by bases 502-2004.

SEQ ID NO: 5 is an amino acid sequence of prM-, M-, and E-peptides encoded by SEQ ID NO: 4 and containing a mutated N-glycosylation site. The proline residue is at position 323 and the sequence is 668 amino acids in length. The prM-peptide is amino acids 1-92, the M-peptide is amino acids 93-167 and the E-peptide is amino acids 168-668.

SEQ ID NO: 6 is a tobacco-optimized DNA sequence encoding M- and E-peptides (Version 2). The sequence is 1728 bases in length and the M-peptide is encoded by bases 1-225. The E-Peptide is encoded by bases 226-1728.

SEQ ID NO: 7 is a tobacco-optimized DNA sequence encoding M- and E-peptides (Version 3). This sequence is 1728 bases in length and the M-peptide is encoded by bases 1-225. The E-peptide is encoded by bases 226-1728.

SEQ ID NO: 8 is a tobacco-optimized DNA sequence encoding chimeric protein including 15 kDa zein ER targeting signal peptide, prM-, M- and E-peptides (Version 2), and KDEL. The sequence is 2106 bases in length and the 15 kDa ER targeting signal is encoded by bases 1-66. The prM-peptide is encoded by bases 67-342, the M-peptide is encoded by bases 343-567, the E-peptide is encoded by bases 568-2070, the KDEL ER retention signal is encoded by bases 2071-2082 and six frame stops are located at bases 2083-2106.

SEQ ID NO: 9 is an amino acid sequence of the chimeric fusion protein encoded by SEQ ID NO: 8. The fusion protein is 694 amino acids in length and contains a 15 kDa zein ER targeting peptide (amino acids 1-22), the prM-peptide (amino acids 23-114), the M-peptide (amino acids 115-189), the E-peptide (amino acids 190-690), an N-glycosylation site (amino acids 343-345) and the KDEL ER retention signal (amino acids 691-694).

SEQ ID NO: 10 is a tobacco-optimized DNA sequence encoding chimeric protein including 15 kDa zein ER targeting signal peptide, prM-, M- and E-peptides with mutated N-glycosylation site (Version 4) and KDEL. The sequence is 2106 bases in length and the kDa ER targeting signal is encoded by bases 1-66, the prM-peptide is encoded by bases 67-342, the M-peptide is encoded by bases 343-567, the E-peptide is encoded by bases 568-2070, the KDEL ER retention signal is encoded by bases 2071-2082 and six frame stops are located at bases 2083-2106.

SEQ ID NO: 11 is an amino acid sequence of the chimeric fusion protein encoded by SEQ ID NO: 10. The polypeptide is 694 amino acids in length and the 15 kDa zein ER targeting peptide is located at amino acids 1-22. The prM-peptide is found at amino acids 23-114, the M-peptide is found at amino acids 115-189, the E-peptide is found at amino acids 190-690 and mutated N-glycosylation site is at amino acids 343-345 and the KDEL ER retention signal is amino acids 691-694.

SEQ ID NO: 12 is a tobacco-optimized DNA sequence encoding chimeric protein including 15 kDa zein ER targeting signal peptide, M- and E-peptides (Version 2) and KDEL. The sequence is 1830 bases in length and the 15 kDa ER targeting signal is encoded by bases 1-66, the M-peptide is encoded by bases 67-291, the E-peptide is encoded by bases 292-1794, the KDEL ER retention signal is encoded by bases 1795-1806 and the six frame stops comprise bases 1807-1830.

SEQ ID NO: 13 is an amino acid sequence of the chimeric fusion protein encoded by SEQ ID NO: 12. This sequence is 602 amino acids long and the 15 kDa zein ER targeting peptide is amino acids 1-22. The M-peptide is located at amino acids 23-97, the E-peptide is located at amino acids 98-598 and the KDEL ER retention signal is found at amino acids 599-602.

SEQ ID NO: 14 is a tobacco-optimized DNA sequence encoding chimeric protein including 15 kDa zein ER targeting signal peptide, M- and E-peptides (Version 3) and KDEL. This sequence is 1832 bases in length, the 15 kDa ER targeting signal is encoded by bases 6-68, the M-peptide is encoded by bases 69-293, the E-peptide is encoded by bases 294-1796, the KDEL ER retention signal is encoded by bases 1797-1808 and six frame stops comprise bases 1809-1832.

SEQ ID NO: 15 is an amino acid sequence of the chimeric fusion protein encoded by SEQ ID NO: 14. The sequence is 601 amino acids in length and the 15 kDa zein ER targeting peptide is amino acids 1-21. The M-peptide is located at amino acids 22-96, the E-peptide is located at amino acids 97-597 and the KDEL ER retention signal is found at amino acids 598-601.

DETAILED DISCLOSURE OF THE INVENTION

The subject application provides the following non-limiting compositions of matter as well as methods of using these compositions of matter in the production of immunogenic polypeptides and methods of inducing immune responses in individuals. Thus, the subject invention provides various compositions of matter comprising:

a) isolated, purified, and/or recombinant polypeptides comprising SEQ ID NO: 5, 9, 11, 13 or 15;

b) a fragment of the polypeptide set forth in SEQ ID NO: 5, 9, 11, 13, 15 or a fragment of SEQ ID NO: 5, 9, 11, 13 or 15 that is "from Y to Z", wherein Y is the N-terminal amino acid of the specified sequence and Z is the C-terminal amino acid of the specified sequence. Thus, for SEQ ID NO: 5, each fragment can be between 5 consecutive amino acids and 667 consecutive amino acids in length. Each fragment containing between 5 and 693 consecutive amino acids of SEQ ID NO: 9 and 11 are specifically contemplated by the subject invention. Likewise, for SEQ ID NO: 13, each polypeptide fragment between 5 and 601 consecutive amino acids is specifically contemplated by the subject invention. Further, each polypeptide fragment spanning between 5 and 600 consecutive amino acids of SEQ ID NO: 15 is also specifically contemplated by the subject invention. Fragments "from Y to Z", wherein Y is the N-terminal amino acid of the specified sequence and Z is the C-terminal amino acid of a specified sequence are provided in Table 9 for SEQ ID NO: 5, Table 10 for SEQ ID NOs: 9 and 11, Table 11 for SEQ ID NO: 13 and Table 12 for SEQ ID NO: 15. Polypeptide fragments as set forth in this application have at least one biological activity that is substantially the same as the corresponding biological activity of the full-length polypeptide of SEQ ID NO: 5, 9, 11, 13 or 15 Various other exemplary polypeptide fragments are set forth in Tables 15 or 16;

c) an E-peptide as set forth in any one of SEQ ID NOs: 5, 9, 11, 13 or 15 or a fragment of an E-peptide as set forth in any one of SEQ ID NOs: 5, 9, 11, 13 or 15 that produces a neutralizing antibody response when administered to an individual;

d) a polypeptide according to any one of embodiments a), b) or c) that further comprises a heterologous polypeptide sequence;

e) a plant-derived polypeptide according to any one of embodiments a), b), c) or d);

f) a composition comprising a carrier and a polypeptide as set forth in any one of a), b), c), d) or e), wherein said carrier is cellular material from the plant, mammalian or bacterial expression system (optionally suspended in a buffer), an adjuvant or a pharmaceutically acceptable excipient;

g) a polynucleotide sequence encoding a polypeptide comprising SEQ ID NO: 5, 9, 11, 13 or 15 or encoding one or more polypeptide fragment of SEQ ID NOs: 5, 9, 11, 13 or 15 as set forth in (b) or (c), optionally wherein said polynucleotide sequence has a G+C content of at least 40% and less than 50% or a G+C content as set forth in Table 13;

h) a polynucleotide sequence that is at least 70% (or a percentage as specified in the Table 14) identical to SEQ ID NO: 1, encodes a polypeptide comprising SEQ ID NO: 2 and has a G+C content of between about 40% and about 50% (or a specific G+C content as specified in Table 13);

i) a polynucleotide sequence at least 8 consecutive nucleotides of a polynucleotide sequence as set forth in (g) or (h);

j) a polynucleotide sequence comprising SEQ ID NO: 3, 4, 6, 7, 8, 10, 12, or 14 or a fragment of at least 8 consecutive nucleotides of SEQ ID NO: 3, 4, 6, 7, 8, 10, 12, or 14;

k) a polynucleotide that is complementary to the polynucleotides set forth in (g), (h), (i), or (j);

l) a polynucleotide that hybridizes under low, intermediate or high stringency with a polynucleotide sequence as set forth in (g), (h), (i), (i) or (k);

m) a genetic construct comprising a polynucleotide sequence as set forth in (g), (h), (i), (i) or (k);

n) a vector comprising a polynucleotide or genetic construct as set forth in (g), (h), (i), (i), (j), (k) or (l);

o) a host cell comprising a vector as set forth in (n), a genetic construct as set forth in (m), or a polynucleotide as set forth in any one of (g), (h), (i), (j) or (k);

p) a transgenic plant, plant cell, or plant part comprising a vector as set forth in (n), a genetic construct as set forth in (m) or a polynucleotide as set forth in any one of (g), (h), (i), (j) or (k); or q) a probe comprising a polynucleotide according to (g), (h), (i), (j), (k) or (l) and, optionally, a label or marker.

In the context of the instant invention, the terms "oligopeptide", "polypeptide", "peptide" and "protein" can be used interchangeably; however, it should be understood that the invention does not relate to the polypeptides in natural form, that is to say that they are not in their natural environment but that the polypeptides may have been isolated or obtained by purification from natural sources or obtained from host cells prepared by genetic manipulation (e.g., the polypeptides, or fragments thereof, are recombinantly produced by host cells, or by chemical synthesis). Polypeptides according to the instant invention may also contain non-natural amino acids, as will be described below. The terms "oligopeptide", "polypeptide", "peptide" and "protein" are also used, in the instant specification, to designate a series of residues, typically L-amino acids, connected one to the other, typically by peptide bonds between the α-amino and carboxyl groups of adjacent amino acids. Linker elements can be joined to the polypeptides of the subject invention through peptide bonds or via chemical bonds (e.g., heterobifunctional chemical linker elements) as set forth below. Additionally, the terms "amino acid(s)" and "residue(s)" can be used interchangeably.

In the context of both polypeptides and polynucleotides, the term "successive" can be used interchangeably with the term "consecutive" or the phrase "contiguous span" throughout the subject application. Thus, in some embodiments, a polynucleotide fragment may be referred to as "a contiguous span of at least X nucleotides, wherein X is any integer value beginning with 5; the upper limit for fragments as set forth herein is one nucleotide less than the total number of nucleotides found in the full-length sequence encoding a particular polypeptide (e.g., a polypeptide comprising SEQ ID NO: 9). A polypeptide fragment, by example, may be referred to as "a contiguous span of at least X amino acids, wherein X is any integer value beginning with 5; the upper limit for such polypeptide fragments is one amino acid less than the total number of amino acids found in the full-length sequence of a particular polypeptide (e.g., 667 for SEQ ID NO: 5, 693 for SEQ ID NO: 9 and 11, 601 amino acids for SEQ ID NO: 13 and 600 amino acids for SEQ ID NO: 15). As used herein, the term "integer" refers to whole numbers in the mathematical sense.

"Nucleotide sequence", "polynucleotide" or "nucleic acid" can be used interchangeably and are understood to mean, according to the present invention, either a double-stranded DNA, a single-stranded DNA or products of transcription of the said DNAs (e.g., RNA molecules). It should also be understood that the present invention does not relate to genomic polynucleotide sequences in their natural environment or natural state. The nucleic acid, polynucleotide, or nucleotide sequences of the invention can be isolated, purified (or partially purified), by separation methods including, but not limited to, ion-exchange chromatography, molecular size exclusion chromatography, or by genetic engineering methods such as amplification, subtractive hybridization, cloning, subcloning or chemical synthesis, or combinations of these genetic engineering methods. The terms "polynucleotide vaccine" and "DNA vaccine" can also be used interchangeably herein.

The terms "comprising", "consisting of" and "consisting essentially of" are defined according to their standard meaning. The terms may be substituted for one another throughout the instant application in order to attach the specific meaning associated with each term. The phrases "isolated" or "biologically pure" refer to material that is substantially or essentially free from components which normally accompany the material as it is found in its native state. Thus, isolated peptides in accordance with the invention preferably do not contain materials normally associated with the peptides in their in situ environment. "Link" or "join" refers to any method known in the art for functionally connecting peptides, including, without limitation, recombinant fusion, covalent bonding, disulfide bonding, ionic bonding, hydrogen bonding, and electrostatic bonding.

Thus, the subject invention provides polypeptides comprising SEQ ID NOs: 5, 9, 11, 13 or 15 and/or polypeptide fragments of SEQ ID NOs: 5, 9, 11, 13 or 15. Polypeptide fragments, according to the subject invention, comprise a contiguous span of at least 5 consecutive amino acids of SEQ ID NOs: 5, 9, 11, 13 or 15. Polypeptide fragments according to the subject invention can be any integer in length from at least 5 consecutive amino acids to 1 amino acid less than a full length polypeptide of SEQ ID NO: 5, 9, 11, 13 or 15. Fragments of SEQ ID NO: 5 can contain any number (integer) of consecutive amino acids between, and including, 5 and 667. For SEQ ID NO: 9 or 11 a polypeptide fragment is any number (integer) of consecutive amino acids between, and including, 5 and 693. For SEQ ID NO: 13, a polypeptide fragment is any number (integer) of consecutive amino acids between, and including, 5 and 601. For SEQ ID NO: 15, a polypeptide fragment is any number (integer) of consecutive amino acids between, and including 5 and 600 amino acids.

Each polypeptide fragment of the subject invention can also be described in terms of its N-terminal and C-terminal positions. Additionally, polypeptide fragments embodiments described herein may be "at least", "equal to", "equal to or less than", "less than", "at least _ but not greater than _" or "from Y to Z", wherein Y is the N-terminal amino acid of the specified sequence and Z is the C-terminal amino acid of the specified sequence, the fragment is at least 5 amino acids in length, and Y and Z are any integer specified (or selected from) those integers identified in the tables specifying the corresponding fragment lengths for each polypeptide disclosed herein (see Tables 9, 10, 11, 12, 15, and 16 [the positions listed in the tables correspond to the amino acid position as provided in the attached sequence listing]). As is apparent from Table 10, the N-terminal amino acid for fragments of SEQ ID NOs: 9 and 11 can be any integer from 1 to 690 and the C-terminal amino acid is any integer from 5 to 694 (depending on the fragment length which is to be any number (integer) of consecutive amino acids between, and including, 5 and 694). For fragments of SEQ ID NO: 5 (shown in Table 9), the N-terminal amino acid can be any integer between 1 and 664 and the C-terminal amino acid is any integer from 5 to 667 (depending on the fragment length which is to be any number (integer) of consecutive amino acids between, and including, 5 and 667). With respect to fragments of SEQ ID NO: 13 (illustrated in Table 11), the N-terminal amino acid can be any integer between 1 and 598 and the C-terminal amino acid is any integer from 5 to 602 (depending on the fragment length which is any number (integer) of consecutive amino acids between, and including, 5 and 601 amino acids). For SEQ ID NO: 15 (provided in Table 12), the N-terminal amino acid can be any integer between 1 and 597 and the C-terminal amino acid is any integer from 5 to 601 (depending on the fragment length which is any number (integer) of consecutive amino acids between, and including, 5 and 600 amino acids). It is noted that all ranges used to describe any embodiment of the present invention are inclusive unless specifically set forth otherwise and that fragments of a given polypeptide can be any integer in length, provided that the length of the polypeptide fragment is at least one amino acid shorter than the polypeptide identified in SEQ ID NO: 5, 9, 11, 13 or 15. To illustrate this concept, the four fragments provided by Table 12 that are 598 amino acids in length are provided. Thus, the various polypeptide fragments are defined as: where Y is position 1 of SEQ ID NO: 15, Z is position 598 of SEQ ID NO: 15 (the peptide is 598 amino acids in length); where Y is position 2 of SEQ ID NO: 15, Z is position 599 of SEQ ID NO: 15 (the peptide is 598 amino acids in length); where Y is position 3 of SEQ ID NO: 15, Z is position 600 of SEQ ID NO: 15 (the peptide is 598 amino acids in length); and where Y is position 4 of SEQ ID NO: 15, Z is position 601 of SEQ ID NO: 15 (the peptide is 598 amino acids in length).

The subject invention also provides for various polypeptide fragments (comprising contiguous spans or consecutive spans of at least five consecutive amino acids) that span particular residues of SEQ ID NO: 5, 9, 11, 13 or 15. For SEQ ID NOs: 9 and 11, preferred fragments include those of at least five consecutive amino acids that include at least one of the amino acids at positions 1-22 [i.e., 1, 2, 3, 4, 5, 6, 7, 8, 9, 10, 11, 12, 13, 14, 15, 16, 17, 18, 19, 20, 21 or all 22 of the amino acids], at least one, two or all three of the amino acids at positions 343-345 of SEQ ID NOs: 9 or 11, and at least one, two, three or all four of amino acids 691 through 694 as set forth in SEQ ID NO: 9 or 11. Non-limiting examples illustrating a few of these combinations of amino acids are set forth in Tables 15 or 16. For SEQ ID NO: 5, certain embodiments provide for any of those fragments of at least five consecutive amino acids that span amino acid 323. For SEQ ID NO: 13, various embodiments of the invention provide polypeptide fragments of at least five consecutive amino acids that span or include: at least one of the amino acids at positions 1-22 of SEQ ID NO: 13; and/or at least one, two, three, or all four of the amino acids at positions 599-602 of SEQ ID NO: 13. With respect to SEQ ID NO: 15, exemplary polypeptide fragments include those that span, or include at least one of the amino acids at positions 1-21 and/or 598-601 of SEQ ID NO: 15. Additional polypeptide fragments are also set forth in Tables 15 and 16. In some aspects of the invention, preferred polypeptide fragments are the complete E-peptide sequence identified in SEQ ID NOs: 5, 9, 11, 13 or 15.

Fragments, as described herein, can be obtained by cleaving the polypeptides of the invention with a proteolytic enzyme (such as trypsin, chymotrypsin, or collagenase) or with a chemical reagent, such as cyanogen bromide (CNBr). Alternatively, polypeptide fragments can be generated in a highly acidic environment, for example at pH 2.5. Such polypeptide fragments may be equally well prepared by chemical synthesis or using hosts transformed with an expression vector according to the invention. The transformed host cells contain a nucleic acid, allowing the expression of these fragments, under the control of appropriate elements for regulation and/or expression of the polypeptide fragments.

In certain preferred embodiments, fragments of the polypeptides disclosed herein retain at least one biological property or biological activity of the full-length polypeptide from which the fragments are derived (such fragments may also be referred to as "biologically active fragments". Thus, both full length polypeptides and fragments of the polypeptides provided by SEQ ID NO: 5, 9, 11, 13 or 15 have one or more of the following properties or biological activities: the ability to: 1) specifically bind to antibodies specific for SEQ ID NO: 5, 9, 11, 13 or 15; 2) specifically bind antibodies found in an animal or human infected with West Nile virus and/or antibodies that neutralize West Nile infectious virus (the ability of the virus to infect a host or target cell); the ability to bind to, and activate T-cell receptors (CTL (cytotoxic T-lymphocyte) and/or HTL (helper T-lymphocyte receptors)) in the context of MHC Class I or Class II antigen that are isolated or derived from an animal or human infected with West Nile virus; 3) the ability to induce an immune response in an animal or human against a West Nile virus; 4) the ability to induce a protective immune response in an animal or human against a West Nile virus; and/or 5) the ability to induce the production of West Nile Virus neutralizing antibodies (also referred to a neutralizing antibodies) in an animal/individual immunized with one or more of said polypeptides.

Where plant expression systems are used for the production of polypeptides provided in the subject application, or fragments thereof, a composition comprising the purified polypeptide can include plant cell components (e.g., cell walls, the cellular matrix of plant cell membranes and carbohydrates, etc.) or plant cell matrix components. Likewise, where eukaryotic or prokaryotic expression systems are used for the production of polypeptides of the subject invention, or fragments thereof, cell membrane or cell wall components of each respective expression system may be present in a composition comprising partially purified polypeptides.

The polypeptides (or fragments thereof) of the invention may be monomeric or multimeric (e.g., dimers, trimers, tetramers and higher multimers). Accordingly, the present invention relates to monomers and multimers of the polypeptides of the invention, their preparation, and compositions containing them. Multimeric polypeptides, as set forth herein, may be formed by hydrophobic, hydrophilic, ionic and/or covalent associations and/or may be indirectly linked, by for example, liposome formation. Thus, in one embodiment, multimers of the invention, such as, for example, homodimers or homotrimers, are formed when polypeptides of the invention contact one another in solution. In another embodiment, heteromultimers of the invention, such as, for example, heterotrimers or heterotetramers, are formed when polypeptides of the invention contact antibodies to the polypeptides of the invention (including antibodies to the heterologous polypeptide sequence in a fusion protein of the invention) in solution. In other embodiments, multimers of the invention are formed by covalent associations with and/or between the polypeptides of the invention. One non-limiting example of such a covalent association is the formation of disulfide bonds between immunoglobulin heavy chains as provided by a fusion protein of the invention that comprises a polypeptide comprising SEQ TD NO: 5, 9, 11, 13 or 15 (or fragments thereof) fused to an Ig heavy chain (see, e.g., U.S. Pat. No. 5,478,925, which disclosure is hereby incorporated by reference in its entirety). Another example of a fusion protein capable of forming covalently associated multimers is oseteoprotegerin (see, e.g., International Publication No. WO 98/49305, herein incorporated by reference in its entirety). In another embodiment, two or more polypeptides of the invention are joined through peptide linkers. Examples include those peptide linkers described in U.S. Pat. No. 5,073,627 (hereby incorporated by reference). Proteins comprising multiple polypeptides of the invention separated by peptide linkers may be produced using conventional recombinant DNA technology.

Other multimeric polypeptides can be formed by fusing the polypeptides of the invention to a leucine zipper or isoleucine zipper polypeptide sequence. Leucine zipper and isoleucine zipper domains are polypeptides that promote multimerization of the proteins in which they are found. Non-limiting examples of leucine zipper domains suitable for producing soluble multimeric proteins of the invention are those described in PCT application WO 94/10308, hereby incorporated by reference. Recombinant fusion proteins comprising a polypeptide of the invention fused to a polypeptide sequence that dimerizes or trimerizes in solution are expressed in suitable host cells, and the resulting soluble multimeric fusion protein is recovered from the culture supernatant using techniques known in the art.

Multimeric polypeptides can also be generated using chemical techniques known in the art. For example, polypeptides desired to be contained in the multimers of the invention may be chemically cross-linked using linker molecules and linker molecule length optimization techniques known in the art (see, e.g., U.S. Pat. No. 5,478,925, which is herein incorporated by reference in its entirety). Additionally, multimeric polypeptides can be generated by introducing disulfide bonds between the cysteine residues located within the sequence of the polypeptides that are being used to construct the multimeric polypeptide (see, e.g., U.S. Pat. No. 5,478,925, which is herein incorporated by reference in its entirety). Further, polypeptides of the invention may be routinely modified by the addition of cysteine or biotin to the C terminus or N-terminus of the polypeptide and techniques known in the art may be applied to generate multimers containing one or more of these modified polypeptides (see, e.g., U.S. Pat. No. 5,478,925, which is herein incorporated by reference in its entirety). Additionally, other techniques known in the art may be applied to generate liposomes containing the polypeptide components desired to be contained in the multimer of the invention (see, e.g., U.S. Pat. No. 5,478,925, which is herein incorporated by reference in its entirety).

The polypeptides provided herein, as well as the fragments thereof, may further comprise linker elements (L) that facilitate the attachment of the fragments to other molecules, amino acids, or polypeptide sequences. The linkers can also be used to attach the polypeptides, or fragments thereof, to solid support matrices for use in affinity purification protocols. Non-limiting examples of "linkers" suitable for the practice of the invention include chemical linkers (such as those sold by Pierce, Rockford, Ill.), or peptides that allow for the connection combinations of polypeptides (see, for example, linkers such as those disclosed in U.S. Pat. Nos. 6,121,424, 5,843,464, 5,750,352, and 5,990,275, hereby incorporated by reference in their entirety).

In other embodiments, the linker element (L) can be an amino acid sequence (a peptide linker). In some embodiments, the peptide linker has one or more of the following characteristics: a) it allows for the free rotation of the polypeptides that it links (relative to each other); b) it is resistant or susceptible to digestion (cleavage) by proteases; and c) it does not interact with the polypeptides it joins together. In various embodiments, a multimeric construct according to the subject invention includes a peptide linker and the peptide linker is 5 to 60 amino acids in length. More preferably, the peptide linker is 10 to 30, amino acids in length; even more preferably, the peptide linker is 10 to 20 amino acids in length. In some embodiments, the peptide linker is 17 amino acids in length.

Peptide linkers suitable for use in the subject invention are made up of amino acids selected from the group consisting of Gly, Ser, Asn, Thr and Ala. Preferably, the peptide linker includes a Gly-Ser element. In a preferred embodiment, the peptide linker comprises $(\text{Ser-Gly-Gly-Gly-Gly})_y$ wherein y is 1, 2, 3, 4, 5, 6, 7, or 8. Other embodiments provide for a peptide linker comprising $((\text{Ser-Gly-Gly-Gly-Gly})_y\text{-Ser-Pro})$. In certain preferred embodiments, y is a value of 3, 4, or 5. In other preferred embodiment, the peptide linker comprises $(\text{Ser-Ser-Ser-Ser-Gly})_y$ or $((\text{Ser-Ser-Ser-Ser-Gly})_y\text{-Ser-Pro})$, wherein y is 1, 2, 3, 4, 5, 6, 7, or 8. In certain preferred embodiments, y is a value of 3, 4, or 5. Where cleavable linker elements are desired, one or more cleavable linker sequences such as Factor Xa or enterokinase (Invitrogen, San Diego Calif.) can be used alone or in combination with the aforementioned linkers.

Multimeric constructs of the subject invention can also comprise a series of repeating elements, optionally interspersed with other elements. As would be appreciated by one skilled in the art, the order in which the repeating elements occur in the multimeric polypeptide is not critical and any arrangement of the repeating elements as set forth herein can be provided by the subject invention. Thus, a "multimeric construct" according to the subject invention can provide a multimeric polypeptide comprising a series of polypeptides or polypeptide fragments that are, optionally, joined together by linker elements (either chemical linker elements or amino acid linker elements).

Fusion proteins according to the subject invention comprise one or more heterologous polypeptide sequences (e.g., tags that facilitate purification of the polypeptides of the invention (see, for example, U.S. Pat. No. 6,342,362, hereby incorporated by reference in its entirety; Altendorf et al., (1999-WWW, 2000); Baneyx, (1999); Eihauer et al., (2001); Jones et al. (1995); Margolin (2000); Puig et al., (2001); Sassenfeld (1990); Sheibani (1999); Skerra et al., (1999); Smith (1998); Smyth et al., (2000); Unger (1997), each of which is hereby incorporated by reference in their entireties), or commercially available tags from vendors such as STRATAGENE (La Jolla, Calif.), NOVAGEN (Madison, Wis.), QIAGEN, Inc., (Valencia, Calif.), or InVitrogen (San Diego, Calif.).

In other embodiments, polypeptides of the subject invention (e.g., SEQ ID NOs: 5, 9, 11, 13, 15 or fragments thereof) can be fused to heterologous polypeptide sequences that have adjuvant activity (a polypeptide adjuvant). Non-limiting examples of such polypeptides include heat shock proteins (hsp) (see, for example, U.S. Pat. No. 6,524,825, the disclosure of which is hereby incorporated by reference in its entirety).

The subject invention also provides biologically active fragments of a polypeptide according to the invention and includes those peptides capable of eliciting an immune response directed against a West Nile virus, said immune response providing components (B-cells, antibodies, and/or components of the cellular immune response (e.g., helper, cytotoxic, and/or suppressor T-cells)) reactive with the fragment of said polypeptide; the intact, full length, unmodified polypeptide disclosed herein; or both a fragment of a polypeptide and the intact, full length, unmodified polypeptides disclosed herein. Certain embodiments provide methods of inducing an antibody response that produces West Nile virus neutralizing antibodies.

The subject application also provides a composition comprising at least one isolated, recombinant, or purified polypeptide comprising SEQ ID NO: 5, 9, 11, 13 or 15 (or a fragment thereof) and at least one additional component. In various aspects of the invention, the additional component is a solid support (for example, microtiter wells, magnetic beads, non-magnetic beads, agarose beads, glass, cellulose, plastics, polyethylene, polypropylene, polyester, nitrocellulose, nylon, or polysulfone). The additional component can also be a pharmaceutically acceptable excipient or adjuvant known to those skilled in the art. In some aspects of the invention, the solid support provides an array of polypeptides of the subject invention or an array of polypeptides comprising combinations of various polypeptides of the subject invention. Other aspects of the invention provide a composition comprising the purified polypeptide that includes plant cell components (e.g., cell walls, the cellular matrix of plant cell membranes and carbohydrates, etc.) or plant cell matrix components. Likewise, where eukaryotic or prokaryotic expression systems are used for the production of polypeptides or fragments of the polypeptides provided by this application, cell membrane or cell wall components of each respective expression system may be present in a composition comprising partially purified polypeptides.

The subject invention also provides methods for eliciting an immune response in an individual comprising the administration of compositions comprising polypeptides according to the subject invention to an individual in amounts sufficient to induce an immune response in the individual. In some embodiments, a "protective" or "therapeutic immune response" is induced in the individual. A "protective immune response" or "therapeutic immune response" refers to an induction in the production of antibodies that neutralize infectious West Nile viruses, or induce a CTL (or $CD8^+$ T cell) and/or an HTL (or $CD4^+$ T cell), and/or an antibody response that prevents, reduces or at least partially arrests disease symptoms, side effects or progression in the individuals. For example, individuals in which a protective immune response has been induced can exhibit reduced mortality and/or exhibit reduced viral shedding as compared to non-immunized control individuals. The protective immune response may also include an antibody response that has been facilitated by the stimulation of helper T cells (or $CD4^+$ T cells). Additional methods of inducing an immune response in an individual are taught in U.S. Pat. No. 6,419,931, hereby incorporated by reference in its entirety. The term CTL can be used interchangeably with $CD8^+$ T-cell(s) and the term HTL can be used interchangeably with $CD4^+$ T-cell(s) throughout the subject application.

Individuals, in the context of this application, refers to birds and/or mammals such as, but not limited to, apes, chimpanzees, orangutans, humans, monkeys or domesticated animals (pets) such as dogs, cats, guinea pigs, hamsters, rabbits, ferrets, cows, horses, goats and sheep. Avian or bird is herein defined as any warm-blooded vertebrate member of the class Aves typically having forelimbs modified into wings, scaly legs, a beak, and bearing young in hard-shelled eggs. For purposes of this specification, preferred groups of birds are domesticated chickens, turkeys, ostriches, ducks, geese, swan, Cornish game hens and exotic birds kept as pets or for display in zoos.

Administering or administer is defined as the introduction of a substance into the body of an individual and includes oral, nasal, ocular, rectal, vaginal and parenteral routes. Compositions may be administered individually or in combination with other agents via any route of administration, including but not limited to subcutaneous (SQ), intramuscular (IM), intravenous (IV), intraperitoneal (IP), intradermal (ID), transdermal, (TD), or via the nasal, ocular, oral, or rectal mucosa.

The composition administered to the individual may, optionally, contain an adjuvant and may be delivered in any manner known in the art for the delivery of immunogen to a subject. Compositions may also be formulated in any carriers, including for example, pharmaceutically acceptable carriers such as those described in E. W. Martin's *Remington's Pharmaceutical Science*, Mack Publishing Company, Easton, Pa. In preferred embodiments, compositions may be formulated in incomplete Freund's adjuvant, complete Freund's adjuvant, or alum. Other non-limiting examples of adjuvants that can be used in the practice of the invention include: oil-water emulsions, Polygen, Carbigen (Carbopol 974P NF) or TiterMax (Block copolymer CRL-8941, squalene and a unique microparticulate stabilizer).

In other embodiments, the subject invention provides for diagnostic assays based upon Western blot formats or standard immunoassays known to the skilled artisan and which utilize a polypeptide comprising, consisting essentially of, or consisting of SEQ ID NO: 5, 9, 11, 13 or 15. For example, antibody-based assays such as enzyme linked immunosorbent assays (ELISAs), radioimmunoassays (RIAs), lateral flow assays, reversible flow chromatographic binding assay (see, for example, U.S. Pat. No. 5,726,010, which is hereby incorporated by reference in its entirety), immunochromatographic strip assays, automated flow assays, and assays utilizing peptide-containing biosensors may be employed for the detection of antibodies that bind to the polypeptides (or fragments thereof) that are provided by the subject invention. The assays and methods for conducting the assays are well-known in the art and the methods may test biological samples (e.g., serum, plasma, or blood) qualitatively (presence or absence of antibody) or quantitatively (comparison of a sample against a standard curve prepared using a polypeptide of the subject invention) for the presence of antibodies that bind to polypeptides of the subject invention.

The antibody-based assays can be considered to be of four types: direct binding assays, sandwich assays, competition assays, and displacement assays. In a direct binding assay, either the antibody or antigen is labeled, and there is a means of measuring the number of complexes formed. In a sandwich assay, the formation of a complex of at least three components (e.g., antibody-antigen-antibody) is measured. In a competition assay, labeled antigen and unlabelled antigen compete for binding to the antibody, and either the bound or the free component is measured. In a displacement assay, the labeled antigen is pre-bound to the antibody, and a change in signal is measured as the unlabelled antigen displaces the bound, labeled antigen from the receptor.

Lateral flow assays can be conducted according to the teachings of U.S. Pat. No. 5,712,170 and the references cited therein. U.S. Pat. No. 5,712,170 and the references cited therein are hereby incorporated by reference in their entireties. Displacement assays and flow immunosensors useful for carrying out displacement assays are described in: Kusterbeck et al., (1990); Kusterbeck et al., (1990a); Ligler et al., (1992); Ogert et al., (1992), all of which are incorporated herein by reference in their entireties. Displacement assays and flow immunosensors are also described in U.S. Pat. No. 5,183,740, which is also incorporated herein by reference in its entirety. The displacement immunoassay, unlike most of the competitive immunoassays used to detect small molecules, can generate a positive signal with increasing antigen concentration.

The subject invention also provides methods of binding an antibody to a polypeptide of the subject invention (e.g., SEQ ID NO: 5, 9, 11, 13 or 15, or an antibody binding fragment thereof) comprising contacting a sample containing an antibody with a polypeptide under conditions that allow for the formation of an antibody-antigen complex. These methods can further comprise the step of detecting the formation of said antibody-antigen complex. In various aspects of this method, an immunoassay is conducted for the detection of West Nile virus specific antibodies in a sample. Non-limiting examples of such immunoassays include enzyme linked immunosorbent assays (ELISAs), radioimmunoassays (RIAs), lateral flow assays, immunochromatographic strip assays, automated flow assays, Western blots, immunoprecipitation assays, reversible flow chromatographic binding assays, agglutination assays, and biosensors. Additional aspects of the invention provide for the use of an array of polypeptides when conducting the aforementioned methods of detecting antibodies specific to West Nile virus (the array can contain at least one of the polypeptides set forth in SEQ ID NOs: 5, 9, 11, 13 or 15 (or fragments thereof) and can also contain other polypeptides of the same or different viral origin).

The subject invention also concerns antibodies that bind to polypeptides of the invention. Antibodies that are immunospecific for the polypeptides as set forth herein are specifically contemplated. In various embodiments, antibodies that do not cross-react with other known West Nile virus polypeptides are preferred. Particularly preferred antibodies do not cross-react with antibodies produced against polypeptides derived from known strains of West Nile virus. The antibodies of the subject invention can be prepared using standard materials and methods known in the art (see, for example, *Monoclonal Antibodies. Principles and Practice,* 1983*; Monoclonal Hybridoma Antibodies: Techniques and Applications,* 1982*; Selected Methods in Cellular Immunology,* 1980*; Immunological Methods, Vol. II,* 1981*; Practical Immunology*, and Kohler et al., 1975; Letchworth and Appleton, 1984). These antibodies can further comprise one or more additional components, such as a solid support, a carrier or pharmaceutically acceptable excipient, or a label.

The term "antibody" includes monoclonal antibodies (including full length monoclonal antibodies), polyclonal antibodies, multispecific antibodies (e.g., bispecific antibodies), and antibody fragments so long as they exhibit the desired biological activity, particularly neutralizing activity. "Antibody fragments" comprise a portion of a full length antibody, generally the antigen binding or variable region thereof.

Examples of antibody fragments include Fab, Fab', $F(ab')_2$, and Fv fragments; diabodies; linear antibodies; single-chain antibody molecules; and multi-specific antibodies formed from antibody fragments. Particularly preferred antibodies according to the subject invention are those that do not bind to the unmodified WNV polypeptides known in the art.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations that typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., (1975), or may be made by recombinant DNA methods (see, e.g., U.S. Pat. No. 4,816,567). The "monoclonal antibodies" may also be isolated from phage antibody libraries using the techniques described in Clackson et al. (1991) and Marks et al. (1991), for example.

The monoclonal antibodies described herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., (1984)). Also included are humanized antibodies that specifically bind to the polypeptides, or fragments thereof, set forth in SEQ ID NO: 5, 9, 11, 13 or 15 (see, for example, U.S. Pat. No. 6,407,213 or 6,417,337, which are hereby incorporated by reference in their entirety, teaching methods of making humanized antibodies).

"Single-chain Fv" or "sFv" antibody fragments comprise the $V_H$ and $V_T$ domains of an antibody, wherein these domains are present in a single polypeptide chain. Generally, the Fv polypeptide further comprises a polypeptide linker between the $V_H$ and $V_L$ domains which enables the sFv to form the desired structure for antigen binding. For a review of sFv see Pluckthun (1994).

The term "diabodies" refers to small antibody fragments with two antigen-binding sites, which fragments comprise a heavy chain variable domain ($V_H$) connected to a light chain variable domain ($V_L$) in the same polypeptide chain ($V_H$-$V_L$). Diabodies are described more fully in, for example, EP 404, 097; WO 93/11161; and Holliger et al. (1993). The term "linear antibodies" refers to the antibodies described in Zapata et al. (1995).

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or non-reducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

As discussed above, "nucleotide sequence", "polynucleotide" or "nucleic acid" can be used interchangeably and are understood to mean, according to the present invention, either a double-stranded DNA, a single-stranded DNA or products of transcription of the said DNAs (e.g., RNA molecules).

The range of percent identity, between 20.00% and 99.99%, is to be taken as including, and providing written description and support for, any fractional percentage, in intervals of 0.01%, between 20.00% and, up to, including 99.99%. These percentages are purely statistical and differences between two nucleic acid sequences can be distributed randomly and over the entire sequence length. For example, homologous sequences can exhibit a percent identity of 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 percent with the sequences of the instant invention. Typically, the percent identity is calculated with reference to the full length, native, and/or naturally occurring polynucleotide. The terms "identical" or percent "identity", in the context of two or more polynucleotide or polypeptide sequences, refer to two or more sequences or subsequences that are the same or have a specified percentage of nucleotides or amino acid residues that are the same, when compared and aligned for maximum correspondence over a comparison window, as measured using a sequence comparison algorithm or by manual alignment and visual inspection.

Both protein and nucleic acid sequence homologies may be evaluated using any of the variety of sequence comparison algorithms and programs known in the art. Such algorithms and programs include, but are by no means limited to, TBLASTN, BLASTP, FASTA, TFASTA, and CLUSTALW (Pearson et al., 1988; Altschul et al., 1990; Thompson et al., 1994; Higgins et al., 1996; Gish et al., 1993). Sequence comparisons are, typically, conducted using default parameters provided by the vendor or using those parameters set forth in the above-identified references, which are hereby incorporated by reference in their entireties.

A "complementary" polynucleotide sequence, as used herein, generally refers to a sequence arising from the hydrogen bonding between a particular purine and a particular pyrimidine in double-stranded nucleic acid molecules (DNA-DNA, DNA-RNA, or RNA-RNA). The major specific pairings are guanine with cytosine and adenine with thymine or uracil. A "complementary" polynucleotide sequence may also be referred to as an "antisense" polynucleotide sequence or an "antisense sequence".

Sequence homology and sequence identity can also be determined by hybridization studies under high stringency, intermediate stringency, and/or low stringency. Various degrees of stringency of hybridization can be employed. The more severe the conditions are, the greater the complementarity that is required for duplex formation. Severity of conditions can be controlled by temperature, probe concentration, probe length, ionic strength, time, and the like. Preferably, hybridization is conducted under low, intermediate, or high stringency conditions by techniques well known in the art, as described, for example, in Keller and Manak (1987).

For example, hybridization of immobilized DNA on Southern blots with $^{32}P$-labeled gene-specific probes can be performed by standard methods (Maniatis et al., 1982). In general, hybridization and subsequent washes can be carried out under intermediate to high stringency conditions that allow for detection of target sequences with homology to the exemplified polynucleotide sequence. For double-stranded DNA gene probes, hybridization can be carried out overnight at 20-25° C. below the melting temperature ($T_m$) of the DNA hybrid in 6×SSPE, 5×Denhardt's solution, 0.1% SDS, 0.1 mg/ml denatured DNA. The melting temperature is described by the following formula (Beltz et al., 1983).

$$Tm=81.5° \text{ C.}+16.6 \text{ Log } [Na^+]+0.41 (\% G+C)-0.61 (\% \text{ formamide})-600/\text{length of duplex in base pairs.}$$

Washes are typically carried out as follows:

(1) twice at room temperature for 15 minutes in 1×SSPE, 0.1% SDS (low stringency wash);

(2) once at $T_m$-20° C. for 15 minutes in 0.2×SSPE, 0.1% SDS (intermediate stringency wash).

For oligonucleotide probes, hybridization can be carried out overnight at 10-20° C. below the melting temperature ($T_m$) of the hybrid in 6×SSPE, 5×Denhardt's solution, 0.1% SDS, 0.1 mg/ml denatured DNA. $T_m$ for oligonucleotide probes can be determined by the following formula:

$$T_m(° \text{ C.})=2(\text{number } T/A \text{ base pairs})+4(\text{number } G/C \text{ base pairs}) \text{ (Suggs et al., 1981).}$$

Washes can be carried out as follows:

(1) twice at room temperature for 15 minutes 1×SSPE, 0.1% SDS (low stringency wash);

(2) once at the hybridization temperature for 15 minutes in 1×SSPE, 0.1% SDS (intermediate stringency wash).

In general, salt and/or temperature can be altered to change stringency. With a labeled DNA fragment >70 or so bases in length, the following conditions can be used:

Low: 1 or 2×SSPE, room temperature

Low: 1 or 2×SSPE, 42° C.

Intermediate: 0.2× or 1×SSPE, 65° C.

High: 0.1×SSPE, 65° C.

By way of another non-limiting example, procedures using conditions of high stringency can also be performed as follows: Pre-hybridization of filters containing DNA is carried out for 8 h to overnight at 65° C. in buffer composed of 6×SSC, 50 mM Tris-HCl (pH 7.5), 1 mM EDTA, 0.02% PVP, 0.02% Ficoll, 0.02% BSA, and 500 μg/ml denatured salmon sperm DNA. Filters are hybridized for 48 h at 65° C., the preferred hybridization temperature, in pre-hybridization mixture containing 100 μg/ml denatured salmon sperm DNA and 5-20×10$^6$ cpm of $^{32}P$-labeled probe. Alternatively, the hybridization step can be performed at 65° C. in the presence of SSC buffer, 1×SSC corresponding to 0.15M NaCl and 0.05 M Na citrate. Subsequently, filter washes can be done at 37° C. for 1 h in a solution containing 2×SSC, 0.01% PVP, 0.01% Ficoll, and 0.01% BSA, followed by a wash in 0.1×SSC at 50° C. for 45 min. Alternatively, filter washes can be performed in a solution containing 2×SSC and 0.1% SDS, or 0.5×SSC and 0.1% SDS, or 0.1×SSC and 0.1% SDS at 68° C. for 15 minute intervals. Following the wash steps, the hybridized probes are detectable by autoradiography. Other conditions of high stringency which may be used are well known in the art and as cited in Sambrook et al. (1989) and Ausubel et al. (1989) are incorporated herein in their entirety.

Another non-limiting example of procedures using conditions of intermediate stringency are as follows: Filters containing DNA are pre-hybridized, and then hybridized at a temperature of 60° C. in the presence of a 5×SSC buffer and labeled probe. Subsequently, filters washes are performed in a solution containing 2×SSC at 50° C. and the hybridized probes are detectable by autoradiography. Other conditions of intermediate stringency which may be used are well known in the art and as cited in Sambrook et al. (1989) and Ausubel et al. (1989) are incorporated herein in their entirety.

Duplex formation and stability depend on substantial complementarity between the two strands of a hybrid and, as noted above, a certain degree of mismatch can be tolerated. Therefore, the probe sequences of the subject invention include mutations (both single and multiple), deletions, insertions of the described sequences, and combinations thereof, wherein said mutations, insertions and deletions permit formation of stable hybrids with the target polynucleotide of interest. Mutations, insertions and deletions can be produced in a given polynucleotide sequence in many ways, and these methods are known to an ordinarily skilled artisan. Other methods may become known in the future.

It is also well known in the art that restriction enzymes can be used to obtain functional fragments of the subject DNA sequences. For example, Bal31 exonuclease can be conveniently used for time-controlled limited digestion of DNA (commonly referred to as "erase-a-base" procedures). See, for example, Maniatis et al. (1982); Wei et al. (1983).

The present invention further comprises fragments of the polynucleotide sequences of the instant invention. Representative fragments of the polynucleotide sequences according to the invention will be understood to mean any nucleotide fragment having at least 5 successive nucleotides, preferably at least 12 successive nucleotides, and still more preferably at least 15, 18, or at least 20 successive nucleotides of the sequence from which it is derived. The upper limit for fragments as set forth herein is the total number of nucleotides found in the full-length sequence encoding a particular polypeptide (e.g., a polypeptide such as that of SEQ ID NO: 5).

In some embodiments, the subject invention includes those fragments capable of hybridizing under various conditions of stringency conditions (e.g., high or intermediate or low stringency) with a nucleotide sequence according to the invention; fragments that hybridize with a nucleotide sequence of the subject invention can be, optionally, labeled as set forth below.

The subject invention provides, in one embodiment, methods for the identification of the presence of nucleic acids according to the subject invention in transformed host cells or in cells isolated from an individual suspected of being infected by West Nile virus. In these varied embodiments, the invention provides for the detection of nucleic acids in a sample (obtained from the individual or from a cell culture) comprising contacting a sample with a nucleic acid (polynucleotide) of the subject invention (such as an RNA, mRNA, DNA, cDNA, or other nucleic acid). In a preferred embodiment, the polynucleotide is a probe that is, optionally, labeled and used in the detection system. Many methods for detection of nucleic acids exist and any suitable method for detection is encompassed by the instant invention. Typical assay formats utilizing nucleic acid hybridization includes, and are not limited to, 1) nuclear run-on assay, 2) slot blot assay, 3) northern blot assay (Alwine et al., 1977, 4) magnetic particle separation, 5) nucleic acid or DNA chips, 6) reverse Northern blot assay, 7) dot blot assay, 8) in situ hybridization, 9) kNase protection assay (Melton et al., 1984) and as described in the 1998 catalog of Ambion, Inc., Austin, Tex., 10) ligase chain reaction, 11) polymerase chain reaction (PCR), 12) reverse transcriptase (RT)-PCR (Berchtold, 1989), 13) differential display RT-PCR (DDRT-PCR) or other suitable combinations of techniques and assays. Labels suitable for use in these detection methodologies include, and are not limited to 1) radioactive labels, 2) enzyme labels, 3) chemiluminescent labels, 4) fluorescent labels, 5) magnetic labels, or other suitable labels, including those set forth below. These methodologies and labels are well known in the art and widely available to the skilled artisan. Likewise, methods of incorporating labels into the nucleic acids are also well known to the skilled artisan.

Thus, the subject invention also provides detection probes (e.g., fragments of the disclosed polynucleotide sequences) for hybridization with a target sequence or the amplicon generated from the target sequence. Such a detection probe will comprise a contiguous/consecutive span of at least 8, 9, 10, 11, 12, 15, 16, 17, 18, 19, 20, 21, 22, 23, 24, 25, 26, 27, 28, 29, 30, 35, 40, 45, 50, 55, 60, 65, 70, 75, 80, 85, 90, 95, or 100 nucleotides. Labeled probes or primers are labeled with a radioactive compound or with another type of label as set forth above (e.g., 1) radioactive labels, 2) enzyme labels, 3) chemiluminescent labels, 4) fluorescent labels, or 5) magnetic labels). Alternatively, non-labeled nucleotide sequences may be used directly as probes or primers; however, the sequences are generally labeled with a radioactive element ($^{32}P$, $^{35}S$, $^{3}H$, $^{121}I$) or with a molecule such as biotin, acetylaminofluorene, digoxigenin, 5-bromo-deoxyuridine, or fluorescein to provide probes that can be used in numerous applications.

Polynucleotides of the subject invention can also be used for the qualitative and quantitative analysis of gene expression using arrays or polynucleotides that are attached to a solid support. As used herein, the term array means a one-, two-, or multi-dimensional arrangement of full length polynucleotides or polynucleotides of sufficient length to permit specific detection of gene expression. Preferably, the fragments are at least 15 nucleotides in length. More preferably, the fragments are at least 100 nucleotides in length. More preferably, the fragments are more than 100 nucleotides in length. In some embodiments the fragments may be more than 500 nucleotides in length.

For example, quantitative analysis of gene expression may be performed with full-length polynucleotides of the subject invention, or fragments thereof, in a complementary DNA microarray as described by Schena et al. (1995, 1996). Polynucleotides, or fragments thereof, are amplified by PCR and arrayed onto silylated microscope slides. Printed arrays are incubated in a humid chamber to allow rehydration of the array elements and rinsed, once in 0.2% SDS for 1 min, twice in water for 1 min and once for 5 min in sodium borohydride solution. The arrays are submerged in water for 2 min at 95° C., transferred into 0.2% SDS for 1 min, rinsed twice with water, air dried and stored in the dark at 25° C. mRNA is isolated from a biological sample and probes are prepared by a single round of reverse transcription. Probes are hybridized to 1 $cm^2$ microarrays under a 14×14 mm glass coverslip for 6-12 hours at 60° C. Arrays are washed for 5 min at 25° C. in low stringency wash buffer (1×SSC/0.2% SDS), then for 10 min at room temperature in high stringency wash buffer (0.1×SSC/0.2% SDS). Arrays are scanned in 0.1×SSC using a fluorescence laser scanning device fitted with a custom filter set. Accurate differential expression measurements are obtained by taking the average of the ratios of two independent hybridizations.

Quantitative analysis of the polynucleotides present in a biological sample can also be performed in complementary DNA arrays as described by Pietu et al. (1996). The polynucleotides of the invention, or fragments thereof, are PCR amplified and spotted on membranes. Then, mRNAs originating from biological samples derived from various tissues or cells are labeled with radioactive nucleotides. After hybridization and washing in controlled conditions, the hybridized mRNAs are detected by phospho-imaging or autoradiography. Duplicate experiments are performed and a quantitative analysis of differentially expressed mRNAs is then performed.

Alternatively, the polynucleotide sequences of the invention may also be used in analytical systems, such as DNA chips. DNA chips and their uses are well known in the art (see for example, U.S. Pat. Nos. 5,561,071; 5,753,439; 6,214,545; Schena 1996; Bianchi et al., 1997; each of which is hereby incorporated by reference in their entireties) and/or are provided by commercial vendors such as Affymetrix, Inc. (Santa Clara, Calif.). In addition, the nucleic acid sequences of the subject invention can be used as molecular weight markers in nucleic acid analysis procedures.

The subject invention also provides compositions of matter that comprise:

a) a polynucleotide sequence encoding a polypeptide comprising SEQ ID NO: 5, 9, 11, 13 or 15 or encoding one or more polypeptide fragment of SEQ ID NOs: 5, 9, 11, 13 or 15 as set forth in Table 9, 10, 11, 12, 15, or 16. In various aspects of the invention, these polynucleotides can have a G+C content of at least 40% and less than 50% or a G+C content as set forth in Table 13;

b) a polynucleotide sequence that is at least 70% (or a percentage as specified in the Table 14) identical to SEQ ID NO: 1, encodes a polypeptide comprising SEQ ID NO: 2 and has a G+C content of between about 40% and about 50% (or a specific G+C content as specified in Table 13);

c) a polynucleotide sequence at least 8 consecutive nucleotides of a polynucleotide sequence as set forth in (a) or (b);

d) a polynucleotide sequence comprising SEQ ID NO: 3, 4, 6, 7, 8, 10, or 12 or a fragment of at least 8 consecutive nucleotides of SEQ ID NO: 3, 4, 6, 7, 8, 10, or 12;

e) a polynucleotide that is complementary to the polynucleotides set forth in (a), (b), (c), or (d);

f) a polynucleotide that hybridizes under low, intermediate or high stringency with a polynucleotide sequence as set forth in (a), (b), (c), (d) or (e);

g) a genetic construct comprising a polynucleotide sequence as set forth in (a), (b), (c), (d) or (e);

h) a vector comprising a polynucleotide or genetic construct as set forth in (a), (b), (c), (d), (e), (f) or (g);

i) a host cell comprising a vector as set forth in (h), a genetic construct as set forth in (g), or a polynucleotide as set forth in any one of (a), (b), (c), (d) or (e);

j) a transgenic plant, plant cell, or plant part comprising a vector as set forth in (h), a genetic construct as set forth in (g) or a polynucleotide as set forth in any one of (a), (b), (c), (d) or (e); or k) a probe comprising a polynucleotide according to (a), (b), (c), (d), (e) or (f) and, optionally, a label or marker.

The subject invention also provides genetic constructs comprising: a) a polynucleotide sequence encoding a polypeptide comprising SEQ ID NO: 5, 9, 11, 13 or 15, or a fragment thereof; b) a polynucleotide sequence having at least about 20% to 99.99% identity to a polynucleotide sequence encoding a polypeptide comprising SEQ ID NO: 5, 9, 11, 13 or 15, or a fragment of SEQ ID NO: 5, 9, 11, 13 or 15, wherein said polypeptide has at least one of the biological activities of a polypeptide comprising SEQ ID NO: 5, 9, 11, 13 or 15, or a fragment thereof; c) a polynucleotide sequence encoding a polypeptide having at least about 20% to 99.99% identity to a polypeptide comprising SEQ ID NO: 5, 9, 11, 13 or 15, or a fragment of SEQ ID NO: 5, 9, 11, 13 or 15, wherein said polypeptide has at least one of the biological activities of a polypeptide comprising SEQ ID NO: 5, 9, 11, 13 or 15, or a fragment thereof; d) a polynucleotide sequence encoding a fragment of a polypeptide comprising SEQ ID NO: 5, 9, 11, 13 or 15, wherein said fragment has at least one of the activities of the polypeptide of SEQ ID NO: 5, 9, 11, 13 or 15; e) a polynucleotide sequence comprising SEQ ID NO: 3, 4, 6, 7, 8, 10, 12, or 14; f) a polynucleotide sequence having at least about 20% to 99.99% identity to the polynucleotide sequence of SEQ ID NO: 3, 4, 6, 7, 8, 10, 12, or 14; g) a polynucleotide sequence encoding multimeric construct; or h) a polynucleotide that is complementary to the polynucleotides set forth in (a), (b), (c), (d), (e), (f), or (g). Genetic constructs of the subject invention can also contain additional regulatory elements such as promoters and enhancers and, optionally, selectable markers.

Also within the scope of the subject instant invention are vectors or expression cassettes containing genetic constructs as set forth herein or polynucleotides encoding the polypeptides, set forth supra, operably linked to regulatory elements. The vectors and expression cassettes may contain additional transcriptional control sequences as well. The vectors and expression cassettes may further comprise selectable markers. The expression cassette may contain at least one additional gene, operably linked to control elements, to be co-transformed into the organism. Alternatively, the additional gene(s) and control element(s) can be provided on multiple expression cassettes. Such expression cassettes are provided with a plurality of restriction sites for insertion of the sequences of the invention to be under the transcriptional regulation of the regulatory regions. The expression cassette (s) may additionally contain selectable marker genes operably linked to control elements.

The expression cassette will include in the 5'-3' direction of transcription, a transcriptional and translational initiation region, a DNA sequence of the invention, and transcriptional and translational termination regions. The transcriptional initiation region, the promoter, may be native or analogous, or foreign or heterologous, to the host cell. Additionally, the promoter may be the natural sequence or alternatively a synthetic sequence. By "foreign" is intended that the transcriptional initiation region is not found in the native plant into which the transcriptional initiation region is introduced. As used herein, a chimeric gene comprises a coding sequence operably linked to a transcriptional initiation region that is heterologous to the coding sequence.

Another aspect of the invention provides vectors for the cloning and/or the expression of a polynucleotide sequence taught herein. Vectors of this invention, including vaccine vectors, can also comprise elements necessary to allow the expression and/or the secretion of the said nucleotide sequences in a given host cell. The vector can contain a promoter, signals for initiation and for termination of translation, as well as appropriate regions for regulation of transcription. In certain embodiments, the vectors can be stably maintained in the host cell and can, optionally, contain signal sequences directing the secretion of translated protein. These different elements are chosen according to the host cell used. Vectors can integrate into the host genome or, optionally, be autonomously-replicating vectors.

The subject invention also provides for the expression of a polypeptide or peptide fragment encoded by a polynucleotide sequence disclosed herein comprising the culture of a host cell transformed with a polynucleotide of the subject invention under conditions that allow for the expression of the polypeptide and, optionally, recovering the expressed polypeptide.

The disclosed polynucleotide sequences can also be regulated by a second nucleic acid sequence so that the protein or peptide is expressed in a host transformed with the recombinant DNA molecule. For example, expression of a protein or peptide may be controlled by any promoter/enhancer element known in the art. Promoters which may be used to control expression include, but are not limited to, the CMV-IE promoter, the SV40 early promoter region (Benoist and Chambon 1981), the promoter contained in the 3' long terminal repeat of Rous sarcoma virus (Yamamoto et al., 1980), the herpes simplex thymidine kinase promoter (Wagner et al., 1981), the regulatory sequences of the metallothionein gene (Brinster et al., 1982); prokaryotic vectors containing promoters such as the β-lactamase promoter (Villa-Kamaroff et al., 1978), or the tac promoter (deBoer et al., 1983); see also "Useful proteins from recombinant bacteria" in Scientific American, 1980, 242:74-94; plant expression vectors comprising the nopaline synthetase promoter region (Herrera-Estrella et al., 1983) or the cauliflower mosaic virus 35S RNA promoter (Gardner et al., 1981), and the promoter of the photosynthetic enzyme ribulose biphosphate carboxylase (Herrera-Estrella et al., 1984); promoter elements from yeast or fungi such as the Gal 4 promoter, the ADC (alcohol dehydrogenase) promoter, PGK (phosphoglycerol kinase) promoter, and/or the alkaline phosphatase promoter.

The vectors according to the invention are, for example, vectors of plasmid or viral origin. In a specific embodiment, a vector is used that comprises a promoter operably linked to a protein or peptide-encoding nucleic acid sequence contained within the disclosed polynucleotide sequences, one or more origins of replication, and, optionally, one or more selectable markers (e.g., an antibiotic resistance gene). Expression vectors comprise regulatory sequences that control gene expression, including gene expression in a desired host cell. Exemplary vectors for the expression of the polypeptides of the invention include the pET-type plasmid vectors (Promega) or pBAD plasmid vectors (Invitrogen) or those provided in the examples below. Furthermore, the vectors according to the invention are useful for transforming host cells so as to clone or express the polynucleotide sequences of the invention.

The invention also encompasses the host cells transformed by a vector according to the invention. These cells may be obtained by introducing into host cells a nucleotide sequence inserted into a vector as defined above, and then culturing the said cells under conditions allowing the replication and/or the expression of the polynucleotide sequences of the subject invention.

The host cell may be chosen from eukaryotic or prokaryotic systems, such as for example bacterial cells, (Gram negative or Gram positive), yeast cells (for example, *Saccharomyces cereviseae* or *Pichia pastoris*), animal cells (such as Chinese hamster ovary (CHO) cells), plant cells, and/or insect cells using baculovirus vectors. In some embodiments, the host cells for expression of the polypeptides include, and are not limited to, those taught in U.S. Pat. Nos. 6,319,691, 6,277, 375, 5,643,570, or 5,565,335, each of which is incorporated by reference in its entirety, including all references cited within each respective patent.

Furthermore, a host cell strain may be chosen which modulates the expression of the inserted sequences, or modifies and processes the gene product in the specific fashion desired. Expression from certain promoters can be elevated in the presence of certain inducers; thus, expression of the genetically engineered polypeptide may be controlled. Furthermore, different host cells have characteristic and specific mechanisms for the translational and post-translational processing and modification (e.g., glycosylation, phosphorylation) of proteins. Appropriate cell lines or host systems can be chosen to ensure the desired modification and processing of the foreign protein expressed. For example, expression in a bacterial system can be used to produce an unglycosylated core protein product. Expression in yeast will produce a glycosylated product. Expression in mammalian cells can be used to ensure "native" glycosylation of a heterologous protein. Furthermore, different vector/host expression systems may effect processing reactions to different extents.

Also provided are transformed plant cells, transgenic seeds, transgenic plant parts and transgenic plants which contain one or more polynucleotide sequence, genetic construct, vector, or expression cassette comprising one or more of the polynucleotides disclosed herein, or biologically active fragments thereof, operably linked to control elements. As used herein, the term "plant" includes algae and higher plants (including, but not limited to trees). Thus, algae, monocots, and dicots may be transformed with genetic constructs of the invention, expression cassettes, or vectors according to the invention. In certain preferred embodiments, tobacco plants or tobacco cell lines are transformed with genetic constructs according to the subject invention.

Thus, polypeptides useful in the production of the compositions or immunization protocols discussed in this application can be derived or obtained from a transgenic plant cell that has been genetically engineered to express a polypeptide comprising (consisting essentially of or consisting of) SEQ ID NO: 5, 9, 11, 13, 15, or fragments thereof. See, for example, U.S. Patent Pub. No: 2004/0268442 A1, the disclosure of which is hereby incorporated by reference in its entirety.

Transgenic plant is herein defined as a plant cell culture, plant cell line, plant tissue culture, lower plant, monocot plant, dicot plant, or progeny or part thereof derived from a transformed plant cell or protoplast, wherein the genome of the transformed plant contains foreign DNA, introduced by laboratory techniques, not originally present in a native, non-transgenic plant cell of the same species. The terms "transgenic plant" and "transformed plant" have sometimes been used in the art as synonymous terms to define a plant whose DNA contains an exogenous DNA molecule. Where appropriate, the polynucleotides encoding the polypeptides set forth herein can be optimized for expression in the transformed plants, plant cells or plant parts. That is, the genes can be synthesized using species-preferred codons corresponding to the species of interest. Methods are available in the art for synthesizing for example, plant-preferred genes. See, for example, U.S. Pat. Nos. 5,380,831 and 5,436,391, and Murray et al. (1989), herein incorporated by reference.

Construction of gene cassettes for expressing polypeptides in plants is readily accomplished utilizing well known methods, such as those disclosed in Sambrook et al. (1989); and Ausubel et al. (1987).

In preparing the constructs of this invention, the various DNA fragments may be manipulated, so as to provide for the DNA sequences in the proper orientation and, as appropriate, in the proper reading frame. Adapters or linkers may be employed for joining the DNA fragments or other manipulations may be involved to provide for convenient restriction sites, removal of superfluous DNA, removal of restriction sites, or the like.

In carrying out the various steps, cloning is employed, so as to amplify a vector containing the promoter/gene of interest for subsequent introduction into the desired host cells. A wide variety of cloning vectors are available, where the cloning vector includes a replication system functional in *Escherichia coli* (*E. coli*) and a marker which allows for selection of the transformed cells. Illustrative vectors include pBR322, pUC series, pACYC184, Bluescript series (Stratagene) etc. Thus, the sequence may be inserted into the vector at an appropriate restriction site(s), the resulting plasmid used to transform the *E. coli* host (e.g., *E. coli* strains HB101, JM101 and DH5$\alpha$), the *E. coli* grown in an appropriate nutrient medium and the cells harvested and lysed and the plasmid recovered. Analysis may involve sequence analysis, restriction analysis, electrophoresis, or the like. After each manipulation, the DNA sequence to be used in the final construct may be restricted and joined to the next sequence, where each of the partial constructs may be cloned in the same or different plasmids.

Vectors are available or can be readily prepared for transformation of plant cells. In general, plasmid or viral vectors should contain all the DNA control sequences necessary for both maintenance and expression of a heterologous DNA sequence in a given host. Such control sequences generally include a leader sequence and a DNA sequence coding for translation start-signal codon, a translation terminator codon, and a DNA sequence coding for a 3' UTR signal controlling messenger RNA processing. Selection of appropriate elements to optimize expression in any particular species is a matter of ordinary skill in the art utilizing the teachings of this disclosure. Finally, the vectors should desirably have a marker gene that is capable of providing a phenotypical property which allows for identification of host cells containing the vector.

The activity of the foreign coding sequence inserted into plant cells is dependent upon the influence of endogenous plant DNA adjacent the insert. Generally, the insertion of heterologous genes appears to be random using any transformation technique; however, technology exists for producing plants with site specific recombination of DNA into plant cells (see WO 91/09957). Any method or combination of methods resulting in the expression of the desired sequence or sequences under the control of the promoter is acceptable.

The present invention is not limited to any particular method for transforming plant cells. Technology for introducing DNA into plant cells is well-known to those of skill in the art. Four basic methods for delivering foreign DNA into plant cells have been described. Chemical methods (Graham and van der Eb, 1973; Zatloukal et al., 1992); physical methods including microinjection (Capecchi, 1980), electroporation (Wong and Neumann 1982; Fromm et al., 1985; U.S. Pat. No. 5,384,253) and the gene gun (Johnston and Tang, 1994; Fynan et al., 1993); viral methods (Clapp, 1993; Lu et al., 1993; Eglitis and Anderson 1988; Eglitis et al., 1988); and receptor-mediated methods (Curiel et al., 1991; Curiel et al., 1992; Wagner et al., 1992).

The introduction of DNA into plant cells by means of electroporation is well-known to those of skill in the art. Plant cell wall-degrading enzymes, such as pectin-degrading enzymes, are used to render the recipient cells more susceptible to transformation by electroporation than untreated cells. To effect transformation by electroporation one may employ either friable tissues such as a suspension culture of cells, or embryogenic callus, or immature embryos or other organized tissues directly. It is generally necessary to partially degrade the cell walls of the target plant material with pectin-degrading enzymes or mechanically wounding in a controlled manner. Such treated plant material is ready to receive foreign DNA by electroporation.

Another method for delivering foreign transforming DNA to plant cells is by microprojectile bombardment. In this method, microparticles are coated with foreign DNA and delivered into cells by a propelling force. Such micro particles are typically made of tungsten, gold, platinum, and similar metals. An advantage of microprojectile bombardment is that neither the isolation of protoplasts (Cristou et al., 1988) nor the susceptibility to *Agrobacterium* infection is required. An illustrative embodiment of a method for delivering DNA into maize cells by acceleration is a Biolistics Particle Delivery System, which can be used to propel particles coated with DNA or cells through a screen onto a filter surface covered with corn cells cultured in suspension. The screen disperses the particles so that they are not delivered to the recipient cells in large aggregates. For the bombardment, cells in suspension are preferably concentrated on filters or solid culture medium. Alternatively, immature embryos or other target cells may be arranged on solid culture medium. The cells to be bombarded are positioned at an appropriate distance below the macroprojectile stopping plate. In bombardment transformation, one may optimize the prebombardment culturing conditions and the bombardment parameters to yield the maximum numbers of stable transformants. Both the physical and biological parameters for bombardment are important in this technology. Physical factors are those that involve manipulating the DNA/microprojectile precipitate or those that affect the flight and velocity of either the microprojectiles. Biological factors include all steps involved in manipulation of cells before and immediately after bombardment, the osmotic adjustment of target cells to help alleviate the trauma associated with bombardment, and also the nature of the transforming DNA, such as linearized DNA or intact supercoiled plasmids.

*Agrobacterium*-mediated transfer is a widely applicable system for introducing foreign DNA into plant cells because the DNA can be introduced into whole plant tissues, eliminating the need to regenerate an intact plant from a protoplast. The use of *Agrobacterium*-mediated plant integrating vectors to introduce DNA into plant cells is well known in the art. See, for example, the methods described in Fraley et al. (1985) and Rogers et al. (1987). Further, the integration of the Ti-DNA is a relatively precise process resulting in few rearrangements. The region of DNA to be transferred is defined by the border sequences, and intervening DNA is usually inserted into the plant genome as described in Spielmann et al. (1986) and Jorgensen et al. (1987).

Modern *Agrobacterium* transformation vectors are capable of replication in *E. coli* as well as *Agrobacterium*, allowing for convenient manipulations. Moreover, recent technological advances in vectors for *Agrobacterium*-mediated gene transfer have improved the arrangement of genes and restriction sites in the vectors to facilitate construction of vectors capable of expressing various proteins or polypeptides. Convenient multi-linker regions flanked by a promoter and a polyadenylation site for direct expression of inserted polypeptide coding genes are suitable for present purposes. In addition, *Agrobacterium* containing both armed and disarmed Ti genes can be used for the transformations.

Transformation of plant protoplasts can be achieved using methods based on calcium phosphate precipitation, polyethylene glycol treatment, electroporation, and combinations of these treatments (see, e.g., Potrykus et al., 1985; Marcotte et al., 1988). Application of these systems to different plant species depends on the ability to regenerate the particular species from protoplasts.

Once the plant cells have been transformed, selected and checked for antigen expression, it is possible in some cases to regenerate whole fertile plants. This will greatly depend on the plant species chosen. Methods for regenerating numerous plant species have been reported in the literature and are well known to the skilled artisan. For practice of the present invention, it is preferable to transform plant cell lines that can be cultured and scaled-up rapidly by avoiding the generally lengthy regeneration step. In addition, the use of plant cell cultures avoids open field production and greatly reduces the chances of gene escape and food contamination. Tobacco suspension cell cultures such as NT-1 and BY-2 (An, 1985) are preferred because these lines are particularly susceptible to handling in culture, are readily transformed, produce stably integrated events and are amenable to cryopreservation.

The tobacco suspension cell line, NT-1, is suitable for the practice of the present invention. NT-1 cells were originally developed from *Nicotiana tabacum* L.cv. bright yellow 2. The NT-1 cell line is widely used and readily available; though, any tobacco suspension cell line is consistent with the practice of the invention. NT-1 cells suitable for use in the examples below are available from the American Type Culture Collection under accession number ATCC No. 74840. See also U.S. Pat. No. 6,140,075, herein incorporated by reference in its entirety.

Many plant cell culture techniques and systems ranging from laboratory-scale shaker flasks to multi-thousand liter bioreactor vessels have been described and are well know in the art of plant cell culture. See for example Fischer, R. et al (1999) and Doran, P. (2000). After the transformed plant cells have been cultured to the mass desired, they are harvested, gently washed and placed in a suitable buffer for disruption. Many different buffers are compatible with the present invention. In general the buffer is an aqueous isotonic buffered salt solution at or near a neutral pH value, with or without detergent to solubilize membrane-bound proteins. Preferred buffers include Dulbecco's Phosphate Buffered Saline, PBS containing 1 mM EDTA, and MOPS (3-(N-Morpholino) propanesulfonic acid).

In one embodiment, cells can be disrupted by sonication. The washed cells are placed in buffer in a range of about 0.01 mg/ml to about 5.0 mg/ml, preferably in a range of about 0.1 mg/ml to about 0.5 mg/ml (washed wet weight cells per volume of buffer). Many commercially available sonication instruments are consistent with the invention and sonication times range from about 5 to about 20 seconds, preferably about 15 to about 20 seconds. The resulting cell fragments may range in size from a few microns to several hundred microns and expose the polypeptide or immunogenic fragments thereof.

The subject invention also concerns DNA vaccine compositions that can be employed to elicit an immune response or a protective immune response. In this aspect of the invention, an amount of a composition comprising recombinant DNA or mRNA encoding a polypeptide as provided herein (or a fragment thereof) is administered to an individual in an amount sufficient to elicit an immune response or protective immune response in said individual. Signal sequences may be deleted from the nucleic acid encoding an antigen of interest and the individual may be monitored for the induction of an immune response according to methods known in the art. A "protective immune response" or "therapeutic immune response" refers to a CTL (or $CD8^+$ T cell), an HTL (or $CD4^+$ T cell), and/or a protective humoral immune response to an antigen that, in some way, prevents or at least partially arrests disease symptoms, side effects or progression. In the context of this invention, such a protective or therapeutic response provides increased survival rates (reduced mortality) in immunized individuals as compared to non-immunized individuals or a reduction in viral shedding in immunized individuals challenged with West Nile virus.

In another embodiment, the subject invention further comprises the administration of polynucleotide (DNA) vaccines in conjunction with a polypeptide antigen, or composition thereof, of the invention. In a preferred embodiment, the antigen is the polypeptide that is encoded by the polynucleotide administered as the polynucleotide vaccine. As a particularly preferred embodiment, the polypeptide antigen is administered as a booster subsequent to the initial administration of the polynucleotide vaccine.

A further embodiment of the subject invention provides for the induction of an immune response to the novel West Nile virus antigens disclosed herein (see, for example, the polypeptides and peptide fragments set forth herein) using a "prime-boost" vaccination regimen known to those skilled in the art. In this aspect of the invention, a DNA vaccine or polypeptide antigen of the subject invention is administered to an individual in an amount sufficient to "prime" the immune response of the individual. The immune response of the individual is then "boosted" via the administration of: 1) one or a combination of: a peptide, polypeptide, and/or full length polypeptide antigen of the subject invention (optionally in conjunction with a immunostimulatory molecule and/or an adjuvant); or 2) a viral vector that contains nucleic acid encoding one, or more, of the same or, optionally, different, antigen constructs, and/or peptide antigens set forth herein. In some alternative embodiments of the invention, a gene encoding an immunostimulatory molecule may be incorporated into the viral vector used to "boost the immune response of the individual. Exemplary immunostimulatory molecules include, and are not limited to, IL-1, IL-2, IL-3, IL-4, IL-5, IL-6, IL-7, IL-8, IL-9, IL-10, IL-11, IL-15, 11-16, 11-18, IL-23, IL-24, erythropoietin, G-CSF, M-CSF, platelet derived growth factor (PDGF), MSF, FLT-3 ligand, EGF, fibroblast growth factor (FGF; e.g., aFGF (FGF-1), bFGF (FGF-2), FGF-3, FGF-4, FGF-5, FGF-6, or FGF-7), insulin-like growth factors (e.g., IGF-1, IGF-2); vascular endothelial growth factor (VEGF); interferons (e.g., IFN-γ, IFN-α, IFN-β); leukemia inhibitory factor (LIF); ciliary neurotrophic factor (CNTF); oncostatin M; stem cell factor (SCF); transforming growth factors (e.g., TGF-α, TGF-β1, TGF-β2, TGF-β3), or chemokines (such as, but not limited to, BCA-1/BLC-1, BRAK/Kec, CXCL16, CXCR3, ENA-78/LIX, Eotaxin-1, Eotaxin-2/MPIF-2, Exodus-2/SLC, Fractalkine/Neurotactin, GROalpha/MGSA, HCC-1, I-TAC, Lymphotactin/ATAC/SCM, MCP-1/MCAF, MCP-3, MCP-4, MDC/STCP-1, ABCD-1, MIP-1α, MIP-1β, MIP-2α/GROβ, MIP-3α/Exodus/LARC, MIP-3β/Exodus-3/ELC, MIP-4/PARC/DC-CK1, PF-4, RANTES, SDF1α, TARC, or TECK). Genes encoding these immunostimulatory molecules are known to those skilled in the art and coding sequences may be obtained from a variety of sources, including various patents databases, publicly available databases (such as the nucleic acid and protein databases found at the National Library of Medicine or the European Molecular Biology Laboratory), the scientific literature, or scientific literature cited in catalogs produced by companies such as Genzyme, Inc., R&D Systems, Inc, or InvivoGen, Inc. [see, for example, the 1995 Cytokine Research Products catalog, Genzyme Diagnostics, Genzyme Corporation, Cambridge Mass.; 2002 or 1995 Catalog of R&D Systems, Inc (Minneapolis, Minn.); or 2002 Catalog of InvivoGen, Inc (San Diego, Calif.) each of which is incorporated by reference in its entirety, including all references cited therein].

Methods of introducing DNA vaccines into individuals are well-known to the skilled artisan. For example, DNA can be injected into skeletal muscle or other somatic tissues (e.g., intramuscular injection). Cationic liposomes or biolistic devices, such as a gene gun, can be used to deliver DNA vaccines. Alternatively, iontophoresis and other means for transdermal transmission can be used for the introduction of DNA vaccines into an individual.

Viral vectors for use in the subject invention can have a portion of the viral genome deleted to introduce new genes without destroying infectivity of the virus. The viral vector of the present invention is, typically, a non-pathogenic virus. At the option of the practitioner, the viral vector can be selected so as to infect a specific cell type, such as professional antigen presenting cells (e.g., macrophage or dendritic cells). Alternatively, a viral vector can be selected that is able to infect any cell in the individual. Exemplary viral vectors suitable for use in the present invention include, but are not limited to poxvirus such as vaccinia virus, avipox virus, fowlpox virus, a highly attenuated vaccinia virus (such as Ankara or MVA [Modified Vaccinia Ankara]), retrovirus, adenovirus, baculovirus and the like. In a preferred embodiment, the viral vector is Ankara or MVA.

General strategies for construction of vaccinia virus expression vectors are known in the art [see, for example, Smith and Moss, 1984; U.S. Pat. No. 4,738,846 (hereby incorporated by reference in its entirety)]. Sutter and Moss (1992) and Sutter et al. (1994) disclose the construction and use as a vector, a non-replicating recombinant Ankara virus (MVA) which can be used as a viral vector in the present invention.

Compositions comprising the subject polynucleotides can include appropriate nucleic acid vaccine vectors (plasmids), which are commercially available (e.g., Vical, San Diego, Calif.) or other nucleic acid vectors (plasmids), which are also commercially available (e.g., Valenti, Burlingame, Calif.). Alternatively, compositions comprising viral vectors and polynucleotides according to the subject invention are provided by the subject invention. In addition, the compositions can include a pharmaceutically acceptable carrier, e.g., saline. The pharmaceutically acceptable carriers are well known in the art and also are commercially available. For example, such acceptable carriers are described in E. W. Martin's *Remington's Pharmaceutical Science*, Mack Publishing Company, Easton, Pa.

All patents, patent applications, provisional applications, and publications referred to or cited herein are incorporated by reference in their entirety, including all figures and tables, to the extent they are not inconsistent with the explicit teachings of this specification.

Following are examples which illustrate procedures for practicing the invention. These examples should not be construed as limiting. All percentages are by weight and all solvent mixture proportions are by volume unless otherwise noted.

Example 1

Optimization of Nucleic Acid Sequence for Expression in Plants

Background To obtain higher levels of expression of a heterologous gene in plants, it may be preferred to re-engineer the protein-encoding sequence of the gene so that it is more efficiently expressed in plant cells. Tobacco is one such plant where it may be preferred to re-design the heterologous protein coding region prior to transformation to increase the expression level of the gene and the level of encoded protein in the plant. Therefore, an additional step in the design of a gene encoding a mammalian virus protein is re-engineering of a heterologous gene for optimal expression.

One motive for the re-engineering of a gene encoding a mammalian virus protein for expression in tobacco is due to the non-optimal G+C content of the native mammalian virus gene. For example, the low G+C content of many native mammalian virus gene(s) (and consequent skewing towards high A+T content) results in the generation of sequences mimicking or duplicating plant gene control sequences that are known to be highly A+T rich. The presence of some A+T-rich sequences within the DNA of gene(s) introduced into plants (e.g., TATA box regions normally found in gene promoters) may result in aberrant transcription of the gene(s). On the other hand, the presence of other regulatory sequences residing in the transcribed mRNA (e.g., polyadenylation signal sequences (AAUAAA), or sequences complementary to small nuclear RNAs involved in pre-mRNA splicing) may lead to RNA instability. Therefore, one goal in the design of genes encoding a mammalian virus protein for tobacco expression, more preferably referred to as plant optimized gene(s), is to generate a DNA sequence having a G+C content close to that of the average of tobacco gene coding regions. Another goal in the design of the plant optimized gene(s) encoding a mammalian virus protein is to generate a DNA sequence in which the sequence modifications do not hinder translation.

The G+C content of the coding regions of 1343 tobacco genes is calculated to be 43.6%. It is therefore preferred, when designing a heterologous gene encoding a mammalian virus protein, to attain a G+C content close to about 44%.

Due to the plasticity afforded by the redundancy/degeneracy of the genetic code (i.e., some amino acids are specified by more than one codon), evolution of the genomes in different organisms or classes of organisms has resulted in differential usage of redundant codons. This "codon bias" is reflected in the mean base composition of protein coding regions. For example, organisms with relatively low G+C contents utilize codons having A or T in the third position of redundant codons, whereas those having higher G+C contents utilize codons having G or C in the third codon position. It is thought that the presence of "minor" codons within an mRNA may reduce the absolute translation rate of that mRNA, especially when the relative abundance of the charged tRNA corresponding to the minor codon is low. An extension of this concept is that the diminution of translation rate by individual minor codons would be at least additive for multiple minor codons. Therefore, mRNAs having high relative contents of minor codons would have correspondingly low translation rates. This rate would be reflected by subsequent low levels of the encoded protein.

To assist in engineering genes encoding a mammalian virus protein for expression in tobacco (or in another plant, such as cotton, maize, or soybean), the codon bias of tobacco genes (or other relevant plant genes) can be determined. The codon bias for tobacco gene protein coding regions is represented by the statistical codon distribution that the plant uses for coding its proteins, and is shown in Table 1, expressed as the frequency (in percentages) with which each codon specifying a single amino acid is used to encode that amino acid. The codons most preferred by the plant are determined, as well as the second, third, or fourth choices of preferred codons when multiple choices exist. A new DNA sequence can then be designed which encodes the amino acid sequence of the mammalian virus protein, but the new DNA sequence differs from the native mammalian virus DNA or RNA sequence (encoding the protein) by the substitution of the plant (first preferred, second preferred, third preferred, or fourth preferred) codons to specify the appropriate amino acid at each position within the protein amino acid sequence. The new sequence can then be analyzed for restriction enzyme recognition sites that might have been created by the modifications. The identified sites are further modified by replacing the relevant codons with first, second, third, or fourth choice preferred codons. Other sites in the sequence which could affect transcription or translation of the gene of interest include the exon:intron junctions (5' or 3'), poly A addition signals, or RNA polymerase termination signals. The modified sequence is further analyzed and further modified to reduce the frequency of TA or CG doublets, and to increase the frequency of TG or CT doublets. In addition to these doublets, sequence blocks that have more than about five consecutive residues of [G+C] or [A+T] can affect transcription or translation of the sequence. Therefore, these sequence blocks are also modified by replacing the codons of first or second choice, etc. with other preferred codons of choice. Rarely used codons are not included to a substantial extent in the gene design, being used only when necessary to accommodate a different design criterion than codon composition per se (e.g. addition or deletion of restriction enzyme recognition sites).

The method described above enables one skilled in the art to design modified gene(s) that are foreign to a particular plant so that the genes are optimally expressed in plants. The method is further described and illustrated in U.S. Pat. No. 5,380,831 and patent application WO 97/13402.

Thus, in order to design plant optimized genes encoding a mammalian virus protein, a DNA sequence is designed to encode the amino acid sequence of said protein utilizing a redundant genetic code established from a codon bias table compiled from the gene sequences for the particular plant or plants. The resulting DNA sequence has a higher degree of codon diversity, a desirable base composition, can contain strategically placed restriction enzyme recognition sites, and lacks sequences that might interfere with transcription of the gene, or translation of the product mRNA. Thus, synthetic genes that are functionally equivalent to the proteins/genes of the subject invention can be used to transform hosts, including plants. Additional guidance regarding the production of synthetic genes can be found in, for example, U.S. Pat. No. 5,380,831.

Once said DNA sequence has been designed on paper or in silico, actual DNA molecules can be synthesized in the laboratory to correspond in sequence precisely to the designed sequence. Such synthetic DNA molecules can be cloned and otherwise manipulated exactly as if they were derived from natural or native sources.

Design of tobacco biased coding regions for WNV prM-M-E peptides. The entire genomic sequence of a flamingo isolate of the West Nile Virus is disclosed as GenBank Accession AF196835. The 2004 base pairs (bp) DNA sequence of the portion of the native viral genome that encodes the prM-, M- and E-peptides of the virus are represented in SEQ ID NO: 1 by nucleotides 1-276 (prM-peptide), 277-501 (M-peptide), and 502-2004 (E-peptide) [SEQ ID NO: 1 comprises bases 466 to 2469 of AF196835]. For the purposes of this example, the native nucleotide sequence will be referred to as Version 1. The amino acid sequences of the prM-, M- and E-peptides encoded by SEQ ID NO: 1 are presented as SEQ ID NO: 2.

Examination of the native genomic DNA sequence of SEQ ID NO: 1 revealed the presence of several sequence motifs that are thought to be detrimental to optimal plant expression, as well as a non-optimal codon composition for expression in tobacco. To improve production of these recombinant proteins in tobacco, a "tobacco-optimized" DNA sequence (SEQ ID NO: 3) was developed that encodes the prM-, M-, and E-peptides of SEQ ID NO: 2

The prM-, M-, and E-peptides (SEQ ID NO: 2) encoded by the native coding region sequence in SEQ ID NO: 1 and by the tobacco-optimized coding region in SEQ ID NO: 3 are identical. In contrast, the native viral DNA sequence and the tobacco-optimized DNA sequence encoding the prM-, M- and E-peptides are only 78.7% identical.

Design of tobacco biased coding regions for WNV prM-M-E peptides with modified N-glycosylation site. It is known within the field of plant protein biochemistry that various sugars or oligosaccharides may be attached to protein molecules (such process being collectively referred to as glycosylation), and that the composition and presentation of such sugar moieties may affect the antigenicity of the protein when introduced into mammals. It is further known that the short amino acid sequences Asparagine-Xaa-Serine, and Asparagine-Xaa-Threonine (abbreviated as Asn-Xaa-Ser/Thr or N-X-S/T, where Xaa and X represent any of the 20 amino acids normally found in proteins) can serve as acceptor sites for glycosylation linkages on proteins, wherein the sugars are attached to the Asn (N) residue. The N-glycosylation acceptor sequence Asn-Tyr-Ser is found as amino acids 321 to 323 in SEQ ID NO: 2, and is a known N-glycosylation site for the E-peptide. SEQ ID NO: 4 discloses a tobacco-optimized DNA sequence encoding the prM, M- and E-peptides, wherein the DNA sequence encoding the N-glycosylation acceptor sequence Asn-Tyr-Ser of the native E-peptide has been mutated to encode Asn-Tyr-Pro. Thus, the only difference between SEQ ID NO: 3 and SEQ ID NO: 4 is the substitution of a proline CCA codon for the AGC Serine codon at bases 967 to 969. The amino acid sequence of the mutated protein, lacking the N-glycosylation acceptor sequence, and encoded by SEQ ID NO: 4, is disclosed as SEQ ID NO: 5.

Tobacco biased WNV M- and E-peptides coding region Version 2. For some utilities, it is desirable to utilize a DNA sequence that encodes only the M- and E-peptides of the West Nile Virus. For expression in tobacco cells, it is sufficient to use the portion of SEQ ID NO: 3 that encodes these peptides (i.e. bases 277-2004 of SEQ ID NO: 3). Thus, the sequence of a tobacco-biased coding region encoding the WNV M- and E-peptides is presented as SEQ ID NO: 6. This sequence encodes residues 93-668 of SEQ ID NO: 2. The native viral DNA sequence encoding the M- and E-peptides (bases 277-2004 of SEQ ID NO: 1) and the tobacco-optimized DNA sequence of SEQ ID NO: 6, which also encodes the M- and E-peptides, are only 78.4% identical, while the encoded proteins are 100% identical.

Design of tobacco-biased WNV M- and E-peptides coding region Version 3. It is often desirable and advantageous to introduce more than a single copy of a gene encoding a protein into a plant cell in order to produce higher levels of the desired protein. The separate copies of the protein coding region may be introduced with each copy under the expression controls of separate promoters and associated transcriptional control elements, or they may be introduced as a unit under the expression control of a single, bidirectional plant promoter. In either instance it is desirable and advantageous that the separate protein coding regions have non-identical DNA sequences. There are two or more biological reasons why this is so. First, it is known that large duplicated DNA sequences are unstable in many bacterial strains used as molecular cloning hosts (e.g. *Escherichia coli*) or in plant transformation (*Agrobacterium tumefaciens*). Thus, the provision of non-identical coding regions specifying identical proteins lessens the opportunity for deleterious rearrangements and/or deletions to occur during these manipulations. Second, it is thought that the expression of duplicated, highly homologous coding regions in transgenic plants may suffer through mechanisms such as gene silencing. The introduction of non-identical coding regions specifying identical proteins thus provides greater opportunity for higher levels of (and more stable) protein production.

Using the principals outlined above, a second tobacco-optimized coding region for the WNV M- and E-peptides was designed and is disclosed as SEQ ID NO: 7. It is emphasized that the protein encoded by SEQ ID NO: 7 is identical to that encoded by bases 277-2004 of the native sequence of SEQ ID NO: 1 (i.e. residues 93-668 of SEQ ID NO: 2), and which is also encoded by the previous tobacco-optimized version disclosed in SEQ ID NO: 6. Comparisons of the second tobacco-optimized sequence disclosed in SEQ ID NO: 7 to bases 277-2004 of the native sequence in SEQ ID NO: 1, and to the first tobacco-optimized version in SEQ ID. NO: 6, reveals that it is 74.6% identical to the corresponding native WNV sequence, and 69.4% identical to the first tobacco-optimized version. Thus, it is apparent that one may generate substantial DNA sequence diversity between different plant-optimized coding region designs, while still remaining within the constraints of the amino acid sequence of the encoded protein, overall codon composition, and the absence of sequences that may be detrimental to plant gene expression. This feature of the invention is illustrated in Table 2, which presents the differential codon compositions of the three disclosed DNA sequences.

Further modifications of the tobacco-optimized WNV prM-, M- and E-peptides coding regions. It is known to those skilled in the field of transgenic plant gene expression that the accretion levels of heterologous proteins are dependent on many variables, one of which is the intracellular location to which the protein is directed during or after translation. Moreover, it is further known that the translocation of a heterologous protein into the endoplasmic reticulum (ER) can have a positive effect on accumulation of the protein, and that a heterologous protein can be targeted for accumulation within the ER by the addition of a short ER targeting peptide to the amino terminus of the protein. The 15 kiloDalton (kDa) zein proteins of maize possess such an ER targeting peptide, and it has been shown that attachment of a 15 kDa zein ER targeting peptide to the amino terminus of a heterologous protein can result in the trafficking of that protein to the ER of monocot cells as well as dicot cells. The most straight-forward method by means of which to attach the ER targeting peptide to the amino terminus of a heterologous protein is to construct a protein coding region that encodes both elements (the ER targeting peptide and the protein coding region) in a single open reading frame which when translated generates a (chimeric) fusion protein containing both domains. It is further known to those skilled in the field that certain short peptide sequences, when present at the carboxy-terminus of ER-localized proteins, can dictate the retention of those proteins within the ER, thus providing for efficient protein accumulation and glycosylation within the ER. One such ER retention signal peptide is the amino acid sequence Lysine-Aspartic Acid-Glutamic Acid-Leucine (abbreviated as KDEL). Thus, one may facilitate the translocation of a heterologous protein to the ER and its retention within the ER by constructing a single open reading frame that encodes all three elements (the ER targeting peptide sequence, the heterologous protein coding region sequence, and the ER retention signal sequence), and which when translated produces a (chimeric) fusion protein that contains all three domains in the listed order from the amino-terminus to the carboxy terminus.

It is also well known to those in the field of transgene expression in plants that certain nucleotide sequence elements flanking (or included within) a coding region for a heterologous protein can affect the translation of the messenger RNA (mRNA) encoding the heterologous protein. One such sequence element that affects translation of the mRNA is the nucleotide sequence surrounding the translation start codon AUG (ATG in the DNA code). In dicot plants, including tobacco, it is known that an optimal translation start sequence context includes the nucleotides GC immediately following the ATG. In the universal genetic code, GCN represents codons specifying Alanine. Thus, an optimal translational start codon context is specified as ATGGCN (encoding Methionine-Alanine). It is further known that an optimal sequence context preceding the translational start codon ATG in dicot mRNAs is represented by AAACA. Finally, it is essential that the open reading frame encoding a protein be terminated with at least one translational termination codon (i.e. TGA, TAA or TAG in the universal DNA genetic code), and even more preferable that multiple translation termination codons be present in not only the same reading frame as the protein coding region (termed the +1 frame), but also in the other five reading frames possible in double-stranded DNA.

SEQ ID NO: 8 discloses the DNA sequence of a complete tobacco-optimized chimeric protein coding region that incorporates the elements mentioned above, comprising a tobacco-optimized sequence encoding the 15 kDa zein ER targeting signal peptide, a tobacco-optimized prM-. M- and E-peptides coding region (disclosed as SEQ ID NO: 3), and a tobacco-optimized KDEL ER retention signal. The chimeric fusion protein encoded by SEQ ID NO: 8 is disclosed as SEQ ID NO: 9. The ER targeting signal encoded by SEQ ID NO: 8 and presented in SEQ ID NO: 9 differs from the native maize 15 kDa zein ER targeting peptide sequence by the addition of an Alanine residue at position #2, to accommodate the consensus translational start codon sequence context described above.

SEQ ID NO: 10 discloses the DNA sequence of a second complete tobacco-optimized chimeric protein coding region that incorporates the elements mentioned above, comprising a tobacco-optimized sequence encoding the 15 kDa zein ER targeting signal peptide, a tobacco-optimized prM-, M- & E-peptides coding region including a mutated N-glycosylation acceptor site as disclosed in SEQ ID NO: 4, and a tobacco-optimized KDEL ER retention signal. The ER targeting signal encoded by SEQ ID NO: 10 is the same as that disclosed in SEQ ID NO: 8. The chimeric fusion protein encoded by SEQ ID NO: 10 is disclosed as SEQ ID NO: 11

SEQ ID NO: 12 discloses the DNA sequence of a third complete tobacco-optimized chimeric protein coding region that incorporates the elements mentioned above, comprising a tobacco-optimized sequence encoding the 15 kDa zein ER targeting signal peptide, a tobacco-optimized M- & E-peptides coding region as disclosed in SEQ ID NO: 6, and a tobacco-optimized KDEL ER retention signal. The ER targeting signal encoded by SEQ ID NO: 12 is the same as that disclosed in SEQ ID NO: 8. The chimeric fusion protein encoded by SEQ ID NO: 12 is disclosed as SEQ ID NO: 13.

SEQ ID NO: 14 discloses the DNA sequence of a fourth complete tobacco-optimized chimeric protein coding region that incorporates the elements mentioned above, comprising a tobacco-optimized sequence encoding the 15 kDa zein ER targeting signal peptide, a tobacco-optimized M- & E-peptides coding region as disclosed in SEQ ID NO: 7, and a tobacco-optimized KDEL ER retention signal. The ER targeting signal encoded by SEQ ID NO: 14 is the same as that disclosed in SEQ ID NO: 8. The chimeric fusion protein encoded by SEQ ID NO: 14 is disclosed as SEQ ID NO: 15.

DNA molecules comprising the DNA sequences disclosed in SEQ ID NO: 8, SEQ ID NO: 10, SEQ ID NO: 12, and SEQ ID NO: 14 were synthesized by a commercial vendor (PicoScript; Houston, Tex.) and the resultant molecules were cloned into plant expression and transformation vectors by standard molecular biological techniques.

Example 2

Plant Expression Vector Construction

Figure 2:
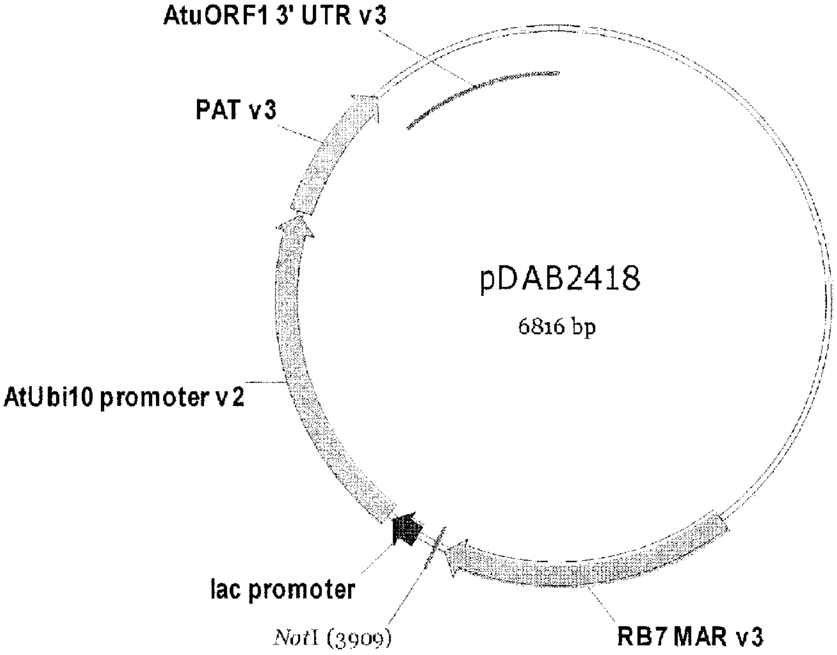
FIG. 2 represents vector pDAB2418. pDAB2418 contains the RB7 matrix attachment region (MAR) (U.S. Pat. No. 5,773,689; U.S. Pat. No. 5,773,695; U.S. Pat. No. 6,239,328, WO 94/07902, and WO 97/27207) and the plant transcription unit where plant selection marker phosphinothricin acetyl transferase (PAT) (U.S. Pat. Nos. 5,879,903; 5,637,489; 5,276,268; and 5,273,894) is driven by the AtUbi10 promoter (Sun C.-W. et al., 1997; Norris, S. R. et al., 1993; Callis, J. et al, 1995) and flanked, downstream by AtuORF1 3' UTR v3 (U.S. Pat. No. 5,428,147; Barker, R. F., et al., 1983; GenBank accession number X00493). A unique NotI site, located between the RB7 MAR gene and the plant AtUbi10 promoter, was used for cloning gene fragments from pDAB2406 containing the CsVMV promoter, gene of interest, and ORF23 3'UTR v1.

Dicot Binary Constructs. Three dicot binary vectors, pDAB2475, pDAB2478, and pDAB2481, for *Agrobacterium*-mediated plant transformation were constructed based on plasmids pDAB2406, pDAB2418, and pDAB2407. pDAB2406 (FIG. 1) contains the cassaya vein mosaic virus (CsVMV) promoter described in WO 97/48819 and an open reading frame 3' untranslated region, ORF23 3'UTR (GenBank accession number X00493) v1. Located between the CsVMV promoter and ORF23 3'UTR v1 are unique sites, NcoI and SacI, which were used for inserting the gene of interest. pDAB2418 (FIG. 2) contains the RB7 matrix attachment region (MAR) (U.S. Pat. No. 5,773,689; U.S. Pat. No. 5,773,695; U.S. Pat. No. 6,239,328, WO 94/07902, and WO 97/27207) and the plant transcription unit where plant selection marker phosphinothricin acetyl transferase (PAT) (U.S. Pat. Nos. 5,879,903; 5,637,489; 5,276,268; and 5,273,894) is driven by the AtUbi10 promoter (Sun C.-W. et al., 1997; Norris, S. R. et al., 1993; Callis, J. et al, 1995) and flanked, downstream by AtuORF1 3, UTR v3 (U.S. Pat. No. 5,428, 147; Barker, R. F., et al., 1983; GenBank accession number X00493). A unique NotI site, located between the RB7 MAR gene and the plant AtUbi10 promoter, was used for cloning gene fragments from pDAB2406 containing the CsVMV promoter, gene of interest, and ORF23 3'UTR v1.

Figure 3:
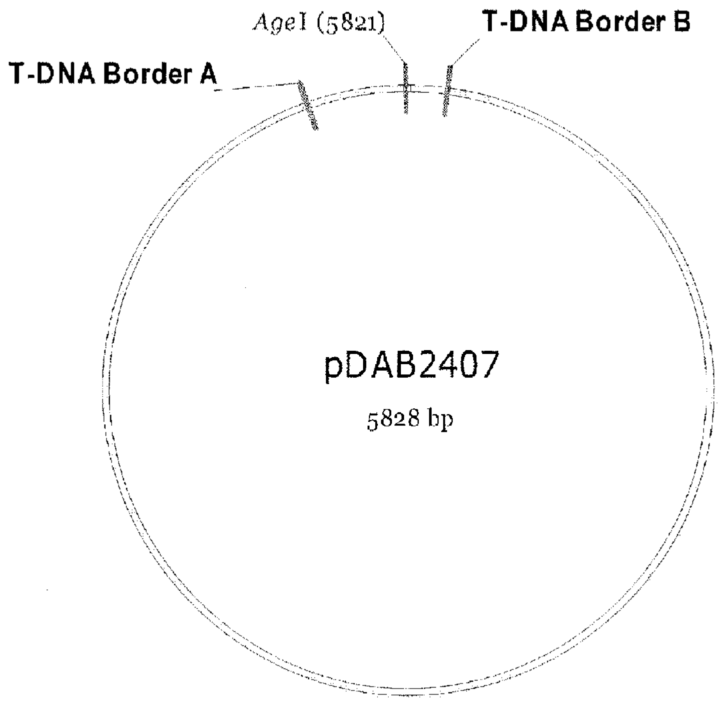
FIG. 3 illustrates a modified basic binary vector, pDAB2407. This binary vector was built by adding an AgeI linker at the unique BamHI site of pBBV (Basic Binary Vector) allowing for AgeI/AgeI ligation of the WNV antigen and selectable marker expression cassettes between the T-DNA borders.

A modified basic binary vector, pDAB2407 (FIG. 3), was built by adding an AgeI linker at the unique BamHI site of pBBV allowing for AgeI/AgeI ligation of the WNV antigen and selectable marker expression cassettes between the T-DNA borders.

Figure 4:
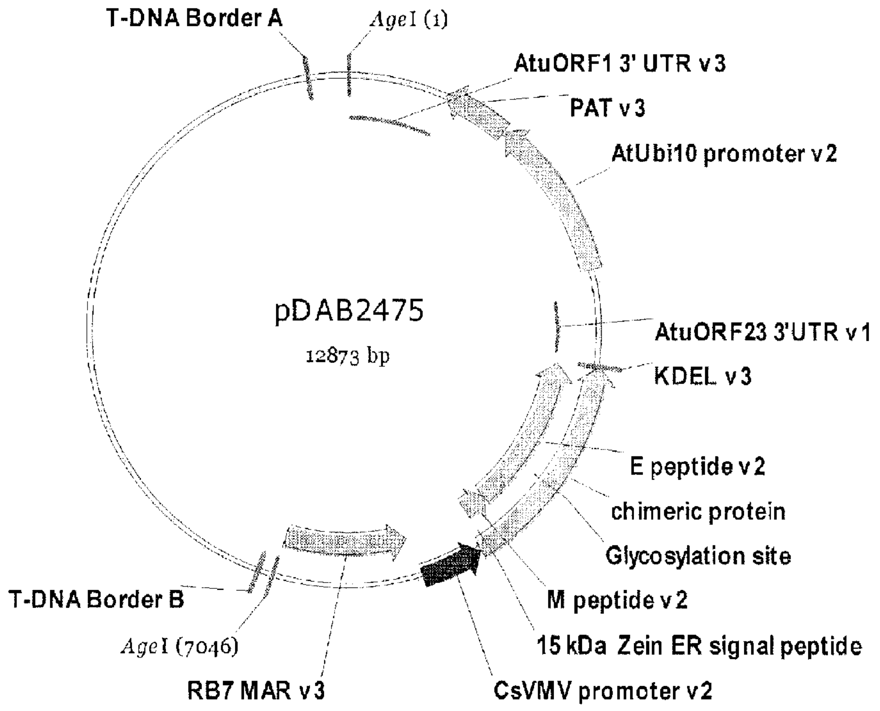
FIG. 4 is a representation of West Nile Virus dicot binary vector pDAB2475 which encodes a chimeric protein consisting of tobacco codon biased West Nile Virus membrane and envelope peptide (version 2) with ER targeting v2 and KDEL retention v3 signals (SEQ ID NO: 12).

West Nile Virus dicot binary vector, pDAB2475 (FIG. 4), encodes a chimeric protein consisting of tobacco codon biased West Nile Virus membrane and envelope peptide (version 2) with ER targeting v2 and KDEL retention v3 signals (SEQ ID NO 12). More specifically, the plant transcription unit (PTU) includes: T-DNA Border B/RB7 MAR v3/CsVMV promoter v2/15 kDa zein ER signal v2-WNV ME v2-KDEL v3/Atu ORF23 3'UTR v1/AtUbi10 promoter v2/PAT v3/AtuORF1 3' UTR v3/T-DNA Border A. As obtained from PicoScript in Stratagene's Bluescript vector, the primary construct was designated as DASPICO20. To isolate the 15 kDa ER signal v2-WNV ME v2-KDEL v3 gene from its Bluescript backbone vector, DASPICO20 was digested with NcoI/SacI and was then inserted into pDAB2406 plasmid at the NcoI and SacI sites by T4 ligase, where the gene fragment was sandwiched between the CsVMV promoter v2 and the ORF23 3 UTR v1, resulting in intermediate vector pDAB2473. To verify a clone with the proper insert, isolated DNA was cut with NcoI/SacI, identified by gel electrophoresis, and bulked up. The CsVMV promoter expression cassette containing ER signal-WNV ME v2-KDEL and ORF23 3'UTR was removed from pDAB2473 with NotI and was T4 ligated at the NotI site of pDAB2418, downstream of the RB7 MARv3 and upstream of the AtUbi10 promoter v2-PAT v3-AtuORF1 3'UTR selectable marker cassette forming the plant transcription units (PTU) in intermediate vector pDAB2474. The PTU components were then excised from pDAB2474 using AgeI digestion and ligated in reverse orientation at the AgeI site of pDAB2407 which resulted in the final dicot binary vector, pDAB2475, where the PTU elements are flanked by T-DNA borders A and B.

Figure 5:
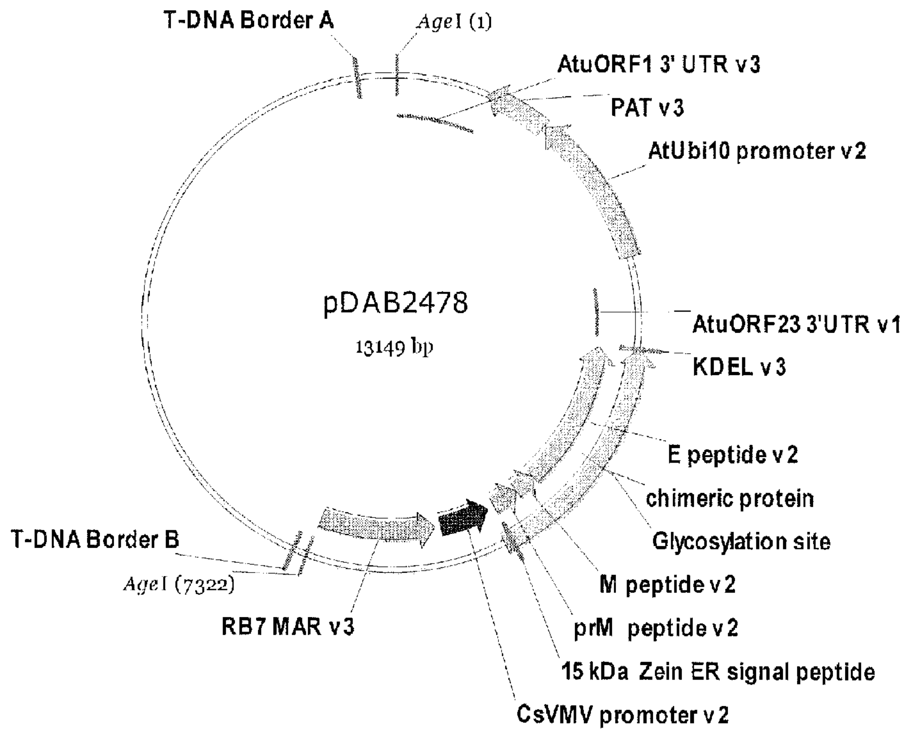
FIG. 5 depicts a dicot binary vector (pDAB2478) encoding a chimeric protein consisting of the tobacco codon biased West Nile Virus pre-membrane v2, membrane and envelope peptides v2 with ER targeting v2 and KDEL retention v3 signals (SEQ ID NO: 8).

The dicot binary vector, pDAB2478 (FIG. 5), encodes a chimeric protein consisting of the tobacco codon biased West Nile Virus pre-membrane v2, membrane and envelope peptides v2 with ER targeting v2 and KDEL retention v3 signals (SEQ ID NO 8). More specifically, the two PTU include: T-DNA Border B/RB7 MAR v3/CsVMV promoter v2/15 kDa zein ER signal v2-prMEv2-KDEL v3/Atu ORF23 3'UTR v1/AtUbi10 promoter v2/PAT v3/AtuORF1 3' UTR v3/T-DNA Border A. As obtained from PICOSCRIPT in Stratagene's Bluescript vector, the primary construct was designated as DASPICO21. To isolate the ER signal v2-prME v2-KDEL v3 gene from its backbone vector, DASPICO21 was digested with NcoI/SacI. The ER signal v2-prME v2-KDEL v3 gene fragment was then T4 ligated into pDAB2406 plasmid at the NcoI and SacI sites where the gene fragment was flanked by the CsVMV promoter and ORF23 3' UTR resulting in intermediate vector pDAB2476. To verify a clone with proper insert, isolated DNA was cut with NcoI/SacI, identified by gel electrophoresis, and bulked up. The CsVMV promoter expression cassette containing ER signal v2-prME v2-KDEL v3 and ORF23 3'UTR was removed from pDAB2476 with NotI and ligated using T4 ligase at the NotI site of pDAB2418, downstream of the RB7 MARv3 gene and upstream of the AtUbi10 promoter v2-PAT v3-AtuORF1 3'UTR selectable marker cassette forming the plant transcription units (PTU) of intermediate construct pDAB2477. The PTU components were then excised from pDAB2477 with AgeI, gel purified, and ligated in reverse orientation at the AgeI site of pDAB2407, which resulted in the final dicot vector, pDAB2478, where the PTU components are flanked by T-DNA borders A and B.

Figure 6:
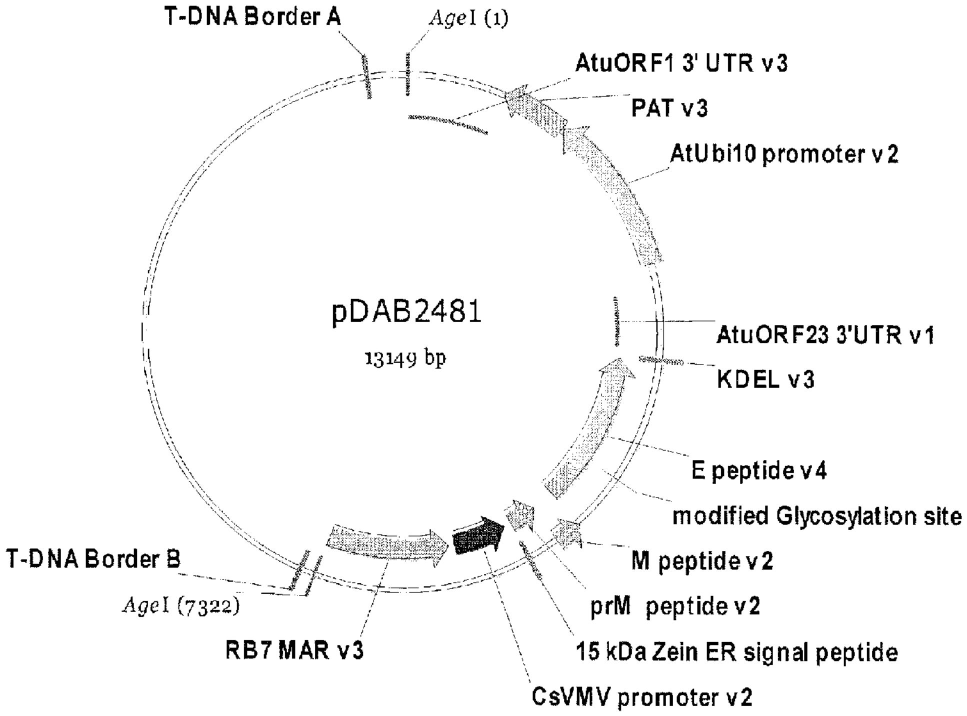
FIG. 6 pertains to a dicot binary vector, pDAB2481, encoding a chimeric protein consisting of the tobacco codon biased West Nile Virus pre-membrane v2, membrane v2, and envelope peptides with a mutated N-glycosylation site (version 4) with ER targeting v2 and KDEL v3 retention signals (SEQ ID NO: 10).

The dicot binary vector, pDAB2481 (FIG. 6), encodes a chimeric protein consisting of the tobacco codon biased West Nile Virus pre-membrane v2, membrane v2, and envelope peptides with a mutated N-glycosylation site (version 4) with ER targeting v2 and KDEL v3 retention signals (SEQ ID NO 10). More specifically, the PTU units include: T-DNA Border B/RB7 MAR v3/CsVMV promoter v2/15 kDa zein ER signal v2-WNV prM v2 E v4 with mutated N-glycosylation site—KDEL v3/Atu ORF23 3'UTR v1/AtUbi10 promoter v2/PAT v3/AtuORF1 3' UTR v3/T-DNA Border A. As obtained from PICOSCRIPT in Stratagene's Bluescript vector, the primary construct was designated as DASPICO22. To isolate the ER signal v2-WNV prM v2 E v4 with mutated N-glycosylation site-KDEL v3 gene from its backbone vector, DASPICO22 was digested with NcoI/SacI and gel purified. The ER signal v2-WNV prM v2 E v4 with mutated N-glycosylation site-KDEL v3 gene fragment was then inserted by T4 ligase into pDAB2406 plasmid at the NcoI and SacI sites, where the gene fragment was sandwiched between the CsVMV promoter v2 and the ORF23 3' UTR v1 resulting in intermediate vector pDAB2479. To verify a clone with insert, isolated DNA was cut with NcoI/SacI, identified by gel electrophoresis, and bulked up. The CsVMV promoter expression cassette containing ER signal v2-WNV prM v2 E v4 with mutated N-glycosylation site-KDEL v3 and ORF23 3'UTR was removed from pDAB2479 with NotI and was ligated at the NotI site of pDAB2418, downstream of the RB7 MARv3 gene and upstream of the AtUbi10 promoter v2-PAT v3-AtuORF1 3'UTR selectable marker cassette forming the PTU components of intermediate construct pDAB2480. The PTU units were then excised from pDAB2480 with AgeI, gel purified, and ligated in reverse orientation at the AgeI site of pDAB2407, which resulted in the final dicot vector, pDAB2481, where the PTU cassette is flanked by T-DNA borders A and B. All final constructs were verified initially by restriction digest, followed by sequencing between the T-DNA borders, which confirmed actual and expected sequence were identical.

Figure 7:
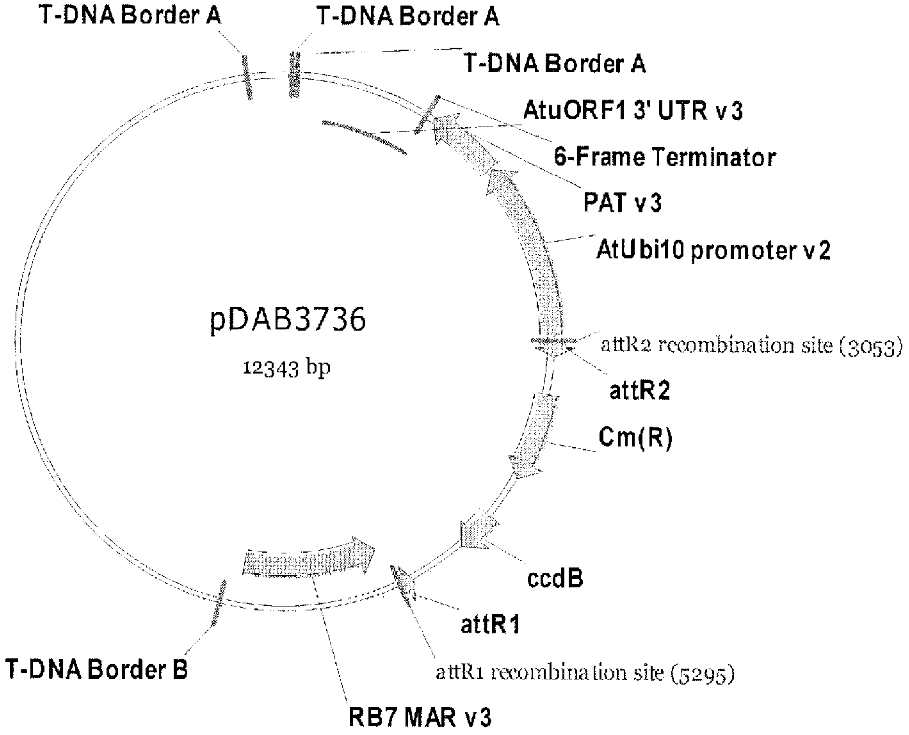
FIGS. 7-11 represent one destination vector, pDAB3736 (FIG. 7), and four donor vectors, pDAB3912 (FIG. 8), pDAB3914 (FIG. 9), pDAB3916 (FIG. 10), and pDAB3724 (FIG. 11) used to build nine binary constructs with the Gateway™ technology.
Figure 8:
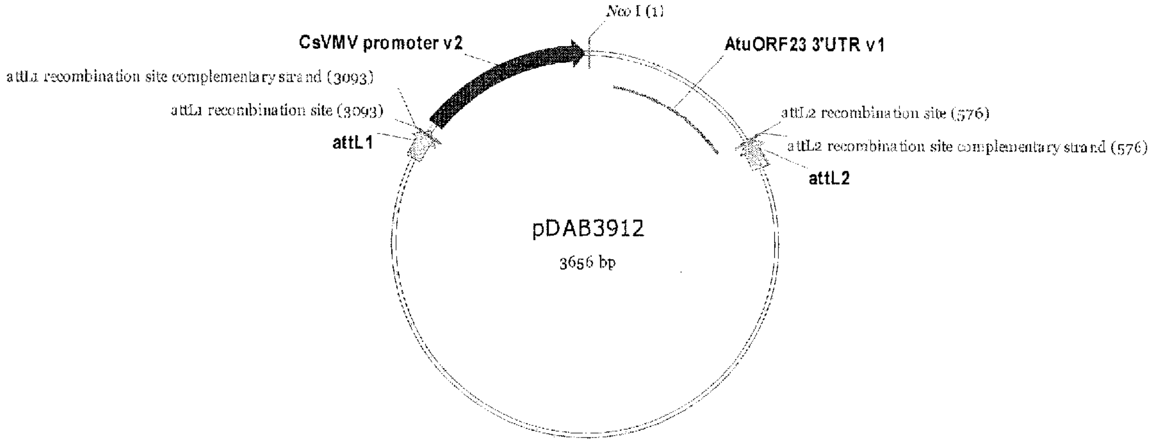
Figure 9:
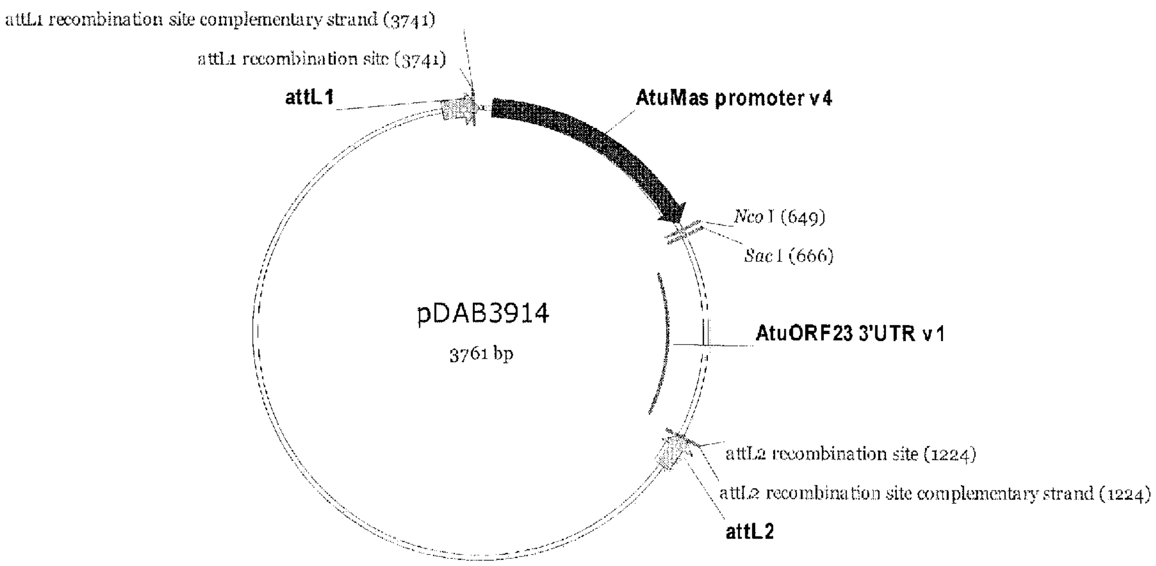
Figure 10:
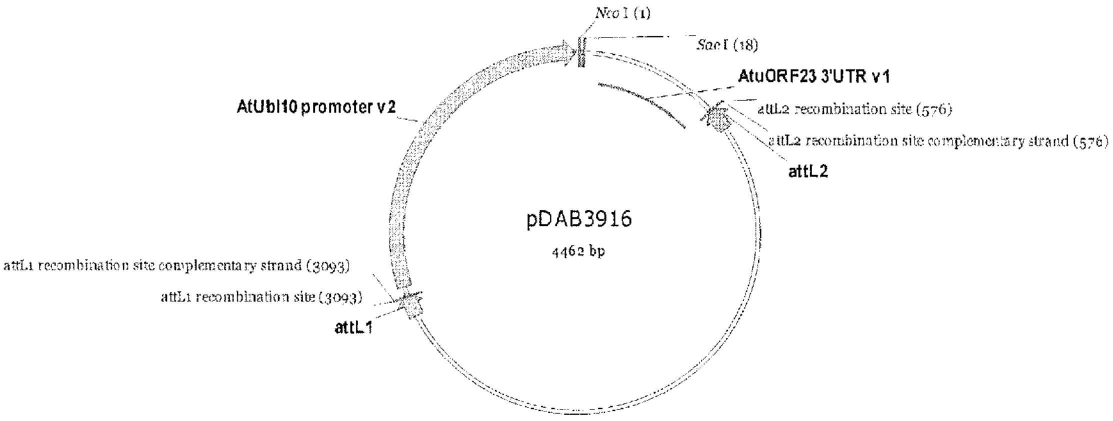
Figure 11:
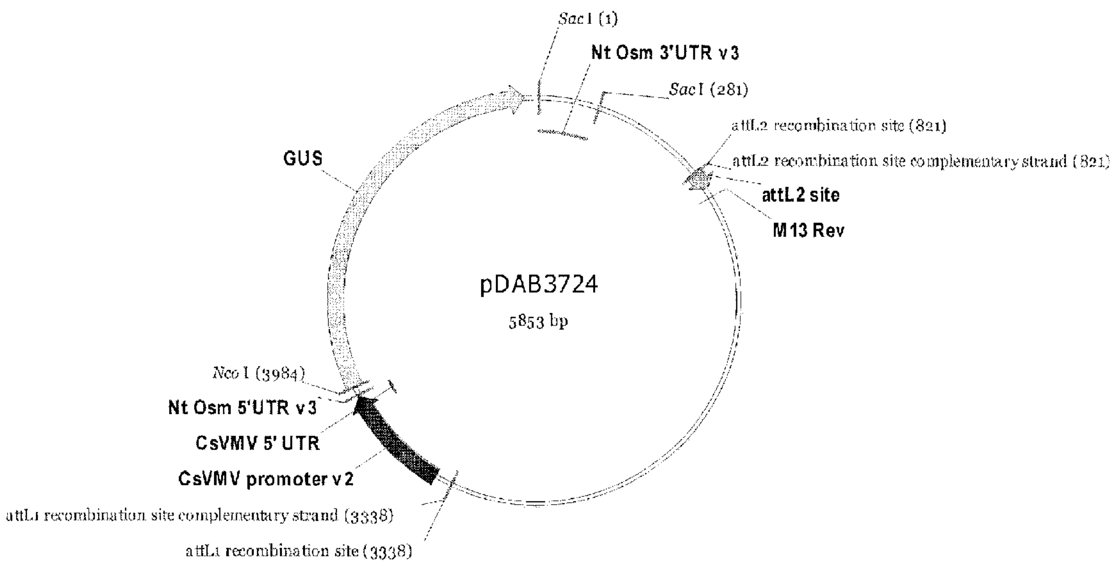

Gateway™ Dicot Binary Constructs. Gateway™ Technology (Invitrogen) was used for cloning the following nine WNV ME dicot binary vectors which contain multiple versions of ME peptide, promoters, and orientation of the gene of interest relative to the promoter and UTR. Both the destination and donor vectors were made following Invitrogen's Gateway™ Technology protocol. One destination vector, pDAB3736 (FIG. 7), and four donor vectors, pDAB3912 (FIG. 8), pDAB3914 (FIG. 9), pDAB3916 (FIG. 10), and pDAB3724 (FIG. 11) make up the backbone of the Gateway™ constructs used to build these nine binary constructs.

Destination vector pDAB3736 was derived from pDAB2407 (FIG. 3) and contains attR sites which recombine with an entry clone in an LR clonase reaction to generate an expression clone. Additionally, pDAB3736 has multiple copies of T-DNA Border A. Within the Border A and Border B regions, there is an RB7 matrix attachment region (MAR) and Gateway™ cloning sites attR1 and attR2. Entry vector pDAB3912 (FIG. 8) contains the CsVMV promoter and ORF23 3'UTR cassette. Located between the promoter and UTR are NcoI and SacI sites where the gene of interest was inserted. The cassette is flanked by Gateway™ cloning sites attL1 and attL2 for generation of entry clones. Another entry vector, pDAB3914 (FIG. 9), contains the AMAS 4OCS promoter (AtuMas promoter) v4 (Genbank accession number X00493) and ORF23 3'UTR cassette. Again, between the promoter and UTR are cloning sites, NcoI and SacI, where the gene of interest was inserted. The cassette is flanked by Gateway™ attL1 and attL2 sites. Like the other donor vectors, pDAB3916 (FIG. 10) is a Gateway™ construct which contains AtUbi10 promoter and ORF23 3'UTR cassette. Between the promoter and UTR are NcoI and SacI sites, where the gene of interest was inserted. The cassette is flanked by Gateway™ cloning sites attL1 and attL2. Gateway donor vector, pDAB3724 (FIG. 11), contains the CsVMV promoter sequentially followed by Nt Osmotin 5' UTR v3 (Genbank accession number S40046), β-Glucuronidase (GUS) reporter gene (Jefferson, 1987), and Nt Osm 3' UTR v3 (Genbank accession number S40046). These elements are flanked by Gateway™ attL1 and attL2 sites. Restriction sites, NcoI and SacI, bordering the GUS gene were used for replacing GUS with the gene of interest.

Figure 12:
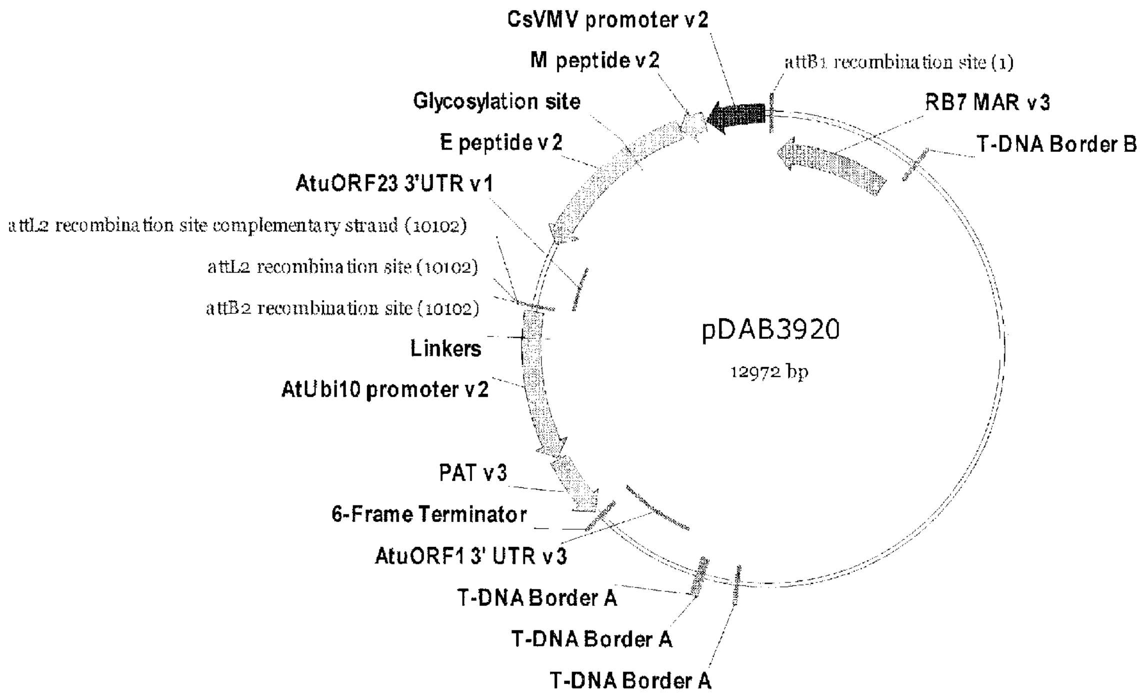
FIG. 12 depicts Gateway™ WNV ME binary vector, pDAB3920. pDAB3920 encodes T-DNA Border B/RB7 MAR v3/CsVMV promoter v2/WNV ME v2/Atu ORF23 3' UTR v1/AtUbi10 promoter v2/PAT v3/Atu ORF1 3' UTR v3/Multiple T-DNA Border A.

Gateway™ WNV ME binary vector, pDAB3920 (FIG. 12), contains the PTU units: T-DNA Border B/RB7 MAR v3/CsVMV promoter v2/WNV ME v2/Atu ORF23 3' UTR v1/AtUbi10 promoter v2/PAT v3/Atu ORF1 3' UTR v3/Multiple T-DNA Border A. Amplification of the WNV ME v2 peptide was accomplished by polymerase chain reaction (PCR). The ER v2 targeting and KDEL v3 retention sequences from DASPICO20 (SEQ ID NO 12) were removed from the ME peptide by using PCR primers (Forward: 5' aga gaa cta gta aaa agg aga aat cca tgg ctt ccc tga cag tgc aaa ctc atg 3'; Reverse: 5' Ccc tcg agg gag ctc tta tca ctt age atg aac att tac ag 3') that primed only to the WNV ME v2 sequence and consisted of an NcoI site in the forward primer and a SacI site in the reverse primer. The WNV ME v2 PCR product was cloned directly into pCR2.1 TOPO vector using Invitrogen's TOPO TA cloning protocol to form pDAB3918. The WNV ME v2 gene was then isolated using NcoI and SacI digestion from the TOPO backbone and ligated using T4 ligase at the NcoI/SacI site of pDAB3912 to form the entry clone, pDAB3919. pDAB3919 was LR Clonased into pDAB3736 to form pDAB3920.

Figure 13:
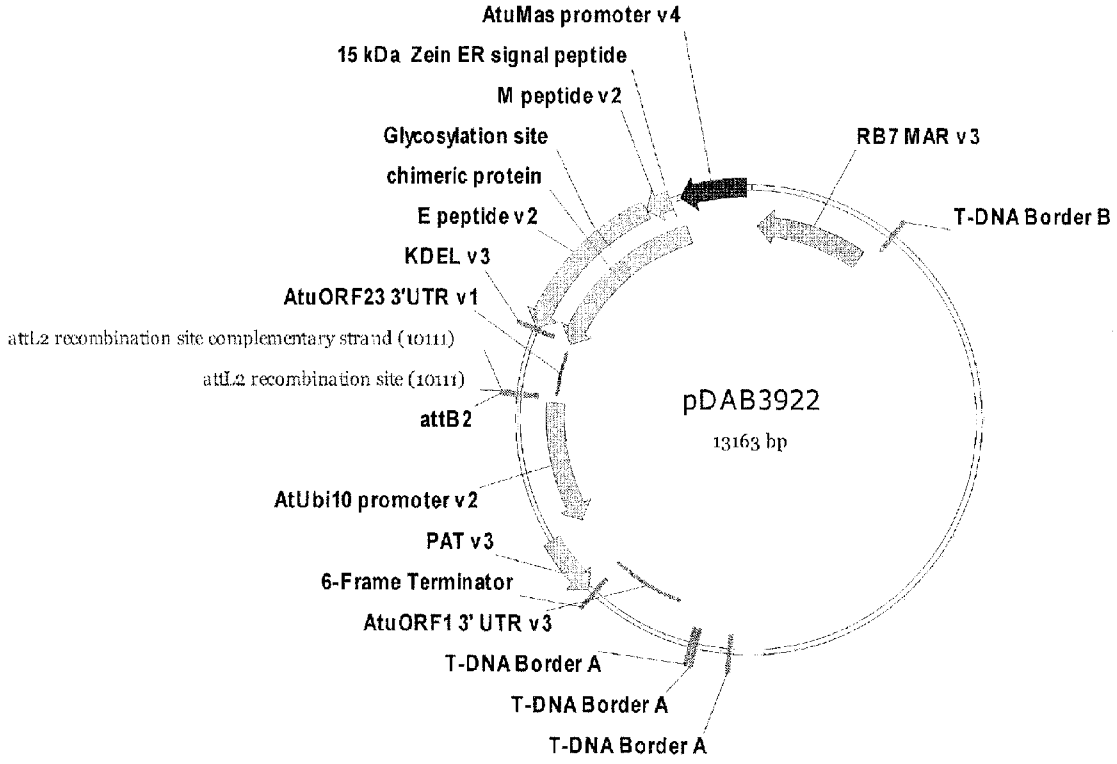
FIG. 13 illustrates Gateway™ binary vector, pDAB3922. pDAB3922 contains the following elements: T-DNA Border B/RB7 MAR v3/AtuMAS 4OCS promoter v4/15 kDa zein ER v2-WNV ME v2-KDELv3/Atu ORF23 3' UTR v1/AtUbi10 promoter v2/PAT v3/Atu ORF1 3' UTR v3/Multiple T-DNA Border A.

Gateway™ binary vector, pDAB3922 (FIG. 13), contains the following elements: T-DNA Border B/RB7 MAR v3/AtuMAS 4OCS promoter v4/15 kDa zein ER v2-WNV ME v2-KDELv3/Atu ORF23 3' UTR v1/AtUbi10 promoter v2/PAT v3/Atu ORF1 3' UTR v3/Multiple T-DNA Border A. The ER signal v2-ME v2-KDEL v3 peptide of DASPICO20 (SEQ ID NO 12) was removed from its backbone plasmid with NcoI and SacI. The excised gene fragment was then inserted at the NcoI/SacI site of pDAB3914 to form entry clone, pDAB3921, with the gene of interest sandwiched between the AtuMAS 4OCS promoter v4 and ORF23 3' UTR v1. pDAB3921 was then LR Clonased into pDAB3736 destination vector to form expression and binary vector, pDAB3922.

Figure 14:
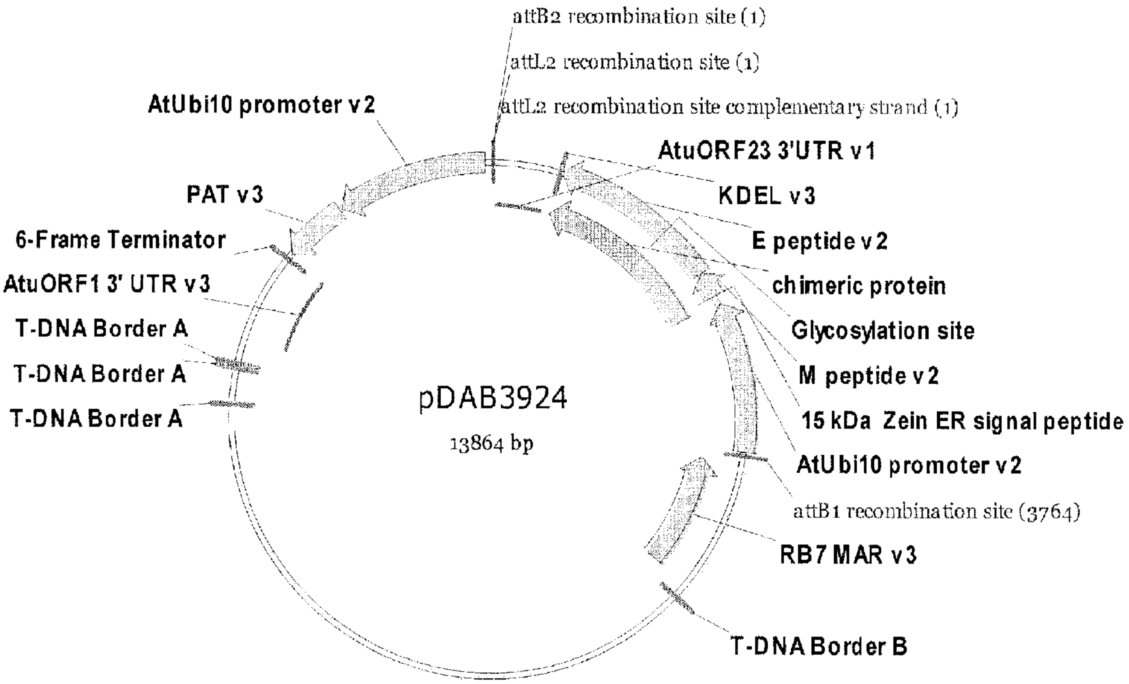
FIG. 14 represents Gateway™ West Nile Virus binary vector, pDAB3924. The pDAB3924 vector contains the following elements: T-DNA Border B/RB7 MAR v3/At Ubi10 promoter (Genbank Accession no L05363) v2/15 kDa zein ER v2-WNV ME v2-KDEL v3/Atu ORF23 3' UTR v1/AtUbi10 promoter v2/PAT v3/Atu ORF1 3' UTR v3/Multiple T-DNA Border A.

Gateway™ West Nile Virus binary vector, pDAB3924 (FIG. 14), contains the following elements: T-DNA Border B/RB7 MAR v3/At Ubi10 promoter (Genbank Accession no L05363) v2/15 kDa zein ER v2-WNV ME v2-KDEL v3/Atu ORF23 3' UTR v1/AtUbi10 promoter v2/PAT v3/Atu ORF1 3' UTR v3/Multiple T-DNA Border A. The ER signal v2-WNV ME v2-KDEL v3 peptide of DASPICO20 (SEQ ID NO 12) was removed from its backbone plasmid with NcoI and SacI. The excised gene fragment was then inserted at the NcoI/SacI site of pDAB3916 to form entry clone, pDAB3923, with the gene of interest sandwiched between the At Ubi10 v2 promoter and ORF23 3' UTR v1. pDAB3923 was then LR Clonased with pDAB3736 destination vector to form dicot binary vector, pDAB3924.

Figure 15:
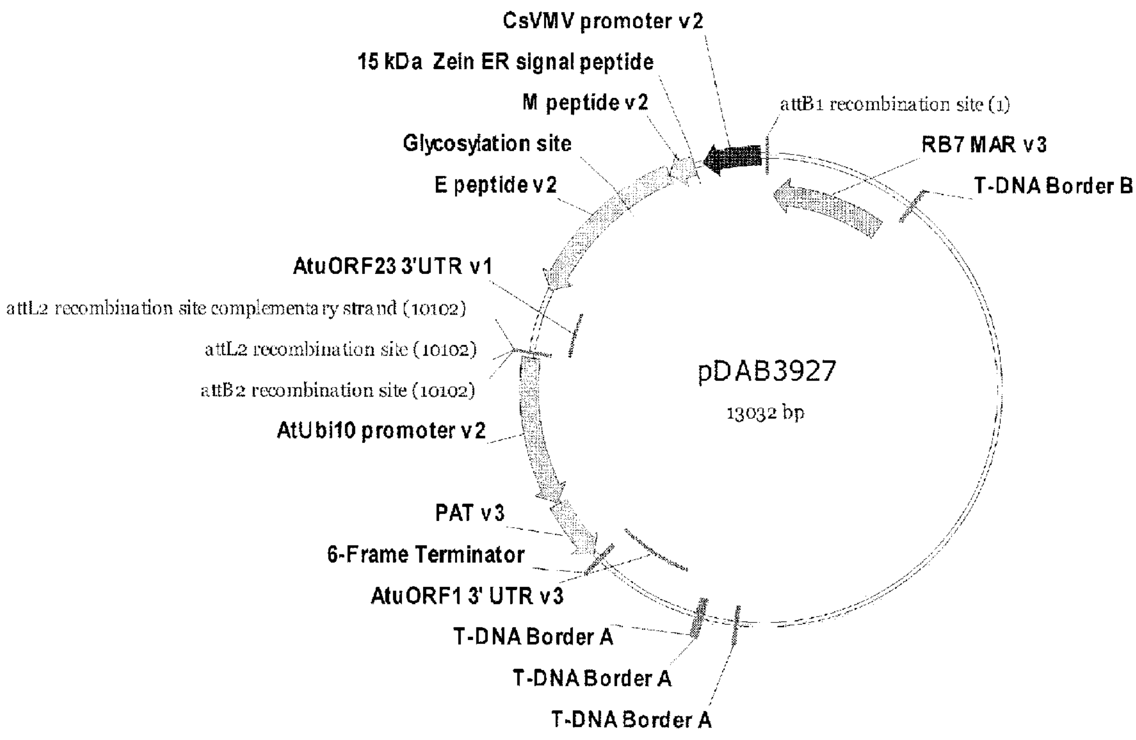
FIG. 15 pertains to a Gateway™ binary vector, pDAB3927 containing the following elements: T-DNA Border B/RB7 MAR v3/CsVMV promoter v2/15 kDa zein ER signal v2-WNV ME v2/Atu ORF23 3' UTR v1/AtUbi10 promoter v2/PAT v3/Atu ORF1 3' UTR v3/Multiple T-DNA Border A.

Gateway™ binary vector, pDAB3927 (FIG. 15), contains the following PTU elements: T-DNA Border B/RB7 MAR v3/CsVMV promoter v2/15 kDa zein ER signal v2-WNV ME v2/Atu ORF23 3' UTR v1/AtUbi10 promoter v2/PAT v3/Atu ORF1 3' UTR v3/Multiple T-DNA Border A. Amplification of the ER signal v2-WNV ME v2 peptide was accomplished by PCR. The KDEL v3 retention sequence from DASPICO20 (SEQ ID NO 12) was removed from the ME v2 peptide by using PCR primers (Forward: 5' cat gcc atg gct aag atg gtc att gtg ctt gtt gtg tgc 3'; Reverse: 5' ccc tcg agg gag ctc tta tca ctt agc atg aac att tac ag 3') that primed only to the ER signal v2-WNV ME v2 sequence and consisted of an NcoI site in the forward primer and a SacI site in the reverse primer for cloning purposes. The ER signal v2-WNV ME v2 PCR product was cloned directly into pCR2.1 TOPO vector using Invitrogen's TOPO TA cloning protocol to form pDAB3925. The ER signal v2-WNV ME v2 gene was then isolated using NcoI and SacI from its TOPO backbone plasmid and was ligated using T4 ligase at the NcoI/SacI site of pDAB3912 to form the entry clone, pDAB3926. pDAB3926 was LR Clonased with destination vector, pDAB3736, to form the final binary vector pDAB3927.

Figure 16:
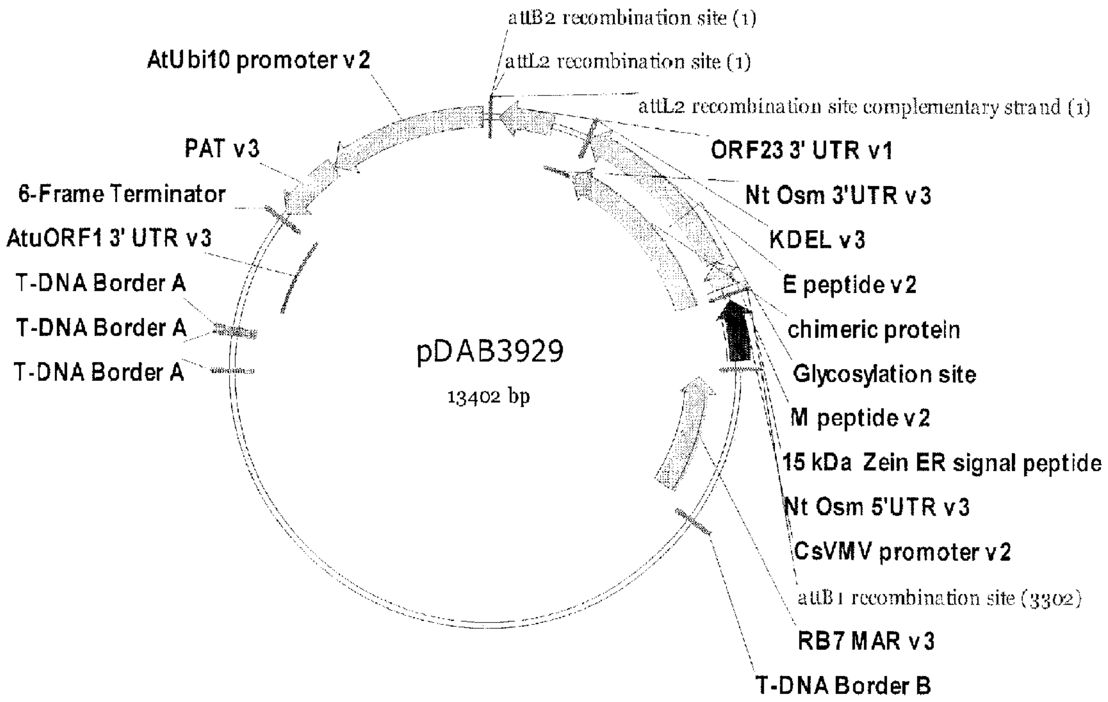
FIG. 16 provides Gateway™ binary vector, pDAB3929. pDAB3929 contains T-DNA Border B/RB7 MAR v3/CsVMV promoter v2/Nt osm 5' UTR v3/15 kDa zein ER v2-WNV ME v2-KDEL v3/Nt osm 3' UTR v3/Atu ORF23 3' UTR v1/AtUbi10 promoter v2/PAT v3/Atu ORF1 3' UTR v3/Multiple T-DNA Border A.

Gateway™ binary vector, pDAB3929 (FIG. 16), contains the following PTU units: T-DNA Border B/RB7 MAR v3/CsVMV promoter v2/Nt osm 5' UTR v3/15 kDa zein ER v2-WNV ME v2-KDEL v3/Nt osm 3' UTR v3/Atu ORF23 3'UTR v1/AtUbi10 promoter v2/PAT v3/Atu ORF1 3' UTR v3/Multiple T-DNA Border A. The ER signal v2-ME v2-KDEL v3 peptide of DASPICO20 (SEQ ID NO 12) was removed from its backbone plasmid with NcoI and SacI. The excised gene fragment was then inserted at the NcoI/SacI site of pDAB3724 (FIG. 11) using T4 ligase to form entry clone, pDAB3928, with the gene of interest sandwiched between the CsVMV/Nt osm 5' UTR and Nt osm 3' UTR v3/ORF23 3'UTR. LR clonase reaction with pDAB3928 and pDAB3736 destination vector resulted in the production of binary vector, pDAB3929.

Figure 17:
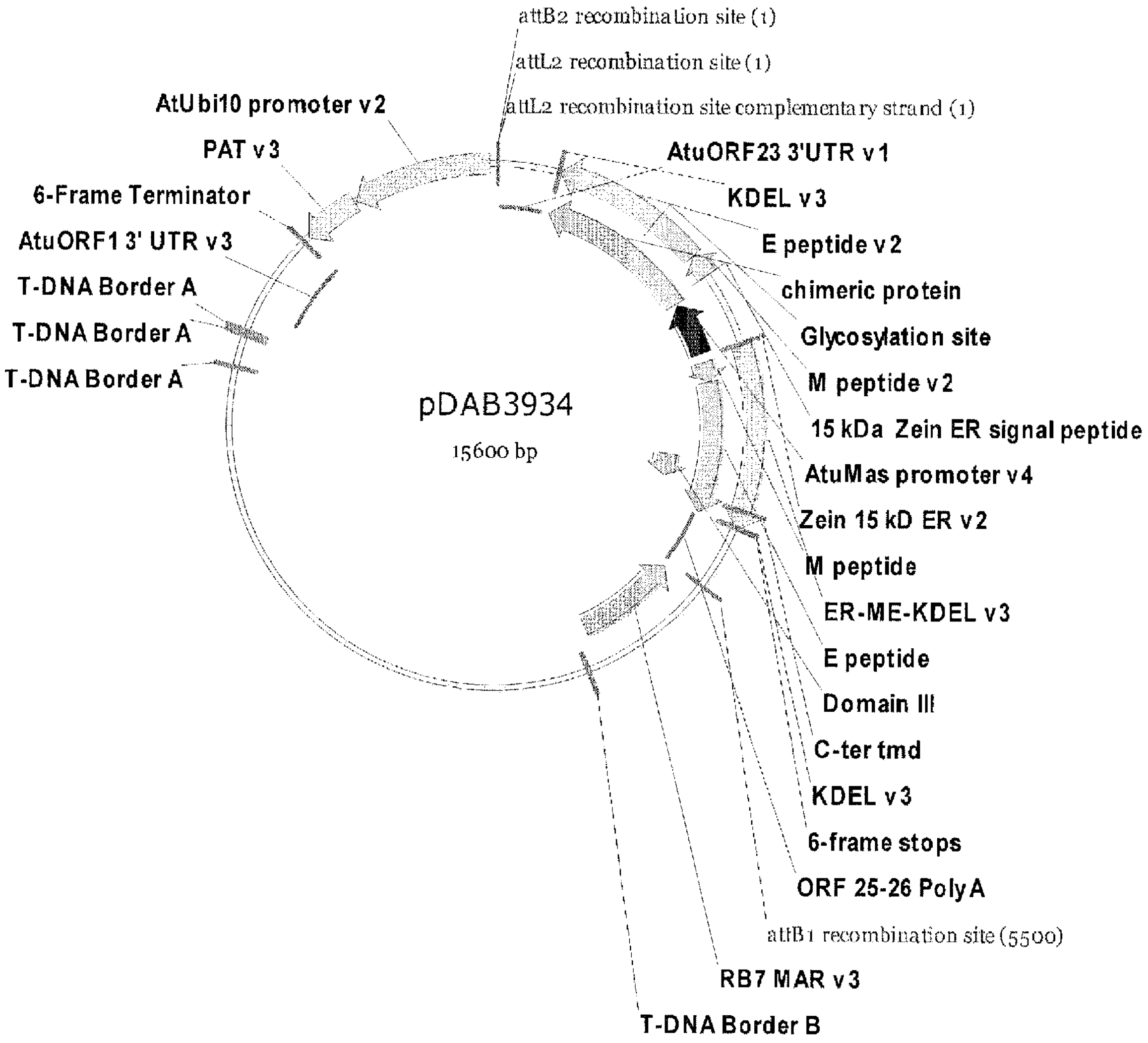
FIG. 17 is Gateway™ binary vector, pDAB3934. This vector contains the following elements: T-DNA Border B/RB7 MAR v3/ORF25/26 3' UTR/KDELv3/WNV ME v3/15 kDa zein ER signal v2 (SEQ ID NO: 14)/AtuMAS 4OCS promoter v4/15 kD zein ER signal v2-WNV ME v2-KDELv3/Atu ORF23 3, UTR v1/AtUbi10 promoter v2/PAT v3/Atu ORF1 3' UTR v3/Multiple T-DNA Border A.

Gateway™ binary vector, pDAB3934 (FIG. 17), contains the following elements: T-DNA Border B/RB7 MAR v3/ORF25/26 3'UTR/KDELv3/WNV ME v3/15 kDa zein ER signal v2 (SEQ ID NO 14)/AtuMAS 4OCS promoter v4/15 kD zein ER signal v2-WNV ME v2-KDELv3/Atu ORF23 3' UTR v1/AtUbi10 promoter v2/PAT v3/Atu ORF1 3' UTR v3/Multiple T-DNA Border A. For generation of this construct, a multiple step cloning process included amplification of the ORF 25/26 poly A UTR from construct p501 (Murai and Kemp, 1982) using primers (Forward: 5' ccc aag ctt ggg tgt cca aca gtc tca ggg tta atg tc 3'; Reverse: ccca agct tgg g tgg cac gtg agg tcc atg egg ctg c) that contained HindIII sites flanking the PCR product. The ORF25/26 poly A PCR product was then cloned into a pCR2.1 TOPO vector to produce pDAB3930. The ER signal v2-WNV ME v2-KDEL v3 of DASPICO20 (SEQ ID NO 12) was removed from its backbone plasmid with NcoI and SacI and was inserted into pDAB3914 at the NcoI/SacI site using T4 ligase to form pDAB3931. SacII was used to remove the ER signal v2-WNV ME v3-KDEL of DASPICO72 (PicoScript, SEQ ID NO 14) from its Bluescript backbone and the gene fragment was then inserted in pDAB3931 at the SacII site in reverse orientation to form pDAB3932. HindIII was used to excise ORF 25/26 poly A PCR product from pDAB3930. The ORF25/26 Poly A UTR was then inserted in reverse orientation into pDAB3932 at its HindIII site to form entry clone, pDAB3933. pDAB3933 was LR Clonased into pDAB3736 to form the expression and binary vector, pDAB3934.

Figure 18:
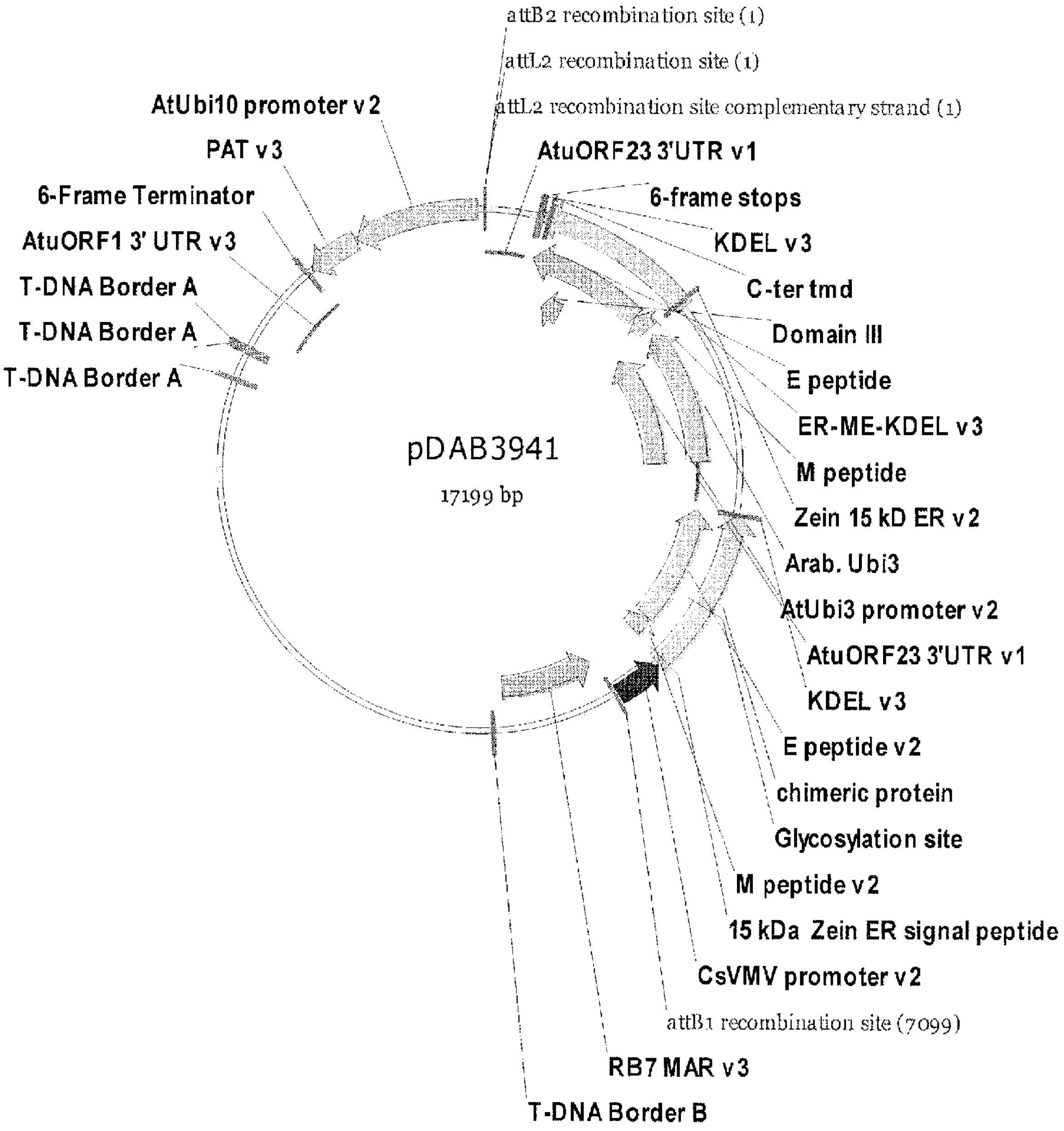
FIG. 18 provides a depiction of Gateway™ binary vector, pDAB3941. pDAB3941 contains the following components: T-DNA Border B/RB7 MAR v3/CsVMV promoter v2/15 kD zein ER v2-WNV ME v2-KDEL v3/Atu ORF23 3'UTR v1/AtUbi3 promoter v2/15 kD zein ER v2-WNV ME v3-KDELv3/Atu ORF23 3' UTR v1/AtUbi10 promoter v2/PAT v3/Atu ORF1 3' UTR v3/Multiple T-DNA Border A.

Gateway™ binary vector, pDAB3941 (FIG. 18), contains the following PTU components: T-DNA Border B/RB7 MAR v3/CsVMV promoter v2/15 kD zein ER v2-WNV ME v2-KDEL v3/Atu ORF23 3'UTR v1/AtUbi3 promoter v2/15 kD zein ER v2-WNV ME v3-KDELv3/Atu ORF23 3' UTR v1/AtUbi10 promoter v2/PAT v3/Atu ORF1 3' UTR v3/Multiple T-DNA Border A. This multiple step cloning process included amplifying the AtUbi3 v2 promoter from another construct using primers (Forward: 5' ccc aag ctt ata aga atg cgg ccg cta aac tat agc ttc gga ttt gga gcc aag tc 3'; Reverse: 5' ccg ctc gag cgg tcc ccg cgg gga gct gaa ata aaa caa tag aac aag tag 3') that contained HindIII/NotI sites at the 5' end of PCR product and SacI/XhoI sites flanking the PCR product at the 3' end. The AtUbi3 v2 PCR product was then cloned into pCR2.1 TOPO vector to make plasmid pDAB3935. An XhoI linker (Sense: cgatccgctcgagcggtagg; Antisense: gtg acc cta ccg etc gag egg atc gag ct) was added to pDAB2406 at the SacI/BstEII site to introduce an XhoI site between the CsVMV v2 promoter and ORF23 3'UTR v1 to make vector, pDAB3936. pDAB3936 was then cut with XhoI and HindIII to remove the CsVMV promoter and retain the backbone vector. PCR product, AtUbi3 v2 promoter, from pDAB3935 was cut with HindIII and XhoI and ligated into pDAB3936 backbone at the HindIII/XhoI site, making pDAB3937. The ER signal v2-ME v2-KDEL v3 peptide of DASPICO20 (SEQ ID NO 12) was removed from its backbone plasmid with NcoI and SacI and ligated into pDAB3912 at the NcoI/SacI site to form plasmid vector, pDAB3939. The ER signal v2-WNV ME v3-KDEL v3 peptide of DASPICO72 (SEQ ID NO 14) was removed from its Bluescript backbone plasmid with SacII-XhoI and was inserted into pDAB3937 at the SacII/XhoI sites to construct pDAB3938. The AtUbi3/ER signal v2-ME v3-KDEL v3/ORF23 gene cassette from pDAB3938 was then excised with NotI and inserted into pDAB3939 at the NotI site to form entry clone, pDAB3940. LR clonase reaction with pDAB3940 and destination vector, pDAB3736, resulted in the formation of dicot binary vector, pDAB3941.

Figure 19:
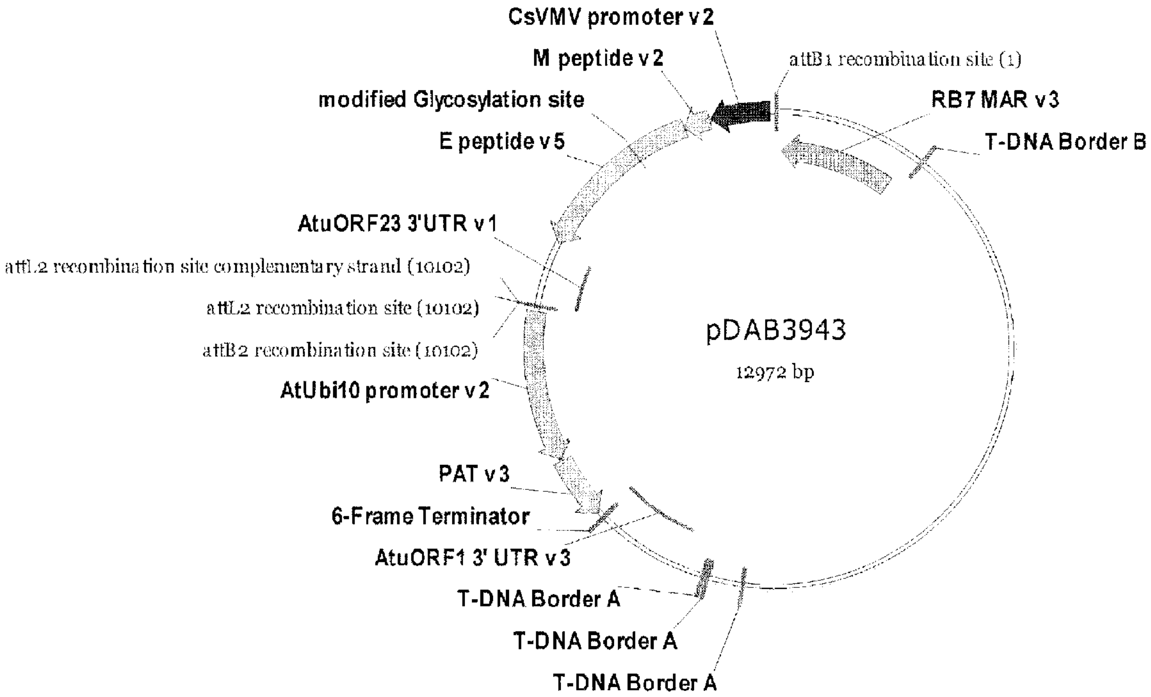
FIG. 19 provides Gateway™ binary vector, pDAB3943. This vector contains the following elements: T-DNA Border B/RB7 MAR v3/CsVMVv2/WNV M v2 E with modified glycosylation site (v5)/Atu ORF23 3' UTR v1/AtUbi10 promoter v2/PAT v3/Atu ORF1 3' UTR v3/Multiple T-DNA Border A.

Gateway™ binary vector, pDAB3943 (FIG. 19), contains the following elements: T-DNA Border B/RB7 MAR v3/CsVMVv2/WNV M v2 E with modified glycosylation site (v5)/ Atu ORF23 3' UTR v1/AtUbi10 promoter v2/PAT v3/Atu ORF1 3' UTR v3/Multiple T-DNA Border A. The cloning process included removing the mutated N-glycosylation site region of the WNV prM v2 E v4 peptide of DASPICO22 (SEQ ID NO 10) using AccI and AvrII restriction enzymes and ligating into pDAB3919 (refer to pDAB3920 cloning strategy) at the AccI/AvrII sites to establish the entry clone, pDAB3942. pDAB3942 was LR Clonased into destination vector, pDAB3736, to make the final dicot binary plasmid, pDAB3943.

All final Gateway binary constructs were verified initially by restriction digest, followed by sequencing between the T-DNA borders, which confirmed actual and expected sequence were identical

Example 3

Transformation of *Agrobacterium* with Plant Expression Vectors

Independently, 1.5-3 μg of plasmid DNA for each WNV construct were added to 50 μl of Electromax® LBA4404 *Agrobacterium tumefaciens* cells (Invitrogen, Carlsbad, Calif.) and gently mixed. The mixture was transferred to cold 0.2 cm Gene Pulser® cuvettes (BioRad Hercules, Calif.) and placed on ice. The cuvettes were then placed in a cold Gene Pulser® rack (BioRad, Hercules, Calif.) and electroporated at the following conditions:

| | |
|---|---|
| Capacitance Output | 25 μFarad |
| Capacitance Extender | 960 μFarad |
| Resistance | 200 ohms |
| Voltage | 2.5 kVolts |

Immediately after electroporation, 950 μl of SOC medium (Invitrogen, Carlsbad, Calif.) was added and the mixture was transferred to a Falcon 2059 tube (Becton Dickinson and Co., Franklin Lakes, N.J.) or equivalent. The transformed cells were then incubated at 28° C. for 1 hour. After incubation, 50 μl, 100 μl, and 200 μl of cells were plated on separate YEP medium plates (10 g yeast extract, 10 g peptone, 5 g NaCl, 10 g sucrose, and 15 g agar in 1 Liter of water) containing antibiotics as appropriate. The plates were grown inverted at 28° C. for approximately 36-48 hours. Single colonies were picked and propagated in 50 ml of liquid YEP (10 g yeast extract, 10 g peptone, 5 g NaCl, and 10 g sucrose in 1 Liter of water), containing antibiotics as appropriate, at 28° C. for approximately 36 hours. Following the Qiagen® low copy mini-prep protocol (Qiagen, Valencia, Calif.), purified plasmid DNA was prepared from the bacterial cultures. DNA integrity was evaluated by restriction digest. Clones with the expected banding patterns were identified and glycerol stocks were prepared by adding 500 μl of bacterial culture to 500 μl of sterile glycerol (Sigma Chemical Co., St. Louis, Mo.) and inverting to mix. Glycerol stocks were frozen on dry ice and stored at −80° C.

Example 4

Stable Transformation of Nicotiana Tabacum Cell Cultures for Expression of WNV Proteins

*Nicotiana tabacum* NT-1 cell cultures were maintained aseptically on a one-week subculture cycle, by adding 2 ml of the NT-1 culture or 1 ml of packed cells into 40 ml NT-1 B media (Table 3) in a 250 ml flask. The suspensions were maintained in the dark at 25±1° C. at 125 rpm.

In preparation for NT-1 culture transformation, a 50% glycerol stock of *Agrobacterium tumefaciens* containing the expression vector of interest was used to initiate a liquid bacterial culture by adding 20-500 μl of glycerol stock to 30 ml YEP liquid medium (10 g yeast extract, 10 g peptone, 5 g NaCl, and 10 g sucrose in 1 liter of water) containing 50 mg/l spectinomycin and 100 μM acetosyringone. The bacterial culture was incubated in the dark at 28° C. at 150-200 rpm until the $OD_{600}$ was 0.5-0.6. This took approximately 18-20 hrs.

On the day of transformation, four days after NT-1 subculture, 20 mM acetosyringone (in ethanol) was added to cell suspensions at a concentration of 1 μl per ml of NT-1 culture. The NT-1 cells were wounded to increase transformation efficiency by drawing them up and down 20 times through a sterile 10 ml standard-bore pipet. Four milliliters of the suspension was transferred into each of 10, 60×20 mm Petri plates. One plate was set aside to be used as a non-transformed control. To each of the remaining 9 plates, 100 μl of *Agrobacterium* suspension was added. The plates were wrapped with parafilm and incubated in the dark at 100 rpm and 25±1° C. for 3 days.

Transgenic events were also created by an alternative method that did not use acetosyringone in either growth of the *Agrobacterium* culture nor was it used during the plant cell transformation process. Four milliliters of the tobacco suspension (unwounded) was transferred into each of 10, 100×25 mm Petri plates. To each of 9 plates, 100 μl of *Agrobacterium* suspension at $OD_{600}$=1.5±0.2 was added, again keeping 1 plate as a non-transformed control. The plates were swirled to mix, wrapped in parafilm and cultured in the dark at 25±1° C. for 3 days without being shaken.

Following the co-cultivation period for either transformation method, all liquid was removed with the cells then resuspended in 8 ml NTC medium (NT-1 B medium containing 500 mg/l carbenicillin, added after autoclaving). One milliliter aliquots of suspension were distributed to each of 8 Petri plates (100×25 mm) containing NTC+B5 medium [NTC medium solidified with 8 g/l TC Agar, supplemented with 5 mg/l phosphinothricylalanyalanine sodium (bialaphos) after autoclaving]. All selection plates, either wrapped with parafilm or left unwrapped, were maintained in the dark at 25-28° C. Before wrapping, liquid was removed from any plates that were excessively wet.

After 2 to 8 weeks, putative transformants appeared as small clusters of callus on a background of dead, non-transformed cells. These viable calli were transferred to fresh NTC+B5 medium, assigned identification numbers, and maintained as individual transformation events. The plates were left unwrapped, incubated in the dark at 28±1° C., and the events were subcultured onto fresh NTC+B5 medium every 2 weeks for a total of 3 passages, after which the carbenicillin was removed from the medium for future subcultures. Portions of each putative transformant were used for protein expression analysis. Selected events were bulked up as callus and established in suspension culture.

Suspensions were initiated by transferring 500 mg of 7-day old, proliferating transgenic callus into a 125-mL flask containing 20 ml NT1B+10 mg/l bialaphos. The cells and liquid were mixed by pipetting 3-5 times with a 50 ml pipet to break up tissue then agitated on a shaker at 130 rpm in the dark at 25±1° C. The suspensions were subcultured on a weekly basis by transferring 1 ml of packed cells into 20 ml NT1B with 10 mg/l bialaphos in a 125 ml flask. The suspensions were maintained in the dark at 25±1° C. at 125 rpm.

Example 5

WNV Protein Expression Analysis

Inactivated WNV reference standard. Reference antigen was prepared by modification of a published method (Blitvich, et al., 2003). WNV was inoculated at a multiplicity of infection of approximately 0.01 into VERO cells in five roller bottles and incubated on a roller rack at 37° C. Two identical bottles of uninoculated VERO cells were fed with the same growth medium (medium 199 with Earles salts, 5% fetal bovine serum, Penicillin/Streptomycin) and incubated under the same conditions. After five days, the inoculated and uninoculated cells were scraped from the inside of their bottles. The medium and cells were placed in 50 ml centrifuge tubes and pelleted at 2000 rpm. Supernatant was discarded and the cells were pooled in 15 ml of growth medium and frozen at −80° C. in 5 equal aliquots.

One tube of infected and one tube of control cells were thawed at 37° C. The cells were pelleted at 3500 rpm for 10 minutes and washed twice in 6 ml of ice-cold borate saline buffer (120 mM sodium chloride, 50 mM boric acid, 24 mM sodium hydroxide, pH 9.0), with centrifugation at 3500 rpm for 10 minutes at 4° C. The cells were resuspended in 900 μl of 0.1% sodium dodecyl sulfate, then 100 μl of Triton X-100 and 2 ml of borate saline buffer were added to the suspension. The suspension was sonicated at 20% output for 30 seconds on ice, transferred to Eppendorf tubes and centrifuged at full speed in a microcentrifuge for 10 minutes. Finally, supernatants were transferred to clean Eppendorf tubes, 500 μl per tube, and frozen at −80° C. Eppendorf tubes containing the WNV-infected material were labeled "WNV/VERO Antigen". Eppendorf tubes containing the uninoculated control cells were labeled "Control VERO Antigen".

Inactivation of WNV was verified by inoculating 50 μl and 25 μl amounts of WNV/VERO Antigen onto monolayers of VERO cells in 150 $cm^2$ flasks, incubating for 5-6 days, then passing the medium onto fresh VERO cells and incubating 6 days. Some VERO cell damage, attributed to the detergent used for inactivation, was observed in the first passage. Absence of cytopathic effects in the second passage indicated successful viral inactivation.

West Nile Virus E Protein Western Blot. A Western blot protocol was developed for detecting E protein using commercially available antibodies. Inactivated West Nile Virus (WNV/VERO Antigen, at 5.1 μg/ml) was prepared in Leammli sample buffer (125 mM Tris-HCl, pH 6.8, 40 mM DTT, 1 mM EDTA, 2% SDS, 10% glycerol) and separated by SDS-PAGE on a 4-12% Bis-Tris gel (Invitrogen, Carlsbad, Calif.). Proteins were transferred to 0.2 μm nitrocellulose membrane by electroblot. Membrane blots were blocked in blocking buffer (WesternBreeze Blocker/Diluent (part A and B), Invitrogen, Carlsbad, Calif.) followed by incubation with a West Nile Virus monoclonal antibody for at least 1 hour (Mab8151 Ms X West Nile/Kunjin Virus, Chemicon International., Temecula, Calif. diluted 1:5000 in blocking buffer or WNV Monoclonal Antibody 7H2, affinity purified, BioReliance Invitrogen BioServices, Rockville, Md., 75 μg/ml in PBS-glycerol diluted 1:500 in blocking buffer). Following three 5 minute wash steps (WesternBreeze Wash Solution (16×), Invitrogen, Carlsbad, Calif.), blots were incubated in detection antibody. For alkaline phosphatase detected blots, a goat anti-mouse alkaline phosphotase labeled antibody (Catalog Number 075-1806, KPL, Gaithersburg, Md.) was diluted in blocking buffer at 1:1000. For horseradish peroxidase detected blots, a goat anti-mouse horseradish peroxidase labeled antibody (Catalog Number 074-1806, KPL, Gaithersburg, Md.) was diluted in blocking buffer at 1:1000. Following incubation with detection antibody, blots were washed and developed with the appropriate substrate: NBT/BCIP Phosphatase Substrate (Catalog Number 50-81-08, KPL, Gaithersburg, Md.) for alkaline phosphatase detection or Pierce SuperSignal (Catalog Number 34080, Pierce, Rockford, Ill.) for horseradish peroxidase to visualize the bands.

West Nile Virus E Protein ELISA. Nunc Maxisorp 96-well microtiter ELISA plates were prepared by Beacon Analytical Systems Inc. (Portland, Me.) by coating plates with Equine anti-WNV (Novartis #215-006, Webster Veterinary Supply, Sterling, Mass.) at a concentration of 2 μg/ml in carbonate buffer, 100 μl per well. Plates were blocked with 1% BSA (Serologicals Corporation Inc., Norcross, Ga.) in PBST (1×PBS containing 0.05% Tween 20, Sigma Cat. No. P-1379), dried, and packed for storage at 4° C. The day of the assay, plates were warmed to room temperature prior to loading samples. WNV reference antigen (WNV/VERO Antigen, at 5.1 μg/ml) was diluted to 200 ng/ml in PBST. Plant samples were pre-diluted in PBST. The diluted reference antigen and test antigen samples were added to the plate by applying 200 μl of sample to duplicate wells in row A and 100 μl of blocking buffer to remaining wells. Serial 2 fold dilutions were made by mixing and transferring 100 μl per well; for a total of 7 dilutions and a blank for the reference antigen and 4 or more dilutions for test samples. Plates were then incubated 1 hour at room temperature. Plates were washed 3× in PBST. Monoclonal antibody (WNV Monoclonal Antibody 7H2, affinity purified, BioReliance Invitrogen BioServices, Rockville, Md., 75 μg/ml in PBS-glycerol) was diluted 1:500 in 1% BSA-PBST and added at 100 μg/well followed by incubation for 1 hour at room temperature. The plates were washed 3× with PBST. Goat anti-Mouse IgG peroxidase-labeled antibody conjugate (BioRad 170-6516, Hercules, Calif.) diluted 1:10,000 in 1% BSA-PBST was added at 100 μl/well and plates were incubated 1 hour at room temperature. The plates were washed 3× in PBST and 100 μl of TMB substrate (BioFX Laboratories Inc., Cowings, Md.) was added to each plate and incubated at room temperature for approximately 5-10 minutes. The reaction was stopped with 1N HCl. Optical density was read at 450 nm minus a 650 nm wavelength reference using a Vmax Kinetic Microplate Reader (Molecular Devices, Sunnyvale, Calif.). Data was transported to SoftMaxPro 4.0 software and the standard curve was fit to a 4 parameter logistic equation for sample quantitation.

Screening Putative Transformants. Callus samples were collected from putative transformants (Example 4) in duplicate at day 7 and day 14 after subculture. For each sample, 200 μl callus was collected from a homogenized pool of callus using a 1 ml syringe (BD, Franklin Lakes, N.J.) with the tip cut off. Samples were collected into 96 well cluster tube boxes (1.2 ml tubes, Costar, Corning, N.Y.), frozen on dry ice and stored at −80° C.

Figure 20:
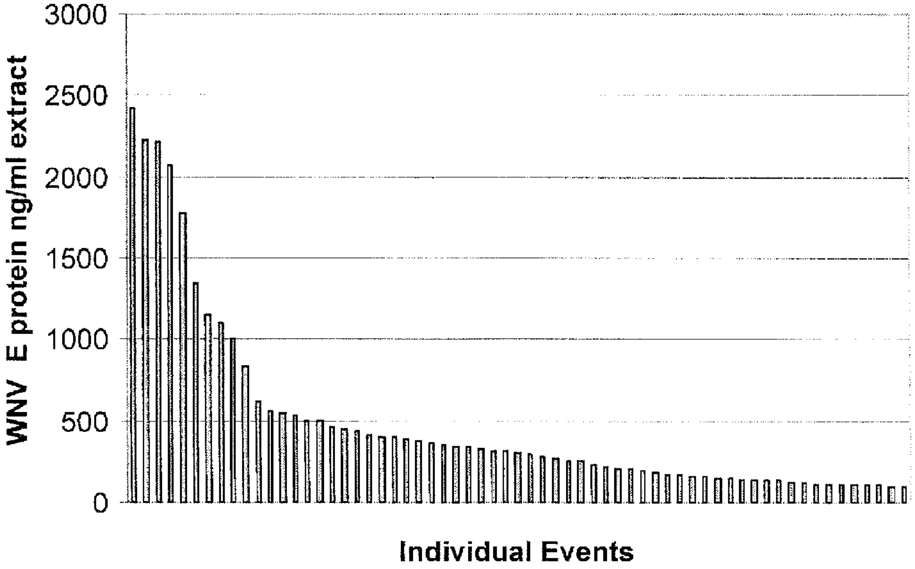
FIG. 20 provides E protein expression of 14 Day callus events transformed with pDAB2475 (ER targeted, ME Version 2, KDEL), as detected by ELISA.
Figure 21:
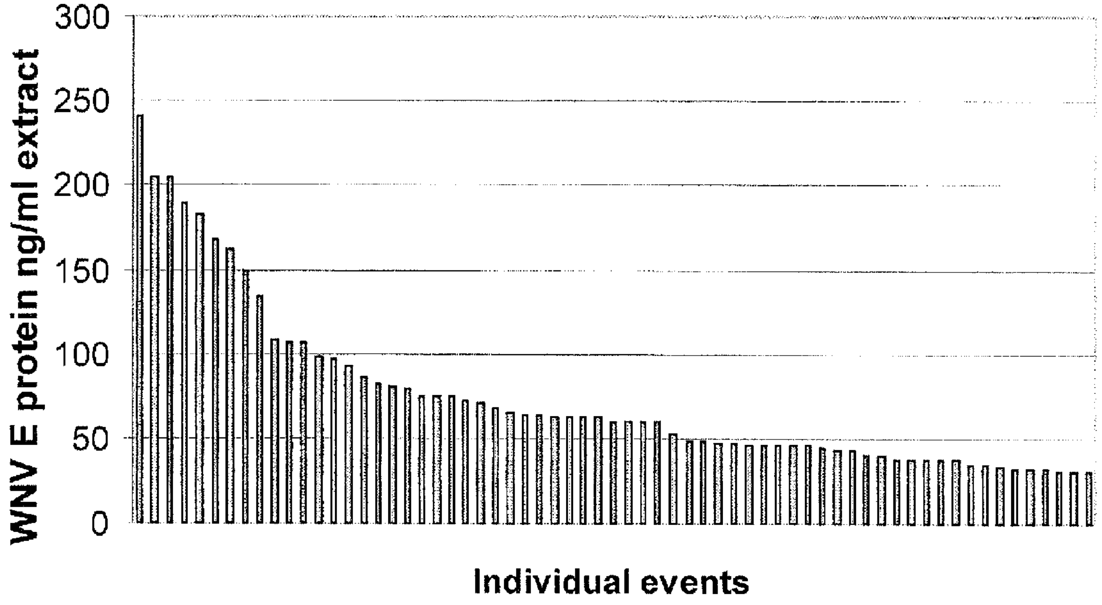
FIG. 21 provides E protein expression of 14 Day callus events transformed with pDAB2478 (ER targeted, prME Version 2, KDEL) as detected by ELISA.
Figure 22:
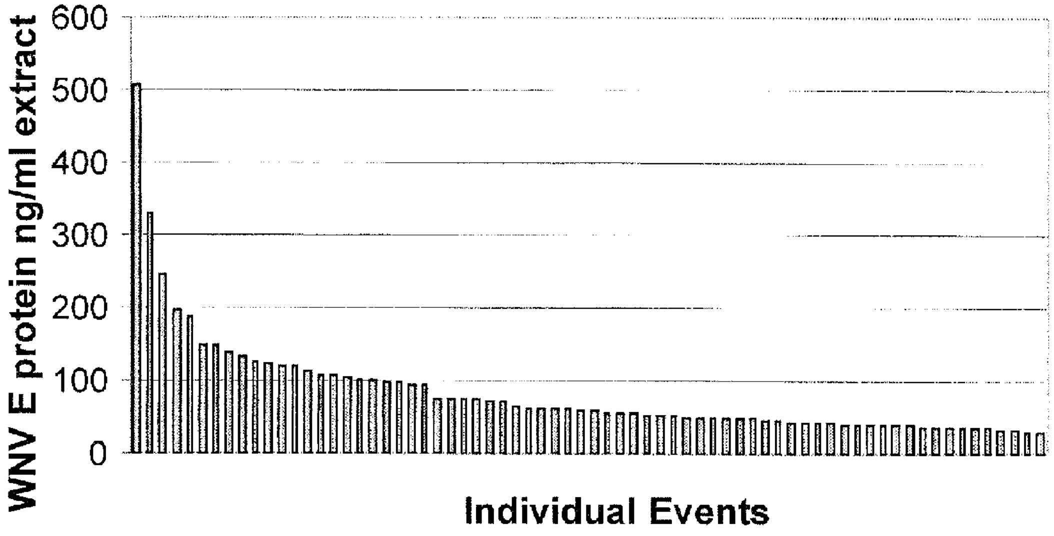
FIG. 22 provides E protein expression of 14 Day callus events transformed with pDAB2481 (ER targeted, prME with modified glycosylation site (Version 4), KDEL) as detected by ELISA.
Figure 23:
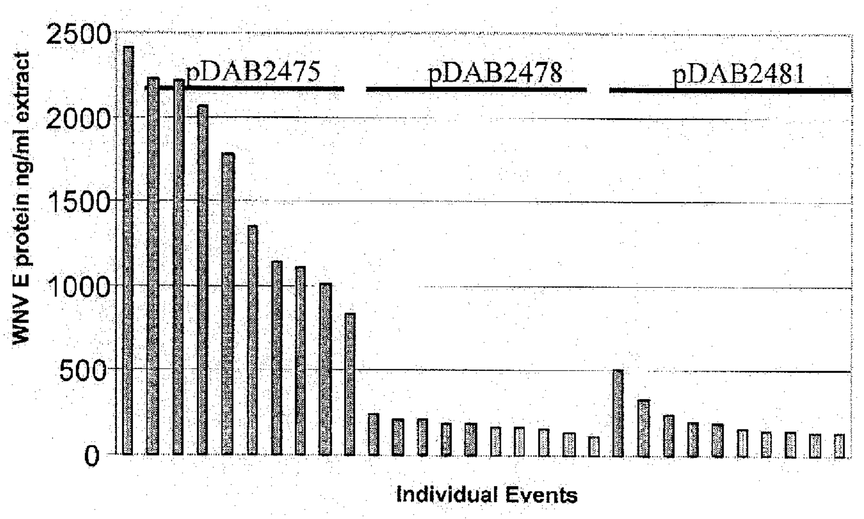
FIG. 23 compares the expression levels between events transformed with pDAB2475, pDAB2478, and pDAB2481. A significantly higher protein recovery potential from pDAB2475 is indicated in the figure.

At the time of analysis, samples were extracted in 0.1% DBDM (n-Dodecyl b-D-maltoside, Sigma D4611) in PBS using a Kleco bead beater (Garcia Machine, Visalia, Calif.). Two steel BB's (Daisy 4.5 mm) were added to each tube along with 200 μl of DBDM-PBS. Samples were agitated at maximum speed for 4 minutes followed by a 10 minute centrifugation at 3000×g. Supernatants were removed to new tubes. The resulting pellet was re-extracted (200 μl buffer, 4 minutes agitation, 10 minute spin). Supernatants from both extractions were pooled and used for analysis. Samples from 14 day callus were analyzed in a 1:10, 1:20, 1:40, 1:80 dilution series. For confirmation of expression ranking, 7 day callus samples were analyzed at a 1:40 dilution. Results of expression screening of events from constructs pDAB2475, pDAB2478, and pDAB2481 are summarized in FIGS. 20-22. Comparison of top expressing events between the 3 vectors (FIG. 23) indicated a significantly higher E protein recovery potential from pDAB2475.

Figure 24:
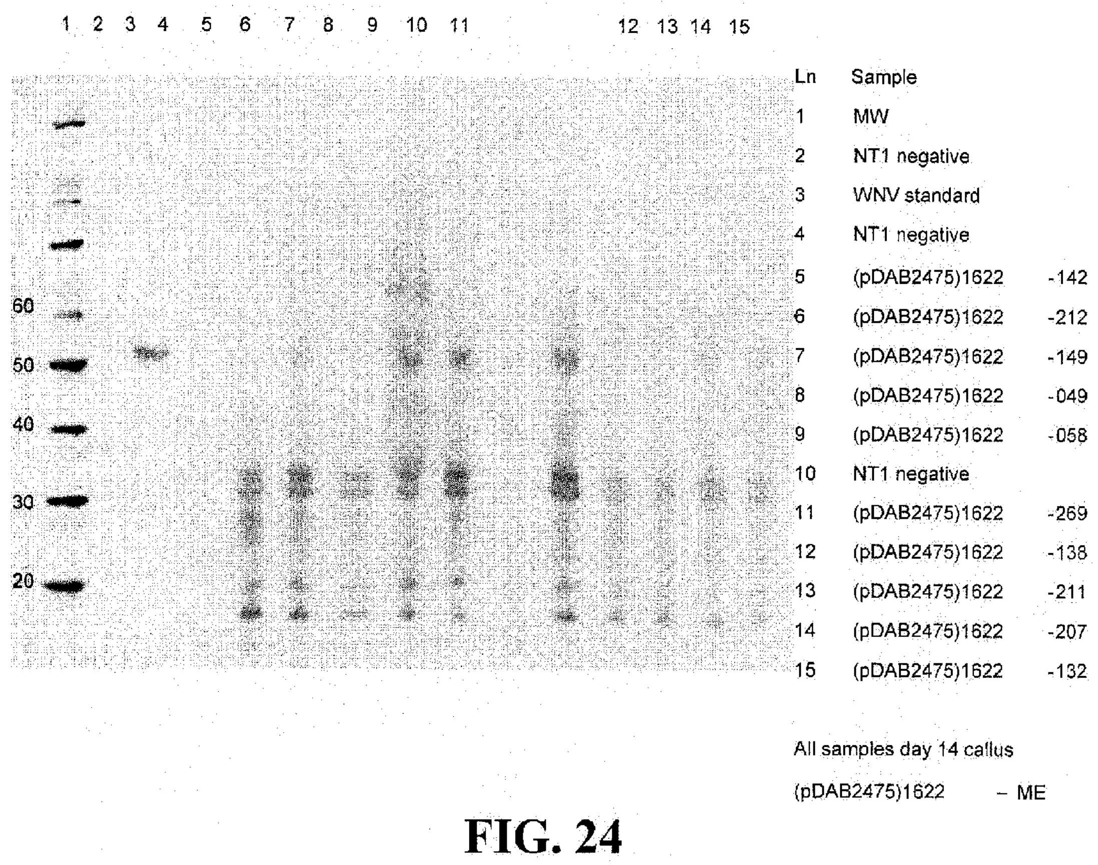
FIG. 24 depicts samples from select events that were analyzed by Western blot (day 14 callus). From many of the pDAB2475 events, full-length E protein was detected at the expected ~54 kDa size of the authentic mature virion E protein.
Figure 25:
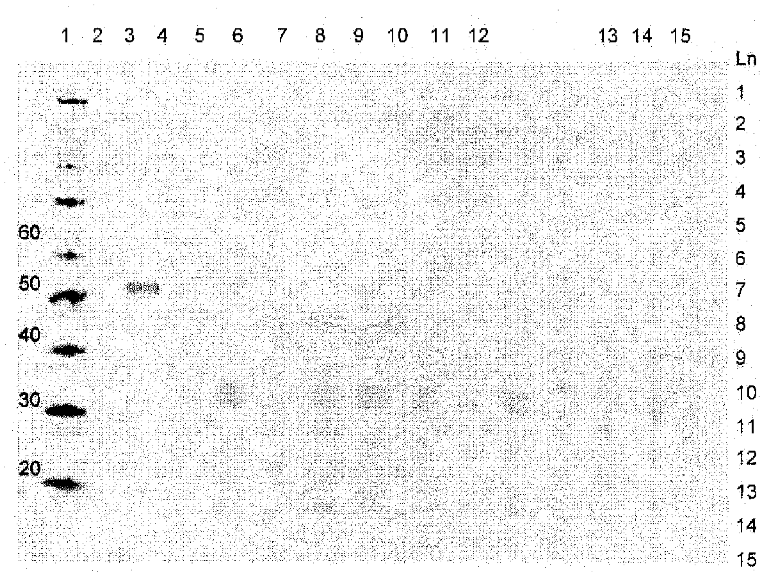
FIGS. 25 and 26 illustrate that fewer events expressing the full-length E protein were detected with the pDAB2478 and pDAB2481 constructs.
Figure 26:
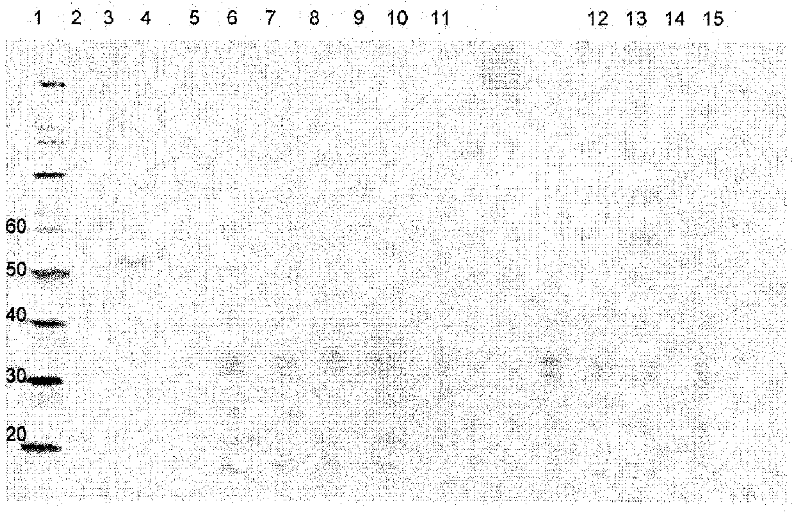

Samples from select events of these constructs were also analyzed by Western blot (day 14 callus). Differences in the banding patterns between constructs were evident. From many of the pDAB2475 events, full-length E protein was detected at the expected ~54 kDa size (FIG. 24). Other bands ~35 kDa and smaller were also reproducibly detected. Fewer events expressing the full-length E protein were detected with pDAB2478 and pDAB2481 constructs (FIGS. 25 and 26).

Figure 27:
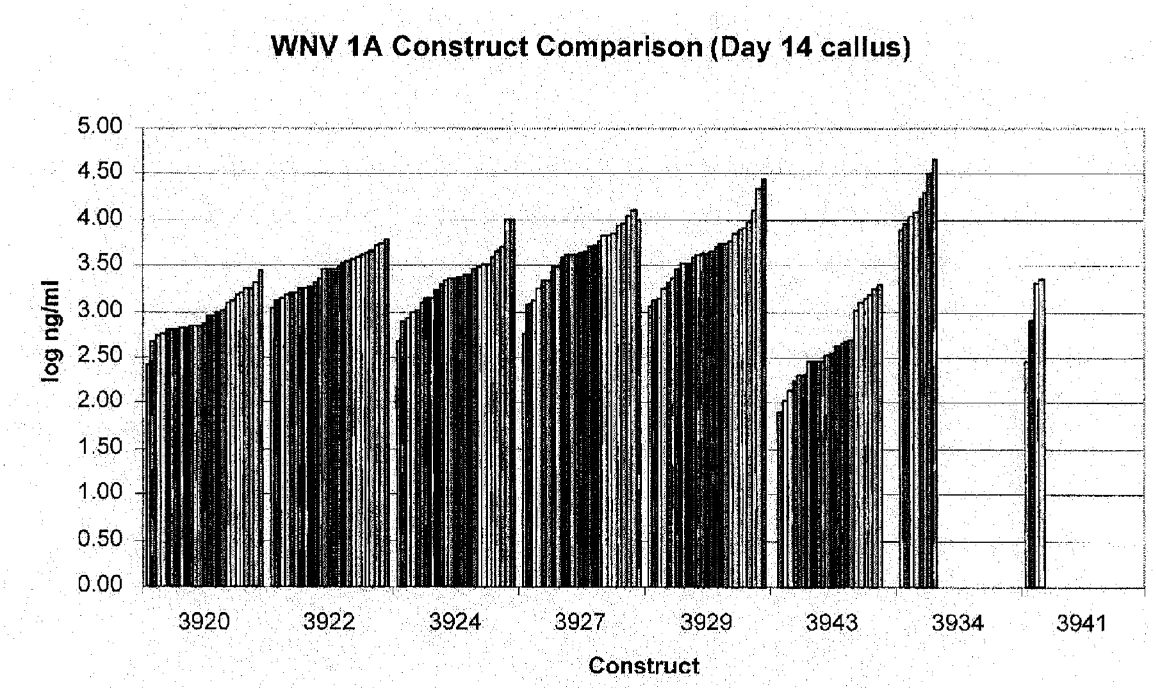
FIG. 27 compares ELISA Results from Day 14 Callus of All Events of pDAB3920, pDAB3922, pDAB3924, pDAB3927, pDAB3929, pDAB3943, pDAB3934 and pDAB3941.
Figure 28:
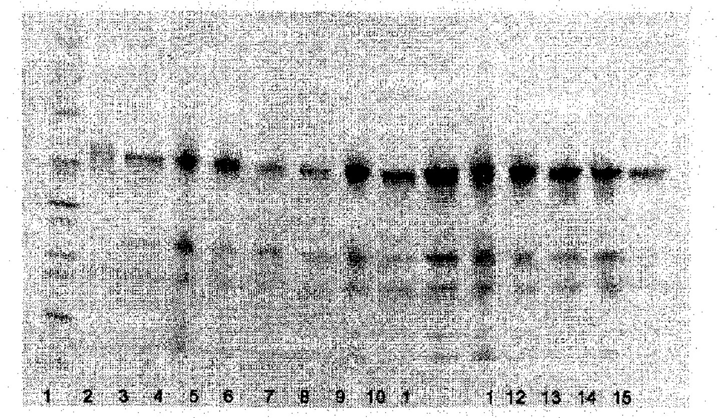
FIG. 28 depicts 14 Day callus samples from events of pDAB3920 and pDAB3922 analyzed by Western blot.
Figure 29:
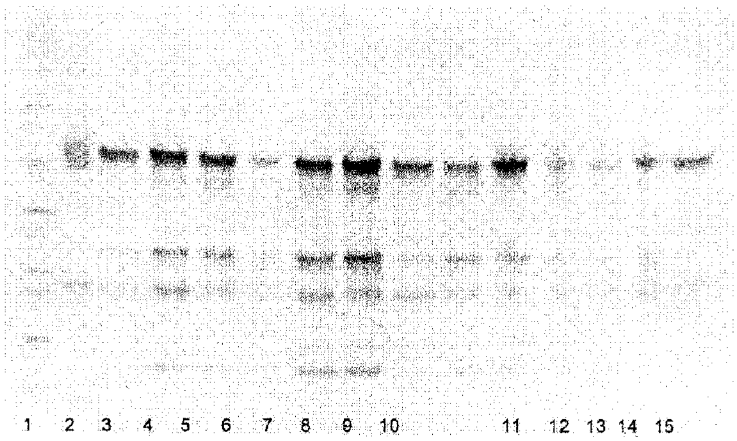
FIG. 29 depicts 14 Day callus samples from events of pDAB3924 and pDAB3927 analyzed by Western blot.
Figure 30:
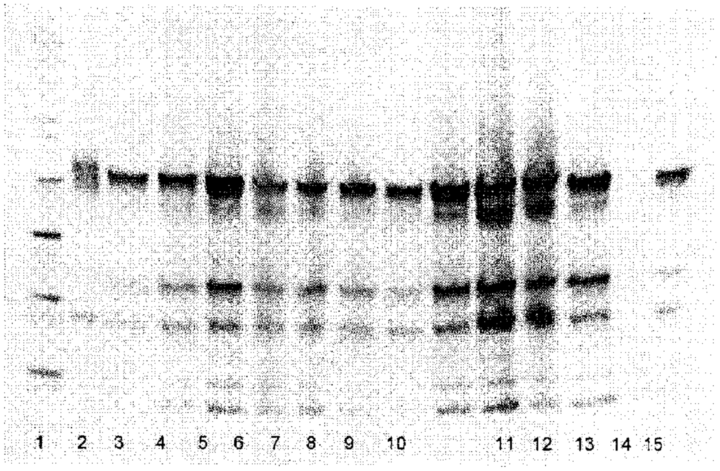
FIG. 30 depicts 14 Day callus samples from events of pDAB3929 and pDAB3934 analyzed by Western blot.

FIG. 27 is a comparative representation of E protein expression from the remaining 8 constructs. All demonstrated expressed E protein in tobacco plant cells, as detected by ELISA. Additionally, Western blot analysis revealed full-length E protein as well as truncations (FIGS. 28-30).

Example 6

Scale-Up of Plant-Cell-Produced WNV Antigens

Cell Culture Scale-up and Fermentation. Transformants from the pDAB2475 and pDAB2481 constructs, expressing full-length E protein were identified for scale-up. *Nicotiana tobacum* NT1 suspension cultures of individual events were scaled up from 20 ml working volume in a 125 ml Erlenmeyer flask to 70 ml and then 140 ml total volume in a 250 ml flask based on "flask packed cell volume". Flask packed cell volume was determined after a 7 day incubation period by aspirating a 10 ml sample under aseptic conditions from a well mixed flask into a serological pipette to a final volume of 10 ml. After 30 seconds of static settling, the volume of the cells in the pipette was multiplied by 10 and recorded as the "flask packed cell volume" to differentiate the measurement from a centrifugal packed cell volume (PCV) measurement. The normal range for flask packed cell volume was variable (15-60%) for individual events, but if a packed cell volume of ≧15% was not achieved within 14 days, the event was discontinued.

Culture maintenance and scale-up was performed by transferring cells from a 7 day flask to a final flask packed cell volume of 5%. For cultures with a 50% packed cell volume, the inoculum transfer volume was 10% v:v. All Erlenmeyer flask cultures were incubated at 26° C. on an orbital shaker with a 2" stroke length at 120 rpm for 7 days. Fermentations utilizing the 2,800 ml Fernbach flask (working volume 1,000 ml) were conducted on an orbital incubator/shaker with a 2" stroke length at 110 rpm for 7 days at 26° C. Fermentations conducted in 101 Braun Biostat C 10 liter fermentors were initiated at an agitation speed of 200 rpm, an air flow of 4 liters per minute, and a vessel temperature of 26° C. Dissolved oxygen was maintained above 30% by a PID control loop that automatically increased the agitation rate between 200 and 450 rpm.

To assess and characterize the fermentor-grown cultures, in-process 10 ml samples were collected in 15 ml graduated centrifuge tubes under aseptic conditions at 24 hour intervals. Of each sample, 10 μl was struck for isolation on tryptic soy agar for assessment of foreign growth. Petri plates were incubated at 30° C. for two days, and then scored for the presence of bacterial or fungal growth. Samples containing foreign growth were verified by light microscopy at 1,000× magnification in subsequent sample collections. Fermentors that were verified to contain foreign growth were autoclaved and the cultures appropriately discarded.

The remainder of each fermentation sample was centrifuged at 2,500×g for 10 minutes to separate the plant cells from the cell culture liquid. The PCV was determined by direct observation of the volume (ml) of packed cells in the tube following centrifugation. The final volume measurement was multiplied by 10 and recorded as the PCV at the time point of collection. Approximately 3-4 ml of the clear supernatant phase from the tube was transferred into a 3 ml syringe and filtered (Corning PTFE #431231) into a clean 1.5 ml microcentrifuge tube. The contents of the tube were analyzed for glucose, pH, acetate, ortho-phosphate, ammonia, sodium, potassium, and lactate using the Bioprofile 300A Biochemistry Analyzer (Nova Biomedical, Boston, Mass.).

For total soluble protein and recombinant protein concentration, the remaining sample of supernatant and packed cells was treated by adding 2-3 mm stainless steel shot, and then placing the 15 ml sample tube in a Geno Grinder for 2 minutes at maximum agitation rate. The cell free fraction was collected after centrifugation at 10,000 rpm for 5 minutes, and the pellet fraction was resuspended in a buffer consisting of PBS, pH 6.8, with 0.1% β-D-dodecyl maltoside. The resuspended pellet was placed back into the Geno Grinder and agitated for 2 minutes. Following centrifugation at 10,000 rpm for 5 minutes, the supernatant fractions were pooled and assayed for total soluble protein using the Bradford method. Extracts were also analyzed for WNV E protein by ELISA and Western blot (see Example 5).

Events from two constructs, pDAB2475 and pDAB2481, were scaled to 10 L stirred tank reactors. A summary of the fermentation batches is presented in Table 4.

Figure 31:
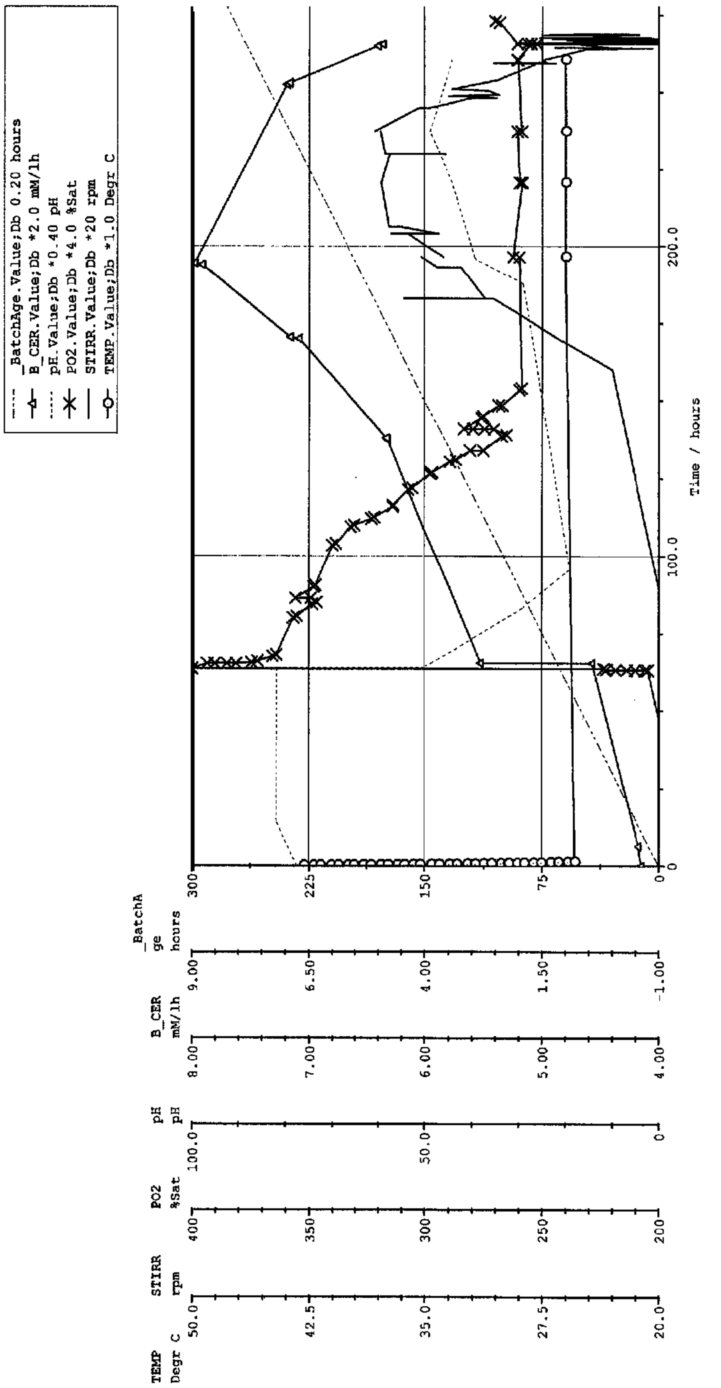
FIG. 31 illustrates on-line fermentation profiles for WNV event 1622-207 during a 10 liter STR fermentation run (Batch ID WNV SRD05006). The reduction in agitator speed rate resulted in the decrease in oxygen uptake rate near the termination of the fermentation.
Figure 32:
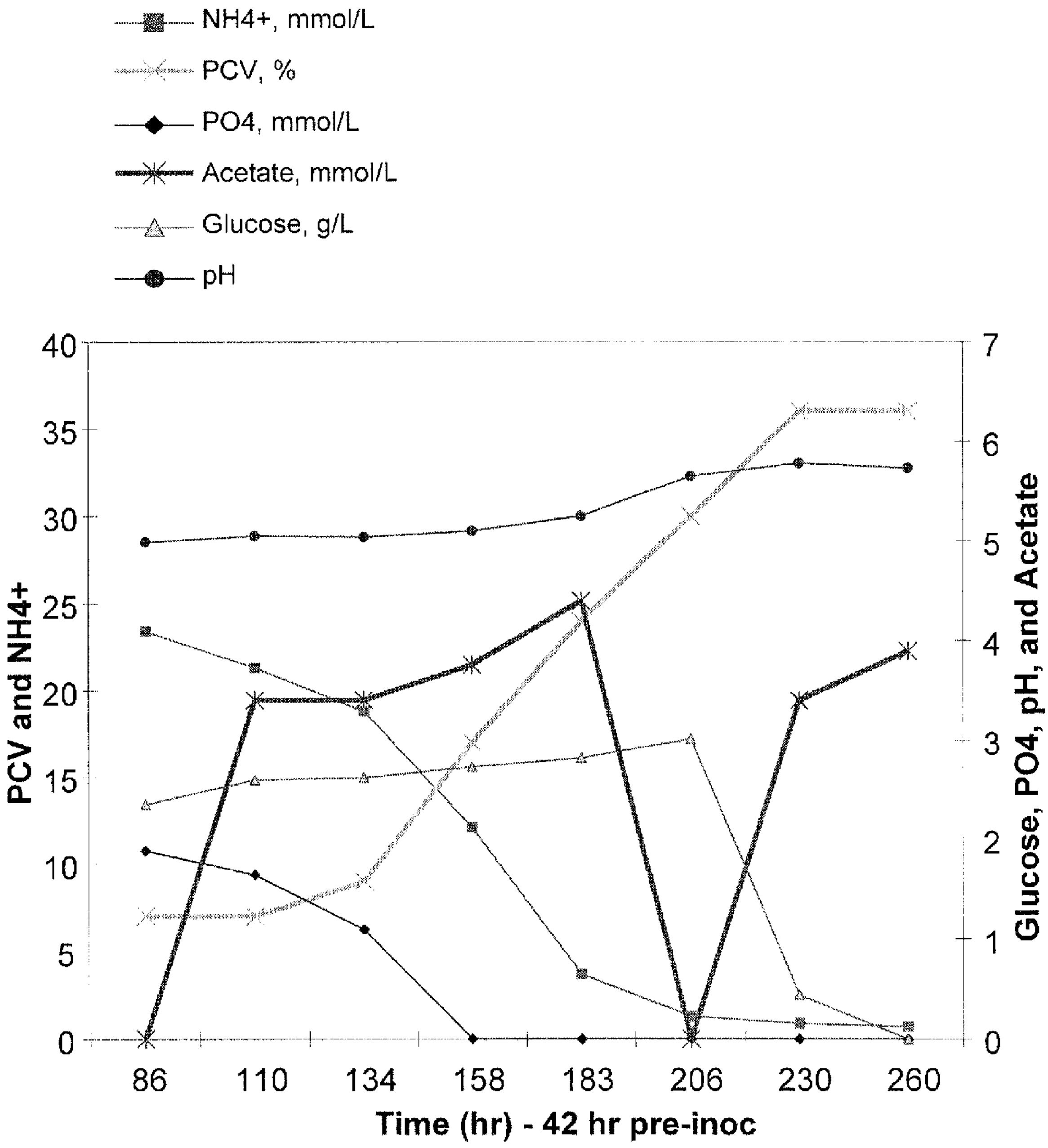
FIG. 32 provides a fermentation residuals analysis for batch ID WNV SRD05006.
Figure 33:
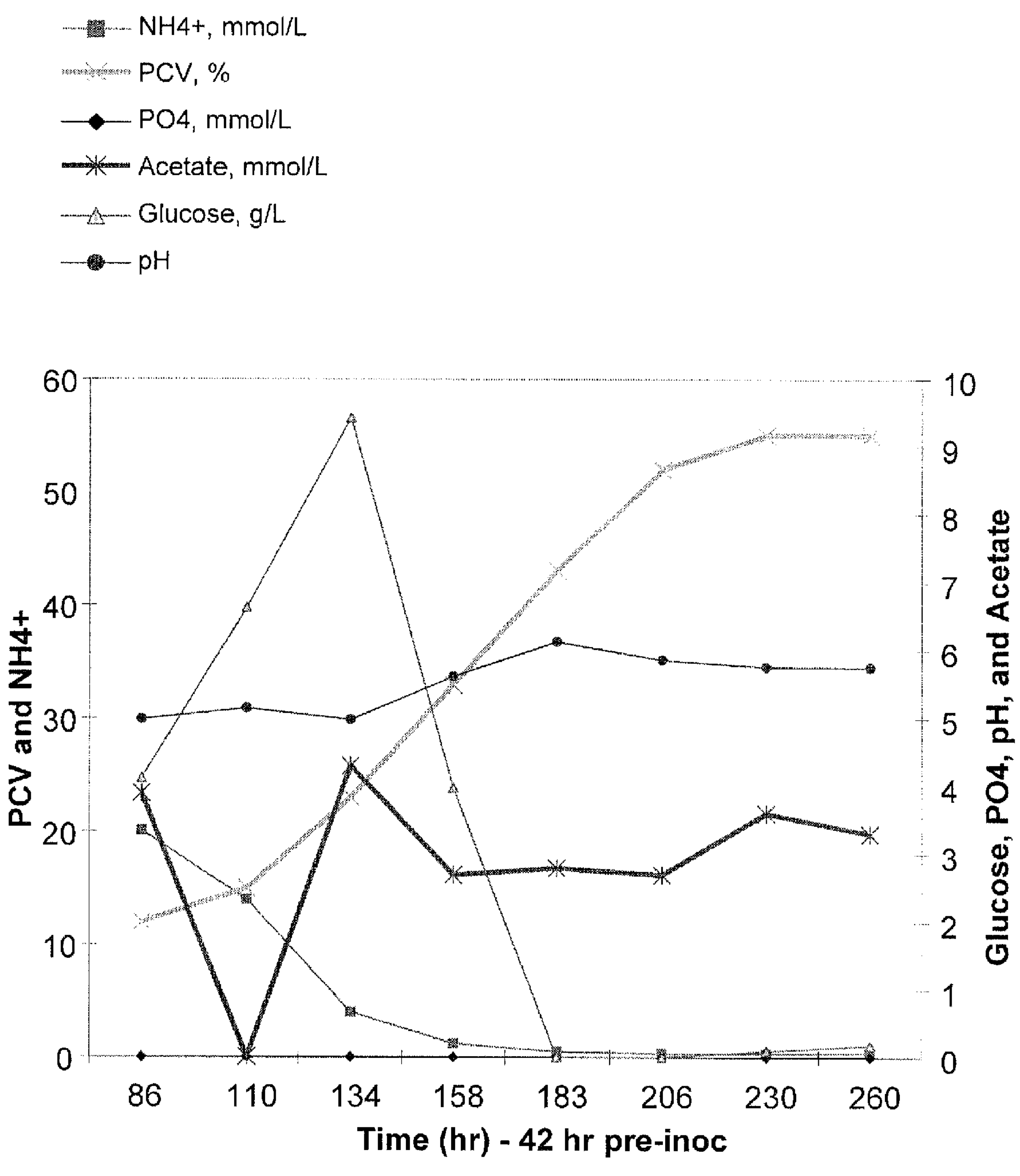
FIG. 33 provides a fermentation residuals analysis for batch ID WNV SRD05007.

Time-based measurements of recombinant protein production in fermentors indicated that the highest volumetric titer was produced at 188 hours for event 1622-207 and 172 hours for event 1702-525. Harvest criteria based on optimum volumetric productivity were developed based on changes in: (1) residual glucose in the fermentor, (2) packed cell volume, (3) respiratory gas analysis, (4) dissolved oxygen, and (5) pH (FIGS. 31-33). The optimum harvest time based on volumetric productivity was similar for all events, and occurred 46 hours after the depletion of glucose. The depletion of carbon source(s) corresponded to an increase in pH from 5.90±0.12−log $H^+$ to 6.5±0.24−log $H^+$, a visible darkening of the fermentation broth, and a >85% reduction in respiratory activity as evidenced by oxygen uptake, carbon dioxide evolution, and dissolved oxygen. Event 1622-207 showed a volumetric titer of 1.570±0.077 (mean±std. dev.) mg 'E' protein/l fermentor working volume and a productivity of 0.200±0.010 (mean±std. dev.) mg 'E' protein/1 fermentor working volume/day (refer to Table 4, Batch WNV-SRD05006).

Figure 34:
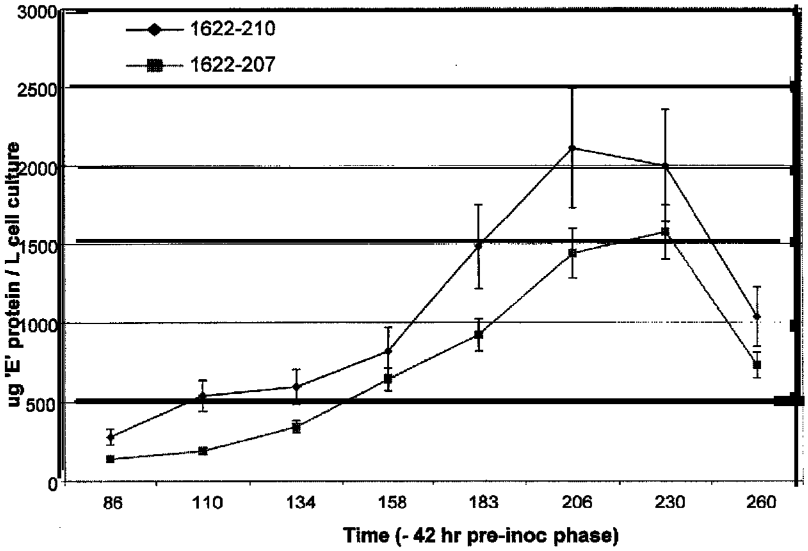
FIG. 34 illustrates the kinetics of ME production in *N. tobacum* NT-1 suspension cells as determined over a period of 9 days for recombinant West Nile Virus events 1622-207 and 1622-210. Production of WNV envelope protein during a 218 hour (9.08 day; subtract the 42 hour pre-inoculation phase from the x-axis time) 10 liter stirred-tank reactor fermentation is depicted. The maximum volumetric productivity of ME events 1622-210 and 1622-207 occurred at 164 hr (206-42 hr), and 188 hr (230-42 hr) post-inoculation respectively.

The kinetics of ME and prME(−) production in *N. tobacum* NT-1 suspension cells were determined over a period of 9 days for recombinant West Nile Virus events 1622-207 and 1622-210 (FIG. 34). Significant losses (up to 50%) in recombinant protein were observed for fermentations that exceeded an 8 day time period (>70 hours beyond the depletion of glucose). Western blots for aged fermentation samples showed significant truncation of the 'E' protein, and a higher percentage of truncated and full length 'E' protein in the 8,000×g supernatant following cell disruption (data not shown). The downward trend in volumetric productivity that is shown in FIG. 34 may be the result of differences in the reactivity of the primary ELISA antibody with truncated 'E' protein, and/or an increased loss of 'E' protein due to changes in the protein's partitioning properties. Additional studies should be performed to investigate this phenomenon.

Example 7

Processing of Plant-Cell-Produced WNV Antigens

Downstream processing of cell cultures grown in 10 liter bioreactors consisted of six procedures that were conducted in parallel. All procedures were completed at 0-4° C. under aseptic conditions. Due to reported pH-induced changes to the quaternary structure of E protein resulting in the formation of an inactive trimer (Modis et al., 2004), the pH of all cell culture and process samples was maintained at 7.0±0.2 by using 50 mM (pH 7.5) 3-(N-Morpholino)propanesulfonic acid (MOPS; pKa=7.2) as a standard buffer for all conditions, unless otherwise stated.

Process method 1 (PM1): The plant suspension cells were harvested from the spent medium using a layer of 30 μm Spectramesh and a 25 cm diameter Buchner funnel. The wet cake was washed with an equal volume of lysis buffer (50 mM MOPS, pH 7.5+1 mM EDTA), filter dried (70 sec. at a vacuum pressure of 25 in. water column), and then resuspended in lysis buffer (50 mM MOPS, pH 7.5+1 mM EDTA) to a final concentration of 33% (w:v). The cell suspension was briefly (3 minutes) homogenized using a Silverson L4R laboratory homogenizer, fitted with a 3 cm rotor-stator head, and operated at 1,500 rpm. The pre-homogenized cells were disrupted by two passes through a Microfludics 110-L cell disrupter, which was operated at 16,000 psi (measured flow path pressure). Following centrifugal clarification of the lysate at 8,000×G for 15 min., the supernatant was decanted from the pellet (discard pellet), and stored at −20° C. until assays were performed.

Process method 2 (PM2): harvested cells were centrifuged at 8,000×G for 15 min., and the spent medium was decanted from the cell paste. The cell pellet was resuspended with 150 mL of lysis buffer, frozen at −20° C. for a minimum of 16 hours, and then thawed in a 25° C. water bath. The thawed cells were resuspended to a final concentration of 33% (w:v) in lysis buffer, and briefly (3 minutes) homogenized using a Silverson L4R laboratory homogenizer, fitted with a 3 cm rotor-stator head, and operated at 1,500 rpm. The homogenized cell slurry was disrupted at 16,000 psi by two passes through a Microfludics 110-L cell disrupter, and the lysate was clarified as described in PM1.

Process method 3 (PM3): Agrimul NRE-1406 (464 g/mol; Cognis Corp., Cincinnati, Ohio) and MOPS, pH 7.5 (final conc. 50 mM) was added directly to the harvested cell culture in a 500 mL Erlenmyer flask to a final concentration of 0.3% (w:v). The flask was stirred on a magnetic stirring plate at 100 rpm using a 5.08 cm stirring bar for 30 minutes. The cell suspension was briefly (3 minutes) homogenized using a Silverson L4R laboratory homogenizer, fitted with a 3 cm rotor-stator head, and operated at 1,500 rpm. The pre-homogenized suspension was disrupted by two passes through a Microfludics 110-L cell disrupter, which was operated at 16,000 psi. Following centrifugal clarification of the lysate at 8,000×g for 15 min., the supernatant was decanted from the pellet (discard pellet), and stored at −20° C. until assays were performed.

Process method 4 (PM4): Process method 4 followed the process described in process method 2, except that 0.3% (w:v) Deriphat 160 (Cognis Corp., Cincinnati, Ohio) was added to thawed cell paste prior to homogenization with the laboratory homogenizer. All other procedures were identical to PM2.

Process method 5 (PM5): Ammonium sulfate precipitation was conducted on the PM2 clarified fraction using three separate fractionation steps: Step 1: A 20% saturated solution (based on a temperature of 25° C.) of ammonium sulfate ($(NH_4)_2SO_4$) was prepared by adding 114 g/l of $(NH_4)_2SO_4$ directly to the PM2 clarified fraction. The solution (measured temp=15° C.) was stirred at 100 rpm for 10 minutes and then centrifuged at 10,000×g for 25 minutes to remove precipitated proteins. The supernatant, which contained West Nile virus E protein and was referred to as the s0-20% fraction, was collected and transferred to step 2. Step 2: A 30% saturated solution of $(NH_4)_2SO_4$ was prepared by adding 59 g/l of $(NH_4)_2SO_4$ directly to the s0-20% fraction. The solution (measured temp=15° C.) was stirred at 100 rpm for 10 minutes and then centrifuged at 10,000×g for 25 minutes to remove precipitated proteins. The supernatant, which contained West Nile virus E protein and was referred to as the s20-30% fraction, was collected and transferred to step 3. Step 3: A 40% saturated solution of $(NH_4)_2SO_4$ was prepared by adding 62 g/l of $(NH_4)_2SO_4$ directly to the s20-30% fraction. The solution (measured temp=8° C.) was stirred at 100 rpm for 10 minutes and then centrifuged at 10,000×g for 25 minutes to remove precipitated proteins. The pellet acquired from the centrifugation step, which contained West Nile virus E protein and was referred to as the p30-40% precipitant, was decanted from the supernatant (discard supernatant), and stored at −20° C. until assays were performed.

Process method 7 (PM7): Process method 7 followed the process described in process method 1, except that the supernatant fraction following cell disruption and centrifugation was discarded and the particulate fraction was further processed to recover recombinant WNV proteins. The particulate fraction was diluted to a final concentration of 20% (w:v) in 50 mM MOPS, pH 7.5 and 1 mM EDTA. Deriphat 160 (an amphoteric surfactant of Monosodium N-Lauryl-beta-Iminodipropionic Acid [Cognis Corporation, Cincinnati, Ohio]) was added directly to the diluted suspension to achieve a detergent to total soluble protein ratio of 1.30±0.14 mg of Deriphat 160 per mg of total soluble protein. In order to expedite the primary processing steps, a correlation based on a linear equation was developed between total soluble protein in the cell free particulate fraction and the harvest packed cell volume for the fermentor. The required amount of Deriphat 160 detergent was rapidly calculated using the final centrifugal packed cell volume measurement based on Equation 1:

$$\text{Deriphat\_}(g)=\%\ \text{Final\_}PCV^{*}\text{Sample\_Vol}(L)^{*}0.0341 \qquad \text{Equation 1}$$

Where:

Deriphat_(g) is the amount of Deriphat 160 added to the resuspended particulate fraction.

% Final_PCV is the centrifugal PCV measurement from the cell culture as a percent.

Sample_Vol (L) is the total volume in liters of the cell culture at harvest.

0.0341=final protein concentration to harvest PCV slope conversion constant.

The suspension was homogenized using a Silverson L4R laboratory homogenizer, fitted with a 3 cm rotor-stator head, and operated at 1,500 rpm for 10 minutes, and then centrifuged at 8,000×g for 25 minutes. The supernatant was decanted from the pellet (discard pellet), and stored at −20° C. until assays were performed.

All preparative (>40 ml) samples were reduced in volume by lyophilization in 3 liter stainless steel trays. Samples were transferred to a stainless steel tray and frozen at −80° C. for 16 hours, then transferred to a model 422116 Genesis Vertis lyophilizer with a condenser temperature of −44° C. and an initial shelf temperature of −10° C. The drying program consisted of 7 timed steps at the following temperatures: −10° C. for 20 minutes, −5° C. for 200 minutes, 0° C. for 400 minutes, 5° C. for 200 minutes, 10° C. for 200 minutes, 15° C. for 200 minutes, and 25° C. for 4000 minutes. The product was considered dry if the final vacuum pressure (using a shelf temperature of 25° C.) could be maintained below 100 mTorr. Dried preparative fractions from the 3 L trays were resuspended in a minimal volume (<40 ml) of sterile distilled water and then transferred to a sterile 100 mL serum vial. The vials were transferred to a −80° C. freezer on an angled (25°) freeze rack for 16 hours. The vials were dried according to the preparative drying program.

Table 5 summarizes the different samples prepared for evaluation in a clinical trial (Study I). These samples represent two plant expression constructs, three events and five process methods, along with negative and positive controls.

Example 8

Formulation of Plant-Cell-Produced WNV Antigens, Study I

Two plant expression constructs, three events and five process methods were used to generate vaccines and negative control vaccines for clinical evaluation of plant-cell-produced WNV antigens in mice. All vaccines were combined with Freund's complete adjuvant for the first dose and Freund's incomplete adjuvant for the second. Inactivated WNV was formulated for use as a positive control.

Formulation of plant-cell-produced antigen. At the initiation of vaccine formulation, preparation of 100 or 50 μg doses was preferred. Therefore, lyophilized plant material was rehydrated in the minimum amount of distilled water required to pass through a syringe needle. With a maximum of 100 μl antigen volume per dose, dose was consequently determined by solubility of the plant material (Table 6). Lyophilized antigen for treatment group 3 was insoluble and removed from the study; lyophilized antigen for group 1 was not concentrated enough to achieve the 100 μg dose in the required 100 μl volume and was also dropped from the study. Negative control preparations were rehydrated with the minimum amount of water required then brought up to approximately 1 ml with additional water.

An aliquot of rehydrated antigen was emulsified with an equal volume of complete Freund's adjuvant (ICN 642851) using two 2 ml glass syringes and a 2⅞ inch 20 gauge microemulsification needle. Vaccines were kept on ice throughout, and rehydrated stock suspensions were frozen at −80° C. immediately after use. For a second use, the previously rehydrated plant material was thawed at room temperature and emulsified with an equal volume of incomplete Freund's adjuvant (ICN 642861) using the same syringes and needles as before. Emulsions were kept on ice and injected immediately following the preparation of all vaccines.

Formulation of reference antigen. From inactivated WNV reference standard (described in Example 5), Triton X-100 was removed with a Chemicon International "Detergent-OUT" spin column prior to formulation for use as a vaccine. Dose was based on WNV E protein concentration at 27.2 μg per mL (Table 6).

Example 9

Generation of WNV-Neutralizing Serum with Plant-Cell-Produced Antigens, Study I Vaccination of mice. Female, CD-1 outbred, SPF mice (Charles River) were acquired and acclimated to the study facilities prior to vaccination. Mice were housed, 5 per cage, and identified by group number with an ear punch. On day 0, at 50 days of age, all mice received a 200 μL dose of the various treatments as described in Table 6 (Example 8). Vaccinations were delivered from a 1 ml syringe with a 27 gauge needle in four sites of 50 μL each subcutaneously in the abdominal region. Due to a delay in the availability of reagents, Group 12 mice were vaccinated one month later than the others and therefore vaccinated at 80 days of age. On day 17, mice received a second 200 μL dose of the various treatments as described in Table 6 (Example 8). Vaccinations were delivered in four sites of 50 μL each subcutaneously in the region of the abdomen. Group 12 was revaccinatedu at 14 days rather than 18. Two mice of group 4 became ill after the second vaccination and one died 30 hours later.

Serum collection. On Day 31, mice were anesthetized by brief exposure to $CO_2$ and exsanguinated by cardiac puncture. Blood was collected into labeled Eppendorf tubes, allowed to clot, and centrifuged to sediment remaining cells. Serum was maintained at −80° C. until the time of assaying. Group 12 mice were exsanguinated on day 28 rather than 32.

WNV Serum Neutralization Assay. All serum neutralization assays were performed in a BL-3 laboratory. Neutralization titers were measured in a constant virus, varying serum assay on VERO cells. Heat-inactivated serum (30 minutes at 56° C.) was diluted from 1:10 in 2-fold steps to 1:1280 in a microtiter plate, two wells per dilution, in Medium 199 with 5% fetal bovine serum (FBS). Stock WNV virus, a Wyoming sage grouse isolate, was diluted to 1:10 in the same medium and an equal volume was added to the serum in each well, giving final serum dilutions of 1:20 to 1:2560. The plates were incubated for 30 minutes to allow the serum to neutralize the virus, and then 12,000 VERO cells in an equal volume of the same medium were added to every well to detect non-neutralized virus. Controls (known positive sera, uninfected wells, and virus titration) were included on a separate plate. The plates were incubated at 37° C. in 5% $CO_2$ for 13 days and observed microscopically at intervals for the presence of cytopathic effect (CPE).

Figure 35:
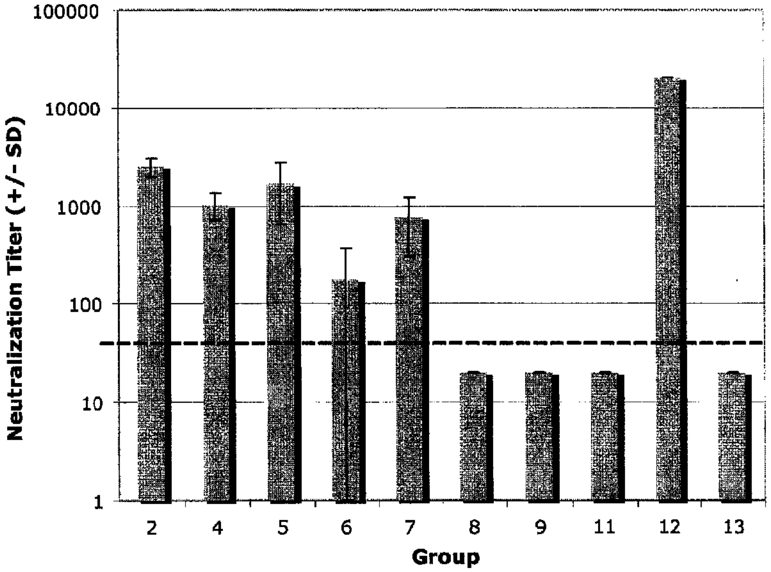
FIG. 35 provides a graphical presentation of WNV serum neutralizing titers from a mouse clinical model study (Study I). The figure was generated by changing neutralization titers of >2560 to 2560 and titers of <20 to 20 and calculating serum neutralization geometric mean titer (GMT) for each treatment group.

The final assay read was at 13 days. The uninfected cell control had no CPE. Neutralization titers of the test samples were expressed as the reciprocal of the final dilution of serum present in the serum-virus mixtures a the 50% endpoint. The WNV back titration was >128 $TCID_{50}$ per well. Rabbit anti-WNV positive control serum had a titer of >2560. Sera from vaccinated mice had neutralization titers as shown in Table 7. By changing neutralization titers of >2560 to 2560 (the maximum titer the assay could measure) and titers of <20 to 20 (the minimum titer the assay could measure) and calculating a geometric mean titer per group, FIG. 35 was generated. FIG. 35 provides a graphical presentation of WNV serum neutralizing titers.

Student's t-test showed that Group 2 titers were statistically higher than all other groups except group 5 and that Groups 4 and 5 were not statistically different. The inactivated WNV positive control (Group 12) was measured in a separate assay with a higher endpoint dilution and therefore was not strictly comparable to the other results.

In conclusion, all preparations of plant-cell-produced WNV E protein used for vaccination, regardless of the amount of E protein present or the process method, engendered neutralizing antibodies. Negative control preparations did not engender neutralizing antibodies (Groups 8, 9, 11, and 13).

In general, the injections were well tolerated by the animals. It is not clear whether the illness and single death following the second injection of Group 4 was due to physical trauma or an adverse reaction to the antigen, the adjuvant, or other components of the vaccine.

Example 10

Generation of WNV-Neutralizing Serum with Plant-Cell-Produced Antigens, Study II To confirm and further understand the efficacy of the plant-cell-produced WNV antigens in the mouse model, an additional group of mice were acquired and immunized with high, medium, and low doses of antigen formulated with five different adjuvants, as listed in Table 8. The transformation event and process method for antigen recovery were not varied. Event (pDAB 2475)1622-207 harvested by PM7 was exclusively used in this study.

Formulation of vaccines. Vaccine formulation was initiated by rehydrating lyophilized WNV plant extract. Sufficient water was added to each of five vials to produce a 125 μg/ml antigen solution. Rehydration was done using sterile water and using sterile needles and syringes for the water addition. The rehydrated solutions were pooled into a new sterile bottle. The solution was then homogenized by 50 passages through a sterile three-way stopcock using two sterile syringes. The homogenized solution was pooled into a new sterile bottle.

Six milliliter batches of each 25 μg/dose vaccine were prepared by first drawing 3.0 ml of antigen solution into a new sterile 10 ml disposable syringe. Next, 3.0 ml of sterilized adjuvant was drawn into a second new sterile disposable syringe. Both syringes were fitted to a new sterile three-way stopcock. The plant extract was then moved into the adjuvant syringe through the stopcock. The vaccine was emulsified by passing the vaccine between the two syringes through 50 cycles. Upon completion of the last cycle the syringe containing the vaccine was removed from the stopcock. The vaccine was transferred into sterile serum vials, sealed and labeled. Packaged vaccines were stored at 4° C. Vaccines were kept at 4° C. until used.

To formulate the 5 μg/dose vaccines, a portion of the original 125 μg/ml plant extract solution was diluted with water to produce a 25 μg/ml solution. This diluted antigen solution was used to formulate these vaccines. The procedure outlined above was repeated for each of the five test vaccines using new sterile syringes and three-way stopcocks for each vaccine.

The 0.5 μg dose vaccines were formulated using a portion of the 25 μg/ml antigen solution diluted to 5 μg/ml. This diluted antigen solution was used to formulate these vaccines. The same procedures previously outlined were used to produce the five trial vaccines at this dose level.

Titer-Max adjuvant is incompatible with neoprene rubber. Vaccines containing Titer-Max adjuvant must not be allowed to come in contact with neoprene rubber. Therefore, all plastic syringes were used during formulation and Teflon faced septa were used to seal the serum vials for the packaged vaccines.

Formulation of Plant Cell Control. Two vials of lyophilized non-transgenic NT-1 Tobacco Cell extract were rehydrated with sterile water to produce a solution similar to the 125 μg/ml antigen solution. This blank control solution was homogenized in the same manner as the antigen solution. The control vaccine was formulated using the same procedures as the 25 μg/dose vaccines. As stated earlier all plastic syringes and a Teflon faced septum were used with this vaccine.

Vaccination of mice. Female, CD-1 outbred, SPF mice (Charles River) were received from a single colony in shipping containers of 40 mice each. Mice were housed 5 per cage, acclimated to the study facilities, and their group number was identified with an ear-punch. At 10-11 weeks of age, all mice received a 200 μL dose of the various treatments as described in Table 8. Vaccinations were delivered from a 1 ml syringe with a 27 gauge needle in four sites of 50 μL each, subcutaneously in the abdominal region.

Within 48 hours after the first vaccination, it was evident that mice in groups 6-8 were reacting locally and systemically to the injection. Mice given carbopol-formulated vaccines stopped eating and drinking, huddled together, and had raised fur. These mice were not given any further vaccinations.

On day 15, mice in groups 1-5 and 9-17 received a second 200 μL dose of the various treatments as described in Table 8. Vaccinations were delivered in four sites of 50 μL each subcutaneously in the region of the abdomen. No adverse reactions were observed in these groups.

Serum collection. On day 22, mice in groups 6-8 were anesthetized by brief exposure to $CO_2$ and exsanguinated by cardiac puncture. On Day 28, mice in all other groups were similarly anesthetized and exsanguinated. Blood was collected into labeled Eppendorf tubes, allowed to clot and centrifuged to sediment remaining cells. Serum was maintained at ≦−80° C.

WNV Serum Neutralization Assay. All serum neutralization assays were performed in a BSL-3 laboratory. Neutralization titers were measured in a constant virus, varying serum assay on VERO cells. Heat-inactivated serum (30 minutes at 56° C.) was appropriately diluted in a microtiter plate, five wells per dilution, in DMEM with 2% fetal bovine serum (FBS). Stock WNV virus, a Wyoming sage grouse isolate, was diluted to obtain a range of 100-300 $TCID_{50}$/25 μl in the same dilution medium and an equal volume was added to the serum in each well. The plates were incubated for 60 minutes to allow the serum to neutralize the virus, and then 20,000-30,000 VERO cells in 150 μl of medium were added to every well to detect non-neutralized virus. Controls (known positive sera, uninfected wells, and virus titration) were included on a separate plate. The plates were incubated at 37° C. in 5% $CO_2$ for 4-7 days and observed microscopically at intervals for the presence of cytopathic effect (CPE). The uninfected cell control had no CPE. The WNV back titration was 194 $TCID_{50}$ per well. Neutralization titers of unknowns were expressed as the reciprocal of the final dilution of serum present in the serum-virus mixtures at the dilution where cells were not infected.

Figure 36:
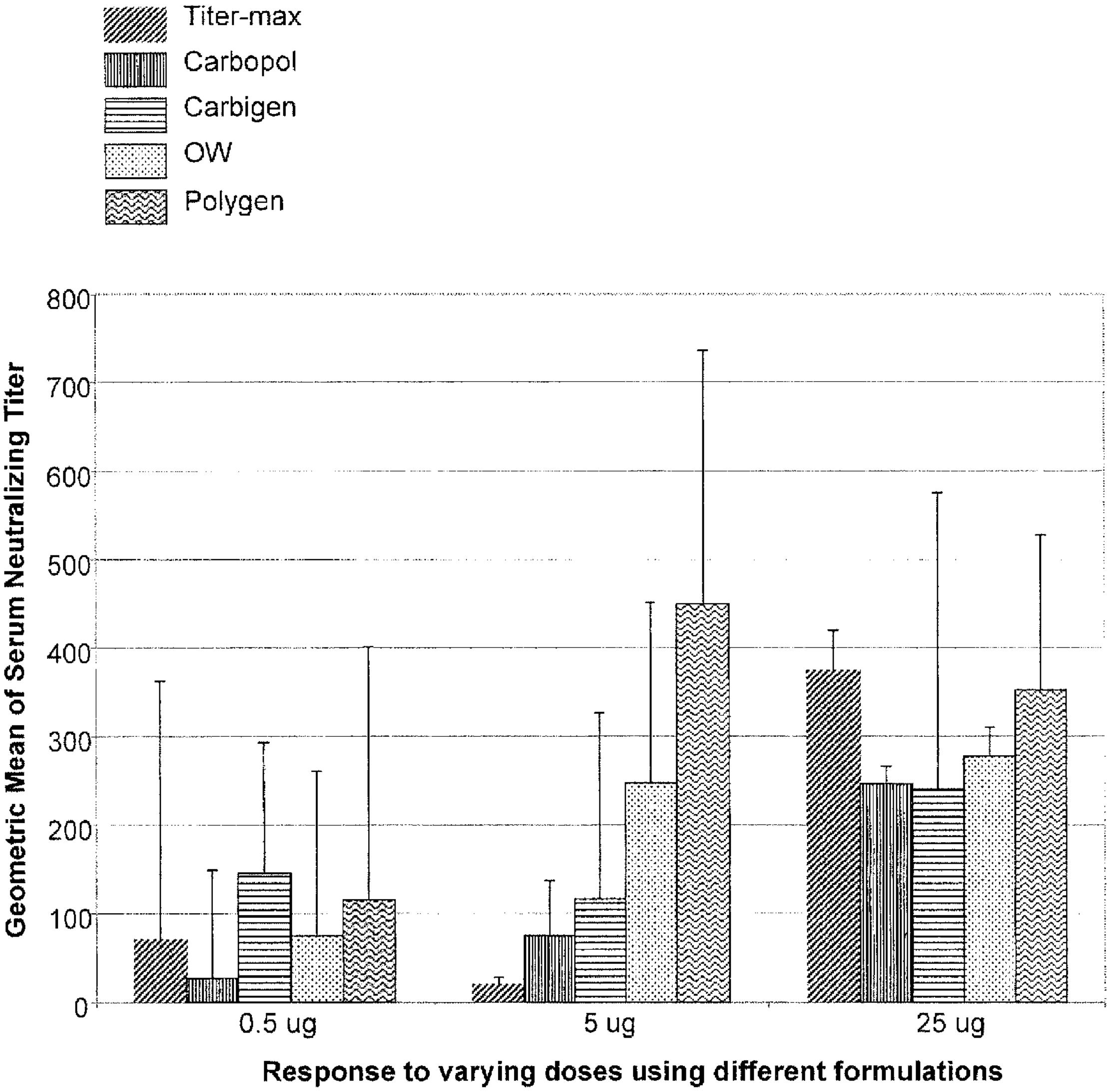
FIG. 36 shows the variable response demonstrated by different doses of antigen and formulation with different adjuvants (Study II).

Many vaccinated mice developed high levels of neutralizing antibodies and response varied with antigen dose and adjuvant (FIG. 36). Antibodies were not engendered in mice given adjuvant and NT-1 cells alone (Group 1, data not shown). It is clear that plant cell-produced WNV E protein was highly immunogenic and possesses at least one epitope required to engender neutralizing antibodies. The fact that a single injection engendered neutralizing antibodies in the mice injected with carbopol formulation (Groups 6-8) suggests that the antigen induced a protective level of IgM. Although the differences between some groups were statistically significant at $p<0.05$, obvious patterns were not clear due to variability inherent within the assay.

Example 11

Demonstration of Protective Efficacy of Plant-Cell-Produced Antigen in Horses To confirm and further understand the efficacy of the plant-cell-produced WNV antigens in the equine species, horses were acquired and vaccinated with high and low doses of antigen formulated with 2 different adjuvants, as listed in Table 17. The transformation event and process method for antigen recovery were not varied. Event (pDAB 2475)1622-207 harvested by PM7 was exclusively used in this study.

Formulation of vaccines. Vaccine formulation was initiated by rehydrating lyophilized WNV plant extract, using the same lot of antigen as in Study II (Example 10). The target concentrations of the vaccines were 10 and 1 μg/ml. The lyophilized antigen was rehydrated with sterile water to 70 ml volume and 20 μg/ml concentration, based on concentration of E protein determined by ELISA prior to extract lyophilization. Following rehydration, the antigen stock solution was homogenized to provide a uniform solution. Homogenization was performed using two 20 ml syringes connected to a three way stopcock. The solution was passed back and forth between the syringes for 50 cycles then placed in a new sterile 100 ml bottle. Once homogenized, the stock was sterile filtered into a new sterile plastic bottle. Sterile filtration was performed using Millipore Sterivex—GV, 0.22 μm filter units (Lot Number H4NN92488). At this point the material was sampled using sterile techniques for both ELISA and Sterility testing. Sterility testing required two weeks to complete and confirmed the solution to be sterile within the limits of the test described below. ELISA assay confirmed the stock solution contained approximately 20 μg/ml. This concentration value was consistent with the previous values for this material.

Carbopol 974 P NF Stock solution. 1×PBS sterile buffer was prepared by first diluting 100 ml Fisher Scientific Brand PBS: Phosphate Buffered Saline 10× solution (Lot No. 044924-36) to 1 liter in DI water. 500 ml of the 1×PBS was transferred into a clean 600 ml beaker fitted with a magnetic stir bar. 5.0 grams of Carbopol 974P NF (Noveon, Lot No. CC52NAB635) was dispersed into the PBS buffer using the magnetic stirrer. The mixture was agitated for 30 minutes to ensure dispersion of the powder. The agitated beaker was fitted with a pH probe, and the pH of the solution was adjusted to be within a pH range of 6.8 to 7.6 using Sodium Hydroxide Solution, 50% w/w (Fisher Brand, Lot No. 0430451-24). Once the pH was adjusted, the solution was allowed to stir for an additional 30 minutes to ensure the pH was stable. This procedure resulted in a 10 mg/ml (10,000 μg/ml) stock solution of neutralized Carbopol 974P NF. The final solution was transferred into various sizes of clean Pyrex Media Bottles and labeled. The bottles were then autoclaved for 45 minutes, 121° C., and 18 psi to ensure sterility. Upon removal from the autoclave, the bottles were sealed and allowed to cool in a hood. Prior to vaccine assembly, one bottle of Carbopol 974P NF stock solution was selected and subjected to sterility testing as described below.

Polygen 30% Stock solution. Polygen is a commercially available adjuvant. The manufacturer of Polygen recommends the product be diluted to a 30% solution prior to formulation. It is also recommended that vaccines be formulated to contain 15% v/v Polygen as the adjuvant package. Polygen 30% Stock Solution was prepared in a BL2 Biosafety cabinet, by transferring 140 ml of sterile water to a sterile 250 ml polycarbonate bottle. 60 ml of Polygen (MVP Laboratories, Inc. Ralston, Nebr., Lot 10011) was added to the sterile water and mixed, resulting in a 30% Polygen solution. This solution was then transferred to a 250 ml Pyrex Media Bottle and autoclaved. Upon removal from the autoclave, the bottle was sealed and transferred to the BL2 hood and allowed to cool to room temperature. This container was tested for sterility prior to vaccine assembly.

Sterile Water Sterile water was prepared by partially filling clean Pyrex Media Bottles with DI water. The bottles were then autoclaved for 45 minutes, 121° C., and 18 psi. Upon removal from the autoclave, the bottles were sealed while still warm and allowed to cool in a hood. Prior to vaccine assembly a bottle of sterile water was selected and subjected to sterility testing as described below.

Sterility Testing. To ensure the axenicity of the formulated vaccines, all sterile raw materials used in the formulation, and the formulated vaccines themselves, were tested for sterility.

Preparation of Agar and Petri Plates Bennett's agar was used for the sterility plating. Bennett's agar was prepared in the following manner:

| Bennett's Agar | Amount |
|---|---|
| Yeast Extract | 1.0 g/L |
| Beef Extract | 1.0 g/L |
| NZ Amine A | 2.0 g/L |
| Glucose | 10.0 g/L |
| Agar | 15.0 g/L |
| DI Water | 1.0 L |

Heat on a stir plate until agar is dissolved. (Lightly covering with foil will facilitate the heating.)

Fill vessels about half full, loosely cap and autoclave on liquid cycle for 20 minutes, 121° C. and 18 psi.

100×15 mm Petri dishes were filled approximately ¾ full with Bennett's agar and allowed to solidify. The plates were prepared at least four days prior to the testing to ensure that they were sterile before using in the testing.

Plating of Raw Materials and Formulated Vaccines A sterile 10 μl inoculating loop was used to obtain a sample of the raw ingredient or formulated vaccine being tested. The quadrant streak method, a common microbiology technique used to obtain single-colony isolates, was used for plating the sample. In an effort to increase the sensitivity of the test, a second plate was established with a 200 μl sample. The sample was uniformly spread across the plate with a sterile cell spreader. The plates were incubated upside down in a 30° C. incubator. They were checked daily (except weekends) for any signs of contaminant growth. Once the plates had remained clean for two weeks, the plated raw material was considered sterile and ready for use.

Two to three weeks prior to the start date of the study the vaccines were assembled. Table 18 shows the calculations for this batch of vaccine and the volumes of each component used. The vaccine was assembled by first pipetting the water and the required adjuvant solution into a sterile 250 ml sterile plastic bottle. The bottle was closed and shaken to mix the two components. The bottle was then opened and the antigen added by pipette. The bottle was again closed and shaken to thoroughly mix the components. The final vaccine was transferred into sterile vials containing either 10 or 25 ml of vaccine. The septum stoppers were placed into the vials using an autoclaved pair of forceps to handle the stopper. Once the stopper was seated onto the vials, they were sealed with an aluminum crimp seal. The vials were labeled with the previously approved label and stored in the refrigerator and maintained at 2-7° C. prior to shipment. One vial of each vaccine was tested for sterility as described in the Sterility Testing section. After sterility testing was completed, the vaccine sample was evaluated for pH, density, and Osmolality. The results of the physical property testing are shown in Table 19.

Vaccination of horses. Forty-six WNV serum neutralizing antibody negative horses (males and females; 6-12 months of age; WNV SN titers≦1:20) were purchased from an outside supplier. The horses were commingled in a mosquito-proof facility and were individually identified by implanted microchips. On Study Day 0, a blood sample was taken from all horses and then all horses received 1 mL of the prescribed treatment as described in Table 17. Vaccinations were administered intramuscularly on the left side of the neck. The blood was processed into serum and stored at −20° F. for further analysis. The horses were monitored daily for any signs of adverse reactivity to the vaccination. No reactions were noted.

On Study Day 14, a blood sample was taken from all horses and then all horses received 1 mL of the prescribed treatment as described in Table 17. Vaccinations were delivered intramuscularly on the right side of the neck. The blood was processed into serum and stored at −20° F. for further analysis. The horses were monitored daily for any signs of adverse reactivity to the vaccination. No reactions were noted.

In addition to the blood samples collected on Study Days 0 and 14, blood samples were also collected from all horses on Study Days 7, 21, 28, 35, 42 and 49. All blood samples were collected from the jugular vein and approximately 12 mL of blood was collected on each sample day. All blood was processed into serum and stored at −20° F. for further analysis.

WNV Serum Neutralization Assay. All serum neutralization assays were performed in a BSL-3 laboratory. Neutralization titers were measured in a constant virus, varying serum assay on VERO cells. Heat-inactivated serum (30 minutes at 56° C.) was appropriately diluted in a microtiter plate, five wells per dilution, in DMEM with 2% fetal bovine serum (FBS). Stock WNV virus, a Wyoming sage grouse isolate, was diluted to obtain a range of 100-300 $TCID_{50}$/25 μl in the same dilution medium and an equal volume was added to the serum in each well. The plates were incubated for 60 minutes to allow the serum to neutralize the virus, and then 20,000-30,000 VERO cells in 150 μl of medium were added to every well to detect non-neutralized virus. Controls (known positive sera, uninfected wells, and virus titration) were included on a separate plate. The plates were incubated at 37° C. in 5% $CO_2$ for 4-7 days and observed microscopically at intervals for the presence of cytopathic effect (CPE). The uninfected cell control had no CPE. Neutralization titers of the test samples were expressed as the reciprocal of the final dilution of serum present in the serum-virus mixtures at the dilution where 50% of the cells were not infected. The WNV back titration was within the range of 50-300. Equine anti-WNV positive control serum had a titer range of 150-450. To calculate the geometric mean titer (GMT), titers≦2 were assigned 2 and titers ≧356 were assigned 356. Sera from vaccinated horses had neutralization titers as shown in Table 20. No serum neutralizing titers were generated in horses receiving the adjuvanted NT-1 cell control vaccines (Groups 1 and 2). Horses receiving the adjuvanted WNV E protein (Groups 3, 4, 5 and 6) generated WNV neutralizing antibody (Table 20). It is clear that plant cell-produced WNV E protein was highly immunogenic and possesses at least one epitope required to engender neutralizing antibodies.

On Study Day 101, all of the horses from Groups 1 and 3 and 2 horses from Group 2 (15 horses total) were shipped to a BSL-3 facility for challenge. On Study Day 105 all horses were challenged by the intrathecal inoculation of 107,000 plaque forming units (pfu) WNV NY99 in 1 mL of PBS. The horses were monitored twice daily for 14 days and blood samples were taken twice daily on Day 1 through 6 and once daily on Day 0 (day of challenge), 7, 10 and 14 post challenge for processing into serum and assessment of viremia. Horses demonstrating severe neurologic symptoms during the 14 day post challenge observation period were humanely euthanized by an overdose of barbiturate. All remaining horses were euthanized at the end of the study (Day 14 through 17). Horses were considered to be infected with WNV and non-protected if they had 2 consecutive positive cultures from the blood samples taken on days 0-7, 10 and 14 post challenge. Additionally, protection from disease was assessed by twice daily clinical monitoring including temperature measurement. Histopathology was performed on sections of the brain from all horses.

Viremia data are presented in Table 21. All non vaccinated control horses (Group 1 and 2) were viremic for at least 2 consecutive days during the post challenge period. No viremia was detected in any of the vaccinated horses during the post challenge monitoring period.

Temperature data are presented in Table 22. Horses were considered to be febrile if 2 consecutive temperature measurements were greater than or equal to 102.5° F. Four of the five non vaccinated control horses (Group 1 and 2) were febrile during the post challenge period. One of the control horses was not considered to be febrile based on the criterion of 2 consecutive temperature measurements of ≧102.5° F.; however, this horse had several independent febrile events and was euthanized due to severe clinical signs prior to the end of the challenge observation period. Nine of the 10 vaccinated horses in Group 3 were afebrile during the post challenge period. One of the 10 vaccinated horses (Group 3) had 2 consecutive temperature measurements ≧102.5° F.

Clinical assessment data are presented in Table 23. Horses were monitored twice daily for clinical signs of disease including lethargy, depression, tremors, decreased appetite, hypersensitivity, reluctance to move, moribund. If no signs of clinical disease were noted and the horses were clinically normal they were assessed as being bright and responsive (BAR). Horses were considered to have clinical signs of WNV if there were 2 consecutive assessments where clinical signs of disease were noted. Three of the five non vaccinated control horses (Group 1 and 2) demonstrated clinical signs of disease. The severity of these clinical signs progressed significantly and these 3 horses were humanely euthanized during the post-challenge period. Two of the 5 control horses did not demonstrate clinical signs of disease. Nine of the 10 vaccinated horses in Group 3 were asymptomatic during the post challenge period. One of the 10 vaccinated horses (Group 3) had 2 consecutive assessments where mild clinical signs of disease were evident. These clinical signs did not progress and the horse returned to BAR.

Histologic examination of 2 sections of the brain (through the pons and through the mid-medulla) was performed on each horse. The results of these histologic examinations are presented in Table 24. The histology was considered to be abnormal if both sections showed signs of mild, moderate or severe changes. Five of the five non vaccinated control horses (Group 1 and 2) were histologically abnormal with both sections examined having moderate to severe histologic changes associated with encephalitis. Three of the 10 vaccinated horses in Group 3 had abnormal histology of the 2 brain sections examined. In 2 of these horses, these abnormal findings were mild in both sections examined. One of the horses had moderate encephalitis noted. No severe lesions were evident. Seven of the 10 vaccinated horses had normal histology or only mild histologic changes in only one of the sections examined. These mild unilateral changes were not considered to be consistent with WNV infection.

It should be understood that the examples and embodiments described herein are for illustrative purposes only and that various modifications or changes in light thereof will be suggested to persons skilled in the art and are to be included within the spirit and purview of this application. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

TABLE 1

Codon distribution in tobacco gene protein coding regions

| Amino Acid | Codon | Tobacco % Usage |
|---|---|---|
| ALA (A) | GCA | 31.0 |
| | GCC | 17.3 |
| | GCG | 8.1 |
| | GCT | 43.6 |
| ARG (R) | AGA | 31.7 |
| | AGG | 24.6 |
| | CGA | 11.9 |
| | CGC | 8.1 |
| | CGG | 7.7 |
| | CGT | 16.0 |
| ASN (N) | AAC | 39.4 |
| | AAT | 60.6 |
| ASP (D) | GAC | 31.1 |
| | GAT | 68.9 |
| CYS (C) | TGC | 42.6 |
| | TGT | 57.4 |
| END | TAA | 42.6 |
| | TAG | 19.6 |
| | TGA | 37.8 |
| GLN (Q) | CAA | 58.9 |
| | CAG | 41.1 |
| GLU (E) | GAA | 55.7 |
| | GAG | 44.3 |
| GLY (G) | GGA | 34.6 |
| | GGC | 16.2 |
| | GGG | 15.4 |
| | GGT | 33.7 |
| HIS (H) | CAC | 38.3 |
| | CAT | 61.7 |
| ILE (I) | ATA | 25.8 |
| | ATC | 24.6 |
| | ATT | 49.6 |
| LEU (L) | CTA | 10.5 |
| | CTC | 13.0 |
| | CTG | 11.2 |
| | CTT | 25.9 |
| | TTA | 15.3 |
| | TTG | 24.0 |
| LYS (K) | AAA | 50.0 |
| | AAG | 50.0 |
| MET (M) | ATG | 100.0 |
| PHE (F) | TTC | 41.9 |
| | TTT | 58.1 |
| PRO (P) | CCA | 38.9 |
| | CCC | 13.6 |
| | CCG | 10.0 |
| | CCT | 37.5 |
| SER (S) | AGC | 12.5 |
| | AGT | 17.3 |

TABLE 1-continued

Codon distribution in tobacco gene protein coding regions

| Amino Acid | Codon | Tobacco % Usage |
|---|---|---|
| | TCA | 22.6 |
| | TCC | 14.1 |
| | TCG | 7.2 |
| | TCT | 26.2 |
| THR (T) | ACA | 32.7 |
| | ACC | 19.1 |
| | ACG | 8.8 |
| | ACT | 39.4 |
| TRP (W) | TGG | 100.0 |
| TYR (Y) | TAC | 41.4 |
| 0 | TAT | 58.6 |
| VAL (V) | GTA | 18.3 |
| | GTC | 17.0 |
| | GTG | 24.3 |
| | GTT | 40.4 |

TABLE 2

Codon composition comparisons of M- & E-peptide coding regions of the native WNV sequence (bases 277-2004 of SEQ ID NO: 1) and two tobacco-optimized gene versions (SEQ ID NO: 6 & SEQ ID NO: 7).

| Amino Acid | Codon | SEQ ID NO: 1 | SEQ ID NO: 6 | SEQ ID NO: 7 |
|---|---|---|---|---|
| ALA (A) | GCA | 10 | 19 | 17 |
| | GCC | 15 | 10 | 10 |
| | GCG | 6 | 0 | 0 |
| | GCT | 21 | 23 | 25 |
| ARG (R) | AGA | 10 | 10 | 8 |
| | AGG | 5 | 7 | 6 |
| | CGA | 0 | 2 | 2 |
| | CGC | 2 | 0 | 0 |
| | CGG | 1 | 0 | 0 |
| | CGT | 3 | 2 | 5 |
| ASN (N) | AAC | 15 | 7 | 8 |
| | AAT | 6 | 14 | 13 |
| ASP (D) | GAC | 16 | 8 | 7 |
| | GAT | 5 | 13 | 14 |
| CYS (C) | TGC | 9 | 5 | 5 |
| | TGT | 3 | 7 | 7 |
| END | TAA | | | |
| | TAG | | | |
| | TGA | | | |
| GLN (Q) | CAA | 6 | 9 | 10 |
| | CAG | 9 | 6 | 5 |
| GLU (E) | GAA | 15 | 14 | 14 |
| | GAG | 10 | 11 | 11 |
| GLY (G) | GGA | 34 | 20 | 20 |
| | GGC | 14 | 11 | 10 |
| | GGG | 8 | 7 | 9 |
| | GGT | 3 | 21 | 20 |
| HIS (H) | CAC | 8 | 4 | 5 |
| 14 | CAT | 6 | 10 | 9 |
| ILE (I) | ATA | 5 | 5 | 6 |
| | ATC | 9 | 5 | 6 |
| | ATT | 7 | 11 | 9 |
| LEU (L) | CTA | 7 | 0 | 0 |
| | CTC | 10 | 8 | 8 |
| | CTG | 9 | 7 | 7 |
| | CTT | 5 | 15 | 16 |
| | TTA | 1 | 9 | 9 |
| | TTG | 22 | 15 | 14 |
| LYS (K) | AAA | 10 | 18 | 14 |
| | AAG | 20 | 12 | 16 |
| MET (M) | ATG | 15 | 15 | 15 |
| PHE (F) | TTC | 11 | 10 | 10 |
| | TTT | 13 | 14 | 14 |
| PRO (P) | CCA | 7 | 8 | 8 |
| | CCC | 2 | 3 | 3 |
| | CCG | 1 | 0 | 0 |

TABLE 2-continued

Codon composition comparisons of M- & E-peptide coding regions of the native WNV sequence (bases 277-2004 of SEQ ID NO: 1) and two tobacco-optimized gene versions (SEQ ID NO: 6 & SEQ ID NO: 7).

| Amino Acid | Codon | SEQ ID NO: 1 | SEQ ID NO: 6 | SEQ ID NO: 7 |
|---|---|---|---|---|
| | CCT | 9 | 8 | 8 |
| SER (S) | AGC | 13 | 6 | 6 |
| | AGT | 3 | 7 | 8 |
| | TCA | 14 | 10 | 10 |
| | TCC | 5 | 7 | 8 |
| | TCG | 3 | 0 | 0 |
| | TCT | 5 | 13 | 11 |
| THR (T) | ACA | 14 | 17 | 18 |
| | ACC | 13 | 11 | 10 |
| | ACG | 9 | 0 | 0 |
| | ACT | 13 | 21 | 21 |
| TRP (W) | TGG | 12 | 12 | 12 |
| TYR (Y) | TAC | 8 | 7 | 7 |
| | TAT | 6 | 7 | 7 |
| VAL (V) | GTA | 1 | 11 | 10 |
| | GTC | 12 | 6 | 9 |
| | GTG | 32 | 11 | 14 |
| | GTT | 10 | 27 | 22 |

TABLE 3

NT-1 B Medium

| Reagent | Per liter |
|---|---|
| MS salts (10X) | 100 ml |
| MES | 0.5 g |
| Thiamine-HCl (1 mg/ml) | 1 ml |
| Myo-inositol | 100 mg |
| $K_2HPO_4$ | 137.4 mg |
| 2,4-D (10 mg/ml) | 222 µl |
| Sucrose | 30 g |
| pH to 5.7 ± 0.03 | |

TABLE 4

Summary of stirred-tank reactor (STR) fermentation runs.

| Event | Batch ID | Fermentor vessel | Harvest PCV % | Harvest volume (L) | Volumetric recovery (mg antigen/L working volume) |
|---|---|---|---|---|---|
| 1622-210δ | WNV SRD05005 | Biostat C20 | 50 | 9.9 | 1.846 |

TABLE 4-continued

Summary of stirred-tank reactor (STR) fermentation runs.

| Event | Batch ID | Fermentor vessel | Harvest PCV % | Harvest volume (L) | Volumetric recovery (mg antigen/L working volume) |
|---|---|---|---|---|---|
| 1622-207δ | WNV SRD05006 | Biostat B10 | 38 | 9.3 | 1.574 |
| 1622-210 | WNV SRD05007 | Bioflo 3000 | 56 | 9.8 | 1.997 |
| 1622-207 | WNV SRD05008 | Biostat B10 | 36 | 9.3 | 1.645 |
| 1622-207 | WNV SRD05009 | Biostat B10 | 38 | 9.4 | 1.492 |
| 1702-525δ | WNV SRD05010 | Biostat KB10 | 41 | 9.5 | 0.966 |

δ = All 1622 events were transformed with pDAB2475, encoding the ME proteins, while all 1702 events were transformed with pDAB2481, encoding the prME proteins with E protein mutated glycosylation site (prME(—)).

TABLE 5

Samples of recombinant West Nile Virus antigen generated for Study I.

| Treatment group, n = 5 | Cell culture event | Process method | E protein Concentration (mg) | Lot ID#, vial label |
|---|---|---|---|---|
| 1 | 1622-207 | PM7 | 3.38 | SRD05005 |
| 2 | 1622-207 | PM7 | 3.38 | SRD05005 |
| 3 | 1622-207 | PM3 | 0.71 | SRD05006 |
| 4 | 1622-210 | PM4 | 0.48 | SRD05007 |
| 5 | 1622-210 | PM2 | 0.51 | SRD05008 |
| 6 | 1702-525 | PM2 & PM3, pooled | 0.93 | SRD05009 |
| 7 | 1602-207 | PM5 | 0.18 | SRD05010 |
| 8 | NT1 wild-type | PM2 | 0 | SRD05011 |
| 9 | NT1 wild-type | PM3 | 0 | SRD05012 |
| 10 | NT1 wild-type | PM4Ψ | 0 | SRD05013Ψ |
| 11 | NT1 wild-type | PM7 | 0 | SRD05014 |
| 12 | Inactivated WNV | Blitvich et al (3) | 2.72 µg/100 µl | SRD05015 |
| 13 | PBS | NA | 0 | SRD05016 |

Ψ = sample omitted due to insufficient sample mass available following lyophilization.

TABLE 6

Samples of recombinant West Nile Virus antigen formulated for Study I.

| Treatment group, n = 5 | Cell culture event | Process method | E protein Concentration (mg) | Lot ID#, vial label | Water added (ml) | Ability to Rehydrate | Approx Dose E protein per mouse (µg) |
|---|---|---|---|---|---|---|---|
| 1 | 1622-207 | PM7 | 3.38 | SRD05005 | — | Not at 100 µg dose desired | — |
| 2 | 1622-207 | PM7 | 3.38 | SRD05005 | 6.8 | Easily | 50 |
| 3 | 1622-207 | PM3 | 0.71 | SRD05006 | 14.2 | Insoluble | — |
| 4 | 1622-210 | PM4 | 0.48 | SRD05007 | 24 | Yes | 3 |
| 5 | 1622-210 | PM2 | 0.51 | SRD05008 | 10.2 | Yes | 5 |
| 6 | 1702-525 | PM2 & PM3, pooled | 0.93 | SRD05009 | 21.6 | Yes | 4 |

TABLE 6-continued

| Samples of recombinant West Nile Virus antigen formulated for Study I. | | | | | | | |
|---|---|---|---|---|---|---|---|
| Treatment group, n = 5 | Cell culture event | Process method | E protein Concentration (mg) | Lot ID#, vial label | Water added (ml) | Ability to Rehydrate | Approx Dose E protein per mouse (μg) |
| 7 | 1602-207 | PM5 | 0.18 | SRD05010 | 3.6 | Yes | 5 |
| 8 | NT1 wild-type | PM2 | 0 | SRD05011 | 1.02 | Yes | 0 |
| 9 | NT1 wild-type | PM3 | 0 | SRD05012 | 1.22 | Yes | 0 |
| 11 | NT1 wild-type | PM7 | 0 | SRD05014 | 3.38 | Yes | 0 |
| 12 | Inactivated WNV | Blitvich et al (3) | 2.72 μg/100 μl | SRD05015 | — | Yes | 2.72 |
| 13 | PBS | NA | 0 | SRD05016 | 0 | Yes | 0 |

TABLE 7

WNV neutralization titers generated from vaccination with plant-cell-produced WNV antigen, Study I.

| Treatment Group | Mouse #1 | Mouse #2 | Mouse #3 | Mouse #4 | Mouse #5 | Mean Titer |
|---|---|---|---|---|---|---|
| 2 | 1280 | 1920 | >2560 | 1920 | >2560 | >2560 |
| 4 | 1280 | 960 | 640 | 1280 | ND | 1040 |
| 5 | >2560 | >2560 | 1280 | 1920 | 80 | 656 |
| 6 | 120 | 480 | 40 | <20 | 240 | 176 |
| 7 | 480 | 480 | 1280 | 320 | 1280 | 768 |

TABLE 7-continued

WNV neutralization titers generated from vaccination with plant-cell-produced WNV antigen, Study I.

| Treatment Group | Mouse #1 | Mouse #2 | Mouse #3 | Mouse #4 | Mouse #5 | Mean Titer |
|---|---|---|---|---|---|---|
| 8 | <20 | <20 | <20 | <20 | <20 | <20 |
| 9 | <20 | <20 | <20 | <20 | <20 | <20 |
| 11 | <20 | <20 | <20 | <20 | <20 | <20 |
| 12 | >20480 | >20480 | >20480 | >20480 | >20480 | >20480 |
| 13 | <20 | <20 | <20 | <20 | <20 | <20 |

TABLE 8

Treatment groups for second mouse study, testing multiple doses and multiple adjuvants (CFA, complete Freund's adjuvant; IFA, incomplete Freund's adjuvant; OW, oil in water)

| GROUP | TREATMENT | ANTIGEN DOSE | ADJUVANT | # ANIMALS |
|---|---|---|---|---|
| 1 | NT-1 plant cell control | NA | Titer-max | 5 |
| 2 | Plant-cell-vaccine (1622-207 event) | 25μ | CFA IFA | 5 |
| 3 | Plant-cell-produced WNV vaccine (1622-207 event) | 25 μg | Titer-max | 10 |
| 4 | Plant-cell-produced WNV vaccine (1622-207 event) | 5 μg | Titer-max | 10 |
| 5 | Plant-cell-produced WNV vaccine (1622-207 event) | 0.5 μg | Titer-max | 10 |
| 6 | Plant-cell-produced WNV vaccine (1622-207 event) | 25 μg | Carbopol | 10 |
| 7 | Plant-cell-produced WNV vaccine (1622-207 event) | 5 μg | Carbopol | 10 |
| 8 | Plant-cell-produced WNV vaccine (1622-207 event) | 0.5 μg | Carbopol | 10 |
| 9 | Plant-cell-produced WNV vaccine (1622-207 event) | 25 μg | Carbigen | 10 |
| 10 | Plant-cell-produced WNV vaccine (1622-207 event) | 5 μg | Carbigen | 10 |
| 11 | Plant-cell-produced WNV vaccine (1622-207 event) | 0.5 μg | Carbigen | 10 |
| 12 | Plant-cell-produced WNV vaccine (1622-207 event) | 25 μg | OW | 10 |
| 13 | Plant-cell-produced WNV vaccine (1622-207 event) | 5 μg | OW | 10 |
| 14 | Plant-cell-produced WNV vaccine (1622-207 event) | 0.5 μg | OW | 10 |
| 15 | Plant-cell-produced WNV vaccine (1622-207 event) | 25 μg | Polygen | 10 |
| 16 | Plant-cell-produced WNV vaccine (1622-207 event) | 5 μg | Polygen | 10 |

TABLE 8-continued

Treatment groups for second mouse study, testing multiple doses and multiple adjuvants (CFA, complete Freund's adjuvant; IFA, incomplete Freund's adjuvant; OW, oil in water)

| GROUP | TREATMENT | ANTIGEN DOSE | ADJUVANT | # ANIMALS |
|---|---|---|---|---|
| 17 | Plant-cell-produced WNV vaccine (1622-207 event) | 0.5 µg | Polygen | 10 |

TABLE 9

Fragments of SEQ ID NO: 5.

| Fragment Length (amino acids) | Y is any integer selected from between, and including: | Z |
|---|---|---|
| 5 | 1 and 664 | Y + 4 |
| 6 | 1 and 663 | Y + 5 |
| 7 | 1 and 662 | Y + 6 |
| 8 | 1 and 661 | Y + 7 |
| 9 | 1 and 660 | Y + 8 |
| 10 | 1 and 659 | Y + 9 |
| 11 | 1 and 658 | Y + 10 |
| 12 | 1 and 657 | Y + 11 |
| 13 | 1 and 656 | Y + 12 |
| 14 | 1 and 655 | Y + 13 |
| 15 | 1 and 654 | Y + 14 |
| 16 | 1 and 653 | Y + 15 |
| 17 | 1 and 652 | Y + 16 |
| 18 | 1 and 651 | Y + 17 |
| 19 | 1 and 650 | Y + 18 |
| 20 | 1 and 649 | Y + 19 |
| 21 | 1 and 648 | Y + 20 |
| 22 | 1 and 647 | Y + 21 |
| 23 | 1 and 646 | Y + 22 |
| 24 | 1 and 645 | Y + 23 |
| 25 | 1 and 644 | Y + 24 |
| 26 | 1 and 643 | Y + 25 |
| 27 | 1 and 642 | Y + 26 |
| 28 | 1 and 641 | Y + 27 |
| 29 | 1 and 640 | Y + 28 |
| 30 | 1 and 639 | Y + 29 |
| 31 | 1 and 638 | Y + 30 |
| 32 | 1 and 637 | Y + 31 |
| 33 | 1 and 636 | Y + 32 |
| 34 | 1 and 635 | Y + 33 |
| 35 | 1 and 634 | Y + 34 |
| 36 | 1 and 633 | Y + 35 |
| 37 | 1 and 632 | Y + 36 |
| 38 | 1 and 631 | Y + 37 |
| 39 | 1 and 630 | Y + 38 |
| 40 | 1 and 629 | Y + 39 |
| 41 | 1 and 628 | Y + 40 |
| 42 | 1 and 627 | Y + 41 |
| 43 | 1 and 626 | Y + 42 |
| 44 | 1 and 625 | Y + 43 |
| 45 | 1 and 624 | Y + 44 |
| 46 | 1 and 623 | Y + 45 |
| 47 | 1 and 622 | Y + 46 |
| 48 | 1 and 621 | Y + 47 |
| 49 | 1 and 620 | Y + 48 |
| 50 | 1 and 619 | Y + 49 |
| 51 | 1 and 618 | Y + 50 |
| 52 | 1 and 617 | Y + 51 |
| 53 | 1 and 616 | Y + 52 |
| 54 | 1 and 615 | Y + 53 |
| 55 | 1 and 614 | Y + 54 |
| 56 | 1 and 613 | Y + 55 |
| 57 | 1 and 612 | Y + 56 |
| 58 | 1 and 611 | Y + 57 |
| 59 | 1 and 610 | Y + 58 |
| 60 | 1 and 609 | Y + 59 |
| 61 | 1 and 608 | Y + 60 |

TABLE 9-continued

Fragments of SEQ ID NO: 5.

| Fragment Length (amino acids) | Y is any integer selected from between, and including: | Z |
|---|---|---|
| 62 | 1 and 607 | Y + 61 |
| 63 | 1 and 606 | Y + 62 |
| 64 | 1 and 605 | Y + 63 |
| 65 | 1 and 604 | Y + 64 |
| 66 | 1 and 603 | Y + 65 |
| 67 | 1 and 602 | Y + 66 |
| 68 | 1 and 601 | Y + 67 |
| 69 | 1 and 600 | Y + 68 |
| 70 | 1 and 599 | Y + 69 |
| 71 | 1 and 598 | Y + 70 |
| 72 | 1 and 597 | Y + 71 |
| 73 | 1 and 596 | Y + 72 |
| 74 | 1 and 595 | Y + 73 |
| 75 | 1 and 594 | Y + 74 |
| 76 | 1 and 593 | Y + 75 |
| 77 | 1 and 592 | Y + 76 |
| 78 | 1 and 591 | Y + 77 |
| 79 | 1 and 590 | Y + 78 |
| 80 | 1 and 589 | Y + 79 |
| 81 | 1 and 588 | Y + 80 |
| 82 | 1 and 587 | Y + 81 |
| 83 | 1 and 586 | Y + 82 |
| 84 | 1 and 585 | Y + 83 |
| 85 | 1 and 584 | Y + 84 |
| 86 | 1 and 583 | Y + 85 |
| 87 | 1 and 582 | Y + 86 |
| 88 | 1 and 581 | Y + 87 |
| 89 | 1 and 580 | Y + 88 |
| 90 | 1 and 579 | Y + 89 |
| 91 | 1 and 578 | Y + 90 |
| 92 | 1 and 577 | Y + 91 |
| 93 | 1 and 576 | Y + 92 |
| 94 | 1 and 575 | Y + 93 |
| 95 | 1 and 574 | Y + 94 |
| 96 | 1 and 573 | Y + 95 |
| 97 | 1 and 572 | Y + 96 |
| 98 | 1 and 571 | Y + 97 |
| 99 | 1 and 570 | Y + 98 |
| 100 | 1 and 569 | Y + 99 |
| 101 | 1 and 568 | Y + 100 |
| 102 | 1 and 567 | Y + 101 |
| 103 | 1 and 566 | Y + 102 |
| 104 | 1 and 565 | Y + 103 |
| 105 | 1 and 564 | Y + 104 |
| 106 | 1 and 563 | Y + 105 |
| 107 | 1 and 562 | Y + 106 |
| 108 | 1 and 561 | Y + 107 |
| 109 | 1 and 560 | Y + 108 |
| 110 | 1 and 559 | Y + 109 |
| 111 | 1 and 558 | Y + 110 |
| 112 | 1 and 557 | Y + 111 |
| 113 | 1 and 556 | Y + 112 |
| 114 | 1 and 555 | Y + 113 |
| 115 | 1 and 554 | Y + 114 |
| 116 | 1 and 553 | Y + 115 |
| 117 | 1 and 552 | Y + 116 |
| 118 | 1 and 551 | Y + 117 |

TABLE 9-continued

| Fragments of SEQ ID NO: 5. | | |
|---|---|---|
| Fragment Length (amino acids) | Y is any integer selected from between, and including: | Z |
| 119 | 1 and 550 | Y + 118 |
| 120 | 1 and 549 | Y + 119 |
| 121 | 1 and 548 | Y + 120 |
| 122 | 1 and 547 | Y + 121 |
| 123 | 1 and 546 | Y + 122 |
| 124 | 1 and 545 | Y + 123 |
| 125 | 1 and 544 | Y + 124 |
| 126 | 1 and 543 | Y + 125 |
| 127 | 1 and 542 | Y + 126 |
| 128 | 1 and 541 | Y + 127 |
| 129 | 1 and 540 | Y + 128 |
| 130 | 1 and 539 | Y + 129 |
| 131 | 1 and 538 | Y + 130 |
| 132 | 1 and 537 | Y + 131 |
| 133 | 1 and 536 | Y + 132 |
| 134 | 1 and 535 | Y + 133 |
| 135 | 1 and 534 | Y + 134 |
| 136 | 1 and 533 | Y + 135 |
| 137 | 1 and 532 | Y + 136 |
| 138 | 1 and 531 | Y + 137 |
| 139 | 1 and 530 | Y + 138 |
| 140 | 1 and 529 | Y + 139 |
| 141 | 1 and 528 | Y + 140 |
| 142 | 1 and 527 | Y + 141 |
| 143 | 1 and 526 | Y + 142 |
| 144 | 1 and 525 | Y + 143 |
| 145 | 1 and 524 | Y + 144 |
| 146 | 1 and 523 | Y + 145 |
| 147 | 1 and 522 | Y + 146 |
| 148 | 1 and 521 | Y + 147 |
| 149 | 1 and 520 | Y + 148 |
| 150 | 1 and 519 | Y + 149 |
| 151 | 1 and 518 | Y + 150 |
| 152 | 1 and 517 | Y + 151 |
| 153 | 1 and 516 | Y + 152 |
| 154 | 1 and 515 | Y + 153 |
| 155 | 1 and 514 | Y + 154 |
| 156 | 1 and 513 | Y + 155 |
| 157 | 1 and 512 | Y + 156 |
| 158 | 1 and 511 | Y + 157 |
| 159 | 1 and 510 | Y + 158 |
| 160 | 1 and 509 | Y + 159 |
| 161 | 1 and 508 | Y + 160 |
| 162 | 1 and 507 | Y + 161 |
| 163 | 1 and 506 | Y + 162 |
| 164 | 1 and 505 | Y + 163 |
| 165 | 1 and 504 | Y + 164 |
| 166 | 1 and 503 | Y + 165 |
| 167 | 1 and 502 | Y + 166 |
| 168 | 1 and 501 | Y + 167 |
| 169 | 1 and 500 | Y + 168 |
| 170 | 1 and 499 | Y + 169 |
| 171 | 1 and 498 | Y + 170 |
| 172 | 1 and 497 | Y + 171 |
| 173 | 1 and 496 | Y + 172 |
| 174 | 1 and 495 | Y + 173 |
| 175 | 1 and 494 | Y + 174 |
| 176 | 1 and 493 | Y + 175 |
| 177 | 1 and 492 | Y + 176 |
| 178 | 1 and 491 | Y + 177 |
| 179 | 1 and 490 | Y + 178 |
| 180 | 1 and 489 | Y + 179 |
| 181 | 1 and 488 | Y + 180 |
| 182 | 1 and 487 | Y + 181 |
| 183 | 1 and 486 | Y + 182 |
| 184 | 1 and 485 | Y + 183 |
| 185 | 1 and 484 | Y + 184 |
| 186 | 1 and 483 | Y + 185 |
| 187 | 1 and 482 | Y + 186 |
| 188 | 1 and 481 | Y + 187 |
| 189 | 1 and 480 | Y + 188 |
| 190 | 1 and 479 | Y + 189 |

TABLE 9-continued

| Fragments of SEQ ID NO: 5. | | |
|---|---|---|
| Fragment Length (amino acids) | Y is any integer selected from between, and including: | Z |
| 191 | 1 and 478 | Y + 190 |
| 192 | 1 and 477 | Y + 191 |
| 193 | 1 and 476 | Y + 192 |
| 194 | 1 and 475 | Y + 193 |
| 195 | 1 and 474 | Y + 194 |
| 196 | 1 and 473 | Y + 195 |
| 197 | 1 and 472 | Y + 196 |
| 198 | 1 and 471 | Y + 197 |
| 199 | 1 and 470 | Y + 198 |
| 200 | 1 and 469 | Y + 199 |
| 201 | 1 and 468 | Y + 200 |
| 202 | 1 and 467 | Y + 201 |
| 203 | 1 and 466 | Y + 202 |
| 204 | 1 and 465 | Y + 203 |
| 205 | 1 and 464 | Y + 204 |
| 206 | 1 and 463 | Y + 205 |
| 207 | 1 and 462 | Y + 206 |
| 208 | 1 and 461 | Y + 207 |
| 209 | 1 and 460 | Y + 208 |
| 210 | 1 and 459 | Y + 209 |
| 211 | 1 and 458 | Y + 210 |
| 212 | 1 and 457 | Y + 211 |
| 213 | 1 and 456 | Y + 212 |
| 214 | 1 and 455 | Y + 213 |
| 215 | 1 and 454 | Y + 214 |
| 216 | 1 and 453 | Y + 215 |
| 217 | 1 and 452 | Y + 216 |
| 218 | 1 and 451 | Y + 217 |
| 219 | 1 and 450 | Y + 218 |
| 220 | 1 and 449 | Y + 219 |
| 221 | 1 and 448 | Y + 220 |
| 222 | 1 and 447 | Y + 221 |
| 223 | 1 and 446 | Y + 222 |
| 224 | 1 and 445 | Y + 223 |
| 225 | 1 and 444 | Y + 224 |
| 226 | 1 and 443 | Y + 225 |
| 227 | 1 and 442 | Y + 226 |
| 228 | 1 and 441 | Y + 227 |
| 229 | 1 and 440 | Y + 228 |
| 230 | 1 and 439 | Y + 229 |
| 231 | 1 and 438 | Y + 230 |
| 232 | 1 and 437 | Y + 231 |
| 233 | 1 and 436 | Y + 232 |
| 234 | 1 and 435 | Y + 233 |
| 235 | 1 and 434 | Y + 234 |
| 236 | 1 and 433 | Y + 235 |
| 237 | 1 and 432 | Y + 236 |
| 238 | 1 and 431 | Y + 237 |
| 239 | 1 and 430 | Y + 238 |
| 240 | 1 and 429 | Y + 239 |
| 241 | 1 and 428 | Y + 240 |
| 242 | 1 and 427 | Y + 241 |
| 243 | 1 and 426 | Y + 242 |
| 244 | 1 and 425 | Y + 243 |
| 245 | 1 and 424 | Y + 244 |
| 246 | 1 and 423 | Y + 245 |
| 247 | 1 and 422 | Y + 246 |
| 248 | 1 and 421 | Y + 247 |
| 249 | 1 and 420 | Y + 248 |
| 250 | 1 and 419 | Y + 249 |
| 251 | 1 and 418 | Y + 250 |
| 252 | 1 and 417 | Y + 251 |
| 253 | 1 and 416 | Y + 252 |
| 254 | 1 and 415 | Y + 253 |
| 255 | 1 and 414 | Y + 254 |
| 256 | 1 and 413 | Y + 255 |
| 257 | 1 and 412 | Y + 256 |
| 258 | 1 and 411 | Y + 257 |
| 259 | 1 and 410 | Y + 258 |
| 260 | 1 and 409 | Y + 259 |
| 261 | 1 and 408 | Y + 260 |
| 262 | 1 and 407 | Y + 261 |

TABLE 9-continued

Fragments of SEQ ID NO: 5.

| Fragment Length (amino acids) | Y is any integer selected from between, and including: | Z |
|---|---|---|
| 263 | 1 and 406 | Y + 262 |
| 264 | 1 and 405 | Y + 263 |
| 265 | 1 and 404 | Y + 264 |
| 266 | 1 and 403 | Y + 265 |
| 267 | 1 and 402 | Y + 266 |
| 268 | 1 and 401 | Y + 267 |
| 269 | 1 and 400 | Y + 268 |
| 270 | 1 and 399 | Y + 269 |
| 271 | 1 and 398 | Y + 270 |
| 272 | 1 and 397 | Y + 271 |
| 273 | 1 and 396 | Y + 272 |
| 274 | 1 and 395 | Y + 273 |
| 275 | 1 and 394 | Y + 274 |
| 276 | 1 and 393 | Y + 275 |
| 277 | 1 and 392 | Y + 276 |
| 278 | 1 and 391 | Y + 277 |
| 279 | 1 and 390 | Y + 278 |
| 280 | 1 and 389 | Y + 279 |
| 281 | 1 and 388 | Y + 280 |
| 282 | 1 and 387 | Y + 281 |
| 283 | 1 and 386 | Y + 282 |
| 284 | 1 and 385 | Y + 283 |
| 285 | 1 and 384 | Y + 284 |
| 286 | 1 and 383 | Y + 285 |
| 287 | 1 and 382 | Y + 286 |
| 288 | 1 and 381 | Y + 287 |
| 289 | 1 and 380 | Y + 288 |
| 290 | 1 and 379 | Y + 289 |
| 291 | 1 and 378 | Y + 290 |
| 292 | 1 and 377 | Y + 291 |
| 293 | 1 and 376 | Y + 292 |
| 294 | 1 and 375 | Y + 293 |
| 295 | 1 and 374 | Y + 294 |
| 296 | 1 and 373 | Y + 295 |
| 297 | 1 and 372 | Y + 296 |
| 298 | 1 and 371 | Y + 297 |
| 299 | 1 and 370 | Y + 298 |
| 300 | 1 and 369 | Y + 299 |
| 301 | 1 and 368 | Y + 300 |
| 302 | 1 and 367 | Y + 301 |
| 303 | 1 and 366 | Y + 302 |
| 304 | 1 and 365 | Y + 303 |
| 305 | 1 and 364 | Y + 304 |
| 306 | 1 and 363 | Y + 305 |
| 307 | 1 and 362 | Y + 306 |
| 308 | 1 and 361 | Y + 307 |
| 309 | 1 and 360 | Y + 308 |
| 310 | 1 and 359 | Y + 309 |
| 311 | 1 and 358 | Y + 310 |
| 312 | 1 and 357 | Y + 311 |
| 313 | 1 and 356 | Y + 312 |
| 314 | 1 and 355 | Y + 313 |
| 315 | 1 and 354 | Y + 314 |
| 316 | 1 and 353 | Y + 315 |
| 317 | 1 and 352 | Y + 316 |
| 318 | 1 and 351 | Y + 317 |
| 319 | 1 and 350 | Y + 318 |
| 320 | 1 and 349 | Y + 319 |
| 321 | 1 and 348 | Y + 320 |
| 322 | 1 and 347 | Y + 321 |
| 323 | 1 and 346 | Y + 322 |
| 324 | 1 and 345 | Y + 323 |
| 325 | 1 and 344 | Y + 324 |
| 326 | 1 and 343 | Y + 325 |
| 327 | 1 and 342 | Y + 326 |
| 328 | 1 and 341 | Y + 327 |
| 329 | 1 and 340 | Y + 328 |
| 330 | 1 and 339 | Y + 329 |
| 331 | 1 and 338 | Y + 330 |
| 332 | 1 and 337 | Y + 331 |
| 333 | 1 and 336 | Y + 332 |
| 334 | 1 and 335 | Y + 333 |

TABLE 9-continued

Fragments of SEQ ID NO: 5.

| Fragment Length (amino acids) | Y is any integer selected from between, and including: | Z |
|---|---|---|
| 335 | 1 and 334 | Y + 334 |
| 336 | 1 and 333 | Y + 335 |
| 337 | 1 and 332 | Y + 336 |
| 338 | 1 and 331 | Y + 337 |
| 339 | 1 and 330 | Y + 338 |
| 340 | 1 and 329 | Y + 339 |
| 341 | 1 and 328 | Y + 340 |
| 342 | 1 and 327 | Y + 341 |
| 343 | 1 and 326 | Y + 342 |
| 344 | 1 and 325 | Y + 343 |
| 345 | 1 and 324 | Y + 344 |
| 346 | 1 and 323 | Y + 345 |
| 347 | 1 and 322 | Y + 346 |
| 348 | 1 and 321 | Y + 347 |
| 349 | 1 and 320 | Y + 348 |
| 350 | 1 and 319 | Y + 349 |
| 351 | 1 and 318 | Y + 350 |
| 352 | 1 and 317 | Y + 351 |
| 353 | 1 and 316 | Y + 352 |
| 354 | 1 and 315 | Y + 353 |
| 355 | 1 and 314 | Y + 354 |
| 356 | 1 and 313 | Y + 355 |
| 357 | 1 and 312 | Y + 356 |
| 358 | 1 and 311 | Y + 357 |
| 359 | 1 and 310 | Y + 358 |
| 360 | 1 and 309 | Y + 359 |
| 361 | 1 and 308 | Y + 360 |
| 362 | 1 and 307 | Y + 361 |
| 363 | 1 and 306 | Y + 362 |
| 364 | 1 and 305 | Y + 363 |
| 365 | 1 and 304 | Y + 364 |
| 366 | 1 and 303 | Y + 365 |
| 367 | 1 and 302 | Y + 366 |
| 368 | 1 and 301 | Y + 367 |
| 369 | 1 and 300 | Y + 368 |
| 370 | 1 and 299 | Y + 369 |
| 371 | 1 and 298 | Y + 370 |
| 372 | 1 and 297 | Y + 371 |
| 373 | 1 and 296 | Y + 372 |
| 374 | 1 and 295 | Y + 373 |
| 375 | 1 and 294 | Y + 374 |
| 376 | 1 and 293 | Y + 375 |
| 377 | 1 and 292 | Y + 376 |
| 378 | 1 and 291 | Y + 377 |
| 379 | 1 and 290 | Y + 378 |
| 380 | 1 and 289 | Y + 379 |
| 381 | 1 and 288 | Y + 380 |
| 382 | 1 and 287 | Y + 381 |
| 383 | 1 and 286 | Y + 382 |
| 384 | 1 and 285 | Y + 383 |
| 385 | 1 and 284 | Y + 384 |
| 386 | 1 and 283 | Y + 385 |
| 387 | 1 and 282 | Y + 386 |
| 388 | 1 and 281 | Y + 387 |
| 389 | 1 and 280 | Y + 388 |
| 390 | 1 and 279 | Y + 389 |
| 391 | 1 and 278 | Y + 390 |
| 392 | 1 and 277 | Y + 391 |
| 393 | 1 and 276 | Y + 392 |
| 394 | 1 and 275 | Y + 393 |
| 395 | 1 and 274 | Y + 394 |
| 396 | 1 and 273 | Y + 395 |
| 397 | 1 and 272 | Y + 396 |
| 398 | 1 and 271 | Y + 397 |
| 399 | 1 and 270 | Y + 398 |
| 400 | 1 and 269 | Y + 399 |
| 401 | 1 and 268 | Y + 400 |
| 402 | 1 and 267 | Y + 401 |
| 403 | 1 and 266 | Y + 402 |
| 404 | 1 and 265 | Y + 403 |
| 405 | 1 and 264 | Y + 404 |
| 406 | 1 and 263 | Y + 405 |

TABLE 9-continued

Fragments of SEQ ID NO: 5.

| Fragment Length (amino acids) | Y is any integer selected from between, and including: | Z |
|---|---|---|
| 407 | 1 and 262 | Y + 406 |
| 408 | 1 and 261 | Y + 407 |
| 409 | 1 and 260 | Y + 408 |
| 410 | 1 and 259 | Y + 409 |
| 411 | 1 and 258 | Y + 410 |
| 412 | 1 and 257 | Y + 411 |
| 413 | 1 and 256 | Y + 412 |
| 414 | 1 and 255 | Y + 413 |
| 415 | 1 and 254 | Y + 414 |
| 416 | 1 and 253 | Y + 415 |
| 417 | 1 and 252 | Y + 416 |
| 418 | 1 and 251 | Y + 417 |
| 419 | 1 and 250 | Y + 418 |
| 420 | 1 and 249 | Y + 419 |
| 421 | 1 and 248 | Y + 420 |
| 422 | 1 and 247 | Y + 421 |
| 423 | 1 and 246 | Y + 422 |
| 424 | 1 and 245 | Y + 423 |
| 425 | 1 and 244 | Y + 424 |
| 426 | 1 and 243 | Y + 425 |
| 427 | 1 and 242 | Y + 426 |
| 428 | 1 and 241 | Y + 427 |
| 429 | 1 and 240 | Y + 428 |
| 430 | 1 and 239 | Y + 429 |
| 431 | 1 and 238 | Y + 430 |
| 432 | 1 and 237 | Y + 431 |
| 433 | 1 and 236 | Y + 432 |
| 434 | 1 and 235 | Y + 433 |
| 435 | 1 and 234 | Y + 434 |
| 436 | 1 and 233 | Y + 435 |
| 437 | 1 and 232 | Y + 436 |
| 438 | 1 and 231 | Y + 437 |
| 439 | 1 and 230 | Y + 438 |
| 440 | 1 and 229 | Y + 439 |
| 441 | 1 and 228 | Y + 440 |
| 442 | 1 and 227 | Y + 441 |
| 443 | 1 and 226 | Y + 442 |
| 444 | 1 and 225 | Y + 443 |
| 445 | 1 and 224 | Y + 444 |
| 446 | 1 and 223 | Y + 445 |
| 447 | 1 and 222 | Y + 446 |
| 448 | 1 and 221 | Y + 447 |
| 449 | 1 and 220 | Y + 448 |
| 450 | 1 and 219 | Y + 449 |
| 451 | 1 and 218 | Y + 450 |
| 452 | 1 and 217 | Y + 451 |
| 453 | 1 and 216 | Y + 452 |
| 454 | 1 and 215 | Y + 453 |
| 455 | 1 and 214 | Y + 454 |
| 456 | 1 and 213 | Y + 455 |
| 457 | 1 and 212 | Y + 456 |
| 458 | 1 and 211 | Y + 457 |
| 459 | 1 and 210 | Y + 458 |
| 460 | 1 and 209 | Y + 459 |
| 461 | 1 and 208 | Y + 460 |
| 462 | 1 and 207 | Y + 461 |
| 463 | 1 and 206 | Y + 462 |
| 464 | 1 and 205 | Y + 463 |
| 465 | 1 and 204 | Y + 464 |
| 466 | 1 and 203 | Y + 465 |
| 467 | 1 and 202 | Y + 466 |
| 468 | 1 and 201 | Y + 467 |
| 469 | 1 and 200 | Y + 468 |
| 470 | 1 and 199 | Y + 469 |
| 471 | 1 and 198 | Y + 470 |
| 472 | 1 and 197 | Y + 471 |
| 473 | 1 and 196 | Y + 472 |
| 474 | 1 and 195 | Y + 473 |
| 475 | 1 and 194 | Y + 474 |
| 476 | 1 and 193 | Y + 475 |
| 477 | 1 and 192 | Y + 476 |
| 478 | 1 and 191 | Y + 477 |

TABLE 9-continued

Fragments of SEQ ID NO: 5.

| Fragment Length (amino acids) | Y is any integer selected from between, and including: | Z |
|---|---|---|
| 479 | 1 and 190 | Y + 478 |
| 480 | 1 and 189 | Y + 479 |
| 481 | 1 and 188 | Y + 480 |
| 482 | 1 and 187 | Y + 481 |
| 483 | 1 and 186 | Y + 482 |
| 484 | 1 and 185 | Y + 483 |
| 485 | 1 and 184 | Y + 484 |
| 486 | 1 and 183 | Y + 485 |
| 487 | 1 and 182 | Y + 486 |
| 488 | 1 and 181 | Y + 487 |
| 489 | 1 and 180 | Y + 488 |
| 490 | 1 and 179 | Y + 489 |
| 491 | 1 and 178 | Y + 490 |
| 492 | 1 and 177 | Y + 491 |
| 493 | 1 and 176 | Y + 492 |
| 494 | 1 and 175 | Y + 493 |
| 495 | 1 and 174 | Y + 494 |
| 496 | 1 and 173 | Y + 495 |
| 497 | 1 and 172 | Y + 496 |
| 498 | 1 and 171 | Y + 497 |
| 499 | 1 and 170 | Y + 498 |
| 500 | 1 and 169 | Y + 499 |
| 501 | 1 and 168 | Y + 500 |
| 502 | 1 and 167 | Y + 501 |
| 503 | 1 and 166 | Y + 502 |
| 504 | 1 and 165 | Y + 503 |
| 505 | 1 and 164 | Y + 504 |
| 506 | 1 and 163 | Y + 505 |
| 507 | 1 and 162 | Y + 506 |
| 508 | 1 and 161 | Y + 507 |
| 509 | 1 and 160 | Y + 508 |
| 510 | 1 and 159 | Y + 509 |
| 511 | 1 and 158 | Y + 510 |
| 512 | 1 and 157 | Y + 511 |
| 513 | 1 and 156 | Y + 512 |
| 514 | 1 and 155 | Y + 513 |
| 515 | 1 and 154 | Y + 514 |
| 516 | 1 and 153 | Y + 515 |
| 517 | 1 and 152 | Y + 516 |
| 518 | 1 and 151 | Y + 517 |
| 519 | 1 and 150 | Y + 518 |
| 520 | 1 and 149 | Y + 519 |
| 521 | 1 and 148 | Y + 520 |
| 522 | 1 and 147 | Y + 521 |
| 523 | 1 and 146 | Y + 522 |
| 524 | 1 and 145 | Y + 523 |
| 525 | 1 and 144 | Y + 524 |
| 526 | 1 and 143 | Y + 525 |
| 527 | 1 and 142 | Y + 526 |
| 528 | 1 and 141 | Y + 527 |
| 529 | 1 and 140 | Y + 528 |
| 530 | 1 and 139 | Y + 529 |
| 531 | 1 and 138 | Y + 530 |
| 532 | 1 and 137 | Y + 531 |
| 533 | 1 and 136 | Y + 532 |
| 534 | 1 and 135 | Y + 533 |
| 535 | 1 and 134 | Y + 534 |
| 536 | 1 and 133 | Y + 535 |
| 537 | 1 and 132 | Y + 536 |
| 538 | 1 and 131 | Y + 537 |
| 539 | 1 and 130 | Y + 538 |
| 540 | 1 and 129 | Y + 539 |
| 541 | 1 and 128 | Y + 540 |
| 542 | 1 and 127 | Y + 541 |
| 543 | 1 and 126 | Y + 542 |
| 544 | 1 and 125 | Y + 543 |
| 545 | 1 and 124 | Y + 544 |
| 546 | 1 and 123 | Y + 545 |
| 547 | 1 and 122 | Y + 546 |
| 548 | 1 and 121 | Y + 547 |
| 549 | 1 and 120 | Y + 548 |
| 550 | 1 and 119 | Y + 549 |

TABLE 9-continued

| Fragments of SEQ ID NO: 5. | | |
|---|---|---|
| Fragment Length (amino acids) | Y is any integer selected from between, and including: | Z |
| 551 | 1 and 118 | Y + 550 |
| 552 | 1 and 117 | Y + 551 |
| 553 | 1 and 116 | Y + 552 |
| 554 | 1 and 115 | Y + 553 |
| 555 | 1 and 114 | Y + 554 |
| 556 | 1 and 113 | Y + 555 |
| 557 | 1 and 112 | Y + 556 |
| 558 | 1 and 111 | Y + 557 |
| 559 | 1 and 110 | Y + 558 |
| 560 | 1 and 109 | Y + 559 |
| 561 | 1 and 108 | Y + 560 |
| 562 | 1 and 107 | Y + 561 |
| 563 | 1 and 106 | Y + 562 |
| 564 | 1 and 105 | Y + 563 |
| 565 | 1 and 104 | Y + 564 |
| 566 | 1 and 103 | Y + 565 |
| 567 | 1 and 102 | Y + 566 |
| 568 | 1 and 101 | Y + 567 |
| 569 | 1 and 100 | Y + 568 |
| 570 | 1 and 99 | Y + 569 |
| 571 | 1 and 98 | Y + 570 |
| 572 | 1 and 97 | Y + 571 |
| 573 | 1 and 96 | Y + 572 |
| 574 | 1 and 95 | Y + 573 |
| 575 | 1 and 94 | Y + 574 |
| 576 | 1 and 93 | Y + 575 |
| 577 | 1 and 92 | Y + 576 |
| 578 | 1 and 91 | Y + 577 |
| 579 | 1 and 90 | Y + 578 |
| 580 | 1 and 89 | Y + 579 |
| 581 | 1 and 88 | Y + 580 |
| 582 | 1 and 87 | Y + 581 |
| 583 | 1 and 86 | Y + 582 |
| 584 | 1 and 85 | Y + 583 |
| 585 | 1 and 84 | Y + 584 |
| 586 | 1 and 83 | Y + 585 |
| 587 | 1 and 82 | Y + 586 |
| 588 | 1 and 81 | Y + 587 |
| 589 | 1 and 80 | Y + 588 |
| 590 | 1 and 79 | Y + 589 |
| 591 | 1 and 78 | Y + 590 |
| 592 | 1 and 77 | Y + 591 |
| 593 | 1 and 76 | Y + 592 |
| 594 | 1 and 75 | Y + 593 |
| 595 | 1 and 74 | Y + 594 |
| 596 | 1 and 73 | Y + 595 |
| 597 | 1 and 72 | Y + 596 |
| 598 | 1 and 71 | Y + 597 |
| 599 | 1 and 70 | Y + 598 |
| 600 | 1 and 69 | Y + 599 |
| 601 | 1 and 68 | Y + 600 |
| 602 | 1 and 67 | Y + 601 |
| 603 | 1 and 66 | Y + 602 |
| 604 | 1 and 65 | Y + 603 |
| 605 | 1 and 64 | Y + 604 |
| 606 | 1 and 63 | Y + 605 |
| 607 | 1 and 62 | Y + 606 |
| 608 | 1 and 61 | Y + 607 |
| 609 | 1 and 60 | Y + 608 |
| 610 | 1 and 59 | Y + 609 |
| 611 | 1 and 58 | Y + 610 |
| 612 | 1 and 57 | Y + 611 |
| 613 | 1 and 56 | Y + 612 |
| 614 | 1 and 55 | Y + 613 |
| 615 | 1 and 54 | Y + 614 |
| 616 | 1 and 53 | Y + 615 |
| 617 | 1 and 52 | Y + 616 |
| 618 | 1 and 51 | Y + 617 |
| 619 | 1 and 50 | Y + 618 |
| 620 | 1 and 49 | Y + 619 |
| 621 | 1 and 48 | Y + 620 |
| 622 | 1 and 47 | Y + 621 |

TABLE 9-continued

| Fragments of SEQ ID NO: 5. | | |
|---|---|---|
| Fragment Length (amino acids) | Y is any integer selected from between, and including: | Z |
| 623 | 1 and 46 | Y + 622 |
| 624 | 1 and 45 | Y + 623 |
| 625 | 1 and 44 | Y + 624 |
| 626 | 1 and 43 | Y + 625 |
| 627 | 1 and 42 | Y + 626 |
| 628 | 1 and 41 | Y + 627 |
| 629 | 1 and 40 | Y + 628 |
| 630 | 1 and 39 | Y + 629 |
| 631 | 1 and 38 | Y + 630 |
| 632 | 1 and 37 | Y + 631 |
| 633 | 1 and 36 | Y + 632 |
| 634 | 1 and 35 | Y + 633 |
| 635 | 1 and 34 | Y + 634 |
| 636 | 1 and 33 | Y + 635 |
| 637 | 1 and 32 | Y + 636 |
| 638 | 1 and 31 | Y + 637 |
| 639 | 1 and 30 | Y + 638 |
| 640 | 1 and 29 | Y + 639 |
| 641 | 1 and 28 | Y + 640 |
| 642 | 1 and 27 | Y + 641 |
| 643 | 1 and 26 | Y + 642 |
| 644 | 1 and 25 | Y + 643 |
| 645 | 1 and 24 | Y + 644 |
| 646 | 1 and 23 | Y + 645 |
| 647 | 1 and 22 | Y + 646 |
| 648 | 1 and 21 | Y + 647 |
| 649 | 1 and 20 | Y + 648 |
| 650 | 1 and 19 | Y + 649 |
| 651 | 1 and 18 | Y + 650 |
| 652 | 1 and 17 | Y + 651 |
| 653 | 1 and 16 | Y + 652 |
| 654 | 1 and 15 | Y + 653 |
| 655 | 1 and 14 | Y + 654 |
| 656 | 1 and 13 | Y + 655 |
| 657 | 1 and 12 | Y + 656 |
| 658 | 1 and 11 | Y + 657 |
| 659 | 1 and 10 | Y + 658 |
| 660 | 1 and 9 | Y + 659 |
| 661 | 1 and 8 | Y + 660 |
| 662 | 1 and 7 | Y + 661 |
| 663 | 1 and 6 | Y + 662 |
| 664 | 1 and 5 | Y + 663 |
| 665 | 1 and 4 | Y + 664 |
| 666 | 1 and 3 | Y + 665 |
| 667 | 1 and 2 | Y + 666 |

TABLE 10

| Fragments of SEQ ID NOs: 9 and 11. | | |
|---|---|---|
| Fragment Length (amino acids) | Y is any integer selected from between, and including: | Z |
| 5 | 1 and 690 | Y + 4 |
| 6 | 1 and 689 | Y + 5 |
| 7 | 1 and 688 | Y + 6 |
| 8 | 1 and 687 | Y + 7 |
| 9 | 1 and 686 | Y + 8 |
| 10 | 1 and 685 | Y + 9 |
| 11 | 1 and 684 | Y + 10 |
| 12 | 1 and 683 | Y + 11 |
| 13 | 1 and 682 | Y + 12 |
| 14 | 1 and 681 | Y + 13 |
| 15 | 1 and 680 | Y + 14 |
| 16 | 1 and 679 | Y + 15 |
| 17 | 1 and 678 | Y + 16 |
| 18 | 1 and 679 | Y + 17 |

TABLE 10-continued

Fragments of SEQ ID NOs: 9 and 11.

| Fragment Length (amino acids) | Y is any integer selected from between, and including: | Z |
|---|---|---|
| 19 | 1 and 676 | Y + 18 |
| 20 | 1 and 675 | Y + 19 |
| 21 | 1 and 674 | Y + 20 |
| 22 | 1 and 673 | Y + 21 |
| 23 | 1 and 672 | Y + 22 |
| 24 | 1 and 671 | Y + 23 |
| 25 | 1 and 670 | Y + 24 |
| 26 | 1 and 669 | Y + 25 |
| 27 | 1 and 668 | Y + 26 |
| 28 | 1 and 667 | Y + 27 |
| 29 | 1 and 666 | Y + 28 |
| 30 | 1 and 665 | Y + 29 |
| 31 | 1 and 664 | Y + 30 |
| 32 | 1 and 663 | Y + 31 |
| 33 | 1 and 662 | Y + 32 |
| 34 | 1 and 661 | Y + 33 |
| 35 | 1 and 660 | Y + 34 |
| 36 | 1 and 659 | Y + 35 |
| 37 | 1 and 658 | Y + 36 |
| 38 | 1 and 657 | Y + 37 |
| 39 | 1 and 656 | Y + 38 |
| 40 | 1 and 655 | Y + 39 |
| 41 | 1 and 654 | Y + 40 |
| 42 | 1 and 653 | Y + 41 |
| 43 | 1 and 652 | Y + 42 |
| 44 | 1 and 651 | Y + 43 |
| 45 | 1 and 650 | Y + 44 |
| 46 | 1 and 649 | Y + 45 |
| 47 | 1 and 648 | Y + 46 |
| 48 | 1 and 647 | Y + 47 |
| 49 | 1 and 646 | Y + 48 |
| 50 | 1 and 645 | Y + 49 |
| 51 | 1 and 644 | Y + 50 |
| 52 | 1 and 643 | Y + 51 |
| 53 | 1 and 642 | Y + 52 |
| 54 | 1 and 641 | Y + 53 |
| 55 | 1 and 640 | Y + 54 |
| 56 | 1 and 639 | Y + 55 |
| 57 | 1 and 638 | Y + 56 |
| 58 | 1 and 637 | Y + 57 |
| 59 | 1 and 636 | Y + 58 |
| 60 | 1 and 635 | Y + 59 |
| 61 | 1 and 634 | Y + 60 |
| 62 | 1 and 633 | Y + 61 |
| 63 | 1 and 632 | Y + 62 |
| 64 | 1 and 631 | Y + 63 |
| 65 | 1 and 630 | Y + 64 |
| 66 | 1 and 629 | Y + 65 |
| 67 | 1 and 628 | Y + 66 |
| 68 | 1 and 627 | Y + 67 |
| 69 | 1 and 626 | Y + 68 |
| 70 | 1 and 625 | Y + 69 |
| 71 | 1 and 624 | Y + 70 |
| 72 | 1 and 623 | Y + 71 |
| 73 | 1 and 622 | Y + 72 |
| 74 | 1 and 621 | Y + 73 |
| 75 | 1 and 620 | Y + 74 |
| 76 | 1 and 619 | Y + 75 |
| 77 | 1 and 618 | Y + 76 |
| 78 | 1 and 617 | Y + 77 |
| 79 | 1 and 616 | Y + 78 |
| 80 | 1 and 615 | Y + 79 |
| 81 | 1 and 614 | Y + 80 |
| 82 | 1 and 613 | Y + 81 |
| 83 | 1 and 612 | Y + 82 |
| 84 | 1 and 611 | Y + 83 |
| 85 | 1 and 610 | Y + 84 |
| 86 | 1 and 609 | Y + 85 |
| 87 | 1 and 608 | Y + 86 |
| 88 | 1 and 607 | Y + 87 |
| 89 | 1 and 606 | Y + 88 |
| 90 | 1 and 605 | Y + 89 |
| 91 | 1 and 604 | Y + 90 |
| 92 | 1 and 603 | Y + 91 |
| 93 | 1 and 602 | Y + 92 |
| 94 | 1 and 601 | Y + 93 |
| 95 | 1 and 600 | Y + 94 |
| 96 | 1 and 599 | Y + 95 |
| 97 | 1 and 598 | Y + 96 |
| 98 | 1 and 597 | Y + 97 |
| 99 | 1 and 596 | Y + 98 |
| 100 | 1 and 595 | Y + 99 |
| 101 | 1 and 594 | Y + 100 |
| 102 | 1 and 593 | Y + 101 |
| 103 | 1 and 592 | Y + 102 |
| 104 | 1 and 591 | Y + 103 |
| 105 | 1 and 590 | Y + 104 |
| 106 | 1 and 589 | Y + 105 |
| 107 | 1 and 588 | Y + 106 |
| 108 | 1 and 587 | Y + 107 |
| 109 | 1 and 586 | Y + 108 |
| 110 | 1 and 585 | Y + 109 |
| 111 | 1 and 584 | Y + 110 |
| 112 | 1 and 583 | Y + 111 |
| 113 | 1 and 582 | Y + 112 |
| 114 | 1 and 581 | Y + 113 |
| 115 | 1 and 580 | Y + 114 |
| 116 | 1 and 579 | Y + 115 |
| 117 | 1 and 578 | Y + 116 |
| 118 | 1 and 577 | Y + 117 |
| 119 | 1 and 576 | Y + 118 |
| 120 | 1 and 575 | Y + 119 |
| 121 | 1 and 574 | Y + 120 |
| 122 | 1 and 573 | Y + 121 |
| 123 | 1 and 572 | Y + 122 |
| 124 | 1 and 571 | Y + 123 |
| 125 | 1 and 570 | Y + 124 |
| 126 | 1 and 569 | Y + 125 |
| 127 | 1 and 568 | Y + 126 |
| 128 | 1 and 567 | Y + 127 |
| 129 | 1 and 566 | Y + 128 |
| 130 | 1 and 565 | Y + 129 |
| 131 | 1 and 564 | Y + 130 |
| 132 | 1 and 563 | Y + 131 |
| 133 | 1 and 562 | Y + 132 |
| 134 | 1 and 561 | Y + 133 |
| 135 | 1 and 560 | Y + 134 |
| 136 | 1 and 559 | Y + 135 |
| 137 | 1 and 558 | Y + 136 |
| 138 | 1 and 557 | Y + 137 |
| 139 | 1 and 556 | Y + 138 |
| 140 | 1 and 555 | Y + 139 |
| 141 | 1 and 554 | Y + 140 |
| 142 | 1 and 553 | Y + 141 |
| 143 | 1 and 552 | Y + 142 |
| 144 | 1 and 551 | Y + 143 |
| 145 | 1 and 550 | Y + 144 |
| 146 | 1 and 549 | Y + 145 |
| 147 | 1 and 548 | Y + 146 |
| 148 | 1 and 547 | Y + 147 |
| 149 | 1 and 546 | Y + 148 |
| 150 | 1 and 545 | Y + 149 |
| 151 | 1 and 544 | Y + 150 |
| 152 | 1 and 543 | Y + 151 |
| 153 | 1 and 542 | Y + 152 |
| 154 | 1 and 541 | Y + 153 |
| 155 | 1 and 540 | Y + 154 |
| 156 | 1 and 539 | Y + 155 |
| 157 | 1 and 538 | Y + 156 |
| 158 | 1 and 537 | Y + 157 |
| 159 | 1 and 536 | Y + 158 |
| 160 | 1 and 535 | Y + 159 |
| 161 | 1 and 534 | Y + 160 |
| 162 | 1 and 533 | Y + 161 |

TABLE 10-continued

| Fragments of SEQ ID NOs: 9 and 11. | | |
|---|---|---|
| Fragment Length (amino acids) | Y is any integer selected from between, and including: | Z |
| 163 | 1 and 532 | Y + 162 |
| 164 | 1 and 531 | Y + 163 |
| 165 | 1 and 530 | Y + 164 |
| 166 | 1 and 529 | Y + 165 |
| 167 | 1 and 528 | Y + 166 |
| 168 | 1 and 527 | Y + 167 |
| 169 | 1 and 526 | Y + 168 |
| 170 | 1 and 525 | Y + 169 |
| 171 | 1 and 524 | Y + 170 |
| 172 | 1 and 523 | Y + 171 |
| 173 | 1 and 522 | Y + 172 |
| 174 | 1 and 521 | Y + 173 |
| 175 | 1 and 520 | Y + 174 |
| 176 | 1 and 519 | Y + 175 |
| 177 | 1 and 518 | Y + 176 |
| 178 | 1 and 517 | Y + 177 |
| 179 | 1 and 516 | Y + 178 |
| 180 | 1 and 515 | Y + 179 |
| 181 | 1 and 514 | Y + 180 |
| 182 | 1 and 513 | Y + 181 |
| 183 | 1 and 512 | Y + 182 |
| 184 | 1 and 511 | Y + 183 |
| 185 | 1 and 510 | Y + 184 |
| 186 | 1 and 509 | Y + 185 |
| 187 | 1 and 508 | Y + 186 |
| 188 | 1 and 507 | Y + 187 |
| 189 | 1 and 506 | Y + 188 |
| 190 | 1 and 505 | Y + 189 |
| 191 | 1 and 504 | Y + 190 |
| 192 | 1 and 503 | Y + 191 |
| 193 | 1 and 502 | Y + 192 |
| 194 | 1 and 501 | Y + 193 |
| 195 | 1 and 500 | Y + 194 |
| 196 | 1 and 499 | Y + 195 |
| 197 | 1 and 498 | Y + 196 |
| 198 | 1 and 497 | Y + 197 |
| 199 | 1 and 496 | Y + 198 |
| 200 | 1 and 495 | Y + 199 |
| 201 | 1 and 494 | Y + 200 |
| 202 | 1 and 493 | Y + 201 |
| 203 | 1 and 492 | Y + 202 |
| 204 | 1 and 491 | Y + 203 |
| 205 | 1 and 490 | Y + 204 |
| 206 | 1 and 489 | Y + 205 |
| 207 | 1 and 488 | Y + 206 |
| 208 | 1 and 487 | Y + 207 |
| 209 | 1 and 486 | Y + 208 |
| 210 | 1 and 485 | Y + 209 |
| 211 | 1 and 484 | Y + 210 |
| 212 | 1 and 483 | Y + 211 |
| 213 | 1 and 482 | Y + 212 |
| 214 | 1 and 481 | Y + 213 |
| 215 | 1 and 480 | Y + 214 |
| 216 | 1 and 479 | Y + 215 |
| 217 | 1 and 478 | Y + 216 |
| 218 | 1 and 477 | Y + 217 |
| 219 | 1 and 476 | Y + 218 |
| 220 | 1 and 475 | Y + 219 |
| 221 | 1 and 474 | Y + 220 |
| 222 | 1 and 473 | Y + 221 |
| 223 | 1 and 472 | Y + 222 |
| 224 | 1 and 471 | Y + 223 |
| 225 | 1 and 470 | Y + 224 |
| 226 | 1 and 469 | Y + 225 |
| 227 | 1 and 468 | Y + 226 |
| 228 | 1 and 467 | Y + 227 |
| 229 | 1 and 466 | Y + 228 |
| 230 | 1 and 465 | Y + 229 |
| 231 | 1 and 464 | Y + 230 |
| 232 | 1 and 463 | Y + 231 |
| 233 | 1 and 462 | Y + 232 |
| 234 | 1 and 461 | Y + 233 |

TABLE 10-continued

| Fragments of SEQ ID NOs: 9 and 11. | | |
|---|---|---|
| Fragment Length (amino acids) | Y is any integer selected from between, and including: | Z |
| 235 | 1 and 460 | Y + 234 |
| 236 | 1 and 459 | Y + 235 |
| 237 | 1 and 458 | Y + 236 |
| 238 | 1 and 457 | Y + 237 |
| 239 | 1 and 456 | Y + 238 |
| 240 | 1 and 455 | Y + 239 |
| 241 | 1 and 454 | Y + 240 |
| 242 | 1 and 453 | Y + 241 |
| 243 | 1 and 452 | Y + 242 |
| 244 | 1 and 451 | Y + 243 |
| 245 | 1 and 450 | Y + 244 |
| 246 | 1 and 449 | Y + 245 |
| 247 | 1 and 448 | Y + 246 |
| 248 | 1 and 447 | Y + 247 |
| 249 | 1 and 446 | Y + 248 |
| 250 | 1 and 445 | Y + 249 |
| 251 | 1 and 444 | Y + 250 |
| 252 | 1 and 443 | Y + 251 |
| 253 | 1 and 442 | Y + 252 |
| 254 | 1 and 441 | Y + 253 |
| 255 | 1 and 440 | Y + 254 |
| 256 | 1 and 439 | Y + 255 |
| 257 | 1 and 438 | Y + 256 |
| 258 | 1 and 437 | Y + 257 |
| 259 | 1 and 436 | Y + 258 |
| 260 | 1 and 435 | Y + 259 |
| 261 | 1 and 434 | Y + 260 |
| 262 | 1 and 433 | Y + 261 |
| 263 | 1 and 432 | Y + 262 |
| 264 | 1 and 431 | Y + 263 |
| 265 | 1 and 430 | Y + 264 |
| 266 | 1 and 429 | Y + 265 |
| 267 | 1 and 428 | Y + 266 |
| 268 | 1 and 427 | Y + 267 |
| 269 | 1 and 426 | Y + 268 |
| 270 | 1 and 425 | Y + 269 |
| 271 | 1 and 424 | Y + 270 |
| 272 | 1 and 423 | Y + 271 |
| 273 | 1 and 422 | Y + 272 |
| 274 | 1 and 421 | Y + 273 |
| 275 | 1 and 420 | Y + 274 |
| 276 | 1 and 419 | Y + 275 |
| 277 | 1 and 418 | Y + 276 |
| 278 | 1 and 417 | Y + 277 |
| 279 | 1 and 416 | Y + 278 |
| 280 | 1 and 415 | Y + 279 |
| 281 | 1 and 414 | Y + 280 |
| 282 | 1 and 413 | Y + 281 |
| 283 | 1 and 412 | Y + 282 |
| 284 | 1 and 411 | Y + 283 |
| 285 | 1 and 410 | Y + 284 |
| 286 | 1 and 409 | Y + 285 |
| 287 | 1 and 408 | Y + 286 |
| 288 | 1 and 407 | Y + 287 |
| 289 | 1 and 406 | Y + 288 |
| 290 | 1 and 405 | Y + 289 |
| 291 | 1 and 404 | Y + 290 |
| 292 | 1 and 403 | Y + 291 |
| 293 | 1 and 402 | Y + 292 |
| 294 | 1 and 401 | Y + 293 |
| 295 | 1 and 400 | Y + 294 |
| 296 | 1 and 399 | Y + 295 |
| 297 | 1 and 398 | Y + 296 |
| 298 | 1 and 397 | Y + 297 |
| 299 | 1 and 396 | Y + 298 |
| 300 | 1 and 395 | Y + 299 |
| 301 | 1 and 394 | Y + 300 |
| 302 | 1 and 393 | Y + 301 |
| 303 | 1 and 392 | Y + 302 |
| 304 | 1 and 391 | Y + 303 |
| 305 | 1 and 390 | Y + 304 |
| 306 | 1 and 389 | Y + 305 |

TABLE 10-continued

Fragments of SEQ ID NOs: 9 and 11.

| Fragment Length (amino acids) | Y is any integer selected from between, and including: | Z |
|---|---|---|
| 307 | 1 and 388 | Y + 306 |
| 308 | 1 and 387 | Y + 307 |
| 309 | 1 and 386 | Y + 308 |
| 310 | 1 and 385 | Y + 309 |
| 311 | 1 and 384 | Y + 310 |
| 312 | 1 and 383 | Y + 311 |
| 313 | 1 and 382 | Y + 312 |
| 314 | 1 and 381 | Y + 313 |
| 315 | 1 and 380 | Y + 314 |
| 316 | 1 and 379 | Y + 315 |
| 317 | 1 and 378 | Y + 316 |
| 318 | 1 and 377 | Y + 317 |
| 319 | 1 and 376 | Y + 318 |
| 320 | 1 and 375 | Y + 319 |
| 321 | 1 and 374 | Y + 320 |
| 322 | 1 and 373 | Y + 321 |
| 323 | 1 and 372 | Y + 322 |
| 324 | 1 and 371 | Y + 323 |
| 325 | 1 and 370 | Y + 324 |
| 326 | 1 and 369 | Y + 325 |
| 327 | 1 and 368 | Y + 326 |
| 328 | 1 and 367 | Y + 327 |
| 329 | 1 and 366 | Y + 328 |
| 330 | 1 and 365 | Y + 329 |
| 331 | 1 and 364 | Y + 330 |
| 332 | 1 and 363 | Y + 331 |
| 333 | 1 and 362 | Y + 332 |
| 334 | 1 and 361 | Y + 333 |
| 335 | 1 and 360 | Y + 334 |
| 336 | 1 and 359 | Y + 335 |
| 337 | 1 and 358 | Y + 336 |
| 338 | 1 and 357 | Y + 337 |
| 339 | 1 and 356 | Y + 338 |
| 340 | 1 and 355 | Y + 339 |
| 341 | 1 and 354 | Y + 340 |
| 342 | 1 and 353 | Y + 341 |
| 343 | 1 and 352 | Y + 342 |
| 344 | 1 and 351 | Y + 343 |
| 345 | 1 and 350 | Y + 344 |
| 346 | 1 and 349 | Y + 345 |
| 347 | 1 and 348 | Y + 346 |
| 348 | 1 and 347 | Y + 347 |
| 349 | 1 and 346 | Y + 348 |
| 350 | 1 and 345 | Y + 349 |
| 351 | 1 and 344 | Y + 350 |
| 352 | 1 and 343 | Y + 351 |
| 353 | 1 and 342 | Y + 352 |
| 354 | 1 and 341 | Y + 353 |
| 355 | 1 and 340 | Y + 354 |
| 356 | 1 and 339 | Y + 355 |
| 357 | 1 and 338 | Y + 356 |
| 358 | 1 and 337 | Y + 357 |
| 359 | 1 and 336 | Y + 358 |
| 360 | 1 and 335 | Y + 359 |
| 361 | 1 and 334 | Y + 360 |
| 362 | 1 and 333 | Y + 361 |
| 363 | 1 and 332 | Y + 362 |
| 364 | 1 and 331 | Y + 363 |
| 365 | 1 and 330 | Y + 364 |
| 366 | 1 and 329 | Y + 365 |
| 367 | 1 and 328 | Y + 366 |
| 368 | 1 and 327 | Y + 367 |
| 369 | 1 and 326 | Y + 368 |
| 370 | 1 and 325 | Y + 369 |
| 371 | 1 and 324 | Y + 370 |
| 372 | 1 and 323 | Y + 371 |
| 373 | 1 and 322 | Y + 372 |
| 374 | 1 and 321 | Y + 373 |
| 375 | 1 and 320 | Y + 374 |
| 376 | 1 and 319 | Y + 375 |
| 377 | 1 and 318 | Y + 376 |
| 378 | 1 and 317 | Y + 377 |
| 379 | 1 and 316 | Y + 378 |
| 380 | 1 and 315 | Y + 379 |
| 381 | 1 and 314 | Y + 380 |
| 382 | 1 and 313 | Y + 381 |
| 383 | 1 and 312 | Y + 382 |
| 384 | 1 and 311 | Y + 383 |
| 385 | 1 and 310 | Y + 384 |
| 386 | 1 and 309 | Y + 385 |
| 387 | 1 and 308 | Y + 386 |
| 388 | 1 and 307 | Y + 387 |
| 389 | 1 and 306 | Y + 388 |
| 390 | 1 and 305 | Y + 389 |
| 391 | 1 and 304 | Y + 390 |
| 392 | 1 and 303 | Y + 391 |
| 393 | 1 and 302 | Y + 392 |
| 394 | 1 and 301 | Y + 393 |
| 395 | 1 and 300 | Y + 394 |
| 396 | 1 and 299 | Y + 395 |
| 397 | 1 and 298 | Y + 396 |
| 398 | 1 and 297 | Y + 397 |
| 399 | 1 and 296 | Y + 398 |
| 400 | 1 and 295 | Y + 399 |
| 401 | 1 and 294 | Y + 400 |
| 402 | 1 and 293 | Y + 401 |
| 403 | 1 and 292 | Y + 402 |
| 404 | 1 and 291 | Y + 403 |
| 405 | 1 and 290 | Y + 404 |
| 406 | 1 and 289 | Y + 405 |
| 407 | 1 and 288 | Y + 406 |
| 408 | 1 and 287 | Y + 407 |
| 409 | 1 and 286 | Y + 408 |
| 410 | 1 and 285 | Y + 409 |
| 411 | 1 and 284 | Y + 410 |
| 412 | 1 and 283 | Y + 411 |
| 413 | 1 and 282 | Y + 412 |
| 414 | 1 and 281 | Y + 413 |
| 415 | 1 and 280 | Y + 414 |
| 416 | 1 and 279 | Y + 415 |
| 417 | 1 and 278 | Y + 416 |
| 418 | 1 and 277 | Y + 417 |
| 419 | 1 and 276 | Y + 418 |
| 420 | 1 and 275 | Y + 419 |
| 421 | 1 and 274 | Y + 420 |
| 422 | 1 and 273 | Y + 421 |
| 423 | 1 and 272 | Y + 422 |
| 424 | 1 and 271 | Y + 423 |
| 425 | 1 and 270 | Y + 424 |
| 426 | 1 and 269 | Y + 425 |
| 427 | 1 and 268 | Y + 426 |
| 428 | 1 and 267 | Y + 427 |
| 429 | 1 and 266 | Y + 428 |
| 430 | 1 and 265 | Y + 429 |
| 431 | 1 and 264 | Y + 430 |
| 432 | 1 and 263 | Y + 431 |
| 433 | 1 and 262 | Y + 432 |
| 434 | 1 and 261 | Y + 433 |
| 435 | 1 and 260 | Y + 434 |
| 436 | 1 and 259 | Y + 435 |
| 437 | 1 and 258 | Y + 436 |
| 438 | 1 and 257 | Y + 437 |
| 439 | 1 and 256 | Y + 438 |
| 440 | 1 and 255 | Y + 439 |
| 441 | 1 and 254 | Y + 440 |
| 442 | 1 and 253 | Y + 441 |
| 443 | 1 and 252 | Y + 442 |
| 444 | 1 and 251 | Y + 443 |
| 445 | 1 and 250 | Y + 444 |
| 446 | 1 and 249 | Y + 445 |
| 447 | 1 and 248 | Y + 446 |
| 448 | 1 and 247 | Y + 447 |
| 449 | 1 and 246 | Y + 448 |
| 450 | 1 and 245 | Y + 449 |

TABLE 10-continued

Fragments of SEQ ID NOs: 9 and 11.

| Fragment Length (amino acids) | Y is any integer selected from between, and including: | Z |
|---|---|---|
| 451 | 1 and 244 | Y + 450 |
| 452 | 1 and 243 | Y + 451 |
| 453 | 1 and 242 | Y + 452 |
| 454 | 1 and 241 | Y + 453 |
| 455 | 1 and 240 | Y + 454 |
| 456 | 1 and 239 | Y + 455 |
| 457 | 1 and 238 | Y + 456 |
| 458 | 1 and 237 | Y + 457 |
| 459 | 1 and 236 | Y + 458 |
| 460 | 1 and 235 | Y + 459 |
| 461 | 1 and 234 | Y + 460 |
| 462 | 1 and 233 | Y + 461 |
| 463 | 1 and 232 | Y + 462 |
| 464 | 1 and 231 | Y + 463 |
| 465 | 1 and 230 | Y + 464 |
| 466 | 1 and 229 | Y + 465 |
| 467 | 1 and 228 | Y + 466 |
| 468 | 1 and 227 | Y + 467 |
| 469 | 1 and 226 | Y + 468 |
| 470 | 1 and 225 | Y + 469 |
| 471 | 1 and 224 | Y + 470 |
| 472 | 1 and 223 | Y + 471 |
| 473 | 1 and 222 | Y + 472 |
| 474 | 1 and 221 | Y + 473 |
| 475 | 1 and 220 | Y + 474 |
| 476 | 1 and 219 | Y + 475 |
| 477 | 1 and 218 | Y + 476 |
| 478 | 1 and 217 | Y + 477 |
| 479 | 1 and 216 | Y + 478 |
| 480 | 1 and 215 | Y + 479 |
| 481 | 1 and 214 | Y + 480 |
| 482 | 1 and 213 | Y + 481 |
| 483 | 1 and 212 | Y + 482 |
| 484 | 1 and 211 | Y + 483 |
| 485 | 1 and 210 | Y + 484 |
| 486 | 1 and 209 | Y + 485 |
| 487 | 1 and 208 | Y + 486 |
| 488 | 1 and 207 | Y + 487 |
| 489 | 1 and 206 | Y + 488 |
| 490 | 1 and 205 | Y + 489 |
| 491 | 1 and 204 | Y + 490 |
| 492 | 1 and 203 | Y + 491 |
| 493 | 1 and 202 | Y + 492 |
| 494 | 1 and 201 | Y + 493 |
| 495 | 1 and 200 | Y + 494 |
| 496 | 1 and 199 | Y + 495 |
| 497 | 1 and 198 | Y + 496 |
| 498 | 1 and 197 | Y + 497 |
| 499 | 1 and 196 | Y + 498 |
| 500 | 1 and 195 | Y + 499 |
| 501 | 1 and 194 | Y + 500 |
| 502 | 1 and 193 | Y + 501 |
| 503 | 1 and 192 | Y + 502 |
| 504 | 1 and 191 | Y + 503 |
| 505 | 1 and 190 | Y + 504 |
| 506 | 1 and 189 | Y + 505 |
| 507 | 1 and 188 | Y + 506 |
| 508 | 1 and 187 | Y + 507 |
| 509 | 1 and 186 | Y + 508 |
| 510 | 1 and 185 | Y + 509 |
| 511 | 1 and 184 | Y + 510 |
| 512 | 1 and 183 | Y + 511 |
| 513 | 1 and 182 | Y + 512 |
| 514 | 1 and 181 | Y + 513 |
| 515 | 1 and 180 | Y + 514 |
| 516 | 1 and 179 | Y + 515 |
| 517 | 1 and 178 | Y + 516 |
| 518 | 1 and 177 | Y + 517 |
| 519 | 1 and 176 | Y + 518 |
| 520 | 1 and 175 | Y + 519 |
| 521 | 1 and 174 | Y + 520 |
| 522 | 1 and 173 | Y + 521 |

TABLE 10-continued

Fragments of SEQ ID NOs: 9 and 11.

| Fragment Length (amino acids) | Y is any integer selected from between, and including: | Z |
|---|---|---|
| 523 | 1 and 172 | Y + 522 |
| 524 | 1 and 171 | Y + 523 |
| 525 | 1 and 170 | Y + 524 |
| 526 | 1 and 169 | Y + 525 |
| 527 | 1 and 168 | Y + 526 |
| 528 | 1 and 167 | Y + 527 |
| 529 | 1 and 166 | Y + 528 |
| 530 | 1 and 165 | Y + 529 |
| 531 | 1 and 164 | Y + 530 |
| 532 | 1 and 163 | Y + 531 |
| 533 | 1 and 162 | Y + 532 |
| 534 | 1 and 161 | Y + 533 |
| 535 | 1 and 160 | Y + 534 |
| 536 | 1 and 159 | Y + 535 |
| 537 | 1 and 158 | Y + 536 |
| 538 | 1 and 157 | Y + 537 |
| 539 | 1 and 156 | Y + 538 |
| 540 | 1 and 155 | Y + 539 |
| 541 | 1 and 154 | Y + 540 |
| 542 | 1 and 153 | Y + 541 |
| 543 | 1 and 152 | Y + 542 |
| 544 | 1 and 151 | Y + 543 |
| 545 | 1 and 150 | Y + 544 |
| 546 | 1 and 149 | Y + 545 |
| 547 | 1 and 148 | Y + 546 |
| 548 | 1 and 147 | Y + 547 |
| 549 | 1 and 146 | Y + 548 |
| 550 | 1 and 145 | Y + 549 |
| 551 | 1 and 144 | Y + 550 |
| 552 | 1 and 143 | Y + 551 |
| 553 | 1 and 142 | Y + 552 |
| 554 | 1 and 141 | Y + 553 |
| 555 | 1 and 140 | Y + 554 |
| 556 | 1 and 139 | Y + 555 |
| 557 | 1 and 138 | Y + 556 |
| 558 | 1 and 137 | Y + 557 |
| 559 | 1 and 136 | Y + 558 |
| 560 | 1 and 135 | Y + 559 |
| 561 | 1 and 134 | Y + 560 |
| 562 | 1 and 133 | Y + 561 |
| 563 | 1 and 132 | Y + 562 |
| 564 | 1 and 131 | Y + 563 |
| 565 | 1 and 130 | Y + 564 |
| 566 | 1 and 129 | Y + 565 |
| 567 | 1 and 128 | Y + 566 |
| 568 | 1 and 127 | Y + 567 |
| 569 | 1 and 126 | Y + 568 |
| 570 | 1 and 125 | Y + 569 |
| 571 | 1 and 124 | Y + 570 |
| 572 | 1 and 123 | Y + 571 |
| 573 | 1 and 122 | Y + 572 |
| 574 | 1 and 121 | Y + 573 |
| 575 | 1 and 120 | Y + 574 |
| 576 | 1 and 119 | Y + 575 |
| 577 | 1 and 118 | Y + 576 |
| 578 | 1 and 117 | Y + 577 |
| 579 | 1 and 116 | Y + 578 |
| 580 | 1 and 115 | Y + 579 |
| 581 | 1 and 114 | Y + 580 |
| 582 | 1 and 113 | Y + 581 |
| 583 | 1 and 112 | Y + 582 |
| 584 | 1 and 111 | Y + 583 |
| 585 | 1 and 110 | Y + 584 |
| 586 | 1 and 109 | Y + 585 |
| 587 | 1 and 108 | Y + 586 |
| 588 | 1 and 107 | Y + 587 |
| 589 | 1 and 106 | Y + 588 |
| 590 | 1 and 105 | Y + 589 |
| 591 | 1 and 104 | Y + 590 |
| 592 | 1 and 103 | Y + 591 |
| 593 | 1 and 102 | Y + 592 |
| 594 | 1 and 101 | Y + 593 |

TABLE 10-continued

Fragments of SEQ ID NOs: 9 and 11.

| Fragment Length (amino acids) | Y is any integer selected from between, and including: | Z |
|---|---|---|
| 595 | 1 and 100 | Y + 594 |
| 596 | 1 and 99 | Y + 595 |
| 597 | 1 and 98 | Y + 596 |
| 598 | 1 and 97 | Y + 597 |
| 599 | 1 and 96 | Y + 598 |
| 600 | 1 and 95 | Y + 599 |
| 601 | 1 and 94 | Y + 600 |
| 602 | 1 and 93 | Y + 601 |
| 603 | 1 and 92 | Y + 602 |
| 604 | 1 and 91 | Y + 603 |
| 605 | 1 and 90 | Y + 604 |
| 606 | 1 and 89 | Y + 605 |
| 607 | 1 and 88 | Y + 606 |
| 608 | 1 and 87 | Y + 607 |
| 609 | 1 and 86 | Y + 608 |
| 610 | 1 and 85 | Y + 609 |
| 611 | 1 and 84 | Y + 610 |
| 612 | 1 and 83 | Y + 611 |
| 613 | 1 and 82 | Y + 612 |
| 614 | 1 and 81 | Y + 613 |
| 615 | 1 and 80 | Y + 614 |
| 616 | 1 and 79 | Y + 615 |
| 617 | 1 and 78 | Y + 616 |
| 618 | 1 and 77 | Y + 617 |
| 619 | 1 and 76 | Y + 618 |
| 620 | 1 and 75 | Y + 619 |
| 621 | 1 and 74 | Y + 620 |
| 622 | 1 and 73 | Y + 621 |
| 623 | 1 and 72 | Y + 622 |
| 624 | 1 and 71 | Y + 623 |
| 625 | 1 and 70 | Y + 624 |
| 626 | 1 and 69 | Y + 625 |
| 627 | 1 and 68 | Y + 626 |
| 628 | 1 and 67 | Y + 627 |
| 629 | 1 and 66 | Y + 628 |
| 630 | 1 and 65 | Y + 629 |
| 631 | 1 and 64 | Y + 630 |
| 632 | 1 and 63 | Y + 631 |
| 633 | 1 and 62 | Y + 632 |
| 634 | 1 and 61 | Y + 633 |
| 635 | 1 and 60 | Y + 634 |
| 636 | 1 and 59 | Y + 635 |
| 637 | 1 and 58 | Y + 636 |
| 638 | 1 and 57 | Y + 637 |
| 639 | 1 and 56 | Y + 638 |
| 640 | 1 and 55 | Y + 639 |
| 641 | 1 and 54 | Y + 640 |
| 642 | 1 and 53 | Y + 641 |
| 643 | 1 and 52 | Y + 642 |
| 644 | 1 and 51 | Y + 643 |
| 645 | 1 and 50 | Y + 644 |
| 646 | 1 and 49 | Y + 645 |
| 647 | 1 and 48 | Y + 646 |
| 648 | 1 and 47 | Y + 647 |
| 649 | 1 and 46 | Y + 648 |
| 650 | 1 and 45 | Y + 649 |
| 651 | 1 and 44 | Y + 650 |
| 652 | 1 and 43 | Y + 651 |
| 653 | 1 and 42 | Y + 652 |
| 654 | 1 and 41 | Y + 653 |
| 655 | 1 and 40 | Y + 654 |
| 656 | 1 and 39 | Y + 655 |
| 657 | 1 and 38 | Y + 656 |
| 658 | 1 and 37 | Y + 657 |
| 659 | 1 and 36 | Y + 658 |
| 660 | 1 and 35 | Y + 659 |
| 661 | 1 and 34 | Y + 660 |
| 662 | 1 and 33 | Y + 661 |
| 663 | 1 and 32 | Y + 662 |
| 664 | 1 and 31 | Y + 663 |
| 665 | 1 and 30 | Y + 664 |
| 666 | 1 and 29 | Y + 665 |

TABLE 10-continued

Fragments of SEQ ID NOs: 9 and 11.

| Fragment Length (amino acids) | Y is any integer selected from between, and including: | Z |
|---|---|---|
| 667 | 1 and 28 | Y + 666 |
| 668 | 1 and 27 | Y + 667 |
| 669 | 1 and 26 | Y + 668 |
| 670 | 1 and 25 | Y + 669 |
| 671 | 1 and 24 | Y + 670 |
| 672 | 1 and 23 | Y + 671 |
| 673 | 1 and 22 | Y + 672 |
| 674 | 1 and 21 | Y + 673 |
| 675 | 1 and 20 | Y + 674 |
| 676 | 1 and 19 | Y + 675 |
| 677 | 1 and 18 | Y + 676 |
| 678 | 1 and 17 | Y + 677 |
| 679 | 1 and 16 | Y + 678 |
| 680 | 1 and 15 | Y + 679 |
| 681 | 1 and 14 | Y + 680 |
| 682 | 1 and 13 | Y + 681 |
| 683 | 1 and 12 | Y + 682 |
| 684 | 1 and 11 | Y + 683 |
| 685 | 1 and 10 | Y + 684 |
| 686 | 1 and 9 | Y + 685 |
| 687 | 1 and 8 | Y + 686 |
| 688 | 1 and 7 | Y + 687 |
| 689 | 1 and 6 | Y + 688 |
| 690 | 1 and 5 | Y + 689 |
| 691 | 1 and 4 | Y + 690 |
| 692 | 1 and 3 | Y + 691 |
| 693 | 1 and 2 | Y + 692 |

TABLE 11

Fragments of SEQ ID NO: 13.

| Fragment Length (amino acids) | Y is any integer selected from between, and including: | Z |
|---|---|---|
| 5 | 1 and 598 | Y + 4 |
| 6 | 1 and 597 | Y + 5 |
| 7 | 1 and 596 | Y + 6 |
| 8 | 1 and 595 | Y + 7 |
| 9 | 1 and 594 | Y + 8 |
| 10 | 1 and 593 | Y + 9 |
| 11 | 1 and 592 | Y + 10 |
| 12 | 1 and 591 | Y + 11 |
| 13 | 1 and 590 | Y + 12 |
| 14 | 1 and 589 | Y + 13 |
| 15 | 1 and 588 | Y + 14 |
| 16 | 1 and 587 | Y + 15 |
| 17 | 1 and 586 | Y + 16 |
| 18 | 1 and 585 | Y + 17 |
| 19 | 1 and 584 | Y + 18 |
| 20 | 1 and 583 | Y + 19 |
| 21 | 1 and 582 | Y + 20 |
| 22 | 1 and 581 | Y + 21 |
| 23 | 1 and 580 | Y + 22 |
| 24 | 1 and 579 | Y + 23 |
| 25 | 1 and 578 | Y + 24 |
| 26 | 1 and 577 | Y + 25 |
| 27 | 1 and 576 | Y + 26 |
| 28 | 1 and 575 | Y + 27 |
| 29 | 1 and 574 | Y + 28 |
| 30 | 1 and 573 | Y + 29 |
| 31 | 1 and 572 | Y + 30 |
| 32 | 1 and 571 | Y + 31 |
| 33 | 1 and 570 | Y + 32 |
| 34 | 1 and 569 | Y + 33 |
| 35 | 1 and 568 | Y + 34 |
| 36 | 1 and 567 | Y + 35 |

TABLE 11-continued

| Fragments of SEQ ID NO: 13. | | |
|---|---|---|
| Fragment Length (amino acids) | Y is any integer selected from between, and including: | Z |
| 37 | 1 and 566 | Y + 36 |
| 38 | 1 and 565 | Y + 37 |
| 39 | 1 and 564 | Y + 38 |
| 40 | 1 and 563 | Y + 39 |
| 41 | 1 and 562 | Y + 40 |
| 42 | 1 and 561 | Y + 41 |
| 43 | 1 and 560 | Y + 42 |
| 44 | 1 and 559 | Y + 43 |
| 45 | 1 and 558 | Y + 44 |
| 46 | 1 and 557 | Y + 45 |
| 47 | 1 and 556 | Y + 46 |
| 48 | 1 and 555 | Y + 47 |
| 49 | 1 and 554 | Y + 48 |
| 50 | 1 and 553 | Y + 49 |
| 51 | 1 and 552 | Y + 50 |
| 52 | 1 and 551 | Y + 51 |
| 53 | 1 and 550 | Y + 52 |
| 54 | 1 and 549 | Y + 53 |
| 55 | 1 and 548 | Y + 54 |
| 56 | 1 and 547 | Y + 55 |
| 57 | 1 and 546 | Y + 56 |
| 58 | 1 and 545 | Y + 57 |
| 59 | 1 and 544 | Y + 58 |
| 60 | 1 and 543 | Y + 59 |
| 61 | 1 and 542 | Y + 60 |
| 62 | 1 and 541 | Y + 61 |
| 63 | 1 and 540 | Y + 62 |
| 64 | 1 and 539 | Y + 63 |
| 65 | 1 and 538 | Y + 64 |
| 66 | 1 and 537 | Y + 65 |
| 67 | 1 and 536 | Y + 66 |
| 68 | 1 and 535 | Y + 67 |
| 69 | 1 and 534 | Y + 68 |
| 70 | 1 and 533 | Y + 69 |
| 71 | 1 and 532 | Y + 70 |
| 72 | 1 and 531 | Y + 71 |
| 73 | 1 and 530 | Y + 72 |
| 74 | 1 and 529 | Y + 73 |
| 75 | 1 and 528 | Y + 74 |
| 76 | 1 and 527 | Y + 75 |
| 77 | 1 and 526 | Y + 76 |
| 78 | 1 and 525 | Y + 77 |
| 79 | 1 and 524 | Y + 78 |
| 80 | 1 and 523 | Y + 79 |
| 81 | 1 and 522 | Y + 80 |
| 82 | 1 and 521 | Y + 81 |
| 83 | 1 and 520 | Y + 82 |
| 84 | 1 and 519 | Y + 83 |
| 85 | 1 and 518 | Y + 84 |
| 86 | 1 and 517 | Y + 85 |
| 87 | 1 and 516 | Y + 86 |
| 88 | 1 and 515 | Y + 87 |
| 89 | 1 and 514 | Y + 88 |
| 90 | 1 and 513 | Y + 89 |
| 91 | 1 and 512 | Y + 90 |
| 92 | 1 and 511 | Y + 91 |
| 93 | 1 and 510 | Y + 92 |
| 94 | 1 and 509 | Y + 93 |
| 95 | 1 and 508 | Y + 94 |
| 96 | 1 and 507 | Y + 95 |
| 97 | 1 and 506 | Y + 96 |
| 98 | 1 and 505 | Y + 97 |
| 99 | 1 and 504 | Y + 98 |
| 100 | 1 and 503 | Y + 99 |
| 101 | 1 and 502 | Y + 100 |
| 102 | 1 and 501 | Y + 101 |
| 103 | 1 and 500 | Y + 102 |
| 104 | 1 and 499 | Y + 103 |
| 105 | 1 and 498 | Y + 104 |
| 106 | 1 and 497 | Y + 105 |
| 107 | 1 and 496 | Y + 106 |
| 108 | 1 and 495 | Y + 107 |

TABLE 11-continued

| Fragments of SEQ ID NO: 13. | | |
|---|---|---|
| Fragment Length (amino acids) | Y is any integer selected from between, and including: | Z |
| 109 | 1 and 494 | Y + 108 |
| 110 | 1 and 493 | Y + 109 |
| 111 | 1 and 492 | Y + 110 |
| 112 | 1 and 491 | Y + 111 |
| 113 | 1 and 490 | Y + 112 |
| 114 | 1 and 489 | Y + 113 |
| 115 | 1 and 488 | Y + 114 |
| 116 | 1 and 487 | Y + 115 |
| 117 | 1 and 486 | Y + 116 |
| 118 | 1 and 485 | Y + 117 |
| 119 | 1 and 484 | Y + 118 |
| 120 | 1 and 483 | Y + 119 |
| 121 | 1 and 482 | Y + 120 |
| 122 | 1 and 481 | Y + 121 |
| 123 | 1 and 480 | Y + 122 |
| 124 | 1 and 479 | Y + 123 |
| 125 | 1 and 478 | Y + 124 |
| 126 | 1 and 477 | Y + 125 |
| 127 | 1 and 476 | Y + 126 |
| 128 | 1 and 475 | Y + 127 |
| 129 | 1 and 474 | Y + 128 |
| 130 | 1 and 473 | Y + 129 |
| 131 | 1 and 472 | Y + 130 |
| 132 | 1 and 471 | Y + 131 |
| 133 | 1 and 470 | Y + 132 |
| 134 | 1 and 469 | Y + 133 |
| 135 | 1 and 468 | Y + 134 |
| 136 | 1 and 467 | Y + 135 |
| 137 | 1 and 466 | Y + 136 |
| 138 | 1 and 465 | Y + 137 |
| 139 | 1 and 464 | Y + 138 |
| 140 | 1 and 463 | Y + 139 |
| 141 | 1 and 462 | Y + 140 |
| 142 | 1 and 461 | Y + 141 |
| 143 | 1 and 460 | Y + 142 |
| 144 | 1 and 459 | Y + 143 |
| 145 | 1 and 458 | Y + 144 |
| 146 | 1 and 457 | Y + 145 |
| 147 | 1 and 456 | Y + 146 |
| 148 | 1 and 455 | Y + 147 |
| 149 | 1 and 454 | Y + 148 |
| 150 | 1 and 453 | Y + 149 |
| 151 | 1 and 452 | Y + 150 |
| 152 | 1 and 451 | Y + 151 |
| 153 | 1 and 450 | Y + 152 |
| 154 | 1 and 449 | Y + 153 |
| 155 | 1 and 448 | Y + 154 |
| 156 | 1 and 447 | Y + 155 |
| 157 | 1 and 446 | Y + 156 |
| 158 | 1 and 445 | Y + 157 |
| 159 | 1 and 444 | Y + 158 |
| 160 | 1 and 443 | Y + 159 |
| 161 | 1 and 442 | Y + 160 |
| 162 | 1 and 441 | Y + 161 |
| 163 | 1 and 440 | Y + 162 |
| 164 | 1 and 439 | Y + 163 |
| 165 | 1 and 438 | Y + 164 |
| 166 | 1 and 437 | Y + 165 |
| 167 | 1 and 436 | Y + 166 |
| 168 | 1 and 435 | Y + 167 |
| 169 | 1 and 434 | Y + 168 |
| 170 | 1 and 433 | Y + 169 |
| 171 | 1 and 432 | Y + 170 |
| 172 | 1 and 431 | Y + 171 |
| 173 | 1 and 430 | Y + 172 |
| 174 | 1 and 429 | Y + 173 |
| 175 | 1 and 428 | Y + 174 |
| 176 | 1 and 427 | Y + 175 |
| 177 | 1 and 426 | Y + 176 |
| 178 | 1 and 425 | Y + 177 |
| 179 | 1 and 424 | Y + 178 |
| 180 | 1 and 423 | Y + 179 |

TABLE 11-continued

Fragments of SEQ ID NO: 13.

| Fragment Length (amino acids) | Y is any integer selected from between, and including: | Z |
|---|---|---|
| 181 | 1 and 422 | Y + 180 |
| 182 | 1 and 421 | Y + 181 |
| 183 | 1 and 420 | Y + 182 |
| 184 | 1 and 419 | Y + 183 |
| 185 | 1 and 418 | Y + 184 |
| 186 | 1 and 417 | Y + 185 |
| 187 | 1 and 416 | Y + 186 |
| 188 | 1 and 415 | Y + 187 |
| 189 | 1 and 414 | Y + 188 |
| 190 | 1 and 413 | Y + 189 |
| 191 | 1 and 412 | Y + 190 |
| 192 | 1 and 411 | Y + 191 |
| 193 | 1 and 410 | Y + 192 |
| 194 | 1 and 409 | Y + 193 |
| 195 | 1 and 408 | Y + 194 |
| 196 | 1 and 407 | Y + 195 |
| 197 | 1 and 406 | Y + 196 |
| 198 | 1 and 405 | Y + 197 |
| 199 | 1 and 404 | Y + 198 |
| 200 | 1 and 403 | Y + 199 |
| 201 | 1 and 402 | Y + 200 |
| 202 | 1 and 401 | Y + 201 |
| 203 | 1 and 400 | Y + 202 |
| 204 | 1 and 399 | Y + 203 |
| 205 | 1 and 398 | Y + 204 |
| 206 | 1 and 397 | Y + 205 |
| 207 | 1 and 396 | Y + 206 |
| 208 | 1 and 395 | Y + 207 |
| 209 | 1 and 394 | Y + 208 |
| 210 | 1 and 393 | Y + 209 |
| 211 | 1 and 392 | Y + 210 |
| 212 | 1 and 391 | Y + 211 |
| 213 | 1 and 390 | Y + 212 |
| 214 | 1 and 389 | Y + 213 |
| 215 | 1 and 388 | Y + 214 |
| 216 | 1 and 387 | Y + 215 |
| 217 | 1 and 386 | Y + 216 |
| 218 | 1 and 385 | Y + 217 |
| 219 | 1 and 384 | Y + 218 |
| 220 | 1 and 383 | Y + 219 |
| 221 | 1 and 382 | Y + 220 |
| 222 | 1 and 381 | Y + 221 |
| 223 | 1 and 380 | Y + 222 |
| 224 | 1 and 379 | Y + 223 |
| 225 | 1 and 378 | Y + 224 |
| 226 | 1 and 377 | Y + 225 |
| 227 | 1 and 376 | Y + 226 |
| 228 | 1 and 375 | Y + 227 |
| 229 | 1 and 374 | Y + 228 |
| 230 | 1 and 373 | Y + 229 |
| 231 | 1 and 372 | Y + 230 |
| 232 | 1 and 371 | Y + 231 |
| 233 | 1 and 370 | Y + 232 |
| 234 | 1 and 369 | Y + 233 |
| 235 | 1 and 368 | Y + 234 |
| 236 | 1 and 367 | Y + 235 |
| 237 | 1 and 366 | Y + 236 |
| 238 | 1 and 365 | Y + 237 |
| 239 | 1 and 364 | Y + 238 |
| 240 | 1 and 363 | Y + 239 |
| 241 | 1 and 362 | Y + 240 |
| 242 | 1 and 361 | Y + 241 |
| 243 | 1 and 360 | Y + 242 |
| 244 | 1 and 359 | Y + 243 |
| 245 | 1 and 358 | Y + 244 |
| 246 | 1 and 357 | Y + 245 |
| 247 | 1 and 356 | Y + 246 |
| 248 | 1 and 355 | Y + 247 |
| 249 | 1 and 354 | Y + 248 |
| 250 | 1 and 353 | Y + 249 |
| 251 | 1 and 352 | Y + 250 |
| 252 | 1 and 351 | Y + 251 |

TABLE 11-continued

Fragments of SEQ ID NO: 13.

| Fragment Length (amino acids) | Y is any integer selected from between, and including: | Z |
|---|---|---|
| 253 | 1 and 350 | Y + 252 |
| 254 | 1 and 349 | Y + 253 |
| 255 | 1 and 348 | Y + 254 |
| 256 | 1 and 347 | Y + 255 |
| 257 | 1 and 346 | Y + 256 |
| 258 | 1 and 345 | Y + 257 |
| 259 | 1 and 344 | Y + 258 |
| 260 | 1 and 343 | Y + 259 |
| 261 | 1 and 342 | Y + 260 |
| 262 | 1 and 341 | Y + 261 |
| 263 | 1 and 340 | Y + 262 |
| 264 | 1 and 339 | Y + 263 |
| 265 | 1 and 338 | Y + 264 |
| 266 | 1 and 337 | Y + 265 |
| 267 | 1 and 336 | Y + 266 |
| 268 | 1 and 335 | Y + 267 |
| 269 | 1 and 334 | Y + 268 |
| 270 | 1 and 333 | Y + 269 |
| 271 | 1 and 332 | Y + 270 |
| 272 | 1 and 331 | Y + 271 |
| 273 | 1 and 330 | Y + 272 |
| 274 | 1 and 329 | Y + 273 |
| 275 | 1 and 328 | Y + 274 |
| 276 | 1 and 327 | Y + 275 |
| 277 | 1 and 326 | Y + 276 |
| 278 | 1 and 325 | Y + 277 |
| 279 | 1 and 324 | Y + 278 |
| 280 | 1 and 323 | Y + 279 |
| 281 | 1 and 322 | Y + 280 |
| 282 | 1 and 321 | Y + 281 |
| 283 | 1 and 320 | Y + 282 |
| 284 | 1 and 319 | Y + 283 |
| 285 | 1 and 318 | Y + 284 |
| 286 | 1 and 317 | Y + 285 |
| 287 | 1 and 316 | Y + 286 |
| 288 | 1 and 315 | Y + 287 |
| 289 | 1 and 314 | Y + 288 |
| 290 | 1 and 313 | Y + 289 |
| 291 | 1 and 312 | Y + 290 |
| 292 | 1 and 311 | Y + 291 |
| 293 | 1 and 310 | Y + 292 |
| 294 | 1 and 309 | Y + 293 |
| 295 | 1 and 308 | Y + 294 |
| 296 | 1 and 307 | Y + 295 |
| 297 | 1 and 306 | Y + 296 |
| 298 | 1 and 305 | Y + 297 |
| 299 | 1 and 304 | Y + 298 |
| 300 | 1 and 303 | Y + 299 |
| 301 | 1 and 302 | Y + 300 |
| 302 | 1 and 301 | Y + 301 |
| 303 | 1 and 300 | Y + 302 |
| 304 | 1 and 299 | Y + 303 |
| 305 | 1 and 298 | Y + 304 |
| 306 | 1 and 297 | Y + 305 |
| 307 | 1 and 296 | Y + 306 |
| 308 | 1 and 295 | Y + 307 |
| 309 | 1 and 294 | Y + 308 |
| 310 | 1 and 293 | Y + 309 |
| 311 | 1 and 292 | Y + 310 |
| 312 | 1 and 291 | Y + 311 |
| 313 | 1 and 290 | Y + 312 |
| 314 | 1 and 289 | Y + 313 |
| 315 | 1 and 288 | Y + 314 |
| 316 | 1 and 287 | Y + 315 |
| 317 | 1 and 286 | Y + 316 |
| 318 | 1 and 285 | Y + 317 |
| 319 | 1 and 284 | Y + 318 |
| 320 | 1 and 283 | Y + 319 |
| 321 | 1 and 282 | Y + 320 |
| 322 | 1 and 281 | Y + 321 |
| 323 | 1 and 280 | Y + 322 |
| 324 | 1 and 279 | Y + 323 |

TABLE 11-continued

| Fragments of SEQ ID NO: 13. | | |
|---|---|---|
| Fragment Length (amino acids) | Y is any integer selected from between, and including: | Z |
| 325 | 1 and 278 | Y + 324 |
| 326 | 1 and 277 | Y + 325 |
| 327 | 1 and 276 | Y + 326 |
| 328 | 1 and 275 | Y + 327 |
| 329 | 1 and 274 | Y + 328 |
| 330 | 1 and 273 | Y + 329 |
| 331 | 1 and 272 | Y + 330 |
| 332 | 1 and 271 | Y + 331 |
| 333 | 1 and 270 | Y + 332 |
| 334 | 1 and 269 | Y + 333 |
| 335 | 1 and 268 | Y + 334 |
| 336 | 1 and 267 | Y + 335 |
| 337 | 1 and 266 | Y + 336 |
| 338 | 1 and 265 | Y + 337 |
| 339 | 1 and 264 | Y + 338 |
| 340 | 1 and 263 | Y + 339 |
| 341 | 1 and 262 | Y + 340 |
| 342 | 1 and 261 | Y + 341 |
| 343 | 1 and 260 | Y + 342 |
| 344 | 1 and 259 | Y + 343 |
| 345 | 1 and 258 | Y + 344 |
| 346 | 1 and 257 | Y + 345 |
| 347 | 1 and 256 | Y + 346 |
| 348 | 1 and 255 | Y + 347 |
| 349 | 1 and 254 | Y + 348 |
| 350 | 1 and 253 | Y + 349 |
| 351 | 1 and 252 | Y + 350 |
| 352 | 1 and 251 | Y + 351 |
| 353 | 1 and 250 | Y + 352 |
| 354 | 1 and 249 | Y + 353 |
| 355 | 1 and 248 | Y + 354 |
| 356 | 1 and 247 | Y + 355 |
| 357 | 1 and 246 | Y + 356 |
| 358 | 1 and 245 | Y + 357 |
| 359 | 1 and 244 | Y + 358 |
| 360 | 1 and 243 | Y + 359 |
| 361 | 1 and 242 | Y + 360 |
| 362 | 1 and 241 | Y + 361 |
| 363 | 1 and 240 | Y + 362 |
| 364 | 1 and 239 | Y + 363 |
| 365 | 1 and 238 | Y + 364 |
| 366 | 1 and 237 | Y + 365 |
| 367 | 1 and 236 | Y + 366 |
| 368 | 1 and 235 | Y + 367 |
| 369 | 1 and 234 | Y + 368 |
| 370 | 1 and 233 | Y + 369 |
| 371 | 1 and 232 | Y + 370 |
| 372 | 1 and 231 | Y + 371 |
| 373 | 1 and 230 | Y + 372 |
| 374 | 1 and 229 | Y + 373 |
| 375 | 1 and 228 | Y + 374 |
| 376 | 1 and 227 | Y + 375 |
| 377 | 1 and 226 | Y + 376 |
| 378 | 1 and 225 | Y + 377 |
| 379 | 1 and 224 | Y + 378 |
| 380 | 1 and 223 | Y + 379 |
| 381 | 1 and 222 | Y + 380 |
| 382 | 1 and 221 | Y + 381 |
| 383 | 1 and 220 | Y + 382 |
| 384 | 1 and 219 | Y + 383 |
| 385 | 1 and 218 | Y + 384 |
| 386 | 1 and 217 | Y + 385 |
| 387 | 1 and 216 | Y + 386 |
| 388 | 1 and 215 | Y + 387 |
| 389 | 1 and 214 | Y + 388 |
| 390 | 1 and 213 | Y + 389 |
| 391 | 1 and 212 | Y + 390 |
| 392 | 1 and 211 | Y + 391 |
| 393 | 1 and 210 | Y + 392 |
| 394 | 1 and 209 | Y + 393 |
| 395 | 1 and 208 | Y + 394 |
| 396 | 1 and 207 | Y + 395 |

TABLE 11-continued

| Fragments of SEQ ID NO: 13. | | |
|---|---|---|
| Fragment Length (amino acids) | Y is any integer selected from between, and including: | Z |
| 397 | 1 and 206 | Y + 396 |
| 398 | 1 and 205 | Y + 397 |
| 399 | 1 and 204 | Y + 398 |
| 400 | 1 and 203 | Y + 399 |
| 401 | 1 and 202 | Y + 400 |
| 402 | 1 and 201 | Y + 401 |
| 403 | 1 and 200 | Y + 402 |
| 404 | 1 and 199 | Y + 403 |
| 405 | 1 and 198 | Y + 404 |
| 406 | 1 and 197 | Y + 405 |
| 407 | 1 and 196 | Y + 406 |
| 408 | 1 and 195 | Y + 407 |
| 409 | 1 and 194 | Y + 408 |
| 410 | 1 and 193 | Y + 409 |
| 411 | 1 and 192 | Y + 410 |
| 412 | 1 and 191 | Y + 411 |
| 413 | 1 and 190 | Y + 412 |
| 414 | 1 and 189 | Y + 413 |
| 415 | 1 and 188 | Y + 414 |
| 416 | 1 and 187 | Y + 415 |
| 417 | 1 and 186 | Y + 416 |
| 418 | 1 and 185 | Y + 417 |
| 419 | 1 and 184 | Y + 418 |
| 420 | 1 and 183 | Y + 419 |
| 421 | 1 and 182 | Y + 420 |
| 422 | 1 and 181 | Y + 421 |
| 423 | 1 and 180 | Y + 422 |
| 424 | 1 and 179 | Y + 423 |
| 425 | 1 and 178 | Y + 424 |
| 426 | 1 and 177 | Y + 425 |
| 427 | 1 and 176 | Y + 426 |
| 428 | 1 and 175 | Y + 427 |
| 429 | 1 and 174 | Y + 428 |
| 430 | 1 and 173 | Y + 429 |
| 431 | 1 and 172 | Y + 430 |
| 432 | 1 and 171 | Y + 431 |
| 433 | 1 and 170 | Y + 432 |
| 434 | 1 and 169 | Y + 433 |
| 435 | 1 and 168 | Y + 434 |
| 436 | 1 and 167 | Y + 435 |
| 437 | 1 and 166 | Y + 436 |
| 438 | 1 and 165 | Y + 437 |
| 439 | 1 and 164 | Y + 438 |
| 440 | 1 and 163 | Y + 439 |
| 441 | 1 and 162 | Y + 440 |
| 442 | 1 and 161 | Y + 441 |
| 443 | 1 and 160 | Y + 442 |
| 444 | 1 and 159 | Y + 443 |
| 445 | 1 and 158 | Y + 444 |
| 446 | 1 and 157 | Y + 445 |
| 447 | 1 and 156 | Y + 446 |
| 448 | 1 and 155 | Y + 447 |
| 449 | 1 and 154 | Y + 448 |
| 450 | 1 and 153 | Y + 449 |
| 451 | 1 and 152 | Y + 450 |
| 452 | 1 and 151 | Y + 451 |
| 453 | 1 and 150 | Y + 452 |
| 454 | 1 and 149 | Y + 453 |
| 455 | 1 and 148 | Y + 454 |
| 456 | 1 and 147 | Y + 455 |
| 457 | 1 and 146 | Y + 456 |
| 458 | 1 and 145 | Y + 457 |
| 459 | 1 and 144 | Y + 458 |
| 460 | 1 and 143 | Y + 459 |
| 461 | 1 and 142 | Y + 460 |
| 462 | 1 and 141 | Y + 461 |
| 463 | 1 and 140 | Y + 462 |
| 464 | 1 and 139 | Y + 463 |
| 465 | 1 and 138 | Y + 464 |
| 466 | 1 and 137 | Y + 465 |
| 467 | 1 and 136 | Y + 466 |
| 468 | 1 and 135 | Y + 467 |

TABLE 11-continued

Fragments of SEQ ID NO: 13.

| Fragment Length (amino acids) | Y is any integer selected from between, and including: | Z |
|---|---|---|
| 469 | 1 and 134 | Y + 468 |
| 470 | 1 and 133 | Y + 469 |
| 471 | 1 and 132 | Y + 470 |
| 472 | 1 and 131 | Y + 471 |
| 473 | 1 and 130 | Y + 472 |
| 474 | 1 and 129 | Y + 473 |
| 475 | 1 and 128 | Y + 474 |
| 476 | 1 and 127 | Y + 475 |
| 477 | 1 and 126 | Y + 476 |
| 478 | 1 and 125 | Y + 477 |
| 479 | 1 and 124 | Y + 478 |
| 480 | 1 and 123 | Y + 479 |
| 481 | 1 and 122 | Y + 480 |
| 482 | 1 and 121 | Y + 481 |
| 483 | 1 and 120 | Y + 482 |
| 484 | 1 and 119 | Y + 483 |
| 485 | 1 and 118 | Y + 484 |
| 486 | 1 and 117 | Y + 485 |
| 487 | 1 and 116 | Y + 486 |
| 488 | 1 and 115 | Y + 487 |
| 489 | 1 and 114 | Y + 488 |
| 490 | 1 and 113 | Y + 489 |
| 491 | 1 and 112 | Y + 490 |
| 492 | 1 and 111 | Y + 491 |
| 493 | 1 and 110 | Y + 492 |
| 494 | 1 and 109 | Y + 493 |
| 495 | 1 and 108 | Y + 494 |
| 496 | 1 and 107 | Y + 495 |
| 497 | 1 and 106 | Y + 496 |
| 498 | 1 and 105 | Y + 497 |
| 499 | 1 and 104 | Y + 498 |
| 500 | 1 and 103 | Y + 499 |
| 501 | 1 and 102 | Y + 500 |
| 502 | 1 and 101 | Y + 501 |
| 503 | 1 and 100 | Y + 502 |
| 504 | 1 and 99 | Y + 503 |
| 505 | 1 and 98 | Y + 504 |
| 506 | 1 and 97 | Y + 505 |
| 507 | 1 and 96 | Y + 506 |
| 508 | 1 and 95 | Y + 507 |
| 509 | 1 and 94 | Y + 508 |
| 510 | 1 and 93 | Y + 509 |
| 511 | 1 and 92 | Y + 510 |
| 512 | 1 and 91 | Y + 511 |
| 513 | 1 and 90 | Y + 512 |
| 514 | 1 and 89 | Y + 513 |
| 515 | 1 and 88 | Y + 514 |
| 516 | 1 and 87 | Y + 515 |
| 517 | 1 and 86 | Y + 516 |
| 518 | 1 and 85 | Y + 517 |
| 519 | 1 and 84 | Y + 518 |
| 520 | 1 and 83 | Y + 519 |
| 521 | 1 and 82 | Y + 520 |
| 522 | 1 and 81 | Y + 521 |
| 523 | 1 and 80 | Y + 522 |
| 524 | 1 and 79 | Y + 523 |
| 525 | 1 and 78 | Y + 524 |
| 526 | 1 and 77 | Y + 525 |
| 527 | 1 and 76 | Y + 526 |
| 528 | 1 and 75 | Y + 527 |
| 529 | 1 and 74 | Y + 528 |
| 530 | 1 and 73 | Y + 529 |
| 531 | 1 and 72 | Y + 530 |
| 532 | 1 and 71 | Y + 531 |
| 533 | 1 and 70 | Y + 532 |
| 534 | 1 and 69 | Y + 533 |
| 535 | 1 and 68 | Y + 534 |
| 536 | 1 and 67 | Y + 535 |
| 537 | 1 and 66 | Y + 536 |
| 538 | 1 and 65 | Y + 537 |
| 539 | 1 and 64 | Y + 538 |
| 540 | 1 and 63 | Y + 539 |

TABLE 11-continued

Fragments of SEQ ID NO: 13.

| Fragment Length (amino acids) | Y is any integer selected from between, and including: | Z |
|---|---|---|
| 541 | 1 and 62 | Y + 540 |
| 542 | 1 and 61 | Y + 541 |
| 543 | 1 and 60 | Y + 542 |
| 544 | 1 and 59 | Y + 543 |
| 545 | 1 and 58 | Y + 544 |
| 546 | 1 and 57 | Y + 545 |
| 547 | 1 and 56 | Y + 546 |
| 548 | 1 and 55 | Y + 547 |
| 549 | 1 and 54 | Y + 548 |
| 550 | 1 and 53 | Y + 549 |
| 551 | 1 and 52 | Y + 550 |
| 552 | 1 and 51 | Y + 551 |
| 553 | 1 and 50 | Y + 552 |
| 554 | 1 and 49 | Y + 553 |
| 555 | 1 and 48 | Y + 554 |
| 556 | 1 and 47 | Y + 555 |
| 557 | 1 and 46 | Y + 556 |
| 558 | 1 and 45 | Y + 557 |
| 559 | 1 and 44 | Y + 558 |
| 560 | 1 and 43 | Y + 559 |
| 561 | 1 and 42 | Y + 560 |
| 562 | 1 and 41 | Y + 561 |
| 563 | 1 and 40 | Y + 562 |
| 564 | 1 and 39 | Y + 563 |
| 565 | 1 and 38 | Y + 564 |
| 566 | 1 and 37 | Y + 565 |
| 567 | 1 and 36 | Y + 566 |
| 568 | 1 and 35 | Y + 567 |
| 569 | 1 and 34 | Y + 568 |
| 570 | 1 and 33 | Y + 569 |
| 571 | 1 and 32 | Y + 570 |
| 572 | 1 and 31 | Y + 571 |
| 573 | 1 and 30 | Y + 572 |
| 574 | 1 and 29 | Y + 573 |
| 575 | 1 and 28 | Y + 574 |
| 576 | 1 and 27 | Y + 575 |
| 577 | 1 and 26 | Y + 576 |
| 578 | 1 and 25 | Y + 577 |
| 579 | 1 and 24 | Y + 578 |
| 580 | 1 and 23 | Y + 579 |
| 581 | 1 and 22 | Y + 580 |
| 582 | 1 and 21 | Y + 581 |
| 583 | 1 and 20 | Y + 582 |
| 584 | 1 and 19 | Y + 583 |
| 585 | 1 and 18 | Y + 584 |
| 586 | 1 and 17 | Y + 585 |
| 587 | 1 and 16 | Y + 586 |
| 588 | 1 and 15 | Y + 587 |
| 589 | 1 and 14 | Y + 588 |
| 590 | 1 and 13 | Y + 589 |
| 591 | 1 and 12 | Y + 590 |
| 592 | 1 and 11 | Y + 591 |
| 593 | 1 and 10 | Y + 592 |
| 594 | 1 and 9 | Y + 593 |
| 595 | 1 and 8 | Y + 594 |
| 596 | 1 and 7 | Y + 595 |
| 597 | 1 and 6 | Y + 596 |
| 598 | 1 and 5 | Y + 597 |
| 599 | 1 and 4 | Y + 598 |
| 600 | 1 and 3 | Y + 599 |
| 601 | 1 and 2 | Y + 600 |

TABLE 12

Fragments of SEQ ID NO: 15.

| Fragment Length (amino acids) | Y is any integer selected from between, and including: | Z |
|---|---|---|
| 5 | 1 and 597 | Y + 4 |
| 6 | 1 and 596 | Y + 5 |
| 7 | 1 and 595 | Y + 6 |
| 8 | 1 and 594 | Y + 7 |
| 9 | 1 and 593 | Y + 8 |
| 10 | 1 and 592 | Y + 9 |
| 11 | 1 and 591 | Y + 10 |
| 12 | 1 and 590 | Y + 11 |
| 13 | 1 and 589 | Y + 12 |
| 14 | 1 and 588 | Y + 13 |
| 15 | 1 and 587 | Y + 14 |
| 16 | 1 and 586 | Y + 15 |
| 17 | 1 and 585 | Y + 16 |
| 18 | 1 and 584 | Y + 17 |
| 19 | 1 and 583 | Y + 18 |
| 20 | 1 and 582 | Y + 19 |
| 21 | 1 and 581 | Y + 20 |
| 22 | 1 and 580 | Y + 21 |
| 23 | 1 and 579 | Y + 22 |
| 24 | 1 and 578 | Y + 23 |
| 25 | 1 and 577 | Y + 24 |
| 26 | 1 and 576 | Y + 25 |
| 27 | 1 and 575 | Y + 26 |
| 28 | 1 and 574 | Y + 27 |
| 29 | 1 and 573 | Y + 28 |
| 30 | 1 and 572 | Y + 29 |
| 31 | 1 and 571 | Y + 30 |
| 32 | 1 and 570 | Y + 31 |
| 33 | 1 and 569 | Y + 32 |
| 34 | 1 and 568 | Y + 33 |
| 35 | 1 and 567 | Y + 34 |
| 36 | 1 and 566 | Y + 35 |
| 37 | 1 and 565 | Y + 36 |
| 38 | 1 and 564 | Y + 37 |
| 39 | 1 and 563 | Y + 38 |
| 40 | 1 and 562 | Y + 39 |
| 41 | 1 and 561 | Y + 40 |
| 42 | 1 and 560 | Y + 41 |
| 43 | 1 and 559 | Y + 42 |
| 44 | 1 and 558 | Y + 43 |
| 45 | 1 and 557 | Y + 44 |
| 46 | 1 and 556 | Y + 45 |
| 47 | 1 and 555 | Y + 46 |
| 48 | 1 and 554 | Y + 47 |
| 49 | 1 and 553 | Y + 48 |
| 50 | 1 and 552 | Y + 49 |
| 51 | 1 and 551 | Y + 50 |
| 52 | 1 and 550 | Y + 51 |
| 53 | 1 and 549 | Y + 52 |
| 54 | 1 and 548 | Y + 53 |
| 55 | 1 and 547 | Y + 54 |
| 56 | 1 and 546 | Y + 55 |
| 57 | 1 and 545 | Y + 56 |
| 58 | 1 and 544 | Y + 57 |
| 59 | 1 and 543 | Y + 58 |
| 60 | 1 and 542 | Y + 59 |
| 61 | 1 and 541 | Y + 60 |
| 62 | 1 and 540 | Y + 61 |
| 63 | 1 and 539 | Y + 62 |
| 64 | 1 and 538 | Y + 63 |
| 65 | 1 and 537 | Y + 64 |
| 66 | 1 and 536 | Y + 65 |
| 67 | 1 and 535 | Y + 66 |
| 68 | 1 and 534 | Y + 67 |
| 69 | 1 and 533 | Y + 68 |
| 70 | 1 and 532 | Y + 69 |
| 71 | 1 and 531 | Y + 70 |
| 72 | 1 and 530 | Y + 71 |
| 73 | 1 and 529 | Y + 72 |
| 74 | 1 and 528 | Y + 73 |
| 75 | 1 and 527 | Y + 74 |
| 76 | 1 and 526 | Y + 75 |

TABLE 12-continued

Fragments of SEQ ID NO: 15.

| Fragment Length (amino acids) | Y is any integer selected from between, and including: | Z |
|---|---|---|
| 77 | 1 and 525 | Y + 76 |
| 78 | 1 and 524 | Y + 77 |
| 79 | 1 and 523 | Y + 78 |
| 80 | 1 and 522 | Y + 79 |
| 81 | 1 and 521 | Y + 80 |
| 82 | 1 and 520 | Y + 81 |
| 83 | 1 and 519 | Y + 82 |
| 84 | 1 and 518 | Y + 83 |
| 85 | 1 and 517 | Y + 84 |
| 86 | 1 and 516 | Y + 85 |
| 87 | 1 and 515 | Y + 86 |
| 88 | 1 and 514 | Y + 87 |
| 89 | 1 and 513 | Y + 88 |
| 90 | 1 and 512 | Y + 89 |
| 91 | 1 and 511 | Y + 90 |
| 92 | 1 and 510 | Y + 91 |
| 93 | 1 and 509 | Y + 92 |
| 94 | 1 and 508 | Y + 93 |
| 95 | 1 and 507 | Y + 94 |
| 96 | 1 and 506 | Y + 95 |
| 97 | 1 and 505 | Y + 96 |
| 98 | 1 and 504 | Y + 97 |
| 99 | 1 and 503 | Y + 98 |
| 100 | 1 and 502 | Y + 99 |
| 101 | 1 and 501 | Y + 100 |
| 102 | 1 and 500 | Y + 101 |
| 103 | 1 and 499 | Y + 102 |
| 104 | 1 and 498 | Y + 103 |
| 105 | 1 and 497 | Y + 104 |
| 106 | 1 and 496 | Y + 105 |
| 107 | 1 and 495 | Y + 106 |
| 108 | 1 and 494 | Y + 107 |
| 109 | 1 and 493 | Y + 108 |
| 110 | 1 and 492 | Y + 109 |
| 111 | 1 and 491 | Y + 110 |
| 112 | 1 and 490 | Y + 111 |
| 113 | 1 and 489 | Y + 112 |
| 114 | 1 and 488 | Y + 113 |
| 115 | 1 and 487 | Y + 114 |
| 116 | 1 and 486 | Y + 115 |
| 117 | 1 and 485 | Y + 116 |
| 118 | 1 and 484 | Y + 117 |
| 119 | 1 and 483 | Y + 118 |
| 120 | 1 and 482 | Y + 119 |
| 121 | 1 and 481 | Y + 120 |
| 122 | 1 and 480 | Y + 121 |
| 123 | 1 and 479 | Y + 122 |
| 124 | 1 and 478 | Y + 123 |
| 125 | 1 and 477 | Y + 124 |
| 126 | 1 and 476 | Y + 125 |
| 127 | 1 and 475 | Y + 126 |
| 128 | 1 and 474 | Y + 127 |
| 129 | 1 and 473 | Y + 128 |
| 130 | 1 and 472 | Y + 129 |
| 131 | 1 and 471 | Y + 130 |
| 132 | 1 and 470 | Y + 131 |
| 133 | 1 and 469 | Y + 132 |
| 134 | 1 and 468 | Y + 133 |
| 135 | 1 and 467 | Y + 134 |
| 136 | 1 and 466 | Y + 135 |
| 137 | 1 and 465 | Y + 136 |
| 138 | 1 and 464 | Y + 137 |
| 139 | 1 and 463 | Y + 138 |
| 140 | 1 and 462 | Y + 139 |
| 141 | 1 and 461 | Y + 140 |
| 142 | 1 and 460 | Y + 141 |
| 143 | 1 and 459 | Y + 142 |
| 144 | 1 and 458 | Y + 143 |
| 145 | 1 and 457 | Y + 144 |
| 146 | 1 and 456 | Y + 145 |
| 147 | 1 and 455 | Y + 146 |
| 148 | 1 and 454 | Y + 147 |

TABLE 12-continued

Fragments of SEQ ID NO: 15.

| Fragment Length (amino acids) | Y is any integer selected from between, and including: | Z |
|---|---|---|
| 149 | 1 and 453 | Y + 148 |
| 150 | 1 and 452 | Y + 149 |
| 151 | 1 and 451 | Y + 150 |
| 152 | 1 and 450 | Y + 151 |
| 153 | 1 and 449 | Y + 152 |
| 154 | 1 and 448 | Y + 153 |
| 155 | 1 and 447 | Y + 154 |
| 156 | 1 and 446 | Y + 155 |
| 157 | 1 and 445 | Y + 156 |
| 158 | 1 and 444 | Y + 157 |
| 159 | 1 and 443 | Y + 158 |
| 160 | 1 and 442 | Y + 159 |
| 161 | 1 and 441 | Y + 160 |
| 162 | 1 and 440 | Y + 161 |
| 163 | 1 and 439 | Y + 162 |
| 164 | 1 and 438 | Y + 163 |
| 165 | 1 and 437 | Y + 164 |
| 166 | 1 and 436 | Y + 165 |
| 167 | 1 and 435 | Y + 166 |
| 168 | 1 and 434 | Y + 167 |
| 169 | 1 and 433 | Y + 168 |
| 170 | 1 and 432 | Y + 169 |
| 171 | 1 and 431 | Y + 170 |
| 172 | 1 and 430 | Y + 171 |
| 173 | 1 and 429 | Y + 172 |
| 174 | 1 and 428 | Y + 173 |
| 175 | 1 and 427 | Y + 174 |
| 176 | 1 and 426 | Y + 175 |
| 177 | 1 and 425 | Y + 176 |
| 178 | 1 and 424 | Y + 177 |
| 179 | 1 and 423 | Y + 178 |
| 180 | 1 and 422 | Y + 179 |
| 181 | 1 and 421 | Y + 180 |
| 182 | 1 and 420 | Y + 181 |
| 183 | 1 and 419 | Y + 182 |
| 184 | 1 and 418 | Y + 183 |
| 185 | 1 and 417 | Y + 184 |
| 186 | 1 and 416 | Y + 185 |
| 187 | 1 and 415 | Y + 186 |
| 188 | 1 and 414 | Y + 187 |
| 189 | 1 and 413 | Y + 188 |
| 190 | 1 and 412 | Y + 189 |
| 191 | 1 and 411 | Y + 190 |
| 192 | 1 and 410 | Y + 191 |
| 193 | 1 and 409 | Y + 192 |
| 194 | 1 and 408 | Y + 193 |
| 195 | 1 and 407 | Y + 194 |
| 196 | 1 and 406 | Y + 195 |
| 197 | 1 and 405 | Y + 196 |
| 198 | 1 and 404 | Y + 197 |
| 199 | 1 and 403 | Y + 198 |
| 200 | 1 and 402 | Y + 199 |
| 201 | 1 and 401 | Y + 200 |
| 202 | 1 and 400 | Y + 201 |
| 203 | 1 and 399 | Y + 202 |
| 204 | 1 and 398 | Y + 203 |
| 205 | 1 and 397 | Y + 204 |
| 206 | 1 and 396 | Y + 205 |
| 207 | 1 and 395 | Y + 206 |
| 208 | 1 and 394 | Y + 207 |
| 209 | 1 and 393 | Y + 208 |
| 210 | 1 and 392 | Y + 209 |
| 211 | 1 and 391 | Y + 210 |
| 212 | 1 and 390 | Y + 211 |
| 213 | 1 and 389 | Y + 212 |
| 214 | 1 and 388 | Y + 213 |
| 215 | 1 and 387 | Y + 214 |
| 216 | 1 and 386 | Y + 215 |
| 217 | 1 and 385 | Y + 216 |
| 218 | 1 and 384 | Y + 217 |
| 219 | 1 and 383 | Y + 218 |
| 220 | 1 and 382 | Y + 219 |

TABLE 12-continued

Fragments of SEQ ID NO: 15.

| Fragment Length (amino acids) | Y is any integer selected from between, and including: | Z |
|---|---|---|
| 221 | 1 and 381 | Y + 220 |
| 222 | 1 and 380 | Y + 221 |
| 223 | 1 and 379 | Y + 222 |
| 224 | 1 and 378 | Y + 223 |
| 225 | 1 and 377 | Y + 224 |
| 226 | 1 and 376 | Y + 225 |
| 227 | 1 and 375 | Y + 226 |
| 228 | 1 and 374 | Y + 227 |
| 229 | 1 and 373 | Y + 228 |
| 230 | 1 and 372 | Y + 229 |
| 231 | 1 and 371 | Y + 230 |
| 232 | 1 and 370 | Y + 231 |
| 233 | 1 and 369 | Y + 232 |
| 234 | 1 and 368 | Y + 233 |
| 235 | 1 and 367 | Y + 234 |
| 236 | 1 and 366 | Y + 235 |
| 237 | 1 and 365 | Y + 236 |
| 238 | 1 and 364 | Y + 237 |
| 239 | 1 and 363 | Y + 238 |
| 240 | 1 and 362 | Y + 239 |
| 241 | 1 and 361 | Y + 240 |
| 242 | 1 and 360 | Y + 241 |
| 243 | 1 and 359 | Y + 242 |
| 244 | 1 and 358 | Y + 243 |
| 245 | 1 and 357 | Y + 244 |
| 246 | 1 and 356 | Y + 245 |
| 247 | 1 and 355 | Y + 246 |
| 248 | 1 and 354 | Y + 247 |
| 249 | 1 and 353 | Y + 248 |
| 250 | 1 and 352 | Y + 249 |
| 251 | 1 and 351 | Y + 250 |
| 252 | 1 and 350 | Y + 251 |
| 253 | 1 and 349 | Y + 252 |
| 254 | 1 and 348 | Y + 253 |
| 255 | 1 and 347 | Y + 254 |
| 256 | 1 and 346 | Y + 255 |
| 257 | 1 and 345 | Y + 256 |
| 258 | 1 and 344 | Y + 257 |
| 259 | 1 and 343 | Y + 258 |
| 260 | 1 and 342 | Y + 259 |
| 261 | 1 and 341 | Y + 260 |
| 262 | 1 and 340 | Y + 261 |
| 263 | 1 and 339 | Y + 262 |
| 264 | 1 and 338 | Y + 263 |
| 265 | 1 and 337 | Y + 264 |
| 266 | 1 and 336 | Y + 265 |
| 267 | 1 and 335 | Y + 266 |
| 268 | 1 and 334 | Y + 267 |
| 269 | 1 and 333 | Y + 268 |
| 270 | 1 and 332 | Y + 269 |
| 271 | 1 and 331 | Y + 270 |
| 272 | 1 and 330 | Y + 271 |
| 273 | 1 and 329 | Y + 272 |
| 274 | 1 and 328 | Y + 273 |
| 275 | 1 and 327 | Y + 274 |
| 276 | 1 and 326 | Y + 275 |
| 277 | 1 and 325 | Y + 276 |
| 278 | 1 and 324 | Y + 277 |
| 279 | 1 and 323 | Y + 278 |
| 280 | 1 and 322 | Y + 279 |
| 281 | 1 and 321 | Y + 280 |
| 282 | 1 and 320 | Y + 281 |
| 283 | 1 and 319 | Y + 282 |
| 284 | 1 and 318 | Y + 283 |
| 285 | 1 and 317 | Y + 284 |
| 286 | 1 and 316 | Y + 285 |
| 287 | 1 and 315 | Y + 286 |
| 288 | 1 and 314 | Y + 287 |
| 289 | 1 and 313 | Y + 288 |
| 290 | 1 and 312 | Y + 289 |
| 291 | 1 and 311 | Y + 290 |
| 292 | 1 and 310 | Y + 291 |

TABLE 12-continued

Fragments of SEQ ID NO: 15.

| Fragment Length (amino acids) | Y is any integer selected from between, and including: | Z |
|---|---|---|
| 293 | 1 and 309 | Y + 292 |
| 294 | 1 and 308 | Y + 293 |
| 295 | 1 and 307 | Y + 294 |
| 296 | 1 and 306 | Y + 295 |
| 297 | 1 and 305 | Y + 296 |
| 298 | 1 and 304 | Y + 297 |
| 299 | 1 and 303 | Y + 298 |
| 300 | 1 and 302 | Y + 299 |
| 301 | 1 and 301 | Y + 300 |
| 302 | 1 and 300 | Y + 301 |
| 303 | 1 and 299 | Y + 302 |
| 304 | 1 and 298 | Y + 303 |
| 305 | 1 and 297 | Y + 304 |
| 306 | 1 and 296 | Y + 305 |
| 307 | 1 and 295 | Y + 306 |
| 308 | 1 and 294 | Y + 307 |
| 309 | 1 and 293 | Y + 308 |
| 310 | 1 and 292 | Y + 309 |
| 311 | 1 and 291 | Y + 310 |
| 312 | 1 and 290 | Y + 311 |
| 313 | 1 and 289 | Y + 312 |
| 314 | 1 and 288 | Y + 313 |
| 315 | 1 and 287 | Y + 314 |
| 316 | 1 and 286 | Y + 315 |
| 317 | 1 and 285 | Y + 316 |
| 318 | 1 and 284 | Y + 317 |
| 319 | 1 and 283 | Y + 318 |
| 320 | 1 and 282 | Y + 319 |
| 321 | 1 and 281 | Y + 320 |
| 322 | 1 and 280 | Y + 321 |
| 323 | 1 and 279 | Y + 322 |
| 324 | 1 and 278 | Y + 323 |
| 325 | 1 and 277 | Y + 324 |
| 326 | 1 and 276 | Y + 325 |
| 327 | 1 and 275 | Y + 326 |
| 328 | 1 and 274 | Y + 327 |
| 329 | 1 and 273 | Y + 328 |
| 330 | 1 and 272 | Y + 329 |
| 331 | 1 and 271 | Y + 330 |
| 332 | 1 and 270 | Y + 331 |
| 333 | 1 and 269 | Y + 332 |
| 334 | 1 and 268 | Y + 333 |
| 335 | 1 and 267 | Y + 334 |
| 336 | 1 and 266 | Y + 335 |
| 337 | 1 and 265 | Y + 336 |
| 338 | 1 and 264 | Y + 337 |
| 339 | 1 and 263 | Y + 338 |
| 340 | 1 and 262 | Y + 339 |
| 341 | 1 and 261 | Y + 340 |
| 342 | 1 and 260 | Y + 341 |
| 343 | 1 and 259 | Y + 342 |
| 344 | 1 and 258 | Y + 343 |
| 345 | 1 and 257 | Y + 344 |
| 346 | 1 and 256 | Y + 345 |
| 347 | 1 and 255 | Y + 346 |
| 348 | 1 and 254 | Y + 347 |
| 349 | 1 and 253 | Y + 348 |
| 350 | 1 and 252 | Y + 349 |
| 351 | 1 and 251 | Y + 350 |
| 352 | 1 and 250 | Y + 351 |
| 353 | 1 and 249 | Y + 352 |
| 354 | 1 and 248 | Y + 353 |
| 355 | 1 and 247 | Y + 354 |
| 356 | 1 and 246 | Y + 355 |
| 357 | 1 and 245 | Y + 356 |
| 358 | 1 and 244 | Y + 357 |
| 359 | 1 and 243 | Y + 358 |
| 360 | 1 and 242 | Y + 359 |
| 361 | 1 and 241 | Y + 360 |
| 362 | 1 and 240 | Y + 361 |
| 363 | 1 and 239 | Y + 362 |
| 364 | 1 and 238 | Y + 363 |

TABLE 12-continued

Fragments of SEQ ID NO: 15.

| Fragment Length (amino acids) | Y is any integer selected from between, and including: | Z |
|---|---|---|
| 365 | 1 and 237 | Y + 364 |
| 366 | 1 and 236 | Y + 365 |
| 367 | 1 and 235 | Y + 366 |
| 368 | 1 and 234 | Y + 367 |
| 369 | 1 and 233 | Y + 368 |
| 370 | 1 and 232 | Y + 369 |
| 371 | 1 and 231 | Y + 370 |
| 372 | 1 and 230 | Y + 371 |
| 373 | 1 and 229 | Y + 372 |
| 374 | 1 and 228 | Y + 373 |
| 375 | 1 and 227 | Y + 374 |
| 376 | 1 and 226 | Y + 375 |
| 377 | 1 and 225 | Y + 376 |
| 378 | 1 and 224 | Y + 377 |
| 379 | 1 and 223 | Y + 378 |
| 380 | 1 and 222 | Y + 379 |
| 381 | 1 and 221 | Y + 380 |
| 382 | 1 and 220 | Y + 381 |
| 383 | 1 and 219 | Y + 382 |
| 384 | 1 and 218 | Y + 383 |
| 385 | 1 and 217 | Y + 384 |
| 386 | 1 and 216 | Y + 385 |
| 387 | 1 and 215 | Y + 386 |
| 388 | 1 and 214 | Y + 387 |
| 389 | 1 and 213 | Y + 388 |
| 390 | 1 and 212 | Y + 389 |
| 391 | 1 and 211 | Y + 390 |
| 392 | 1 and 210 | Y + 391 |
| 393 | 1 and 209 | Y + 392 |
| 394 | 1 and 208 | Y + 393 |
| 395 | 1 and 207 | Y + 394 |
| 396 | 1 and 206 | Y + 395 |
| 397 | 1 and 205 | Y + 396 |
| 398 | 1 and 204 | Y + 397 |
| 399 | 1 and 203 | Y + 398 |
| 400 | 1 and 202 | Y + 399 |
| 401 | 1 and 201 | Y + 400 |
| 402 | 1 and 200 | Y + 401 |
| 403 | 1 and 199 | Y + 402 |
| 404 | 1 and 198 | Y + 403 |
| 405 | 1 and 197 | Y + 404 |
| 406 | 1 and 196 | Y + 405 |
| 407 | 1 and 195 | Y + 406 |
| 408 | 1 and 194 | Y + 407 |
| 409 | 1 and 193 | Y + 408 |
| 410 | 1 and 192 | Y + 409 |
| 411 | 1 and 191 | Y + 410 |
| 412 | 1 and 190 | Y + 411 |
| 413 | 1 and 189 | Y + 412 |
| 414 | 1 and 188 | Y + 413 |
| 415 | 1 and 187 | Y + 414 |
| 416 | 1 and 186 | Y + 415 |
| 417 | 1 and 185 | Y + 416 |
| 418 | 1 and 184 | Y + 417 |
| 419 | 1 and 183 | Y + 418 |
| 420 | 1 and 182 | Y + 419 |
| 421 | 1 and 181 | Y + 420 |
| 422 | 1 and 180 | Y + 421 |
| 423 | 1 and 179 | Y + 422 |
| 424 | 1 and 178 | Y + 423 |
| 425 | 1 and 177 | Y + 424 |
| 426 | 1 and 176 | Y + 425 |
| 427 | 1 and 175 | Y + 426 |
| 428 | 1 and 174 | Y + 427 |
| 429 | 1 and 173 | Y + 428 |
| 430 | 1 and 172 | Y + 429 |
| 431 | 1 and 171 | Y + 430 |
| 432 | 1 and 170 | Y + 431 |
| 433 | 1 and 169 | Y + 432 |
| 434 | 1 and 168 | Y + 433 |
| 435 | 1 and 167 | Y + 434 |
| 436 | 1 and 166 | Y + 435 |

TABLE 12-continued

| Fragments of SEQ ID NO: 15. | | |
|---|---|---|
| Fragment Length (amino acids) | Y is any integer selected from between, and including: | Z |
| 437 | 1 and 165 | Y + 436 |
| 438 | 1 and 164 | Y + 437 |
| 439 | 1 and 163 | Y + 438 |
| 440 | 1 and 162 | Y + 439 |
| 441 | 1 and 161 | Y + 440 |
| 442 | 1 and 160 | Y + 441 |
| 443 | 1 and 159 | Y + 442 |
| 444 | 1 and 158 | Y + 443 |
| 445 | 1 and 157 | Y + 444 |
| 446 | 1 and 156 | Y + 445 |
| 447 | 1 and 155 | Y + 446 |
| 448 | 1 and 154 | Y + 447 |
| 449 | 1 and 153 | Y + 448 |
| 450 | 1 and 152 | Y + 449 |
| 451 | 1 and 151 | Y + 450 |
| 452 | 1 and 150 | Y + 451 |
| 453 | 1 and 149 | Y + 452 |
| 454 | 1 and 148 | Y + 453 |
| 455 | 1 and 147 | Y + 454 |
| 456 | 1 and 146 | Y + 455 |
| 457 | 1 and 145 | Y + 456 |
| 458 | 1 and 144 | Y + 457 |
| 459 | 1 and 143 | Y + 458 |
| 460 | 1 and 142 | Y + 459 |
| 461 | 1 and 141 | Y + 460 |
| 462 | 1 and 140 | Y + 461 |
| 463 | 1 and 139 | Y + 462 |
| 464 | 1 and 138 | Y + 463 |
| 465 | 1 and 137 | Y + 464 |
| 466 | 1 and 136 | Y + 465 |
| 467 | 1 and 135 | Y + 466 |
| 468 | 1 and 134 | Y + 467 |
| 469 | 1 and 133 | Y + 468 |
| 470 | 1 and 132 | Y + 469 |
| 471 | 1 and 131 | Y + 470 |
| 472 | 1 and 130 | Y + 471 |
| 473 | 1 and 129 | Y + 472 |
| 474 | 1 and 128 | Y + 473 |
| 475 | 1 and 127 | Y + 474 |
| 476 | 1 and 126 | Y + 475 |
| 477 | 1 and 125 | Y + 476 |
| 478 | 1 and 124 | Y + 477 |
| 479 | 1 and 123 | Y + 478 |
| 480 | 1 and 122 | Y + 479 |
| 481 | 1 and 121 | Y + 480 |
| 482 | 1 and 120 | Y + 481 |
| 483 | 1 and 119 | Y + 482 |
| 484 | 1 and 118 | Y + 483 |
| 485 | 1 and 117 | Y + 484 |
| 486 | 1 and 116 | Y + 485 |
| 487 | 1 and 115 | Y + 486 |
| 488 | 1 and 114 | Y + 487 |
| 489 | 1 and 113 | Y + 488 |
| 490 | 1 and 112 | Y + 489 |
| 491 | 1 and 111 | Y + 490 |
| 492 | 1 and 110 | Y + 491 |
| 493 | 1 and 109 | Y + 492 |
| 494 | 1 and 108 | Y + 493 |
| 495 | 1 and 107 | Y + 494 |
| 496 | 1 and 106 | Y + 495 |
| 497 | 1 and 105 | Y + 496 |
| 498 | 1 and 104 | Y + 497 |
| 499 | 1 and 103 | Y + 498 |
| 500 | 1 and 102 | Y + 499 |
| 501 | 1 and 101 | Y + 500 |
| 502 | 1 and 100 | Y + 501 |
| 503 | 1 and 99 | Y + 502 |
| 504 | 1 and 98 | Y + 503 |
| 505 | 1 and 97 | Y + 504 |
| 506 | 1 and 96 | Y + 505 |
| 507 | 1 and 95 | Y + 506 |
| 508 | 1 and 94 | Y + 507 |

TABLE 12-continued

| Fragments of SEQ ID NO: 15. | | |
|---|---|---|
| Fragment Length (amino acids) | Y is any integer selected from between, and including: | Z |
| 509 | 1 and 93 | Y + 508 |
| 510 | 1 and 92 | Y + 509 |
| 511 | 1 and 91 | Y + 510 |
| 512 | 1 and 90 | Y + 511 |
| 513 | 1 and 89 | Y + 512 |
| 514 | 1 and 88 | Y + 513 |
| 515 | 1 and 87 | Y + 514 |
| 516 | 1 and 86 | Y + 515 |
| 517 | 1 and 85 | Y + 516 |
| 518 | 1 and 84 | Y + 517 |
| 519 | 1 and 83 | Y + 518 |
| 520 | 1 and 82 | Y + 519 |
| 521 | 1 and 81 | Y + 520 |
| 522 | 1 and 80 | Y + 521 |
| 523 | 1 and 79 | Y + 522 |
| 524 | 1 and 78 | Y + 523 |
| 525 | 1 and 77 | Y + 524 |
| 526 | 1 and 76 | Y + 525 |
| 527 | 1 and 75 | Y + 526 |
| 528 | 1 and 74 | Y + 527 |
| 529 | 1 and 73 | Y + 528 |
| 530 | 1 and 72 | Y + 529 |
| 531 | 1 and 71 | Y + 530 |
| 532 | 1 and 70 | Y + 531 |
| 533 | 1 and 69 | Y + 532 |
| 534 | 1 and 68 | Y + 533 |
| 535 | 1 and 67 | Y + 534 |
| 536 | 1 and 66 | Y + 535 |
| 537 | 1 and 65 | Y + 536 |
| 538 | 1 and 64 | Y + 537 |
| 539 | 1 and 63 | Y + 538 |
| 540 | 1 and 62 | Y + 539 |
| 541 | 1 and 61 | Y + 540 |
| 542 | 1 and 60 | Y + 541 |
| 543 | 1 and 59 | Y + 542 |
| 544 | 1 and 58 | Y + 543 |
| 545 | 1 and 57 | Y + 544 |
| 546 | 1 and 56 | Y + 545 |
| 547 | 1 and 55 | Y + 546 |
| 548 | 1 and 54 | Y + 547 |
| 549 | 1 and 53 | Y + 548 |
| 550 | 1 and 52 | Y + 549 |
| 551 | 1 and 51 | Y + 550 |
| 552 | 1 and 50 | Y + 551 |
| 553 | 1 and 49 | Y + 552 |
| 554 | 1 and 48 | Y + 553 |
| 555 | 1 and 47 | Y + 554 |
| 556 | 1 and 46 | Y + 555 |
| 557 | 1 and 45 | Y + 556 |
| 558 | 1 and 44 | Y + 557 |
| 559 | 1 and 43 | Y + 558 |
| 560 | 1 and 42 | Y + 559 |
| 561 | 1 and 41 | Y + 560 |
| 562 | 1 and 40 | Y + 561 |
| 563 | 1 and 39 | Y + 562 |
| 564 | 1 and 38 | Y + 563 |
| 565 | 1 and 37 | Y + 564 |
| 566 | 1 and 36 | Y + 565 |
| 567 | 1 and 35 | Y + 566 |
| 568 | 1 and 34 | Y + 567 |
| 569 | 1 and 33 | Y + 568 |
| 570 | 1 and 32 | Y + 569 |
| 571 | 1 and 31 | Y + 570 |
| 572 | 1 and 30 | Y + 571 |
| 573 | 1 and 29 | Y + 572 |
| 574 | 1 and 28 | Y + 573 |
| 575 | 1 and 27 | Y + 574 |
| 576 | 1 and 26 | Y + 575 |
| 577 | 1 and 25 | Y + 576 |
| 578 | 1 and 24 | Y + 577 |
| 579 | 1 and 23 | Y + 578 |
| 580 | 1 and 22 | Y + 579 |

TABLE 12-continued

| Fragments of SEQ ID NO: 15. | | |
|---|---|---|
| Fragment Length (amino acids) | Y is any integer selected from between, and including: | Z |
| 581 | 1 and 21 | Y + 580 |
| 582 | 1 and 20 | Y + 581 |
| 583 | 1 and 19 | Y + 582 |
| 584 | 1 and 18 | Y + 583 |
| 585 | 1 and 17 | Y + 584 |
| 586 | 1 and 16 | Y + 585 |
| 587 | 1 and 15 | Y + 586 |
| 588 | 1 and 14 | Y + 587 |
| 589 | 1 and 13 | Y + 588 |
| 590 | 1 and 12 | Y + 589 |
| 591 | 1 and 11 | Y + 590 |
| 592 | 1 and 10 | Y + 591 |
| 593 | 1 and 9 | Y + 592 |
| 594 | 1 and 8 | Y + 593 |
| 595 | 1 and 7 | Y + 594 |
| 596 | 1 and 6 | Y + 595 |
| 597 | 1 and 5 | Y + 596 |
| 598 | 1 and 4 | Y + 597 |
| 599 | 1 and 3 | Y + 598 |
| 600 | 1 and 2 | Y + 599 |

TABLE 13

| G + C Content (%) |
|---|
| 40.0 |
| 40.1 |
| 40.2 |
| 40.3 |
| 40.4 |
| 40.5 |
| 40.6 |
| 40.7 |
| 40.8 |
| 40.9 |
| 41.0 |
| 41.1 |
| 41.2 |
| 41.3 |
| 41.4 |
| 41.5 |
| 41.6 |
| 41.7 |
| 41.8 |
| 41.9 |
| 42.0 |
| 42.1 |
| 42.2 |
| 42.3 |
| 42.4 |
| 42.5 |
| 42.6 |
| 42.7 |
| 42.8 |
| 42.9 |
| 43.0 |
| 43.1 |
| 43.2 |
| 43.3 |
| 43.4 |
| 43.5 |
| 43.6 |
| 43.7 |
| 43.8 |
| 43.9 |
| 44.0 |
| 44.1 |
| 44.2 |
| 44.3 |

TABLE 13-continued

| G + C Content (%) |
|---|
| 44.4 |
| 44.5 |
| 44.6 |
| 44.7 |
| 44.8 |
| 44.9 |
| 45.0 |
| 45.1 |
| 45.2 |
| 45.3 |
| 45.4 |
| 45.5 |
| 45.6 |
| 45.7 |
| 45.8 |
| 45.9 |
| 46.0 |
| 46.1 |
| 46.2 |
| 46.3 |
| 46.4 |
| 46.5 |
| 46.6 |
| 46.7 |
| 46.8 |
| 46.9 |
| 47.0 |
| 47.1 |
| 47.2 |
| 47.3 |
| 47.4 |
| 47.5 |
| 47.6 |
| 47.7 |
| 47.8 |
| 47.9 |
| 48.0 |
| 48.1 |
| 48.2 |
| 48.3 |
| 48.4 |
| 48.5 |
| 48.6 |
| 48.7 |
| 48.8 |
| 48.9 |
| 49.0 |
| 49.1 |
| 49.2 |
| 49.3 |
| 49.4 |
| 49.5 |
| 49.6 |
| 49.7 |
| 49.8 |
| 49.9 |
| 50.0 |

TABLE 14

| Percent Identity |
|---|
| 70.0 |
| 70.1 |
| 70.2 |
| 70.3 |
| 70.4 |
| 70.5 |
| 70.6 |
| 70.7 |
| 70.8 |
| 70.9 |
| 71.0 |
| 71.1 |

TABLE 14-continued

| Percent Identity |
| --- |
| 71.2 |
| 71.3 |
| 71.4 |
| 71.5 |
| 71.6 |
| 71.7 |
| 71.8 |
| 71.9 |
| 72.0 |
| 72.1 |
| 72.2 |
| 72.3 |
| 72.4 |
| 72.5 |
| 72.6 |
| 72.7 |
| 72.8 |
| 72.9 |
| 73.0 |
| 73.1 |
| 73.2 |
| 73.3 |
| 73.4 |
| 73.5 |
| 73.6 |
| 73.7 |
| 73.8 |
| 73.9 |
| 74.0 |
| 74.1 |
| 74.2 |
| 74.3 |
| 74.4 |
| 74.5 |
| 74.6 |
| 74.7 |
| 74.8 |
| 74.9 |
| 75.0 |
| 75.1 |
| 75.2 |
| 75.3 |
| 75.4 |
| 75.5 |
| 75.6 |
| 75.7 |
| 75.8 |
| 75.9 |
| 76.0 |
| 76.1 |
| 76.2 |
| 76.3 |
| 76.4 |
| 76.5 |
| 76.6 |
| 76.7 |
| 76.8 |
| 76.9 |
| 77.0 |
| 77.1 |
| 77.2 |
| 77.3 |
| 77.4 |
| 77.5 |
| 77.6 |
| 77.7 |
| 77.8 |
| 77.9 |
| 78.0 |
| 78.1 |
| 78.2 |
| 78.3 |
| 78.4 |
| 78.5 |
| 78.6 |
| 78.7 |
| 78.8 |

TABLE 14-continued

| Percent Identity |
| --- |
| 78.9 |
| 79.0 |
| 79.1 |
| 79.2 |
| 79.3 |
| 79.4 |
| 79.5 |
| 79.6 |
| 79.7 |
| 79.8 |
| 79.9 |
| 80.0 |
| 80.1 |
| 80.2 |
| 80.3 |
| 80.4 |
| 80.5 |
| 80.6 |
| 80.7 |
| 80.8 |
| 80.9 |
| 81.0 |
| 81.1 |
| 81.2 |
| 81.3 |
| 81.4 |
| 81.5 |
| 81.6 |
| 81.7 |
| 81.8 |
| 81.9 |
| 82.0 |
| 82.1 |
| 82.2 |
| 82.3 |
| 82.4 |
| 82.5 |
| 82.6 |
| 82.7 |
| 82.8 |
| 82.9 |
| 83.0 |
| 83.1 |
| 83.2 |
| 83.3 |
| 83.4 |
| 83.5 |
| 83.6 |
| 83.7 |
| 83.8 |
| 83.9 |
| 84.0 |
| 84.1 |
| 84.2 |
| 84.3 |
| 84.4 |
| 84.5 |
| 84.6 |
| 84.7 |
| 84.8 |
| 84.9 |
| 85.0 |
| 85.1 |
| 85.2 |
| 85.3 |
| 85.4 |
| 85.5 |
| 85.6 |
| 85.7 |
| 85.8 |
| 85.9 |
| 86.0 |
| 86.1 |
| 86.2 |
| 86.3 |
| 86.4 |
| 86.5 |

TABLE 14-continued

| Percent Identity |
|---|
| 86.6 |
| 86.7 |
| 86.8 |
| 86.9 |
| 87.0 |
| 87.1 |
| 87.2 |
| 87.3 |
| 87.4 |
| 87.5 |
| 87.6 |
| 87.7 |
| 87.8 |
| 87.9 |
| 88.0 |
| 88.1 |
| 88.2 |
| 88.3 |
| 88.4 |
| 88.5 |
| 88.6 |
| 88.7 |
| 88.8 |
| 88.9 |
| 89.0 |
| 89.1 |
| 89.2 |
| 89.3 |
| 89.4 |
| 89.5 |
| 89.6 |
| 89.7 |
| 89.8 |
| 89.9 |
| 90.0 |
| 90.1 |
| 90.2 |
| 90.3 |
| 90.4 |
| 90.5 |
| 90.6 |
| 90.7 |
| 90.8 |
| 90.9 |
| 91.0 |
| 91.1 |
| 91.2 |
| 91.3 |
| 91.4 |
| 91.5 |
| 91.6 |
| 91.7 |
| 91.8 |
| 91.9 |
| 92.0 |
| 92.1 |
| 92.2 |
| 92.3 |
| 92.4 |
| 92.5 |
| 92.6 |
| 92.7 |
| 92.8 |
| 92.9 |
| 93.0 |
| 93.1 |
| 93.2 |
| 93.3 |
| 93.4 |
| 93.5 |
| 93.6 |
| 93.7 |
| 93.8 |
| 93.9 |
| 94.0 |
| 94.1 |
| 94.2 |
| 94.3 |
| 94.4 |
| 94.5 |
| 94.6 |
| 94.7 |
| 94.8 |
| 94.9 |
| 95.0 |
| 95.1 |
| 95.2 |
| 95.3 |
| 95.4 |
| 95.5 |
| 95.6 |
| 95.7 |
| 95.8 |
| 95.9 |
| 96.0 |
| 96.1 |
| 96.2 |
| 96.3 |
| 96.4 |
| 96.5 |
| 96.6 |
| 96.7 |
| 96.8 |
| 96.9 |
| 97.0 |
| 97.1 |
| 97.2 |
| 97.3 |
| 97.4 |
| 97.5 |
| 97.6 |
| 97.7 |
| 97.8 |
| 97.9 |
| 98.0 |
| 98.1 |
| 98.2 |
| 98.3 |
| 98.4 |
| 98.5 |
| 98.6 |
| 98.7 |
| 98.8 |
| 98.9 |
| 99.0 |
| 99.1 |
| 99.2 |
| 99.3 |
| 99.4 |
| 99.5 |
| 99.6 |
| 99.7 |
| 99.8 |
| 99.9 |
| 100.0 |

TABLE 15

Exemplary fragments or polypeptide spans containing the following consecutive amino acids of SEQ ID NO: 9.

| Exemplary Polypeptides or Fragments | | | | | |
|---|---|---|---|---|---|
| 1 | 1-22 | | | | |
| 2 | 1-22 | 343 | | | |
| 3 | 1-22 | 343 | 344 | | |
| 4 | 1-22 | 343 | 344 | 345 | |
| 5 | 1-22 | 343 | 344 | 345 | 691-694 |
| 6 | | 343 | | | |

TABLE 15-continued

| Exemplary fragments or polypeptide spans containing the following consecutive amino acids of SEQ ID NO: 9. | | | | |
|---|---|---|---|---|
| Exemplary Polypeptides or Fragments | | | | |
| 7 | 343 | 344 | | |
| 8 | 343 | 344 | 345 | |
| 9 | 343 | 344 | 345 | 691-694 |
| 10 | | 344 | | |
| 11 | | 344 | 345 | 691-694 |
| 12 | | | 345 | |
| 13 | | | 345 | 691-694 |
| 14 | | | | 691-694 |

TABLE 16

Various Exemplary Fragments of SEQ ID NOs: 5, 9, 11, 13 and 15.

| SEQ ID NO: | N-terminal amino acid residue | C-terminal amino acid residue |
|---|---|---|
| 5 | 93 | 668 |
| 5 | 168 | 668 |
| 9 or 11 | 1 | 114 |
| 9 or 11 | 2 | 114 |
| 9 or 11 | 3 | 114 |
| 9 or 11 | 4 | 114 |
| 9 or 11 | 5 | 114 |
| 9 or 11 | 6 | 114 |
| 9 or 11 | 7 | 114 |
| 9 or 11 | 8 | 114 |
| 9 or 11 | 9 | 114 |
| 9 or 11 | 10 | 114 |
| 9 or 11 | 11 | 114 |
| 9 or 11 | 12 | 114 |
| 9 or 11 | 13 | 114 |
| 9 or 11 | 14 | 114 |
| 9 or 11 | 15 | 114 |
| 9 or 11 | 16 | 114 |
| 9 or 11 | 17 | 114 |
| 9 or 11 | 18 | 114 |
| 9 or 11 | 19 | 114 |
| 9 or 11 | 20 | 114 |
| 9 or 11 | 21 | 114 |
| 9 or 11 | 22 | 114 |
| 9 or 11 | 1 | 189 |
| 9 or 11 | 2 | 189 |
| 9 or 11 | 3 | 189 |
| 9 or 11 | 4 | 189 |
| 9 or 11 | 5 | 189 |
| 9 or 11 | 6 | 189 |
| 9 or 11 | 7 | 189 |
| 9 or 11 | 8 | 189 |
| 9 or 11 | 9 | 189 |
| 9 or 11 | 10 | 189 |
| 9 or 11 | 11 | 189 |
| 9 or 11 | 12 | 189 |
| 9 or 11 | 13 | 189 |
| 9 or 11 | 14 | 189 |
| 9 or 11 | 15 | 189 |
| 9 or 11 | 16 | 189 |
| 9 or 11 | 17 | 189 |
| 9 or 11 | 18 | 189 |
| 9 or 11 | 19 | 189 |
| 9 or 11 | 20 | 189 |
| 9 or 11 | 21 | 189 |
| 9 or 11 | 22 | 189 |
| 9 or 11 | 1 | 690 |
| 9 or 11 | 2 | 690 |
| 9 or 11 | 3 | 690 |
| 9 or 11 | 4 | 690 |
| 9 or 11 | 5 | 690 |

TABLE 16-continued

Various Exemplary Fragments of SEQ ID NOs: 5, 9, 11, 13 and 15.

| SEQ ID NO: | N-terminal amino acid residue | C-terminal amino acid residue |
|---|---|---|
| 9 or 11 | 6 | 690 |
| 9 or 11 | 7 | 690 |
| 9 or 11 | 8 | 690 |
| 9 or 11 | 9 | 690 |
| 9 or 11 | 10 | 690 |
| 9 or 11 | 11 | 690 |
| 9 or 11 | 12 | 690 |
| 9 or 11 | 13 | 690 |
| 9 or 11 | 14 | 690 |
| 9 or 11 | 15 | 690 |
| 9 or 11 | 16 | 690 |
| 9 or 11 | 17 | 690 |
| 9 or 11 | 18 | 690 |
| 9 or 11 | 19 | 690 |
| 9 or 11 | 20 | 690 |
| 9 or 11 | 21 | 690 |
| 9 or 11 | 22 | 690 |
| 9 or 11 | 1 | 691 |
| 9 or 11 | 2 | 691 |
| 9 or 11 | 3 | 691 |
| 9 or 11 | 4 | 691 |
| 9 or 11 | 5 | 691 |
| 9 or 11 | 6 | 691 |
| 9 or 11 | 7 | 691 |
| 9 or 11 | 8 | 691 |
| 9 or 11 | 9 | 691 |
| 9 or 11 | 10 | 691 |
| 9 or 11 | 11 | 691 |
| 9 or 11 | 12 | 691 |
| 9 or 11 | 13 | 691 |
| 9 or 11 | 14 | 691 |
| 9 or 11 | 15 | 691 |
| 9 or 11 | 16 | 691 |
| 9 or 11 | 17 | 691 |
| 9 or 11 | 18 | 691 |
| 9 or 11 | 19 | 691 |
| 9 or 11 | 20 | 691 |
| 9 or 11 | 21 | 691 |
| 9 or 11 | 22 | 691 |
| 9 or 11 | 1 | 692 |
| 9 or 11 | 2 | 692 |
| 9 or 11 | 3 | 692 |
| 9 or 11 | 4 | 692 |
| 9 or 11 | 5 | 692 |
| 9 or 11 | 6 | 692 |
| 9 or 11 | 7 | 692 |
| 9 or 11 | 8 | 692 |
| 9 or 11 | 9 | 692 |
| 9 or 11 | 10 | 692 |
| 9 or 11 | 11 | 692 |
| 9 or 11 | 12 | 692 |
| 9 or 11 | 13 | 692 |
| 9 or 11 | 14 | 692 |
| 9 or 11 | 15 | 692 |
| 9 or 11 | 16 | 692 |
| 9 or 11 | 17 | 692 |
| 9 or 11 | 18 | 692 |
| 9 or 11 | 19 | 692 |
| 9 or 11 | 20 | 692 |
| 9 or 11 | 21 | 692 |
| 9 or 11 | 22 | 692 |
| 9 or 11 | 1 | 693 |
| 9 or 11 | 2 | 693 |
| 9 or 11 | 3 | 693 |
| 9 or 11 | 4 | 693 |
| 9 or 11 | 5 | 693 |
| 9 or 11 | 6 | 693 |
| 9 or 11 | 7 | 693 |
| 9 or 11 | 8 | 693 |
| 9 or 11 | 9 | 693 |
| 9 or 11 | 10 | 693 |
| 9 or 11 | 11 | 693 |

TABLE 16-continued

Various Exemplary Fragments of SEQ ID NOs: 5, 9, 11, 13 and 15.

| SEQ ID NO: | N-terminal amino acid residue | C-terminal amino acid residue |
|---|---|---|
| 9 or 11 | 12 | 693 |
| 9 or 11 | 13 | 693 |
| 9 or 11 | 14 | 693 |
| 9 or 11 | 15 | 693 |
| 9 or 11 | 16 | 693 |
| 9 or 11 | 17 | 693 |
| 9 or 11 | 18 | 693 |
| 9 or 11 | 19 | 693 |
| 9 or 11 | 20 | 693 |
| 9 or 11 | 21 | 693 |
| 9 or 11 | 22 | 693 |
| 9 or 11 | 1 | 694 |
| 9 or 11 | 2 | 694 |
| 9 or 11 | 3 | 694 |
| 9 or 11 | 4 | 694 |
| 9 or 11 | 5 | 694 |
| 9 or 11 | 6 | 694 |
| 9 or 11 | 7 | 694 |
| 9 or 11 | 8 | 694 |
| 9 or 11 | 9 | 694 |
| 9 or 11 | 10 | 694 |
| 9 or 11 | 11 | 694 |
| 9 or 11 | 12 | 694 |
| 9 or 11 | 13 | 694 |
| 9 or 11 | 14 | 694 |
| 9 or 11 | 15 | 694 |
| 9 or 11 | 16 | 694 |
| 9 or 11 | 17 | 694 |
| 9 or 11 | 18 | 694 |
| 9 or 11 | 19 | 694 |
| 9 or 11 | 20 | 694 |
| 9 or 11 | 21 | 694 |
| 9 or 11 | 22 | 694 |
| 9 or 11 | 23 | 690 |
| 9 or 11 | 23 | 691 |
| 9 or 11 | 23 | 692 |
| 9 or 11 | 23 | 693 |
| 9 or 11 | 23 | 694 |
| 9 or 11 | 115 | 690 |
| 9 or 11 | 115 | 691 |
| 9 or 11 | 115 | 692 |
| 9 or 11 | 115 | 693 |
| 9 or 11 | 115 | 694 |
| 9 or 11 | 190 | 690 |
| 9 or 11 | 190 | 691 |
| 9 or 11 | 190 | 692 |
| 9 or 11 | 190 | 693 |
| 9 or 11 | 190 | 694 |
| 13 | 1 | 97 |
| 13 | 2 | 97 |
| 13 | 3 | 97 |
| 13 | 4 | 97 |
| 13 | 5 | 97 |
| 13 | 6 | 97 |
| 13 | 7 | 97 |
| 13 | 8 | 97 |
| 13 | 9 | 97 |
| 13 | 10 | 97 |
| 13 | 11 | 97 |
| 13 | 12 | 97 |
| 13 | 13 | 97 |
| 13 | 14 | 97 |
| 13 | 15 | 97 |
| 13 | 16 | 97 |
| 13 | 17 | 97 |
| 13 | 18 | 97 |
| 13 | 19 | 97 |
| 13 | 20 | 97 |
| 13 | 21 | 97 |
| 13 | 22 | 97 |
| 13 | 1 | 598 |
| 13 | 2 | 598 |

TABLE 16-continued

Various Exemplary Fragments of SEQ ID NOs: 5, 9, 11, 13 and 15.

| SEQ ID NO: | N-terminal amino acid residue | C-terminal amino acid residue |
|---|---|---|
| 13 | 3 | 598 |
| 13 | 4 | 598 |
| 13 | 5 | 598 |
| 13 | 6 | 598 |
| 13 | 7 | 598 |
| 13 | 8 | 598 |
| 13 | 9 | 598 |
| 13 | 10 | 598 |
| 13 | 11 | 598 |
| 13 | 12 | 598 |
| 13 | 13 | 598 |
| 13 | 14 | 598 |
| 13 | 15 | 598 |
| 13 | 16 | 598 |
| 13 | 17 | 598 |
| 13 | 18 | 598 |
| 13 | 19 | 598 |
| 13 | 20 | 598 |
| 13 | 21 | 598 |
| 13 | 22 | 598 |
| 13 | 1 | 599 |
| 13 | 2 | 599 |
| 13 | 3 | 599 |
| 13 | 4 | 599 |
| 13 | 5 | 599 |
| 13 | 6 | 599 |
| 13 | 7 | 599 |
| 13 | 8 | 599 |
| 13 | 9 | 599 |
| 13 | 10 | 599 |
| 13 | 11 | 599 |
| 13 | 12 | 599 |
| 13 | 13 | 599 |
| 13 | 14 | 599 |
| 13 | 15 | 599 |
| 13 | 16 | 599 |
| 13 | 17 | 599 |
| 13 | 18 | 599 |
| 13 | 19 | 599 |
| 13 | 20 | 599 |
| 13 | 21 | 599 |
| 13 | 22 | 599 |
| 13 | 1 | 600 |
| 13 | 2 | 600 |
| 13 | 3 | 600 |
| 13 | 4 | 600 |
| 13 | 5 | 600 |
| 13 | 6 | 600 |
| 13 | 7 | 600 |
| 13 | 8 | 600 |
| 13 | 9 | 600 |
| 13 | 10 | 600 |
| 13 | 11 | 600 |
| 13 | 12 | 600 |
| 13 | 13 | 600 |
| 13 | 14 | 600 |
| 13 | 15 | 600 |
| 13 | 16 | 600 |
| 13 | 17 | 600 |
| 13 | 18 | 600 |
| 13 | 19 | 600 |
| 13 | 20 | 600 |
| 13 | 21 | 600 |
| 13 | 22 | 600 |
| 13 | 1 | 601 |
| 13 | 2 | 601 |
| 13 | 3 | 601 |
| 13 | 4 | 601 |
| 13 | 5 | 601 |
| 13 | 6 | 601 |
| 13 | 7 | 601 |
| 13 | 8 | 601 |

TABLE 16-continued

Various Exemplary Fragments of SEQ ID NOs: 5, 9, 11, 13 and 15.

| SEQ ID NO: | N-terminal amino acid residue | C-terminal amino acid residue |
|---|---|---|
| 13 | 9 | 601 |
| 13 | 10 | 601 |
| 13 | 11 | 601 |
| 13 | 12 | 601 |
| 13 | 13 | 601 |
| 13 | 14 | 601 |
| 13 | 15 | 601 |
| 13 | 16 | 601 |
| 13 | 17 | 601 |
| 13 | 18 | 601 |
| 13 | 19 | 601 |
| 13 | 20 | 601 |
| 13 | 21 | 601 |
| 13 | 22 | 601 |
| 13 | 1 | 602 |
| 13 | 2 | 602 |
| 13 | 3 | 602 |
| 13 | 4 | 602 |
| 13 | 5 | 602 |
| 13 | 6 | 602 |
| 13 | 7 | 602 |
| 13 | 8 | 602 |
| 13 | 9 | 602 |
| 13 | 10 | 602 |
| 13 | 11 | 602 |
| 13 | 12 | 602 |
| 13 | 13 | 602 |
| 13 | 14 | 602 |
| 13 | 15 | 602 |
| 13 | 16 | 602 |
| 13 | 17 | 602 |
| 13 | 18 | 602 |
| 13 | 19 | 602 |
| 13 | 20 | 602 |
| 13 | 21 | 602 |
| 13 | 22 | 602 |
| 13 | 23 | 599 |
| 13 | 23 | 600 |
| 13 | 23 | 601 |
| 13 | 23 | 602 |
| 13 | 98 | 599 |
| 13 | 98 | 600 |
| 13 | 98 | 601 |
| 13 | 98 | 602 |
| 15 | 1 | 96 |
| 15 | 2 | 96 |
| 15 | 3 | 96 |
| 15 | 4 | 96 |
| 15 | 5 | 96 |
| 15 | 6 | 96 |
| 15 | 7 | 96 |
| 15 | 8 | 96 |
| 15 | 9 | 96 |
| 15 | 10 | 96 |
| 15 | 11 | 96 |
| 15 | 12 | 96 |
| 15 | 13 | 96 |
| 15 | 14 | 96 |
| 15 | 15 | 96 |
| 15 | 16 | 96 |
| 15 | 17 | 96 |
| 15 | 18 | 96 |
| 15 | 19 | 96 |
| 15 | 20 | 96 |
| 15 | 21 | 96 |
| 15 | 1 | 597 |
| 15 | 2 | 597 |
| 15 | 3 | 597 |
| 15 | 4 | 597 |
| 15 | 5 | 597 |
| 15 | 6 | 597 |
| 15 | 7 | 597 |

TABLE 16-continued

Various Exemplary Fragments of SEQ ID NOs: 5, 9, 11, 13 and 15.

| SEQ ID NO: | N-terminal amino acid residue | C-terminal amino acid residue |
|---|---|---|
| 15 | 8 | 597 |
| 15 | 9 | 597 |
| 15 | 10 | 597 |
| 15 | 11 | 597 |
| 15 | 12 | 597 |
| 15 | 13 | 597 |
| 15 | 14 | 597 |
| 15 | 15 | 597 |
| 15 | 16 | 597 |
| 15 | 17 | 597 |
| 15 | 18 | 597 |
| 15 | 19 | 597 |
| 15 | 20 | 597 |
| 15 | 21 | 597 |
| 15 | 1 | 598 |
| 15 | 2 | 598 |
| 15 | 3 | 598 |
| 15 | 4 | 598 |
| 15 | 5 | 598 |
| 15 | 6 | 598 |
| 15 | 7 | 598 |
| 15 | 8 | 598 |
| 15 | 9 | 598 |
| 15 | 10 | 598 |
| 15 | 11 | 598 |
| 15 | 12 | 598 |
| 15 | 13 | 598 |
| 15 | 14 | 598 |
| 15 | 15 | 598 |
| 15 | 16 | 598 |
| 15 | 17 | 598 |
| 15 | 18 | 598 |
| 15 | 19 | 598 |
| 15 | 20 | 598 |
| 15 | 21 | 598 |
| 15 | 1 | 599 |
| 15 | 2 | 599 |
| 15 | 3 | 599 |
| 15 | 4 | 599 |
| 15 | 5 | 599 |
| 15 | 6 | 599 |
| 15 | 7 | 599 |
| 15 | 8 | 599 |
| 15 | 9 | 599 |
| 15 | 10 | 599 |
| 15 | 11 | 599 |
| 15 | 12 | 599 |
| 15 | 13 | 599 |
| 15 | 14 | 599 |
| 15 | 15 | 599 |
| 15 | 16 | 599 |
| 15 | 17 | 599 |
| 15 | 18 | 599 |
| 15 | 19 | 599 |
| 15 | 20 | 599 |
| 15 | 21 | 599 |
| 15 | 1 | 599 |
| 15 | 2 | 599 |
| 15 | 3 | 599 |
| 15 | 4 | 599 |
| 15 | 5 | 599 |
| 15 | 6 | 599 |
| 15 | 7 | 599 |
| 15 | 8 | 599 |
| 15 | 9 | 599 |
| 15 | 10 | 599 |
| 15 | 11 | 599 |
| 15 | 12 | 599 |
| 15 | 13 | 599 |
| 15 | 14 | 599 |
| 15 | 15 | 599 |
| 15 | 16 | 599 |

TABLE 16-continued

| Various Exemplary Fragments of SEQ ID NOs: 5, 9, 11, 13 and 15. | | |
|---|---|---|
| SEQ ID NO: | N-terminal amino acid residue | C-terminal amino acid residue |
| 15 | 17 | 599 |
| 15 | 18 | 599 |
| 15 | 19 | 599 |
| 15 | 20 | 599 |
| 15 | 21 | 599 |
| 15 | 1 | 600 |
| 15 | 2 | 600 |
| 15 | 3 | 600 |
| 15 | 4 | 600 |
| 15 | 5 | 600 |
| 15 | 6 | 600 |
| 15 | 7 | 600 |
| 15 | 8 | 600 |
| 15 | 9 | 600 |
| 15 | 10 | 600 |
| 15 | 11 | 600 |
| 15 | 12 | 600 |
| 15 | 13 | 600 |
| 15 | 14 | 600 |
| 15 | 15 | 600 |
| 15 | 16 | 600 |
| 15 | 17 | 600 |
| 15 | 18 | 600 |
| 15 | 19 | 600 |
| 15 | 20 | 600 |
| 15 | 21 | 600 |
| 15 | 1 | 601 |
| 15 | 2 | 601 |
| 15 | 3 | 601 |
| 15 | 4 | 601 |
| 15 | 5 | 601 |
| 15 | 6 | 601 |
| 15 | 7 | 601 |
| 15 | 8 | 601 |
| 15 | 9 | 601 |
| 15 | 10 | 601 |
| 15 | 11 | 601 |
| 15 | 12 | 601 |
| 15 | 13 | 601 |
| 15 | 14 | 601 |
| 15 | 15 | 601 |
| 15 | 16 | 601 |
| 15 | 17 | 601 |
| 15 | 18 | 601 |
| 15 | 19 | 601 |
| 15 | 20 | 601 |
| 15 | 21 | 601 |
| 15 | 22 | 598 |
| 15 | 22 | 599 |
| 15 | 22 | 600 |
| 15 | 22 | 601 |
| 15 | 97 | 598 |
| 15 | 97 | 599 |
| 15 | 97 | 600 |
| 15 | 97 | 601 |

TABLE 17

Treatment groups for equine efficacy study, testing two dose levels and 2 different adjuvants (Polygen ™ and Carbopol)

| GROUP | TREATMENT | ANTIGEN DOSE | ADJUVANT | # HORSES |
|---|---|---|---|---|
| 1 | Plant cell control 1 | NA | Carbopol | 3 |
| 2 | Plant cell control 2 | NA | Polygen ™ | 3 |
| 3 | Plant-cell-produced WNV vaccine - High Dose PM7 | 10 µg | Carbopol | 10 |
| 4 | Plant-cell-produced WNV vaccine- Low Dose PM7 | 1 µg | Carbopol | 10 |
| 5 | Plant-cell-produced WNV vaccine - High Dose PM7 | 10 µg | Polygen ™ | 10 |
| 6 | Plant-cell-produced WNV vaccine - Low Dose PM7 | 1 µg | Polygen ™ | 10 |

TABLE 18

Vaccine composition for equine efficacy study, testing two dose levels and 2 different adjuvants (Polygen ™ and Carbopol)
WNV Calculations for Protocol 61004
Denotes Required Input

| | |
|---|---|
| Target Dose (ug/dose) | 10 |
| Target Injection Volume (ul) | 1000 |
| Volume/Vaccine needed (ml) | 120 |
| # inj/ml | 1 |

TABLE 18-continued

Vaccine composition for equine efficacy study, testing two dose levels and 2 different adjuvants (Polygen ™ and Carbopol)
WNV Calculations for Protocol 61004
Denotes Required Input

| Stock Solutions | | |
|---|---|---|
| Bulk Antigen content: (ug/ml) | 20 | NB C2004-6A |
| Carbopol Stock | 1000 | Lot CC52NAB635 |
| Polygen 30% stock | 30 | MVP Lot 10011 |

| Formulation Targets: | ug/ml Vac. | ug/dose |
|---|---|---|
| High Antigen (ug/ml) | 10 | 10 |
| Low Antigen (ug/ml) | 1 | 1 |
| Carbopol | 4000 | 4000 |
| Polygen 30% | 15 | 15 |
| Blank Antigen | | |

| Antigen Rehydration | |
|---|---|
| Desired Rehydrated Concentration | 20 |
| Assay before lyophilization (ug/ml) | 20 |
| Original Volume | 70 |
| total ug/vial | 1400 |
| Rehydration Volume | 70 |
| Rehydrated concentration | 20 |
| Total Vials to rehydrate | 1.7 |

NOTES:
If not rehydrating antigen enter antigen assay cell B9
Polygen Values are % volume, Target is 15% Polygen in Vaccine
All Volumes are in ml

| Formulation | NT-1 Control + Carbopol | NT-1 Control + Polygen | High Dose + Carbopol | Low Dose + Carbopol | High Dose + Polygen | Low Dose + Polygen |
|---|---|---|---|---|---|---|
| Volume to produce | 120 | 120 | 120 | 120 | 120 | 120 |
| Blank NT-1 | 60.000 | 60.000 | | | | |
| Antigen-High Dose | | | 60.000 | | 60.000 | |
| Antigen-Low Dose | | | | 6.000 | | 6.000 |
| Carbopol Stock | 48.000 | | 48.000 | 48.000 | | |
| Polygen 30% Stock | | 60.000 | | | 60.000 | 60.000 |
| Water | 12.000 | 0.000 | 12.000 | 66.000 | 0.000 | 54.000 |
| Total | 120.000 | 120.000 | 120.000 | 120.000 | 120.000 | 120.000 |
| Serial No. | C1670-40-A | C1670-40-B | C1670-40-C | C1670-40-D | C1670-40-E | C1670-40-F |

TABLE 19

Physical Properties of Serology Study Vaccines

| Serial Number | Density @ 20° C. | pH | Osmolality |
|---|---|---|---|
| C1670-40-A | 1.0080 | 7.66 | 222 |
| C1670-40-B | 1.0040 | 7.79 | 136 |
| C1670-40-C | 1.0088 | 7.41 | 220 |
| C1670-40-D | 1.0055 | 7.29 | 157 |
| C1670-40-E | 1.0046 | 7.54 | 127 |
| C1670-40-F | 1.0010 | 7.28 | 60 |
| PM7 NT-1 Control | 1.0040 | 8.47 | 143 |
| Bulk Antigen | 1.0057 | 7.97 | 141 |

TABLE 20

| West Nile Virus Serum Neutralizing Titers, equine efficacy study | | | | | | | | | |
|---|---|---|---|---|---|---|---|---|---|
| Group # | Horse # | Day 0 | Day 7 | Day 14 | Day 21 | Day 28 | Day 35 | Day 42 | Day 49 |
| 1 | 132663371 | 2 | 2 | 3 | 4 | 2 | 2 | 2 | 2 |
| 1 | 133134514 | 2 | 2 | 2 | 2 | 2 | 2 | 2 | 2 |
| 1 | 133218532 | 2 | 2 | 2 | 3 | 2 | 2 | 2 | 2 |
| GMT | | 2.0 | 2.0 | 2.3 | 2.9 | 2.0 | 2.0 | 2.0 | 2.0 |
| STD | | 0.0 | 0.0 | 0.6 | 1.0 | 0.0 | 0.0 | 0.0 | 0.0 |
| 2 | 132761220 | 2 | 2 | 2 | 3 | 2 | 2 | 2 | 2 |
| 2 | 133125371 | 2 | 2 | 2 | 2 | 2 | 2 | 2 | 2 |
| 2 | 133339624 | 2 | 2 | 2 | 2 | 2 | 2 | 2 | 2 |
| GMT | | 2.0 | 2.0 | 2.0 | 2.3 | 2.0 | 2.0 | 2.0 | 2.0 |
| STD | | 0.0 | 0.0 | 0.0 | 0.6 | 0.0 | 0.0 | 0.0 | 0.0 |
| 3 | 132713454 | 2 | 13 | 22 | 21 | 32 | 32 | 27 | 32 |
| 3 | 132725167 | 2 | 22 | 46 | 49 | 89 | 128 | 49 | 51 |
| 3 | 133132466 | 2 | 2 | 2 | 4 | 7 | 22 | 12 | 14 |
| 3 | 133167527 | 2 | 3 | 22 | 22 | 54 | 41 | 32 | 38 |
| 3 | 133169647 | 2 | 2 | 5 | 6 | 22 | 21 | 10 | 9 |
| 3 | 133215467 | 2 | 3 | 6 | 13 | 21 | 27 | 16 | 22 |
| 3 | 133216291 | 2 | 6 | 12 | 16 | 20 | 25 | 11 | 1 |
| 3 | 133334763 | 2 | 163 | 326 | 282 | 101 | 157 | 89 | 57 |
| 3 | 133352724 | 2 | 2 | 6 | 18 | 21 | 18 | 11 | 9 |
| 3 | 133353395 | 2 | 2 | 6 | 8 | 20 | 36 | 24 | 24 |
| GMT | | 2.0 | 5.8 | 13.4 | 18.5 | 29.0 | 37.4 | 21.5 | 22.5 |
| STD | | 0.0 | 50.0 | 99.5 | 84.6 | 32.1 | 49.4 | 24.7 | 17.0 |
| 4 | 132714272 | 2 | 2 | 6 | 11 | 45 | 54 | 41 | 45 |
| 4 | 132724335 | 2 | 11 | 112 | 97 | 355 | 256 | 300 | 163 |
| 4 | 132725096 | 2 | 2 | 3 | 8 | 41 | 45 | 25 | 24 |
| 4 | 132752597 | 2 | 5 | 32 | 49 | 71 | 45 | 32 | 45 |
| 4 | 132863266 | 3 | 3 | 9 | 7 | 22 | 25 | 24 | 32 |
| 4 | 133125091 | 2 | 12 | 89 | 140 | 202 | 178 | 81 | 162 |
| 4 | 133133383 | 2 | 2 | 3 | 6 | 73 | 108 | 73 | 56 |
| 4 | 133133523 | 2 | 2 | 10 | 19 | 54 | 97 | 128 | 89 |
| 4 | 133167760 | 2 | 2 | 7 | 22 | 45 | 45 | 36 | 36 |
| 4 | 133213152 | 5 | 5 | 6 | 21 | 20 | 25 | 8 | 27 |
| GMT | | 2.3 | 3.5 | 12.1 | 21.5 | 61.2 | 65.6 | 46.9 | 53.7 |
| STD | | 1.0 | 3.8 | 39.6 | 45.4 | 105.7 | 75.6 | 86.7 | 53.2 |
| 5 | 132668226 | 2 | 2 | 3 | 3 | 16 | 21 | 4 | 6 |
| 5 | 132675665 | 2 | 2 | 2 | 3 | 3 | 4 | 2 | 2 |
| 5 | 132725594 | 2 | 2 | 2 | 2 | 3 | 3 | 2 | 2 |
| 5 | 132844457 | 2 | 2 | 3 | 2 | 2 | 6 | 2 | 2 |
| 5 | 133126771 | 2 | 3 | 5 | 6 | 3 | 5 | 3 | 2 |
| 5 | 133131652 | 2 | 2 | 2 | 2 | 2 | 2 | 2 | 2 |
| 5 | 133164716 | 2 | 4 | 5 | 6 | 5 | 7 | 4 | 6 |
| 5 | 133223315 | 2 | 2 | 2 | 3 | 2 | 2 | 2 | 2 |
| 5 | 133333646 | 2 | 18 | 25 | 14 | 8 | 18 | 6 | 6 |
| 5 | 133349224 | 2 | 5 | 8 | 9 | 3 | 6 | 5 | 2 |
| GMT | | 2.0 | 3.0 | 3.9 | 4.0 | 3.6 | 5.4 | 2.9 | 2.8 |
| STD | | 0.0 | 5.0 | 7.1 | 3.9 | 4.4 | 6.6 | 1.5 | 1.9 |
| 6 | 132652471 | 2 | 3 | 6 | 10 | 9 | 16 | 10 | 6 |
| 6 | 132722692 | 2 | 2 | 2 | 3 | 5 | 7 | 10 | 4 |
| 6 | 132722714 | 2 | 2 | 3 | 4 | 10 | 20 | 6 | 3 |
| 6 | 132728113 | 2 | 2 | 2 | 9 | 14 | 22 | 11 | 22 |
| 6 | 132735313 | 2 | 6 | 7 | 11 | 10 | 7 | 6 | 6 |
| 6 | 132822260 | 2 | 3 | 5 | 6 | 6 | 7 | 6 | 4 |
| 6 | 133125493 | 2 | 3 | 5 | 6 | 7 | 9 | 5 | 4 |
| 6 | 133126691 | 2 | 2 | 5 | 10 | 11 | 14 | 10 | 12 |
| 6 | 133136216 | 2 | 2 | 2 | 3 | 4 | 6 | 3 | 3 |
| 6 | 133162564 | 2 | 2 | 2 | 45 | 3 | 6 | 3 | 5 |
| GMT | | 2.0 | 2.5 | 3.5 | 7.5 | 7.2 | 10.1 | 6.4 | 5.5 |
| STD | | 0.0 | 1.3 | 1.9 | 12.4 | 3.5 | 6.1 | 3.0 | 5.9 |

TABLE 21

| Viremia Data, equine efficacy study<br>Viremia (pfu/mL serum) | | | | | | | | |
|---|---|---|---|---|---|---|---|---|
| Day post challenge | Group 1 Horse | | | Group 2 Horse | | Group 3 Horse | | |
| (am/pm) | 132663371 | 133134514 | 133218532 | 132761220 | 133339624 | 133167527 | 133353395 | 133334763 |
| 0.0 | <5 | <5 | <5 | <5 | <5 | <5 | <5 | <5 |
| 1 (am) | <5 | <5 | <5 | <5 | <5 | <5 | <5 | <5 |
| 1 (pm) | <5 | <5 | <5 | <5 | <5 | <5 | <5 | <5 |

TABLE 21-continued

Viremia Data, equine efficacy study
Viremia (pfu/mL serum)

| | | | | | | | | |
|---|---|---|---|---|---|---|---|---|
| 2 (am) | 50 | 60 | 5 | 70 | 100 | <5 | <5 | <5 |
| 2 (pm) | 5 | 140 | 5 | 5 | 425 | <5 | <5 | <5 |
| 3 (am) | <5 | 75 | <5 | 40 | 340 | <5 | <5 | <5 |
| 3 (pm) | 5 | 25 | 10 | 10 | 375 | <5 | <5 | <5 |
| 4 (am) | <5 | 50 | <5 | 25 | 350 | <5 | <5 | <5 |
| 4 (pm) | <5 | 45 | <5 | <5 | 115 | <5 | <5 | <5 |
| 5 (am) | <5 | <5 | <5 | <5 | 5 | <5 | <5 | <5 |
| 5 (pm) | <5 | <5 | <5 | <5 | <5 | <5 | <5 | <5 |
| 6 (am) | <5 | <5 | <5 | <5 | <5 | <5 | <5 | <5 |
| 6 (pm) | <5 | <5 | <5 | <5 | <5 | <5 | <5 | <5 |
| 7 (am) | <5 | <5 | <5 | <5 | <5 | <5 | <5 | <5 |
| 10 (am) | <5 | <5 | <5 | <5 | <5 | <5 | <5 | <5 |
| 14 (am) | <5 | — | <5 | — | — | <5 | <5 | <5 |

| Day post challenge | Group 3 Horse | | | | | | |
|---|---|---|---|---|---|---|---|
| (am/pm) | 133169647 | 133132466 | 133215467 | 133352724 | 132725167 | 132713454 | 133216291 |
| 0.0 | <5 | <5 | <5 | <5 | <5 | <5 | <5 |
| 1 (am) | <5 | <5 | <5 | <5 | <5 | <5 | <5 |
| 1 (pm) | <5 | <5 | <5 | <5 | <5 | <5 | <5 |
| 2 (am) | <5 | <5 | <5 | <5 | <5 | <5 | <5 |
| 2 (pm) | <5 | <5 | <5 | <5 | <5 | <5 | <5 |
| 3 (am) | <5 | <5 | <5 | <5 | <5 | <5 | <5 |
| 3 (pm) | <5 | <5 | <5 | <5 | <5 | <5 | <5 |
| 4 (am) | <5 | <5 | <5 | <5 | <5 | <5 | <5 |
| 4 (pm) | <5 | <5 | <5 | <5 | <5 | <5 | <5 |
| 5 (am) | <5 | <5 | <5 | <5 | <5 | <5 | <5 |
| 5 (pm) | <5 | <5 | <5 | <5 | ND | <5 | <5 |
| 6 (am) | <5 | <5 | <5 | <5 | <5 | <5 | <5 |
| 6 (pm) | <5 | <5 | <5 | <5 | <5 | <5 | <5 |
| 7 (am) | <5 | <5 | <5 | <5 | <5 | <5 | <5 |
| 10 (am) | <5 | <5 | <5 | <5 | <5 | <5 | <5 |
| 14 (am) | <5 | <5 | <5 | <5 | <5 | <5 | <5 |

TABLE 22

Temperature Data, equine efficacy study
Temperature Post Challenge

| | Group 1 Horse | | | Group 2 Horse | | Group 3 Horse | | |
|---|---|---|---|---|---|---|---|---|
| Day | 132663371 | 133134514 | 133218532 | 132761220 | 133339624 | 133167527 | 133353395 | 133334763 |
| −1 (am) | 101.4 | 100.6 | 102.2 | 100.8 | 102.5 | 101.0 | 101.1 | 100.9 |
| 0 (am) | 101.8 | 101.3 | 102.2 | 101.5 | 102.1 | 101.0 | 101.6 | 101.7 |
| 1 (am) | 101.6 | 100.2 | 100.9 | 100.4 | 100.4 | 101.6 | 101.0 | 101.8 |
| 1 (pm) | 101.6 | 101.2 | 102.6 | 100.6 | 100.9 | 101.4 | 100.2 | 102.6 |
| 2 (am) | 100.2 | 100.6 | 100.8 | 99.6 | 101.0 | 100.2 | 100.6 | 102.0 |
| 2 (pm) | 102.0 | 99.8 | 99.6 | 100.0 | 100.9 | 102.8 | 100.6 | 102.4 |
| 3 (am) | 101.2 | 100.0 | 100.2 | 100.8 | 100.2 | 100.6 | 99.2 | 101.2 |
| 3 (pm) | 100.0 | 100.3 | 99.7 | 99.9 | 100.3 | 102.3 | 101.0 | 101.4 |
| 4 (am) | 100.2 | 99.8 | 100.2 | 100.3 | 100.7 | 100.1 | 100.7 | 101.2 |
| 4 (pm) | 99.9 | 100.6 | 100.7 | 100.0 | 101.2 | 100.8 | 100.2 | 101.4 |
| 5 (am) | 100.2 | 100.3 | 99.7 | 100.2 | 100.1 | 99.8 | 100.3 | 101.4 |
| 5 (pm) | 100.5 | 100.7 | 99.8 | 100.6 | 100.2 | 100.1 | 101.0 | 102.2 |
| 6 (am) | 99.9 | 100.5 | 99.9 | 99.5 | 100.2 | 99.7 | 100.6 | 100.8 |
| 6 (pm) | 99.6 | 100.1 | 101.4 | 100.9 | 99.8 | 100.6 | 100.2 | 101.8 |
| 7 (am) | 100.6 | 100.4 | 100.6 | 100.2 | 99.6 | 100.1 | 9.8 | 100.4 |
| 7 (pm) | 100.2 | 101.4 | 100.2 | 101.0 | 99.8 | 100.6 | 100.2 | 102.4 |
| 8 (am) | 100.6 | 100.5 | 100.0 | 100.1 | 100.7 | 100.3 | 99.5 | 101.0 |
| 8 (pm) | 102.2 | 101.0 | 101.2 | 101.0 | 101.4 | 99.6 | 100.0 | 101.0 |
| 9 (am) | 103.0 | 101.1 | 101.6 | 100.0 | 101.6 | 100.8 | 99.6 | 100.7 |
| 9 (pm) | 104.0 | 103.4 | 103.6 | 101.6 | 104.4 | 102.6 | 100.2 | 100.0 |
| 10 (am) | 102.5 | 103.7 | 104.0 | 102.4 | 104.2 | 100.6 | 100.1 | 100.2 |
| 10 (pm) | 102.8 | | 103.7 | 104.6 | | 100.8 | 101.0 | 102.1 |
| 11 (am) | 101.4 | | 101.6 | 102.0 | | 100.7 | 100.2 | 100.1 |
| 11 (pm) | 101.8 | | 103.2 | 103.2 | | 100.6 | 101.0 | 100.0 |
| 12 (am) | 100.2 | | 101.2 | 100.7 | | 100.1 | 100.5 | 100.6 |
| 12 (pm) | 100.0 | | 101.0 | | | 100.2 | 99.8 | 99.9 |
| 13 (am) | 100.6 | | 100.8 | | | 100.6 | 100.0 | 100.2 |

TABLE 22-continued

Temperature Data, equine efficacy study
Temperature Post Challenge

| | | | | | |
|---|---|---|---|---|---|
| 13 (pm) | 100.2 | 99.6 | 99.9 | 100.7 | 101.6 |
| 14 (am) | 100.8 | 99.6 | 100.0 | 100.6 | 101.0 |

| | Group 3 Horse | | | | | | |
|---|---|---|---|---|---|---|---|
| Day | 133169647 | 133132466 | 133215467 | 133352724 | 132725167 | 132713454 | 133216291 |
| −1 (am) | 101.0 | 101.7 | 100.6 | 100.9 | 101.2 | 100.6 | 102.2 |
| 0 (am) | 100.4 | 102.0 | 100.6 | 100.5 | 100.8 | 100.7 | 101.2 |
| 1 (am) | 100.2 | 101.6 | 101.3 | 101.6 | 101.8 | 100.4 | 100.2 |
| 1 (pm) | 101.2 | 101.0 | 101.2 | 100.2 | 101.6 | 100.8 | 100.2 |
| 2 (am) | 100.0 | 100.2 | 100.8 | 101.0 | 100.2 | 100.1 | 100.9 |
| 2 (pm) | 99.6 | 100.2 | 99.8 | 100.6 | 102.0 | 101.6 | 100.6 |
| 3 (am) | 100.6 | 99.6 | 100.8 | 100.2 | 100.0 | 100.1 | 100.2 |
| 3 (pm) | 99.8 | 100.0 | 100.2 | 99.8 | 100.9 | 100.1 | 100.3 |
| 4 (am) | 101.0 | 99.6 | 100.6 | 101.2 | 100.2 | 100.5 | 100.6 |
| 4 (pm) | 99.6 | 100.0 | 100.6 | 100.0 | 101.0 | 100.2 | 100.3 |
| 5 (am) | 99.6 | 102.0 | 100.0 | 100.2 | 100.1 | 100.4 | 99.8 |
| 5 (pm) | 100.8 | 100.3 | 100.2 | 99.9 | ND | 100.0 | 100.5 |
| 6 (am) | 99.8 | 99.6 | 100.1 | 99.6 | 99.9 | 100.1 | 100.2 |
| 6 (pm) | 100.0 | 100.6 | 100.6 | 100.0 | 100.2 | 100.2 | 100.7 |
| 7 (am) | 100.2 | 102.2 | 100.0 | 99.4 | 100.6 | 100.7 | 99.9 |
| 7 (pm) | 100.2 | 100.6 | 101.0 | 100.4 | 100.6 | 100.0 | 100.6 |
| 8 (am) | 99.6 | 99.2 | 99.7 | 99.6 | 100.1 | 100.2 | 99.9 |
| 8 (pm) | 100.2 | 100.6 | 100.6 | 99.8 | 100.2 | 100.0 | 100.6 |
| 9 (am) | 100.3 | 100.1 | 99.8 | 100.0 | 100.1 | 100.5 | 100.2 |
| 9 (pm) | 102.0 | 100.4 | 100.8 | 100.2 | 101.8 | 99.9 | 100.6 |
| 10 (am) | 100.2 | 100.0 | 100.0 | 100.4 | 101.5 | 99.4 | 100.9 |
| 10 (pm) | 100.8 | 102.8 | 100.6 | 100.2 | 100.3 | 100.6 | 101.4 |
| 11 (am) | 101.0 | 100.9 | 100.0 | 99.8 | 99.6 | 100.2 | 101.6 |
| 11 (pm) | 101.4 | 102.2 | 101.0 | 100.9 | 100.5 | 101.4 | 102.2 |
| 12 (am) | 100.3 | 102.0 | 99.6 | 100.1 | 101.4 | 100.6 | 102.7 |
| 12 (pm) | 100.2 | 100.6 | 100.0 | 100.5 | 100.2 | 101.7 | 103.0 |
| 13 (am) | 100.3 | 100.0 | 100.0 | 100.0 | 99.6 | 101.0 | 101.8 |
| 13 (pm) | 100.2 | 100.0 | 100.3 | 100.6 | 100.5 | 100.8 | 103.0 |
| 14 (am) | 100.4 | 100.2 | 100.7 | 100.5 | 100.2 | 100.3 | 101.2 |

TABLE 23

Clinical Assessment Data, equine efficacy study

| Horse | Group | Day −1 | Day 0 | Day 1 | Day 2 | Day 3 | Day 4 | Day 5 | Day 6 | Day 7 | Day 8 |
|---|---|---|---|---|---|---|---|---|---|---|---|
| 132663371 | 1 | BAR | BAR | BAR | BAR | BAR | BAR | BAR | BAR | BAR | BAR |
| 133134514 | 1 | BAR | BAR | BAR | BAR | BAR | BAR | BAR | BAR | BAR | BAR |
| 133218532 | 1 | BAR | BAR | BAR | BAR | BAR | BAR | BAR | BAR | BAR | BAR |
| 132761220 | 2 | BAR | BAR | BAR | BAR | BAR | BAR | BAR | BAR | BAR | BAR |
| 133339624 | 2 | BAR | BAR | BAR | BAR | BAR | BAR | BAR | BAR | BAR | BAR |
| 133167527 | 3 | BAR | BAR | BAR | BAR | BAR | BAR | BAR | BAR | BAR | BAR |
| 133353395 | 3 | BAR | BAR | BAR | BAR | BAR | BAR | BAR | BAR | BAR | BAR |
| 133334763 | 3 | BAR | BAR | BAR | BAR | BAR | BAR | BAR | BAR | BAR | BAR |
| 133169647 | 3 | BAR | BAR | BAR | BAR | BAR | BAR | BAR | BAR | BAR | BAR |
| 133132466 | 3 | BAR | BAR | BAR | BAR | BAR | BAR | BAR | BAR | hypersensitive | BAR |
| 133215467 | 3 | BAR | BAR | BAR | BAR | BAR | BAR | BAR | BAR | BAR | BAR |
| 133352724 | 3 | BAR | BAR | BAR | BAR | BAR | BAR | BAR | BAR | BAR | BAR |
| 132725167 | 3 | BAR | BAR | BAR | BAR | BAR | BAR | BAR | dull and lethargic | lethargic | BAR |
| 132713454 | 3 | BAR | BAR | BAR | BAR | BAR | BAR | BAR | BAR | BAR | BAR |
| 133216291 | 3 | BAR | BAR | BAR | BAR | BAR | BAR | BAR | BAR | BAR | BAR |

| Horse | Group | Day 9 | Day 10 | Day 11 | Day 12 | Day 13 | Day 14 |
|---|---|---|---|---|---|---|---|
| 132663371 | 1 | BAR | BAR | BAR | BAR | BAR | BAR |
| 133134514 | 1 | BAR | am - dull and slow. pm - very dull, weak euthanized | Dead | Dead | Dead | Dead |
| 133218532 | 1 | BAR | BAR | mild depression | BAR | BAR | BAR |
| 132761220 | 2 | BAR | lip tremors | Mild lip tremors, decreased appetite | lip/head tremors, hypersensitive, reluctant to move neck; euthanized | Dead | Dead |
| 133339624 | 2 | BAR | Head tremors, | Dead | Dead | Dead | Dead |

TABLE 23-continued

Clinical Assessment Data, equine efficacy study

| | | | | | | | |
|---|---|---|---|---|---|---|---|
| | | | severe weakness, chewing; euthanized | | | | |
| 133167527 | 3 | BAR | BAR | BAR | BAR | BAR | BAR |
| 133353395 | 3 | BAR | BAR | BAR | BAR | BAR | BAR |
| 133334763 | 3 | BAR | BAR | BAR | BAR | BAR | BAR |
| 133169647 | 3 | BAR | BAR | BAR | BAR | BAR | BAR |
| 133132466 | 3 | BAR | BAR | BAR | BAR | BAR | BAR |
| 133215467 | 3 | BAR | BAR | BAR | BAR | BAR | BAR |
| 133352724 | 3 | BAR | BAR | BAR | BAR | BAR | BAR |
| 132725167 | 3 | BAR | BAR | BAR | BAR | BAR | BAR |
| 132713454 | 3 | BAR | BAR | BAR | BAR | BAR | BAR |
| 133216291 | 3 | BAR | BAR | Slight hypersensitivity | BAR | BAR | BAR |

TABLE 24

Histologic Examination Findings, equine efficacy study

| Horse | Group | Day Euthanized | Histology Findings |
|---|---|---|---|
| 132663371 | 1 | 15 | mild to moderate encephalitis both sections |
| 133134514 | 1 | 10 | severe encephalitis both sections |
| 133218532 | 1 | 14 | moderate to severe encephalitis both sections |
| 132761220 | 2 | 12 | severe encephalitis both sections |
| 133339624 | 2 | 10 | severe encephalitis both sections |
| 133167527 | 3 | 17 | normal |
| 133353395 | 3 | 17 | mild encephalitis one section |
| 133334763 | 3 | 14 | mild encephalitis one section |
| 133169647 | 3 | 14 | normal |
| 133132466 | 3 | 17 | mild encephalitis both sections |
| 133215467 | 3 | 14 | mild encephalitis both sections |
| 133352724 | 3 | 15 | mild encephalitis one section |
| 132725167 | 3 | 14 | normal |
| 132713454 | 3 | 17 | mild encephalitis one section |
| 133216291 | 3 | 15 | moderate encephalitis both sections |

REFERENCES

U.S. Pat. No. 5,773,689
U.S. Pat. No. 5,773,695
U.S. Pat. No. 6,239,328
U.S. Pat. No. 5,879,903
U.S. Pat. No. 5,637,489
U.S. Pat. No. 5,276,268
U.S. Pat. No. 5,273,894
U.S. Pat. No. 5,478,925
U.S. Pat. No. 5,073,627
U.S. Pat. No. 6,121,424
U.S. Pat. No. 5,843,464
U.S. Pat. No. 5,750,352
U.S. Pat. No. 5,990,275
U.S. Pat. No. 6,342,362
U.S. Pat. No. 6,524,825
U.S. Pat. No. 6,419,931
U.S. Pat. No. 5,712,170
U.S. Pat. No. 5,183,740
U.S. Pat. No. 4,816,567
U.S. Pat. No. 5,380,831
U.S. Pat. No. 5,436,391
U.S. Pat. No. 6,319,691
U.S. Pat. No. 6,277,375
U.S. Pat. No. 5,643,570
U.S. Pat. No. 5,565,335
U.S. Pat. No. 5,561,071
U.S. Pat. No. 5,753,439
U.S. Pat. No. 6,214,545
U.S. Pat. No. 5,384,253
U.S. Pat. No. 5,428,147
U.S. Patent Publication No. 2004/0268442 A1
EP 404,097
WO 93/11161
WO 94/10308
WO 94/07902
WO 97/27207
WO 98/49305
WO 91/09957

Altendorf et al. (1999-WWW, 2000) "Structure and Function of the $F_o$ Complex of the ATP Synthase from *Escherichia Coli*" *J. of Experimental Biology* 203:19-28.

Altschul, S. F. et al. (1990) "Basic Local Alignment Search Tool" *J. Mol. Biol.* 215(3):403-410.

Alwine, J. C. et al. (1977) "Method for detection of specific RNAs in agarose gels by transfer to diazobenzyloxymethyl-paper and hybridization with DNA probes" *Proc. Natl. Acad. Sci.* 74:5350-5354.

An, G. (1985) "High Efficiency Transformation of Cultured Tobacco Cells" *Plant Physiol.,* 79:568-570.

Ausubel, M. et al. (1987) Current Protocols in Molecular Biology, John Wiley and Sons, New York, N.Y.

Ausubel, M. et al. (1989) Current Protocols in Molecular Biology, Green Publishing Associates and Wiley Interscience, N.Y.

Baneyx, F. (1999) "Recombinant Protein Expression in *Escherichia coli*" *Biotechnology* 10:411-21.

Barker, R. F. et al. (1983) "Nucleotide sequence of the T-DNA region from the *Agrobacterium tumefaciens* octopine Ti plasmid pTi15955" *Plant Molecular Biology* 2:335-350.

Beasley, D. W., and A. D. Barrett (2002) "Identification of neutralizing epitopes within structural domain III of the West Nile virus envelope protein" *J Virol* 76:13097-13100.

Beltz, G. et al. (1983) "Isolation of multigene families and determination of homologies by filter hybridization methods" *Methods of Enzymology*, R. Wu, L. Grossman and K. Moldave [eds.] Academic Press, New York 100:266-285.

Benoist, C., Chambon, P. (1981) "In vivo sequence requirements of the SV40 early promoter region" *Nature* 290:304-310.

Berchtold, M. W. (1989) "A simple method for direct cloning and sequencing cDNA by the use of a single specific oligonucleotide and oligo(dT) in a polymerase chain reaction (PCR)" *Nuc. Acids. Res.* 17:453.

Bianchi, N. et al. (1997) "Biosensor technology and surface plasmon resonance for real-time detection of HIV-1 genomic sequences amplified by polymerase chain reaction" *Clin. Diagn. Virol.* 8(3):199-208.

Blitvich, B. J. et al. (2003) "Epitope-blocking enzyme-linked immunosorbent assays for the detection of serum antibodies to West Nile virus in multiple avian species" *J. Clin. Microbiol.* 41(3):1041-1047.

Bray, M., B. T. Zhao, L. Markoff, K. H. Eckels, R. M. Chanock, and C. J. Lai (1989) "Mice immunized with recombinant vaccinia virus expressing dengue 4 virus structural proteins with or without nonstructural protein NS1 are protected against fatal dengue virus encephalitis" *J Virol* 63:2853-2856.

Bressanelli, S., K. Stiasny, S. L. Allison, E. A. Stura, S. Duquerroy, J. Lescar, F. X. Heinz, and F. A. Rey (2004) "Structure of a flavivirus envelope glycoprotein in its low-pH-induced membrane fusion conformation" *Embo J* 23:728-738.

Brinster, R. I. et al. (1982) "Regulation of metallothionein-thymidine kinase fusion plasmids injected into mouse eggs" *Nature* 296:39-42.

Callis, J. et al. (1995) "Structure and Evolution of Genes Encoding Polyubiquitin and Ubiquitin-Like Proteins in *Arabidopsis thaliana* Ecotype Columbia" *Genetics* 139 (2):921-939.

Cammack, N., and E. A. Gould (1986) "Topographical analysis of epitope relationships on the envelope glycoprotein of yellow fever 17D vaccine and the wild type Asibi parent virus" *Virology* 150:333-341.

Capecchi, M. R. (1980) "High efficiency transformation by direct microinjection of DNA into cultured mammalian cells" *Cell* 22(2):479-488.

Cecilia, D., and E. A. Gould (1991) "Nucleotide changes responsible for loss of neuroinvasiveness in Japanese encephalitis virus neutralization-resistant mutants" *Virology* 181:70-77.

Clackson, T. et al. (1991) "Making Antibody Fragments Using Phage Display Libraries" *Nature* 352:624-628.

Clapp, J. F. (1993) "Somatic gene therapy into hematopoietic cells. Current status and future implications" *Clin. Perinatol.* 20(1):155-168.

Curiel, D. T. et al. (1991) "Adenovirus Enhancement of Transferrin-Polylysine-Mediated Gene Delivery" *Proc. Natl. Acad. Sci. USA* 88(19):8850-8854.

Curiel, D. T. et al. (1992) "High-efficiency gene transfer mediated by adenovirus coupled to DNA-polylysine complexes" *Hum. Gen. Ther.* 3(2):147-154.

deBoer, H. A. et al. (1983) "The tac promoter: a functional hybrid derived from the trp and lac promoters" *Proc. Natl. Acad. Sci. U.S.A.* 80(1):21-25.

Doran, P. M. (2000) "Foreign protein production in plant tissue cultures" *Current Opinions in Biotechnology,* 11:199-204.

Eglitis, M. A. et al. (1988) "Retroviral-mediated gene transfer into hemopoietic cells" *Avd. Exp. Med. Biol.* 241:19-27.

Eglitis, M. A., Anderson, W. F. (1988) "Retroviral Vectors for Introduction of Genes into Mammalian Cells" *Biotechniques* 6(7):608-614.

Eihauer, A. et al. (2001) "The FLAG™ Peptide, a Versatile Fusion Tag for the Purification of Recombinant Proteins" *J. Biochem Biophys Methods* 49:455-65.

Fischer, R. et al. (1999) "Towards molecular farming in the future: *Pichia pastoris*-based production of single-chain antibody fragments" *Biotechnol. Appl. Biochem.* 30:109-112.

Fraley, R. T. et al. (1985) "The SEV system: A new disarmed Ti plasmid vector system for plant transformation" *Biotechnology* 3:629-635.

Fromm, M. et al. (1985) "Expression of Genes Transferred into Monocot and Dicot Plant Cells by Electroporation" *Proc. Natl. Acad. Sci. USA* 82(17):5824-5828.

Fynan, E. F. et al. (1993) "DNA Vaccines: Protective Immunizations by Parenteral, Mucosal, and Gene-Gun Inoculations" *Proc. Natl. Acad. Sci. USA,* 90(24):11478-11482.

Gao, G. F., M. H. Hussain, H. W. Reid, and E. A. Gould (1994) "Identification of naturally occurring monoclonal antibody escape variants of louping ill virus" *J Gen Virol* 75 (Pt 3):609-614.

Gardner, R. C. et al. (1981) "The complete nucleotide sequence of an infectious clone of cauliflower mosaic virus by M13 mp 7 shotgun sequencing" *Nucl. Acids Res.* 9(12): 2871-2888.

Graham, F. L., van der Eb, A. J. (1973) "Transformation of rat cells by DNA of human adenovirus 5" *Virology* 54(02): 536-539.

Gish, W. et al. (1993) "Identification of protein coding regions by database similarity search" *Nature Genetics* 3:266-272.

Guirakhoo, F., F. X. Heinz, and C. Kunz (1989) "Epitope model of tick-borne encephalitis virus envelope glycoprotein E: analysis of structural properties, role of carbohydrate side chain, and conformational changes occurring at acidic pH" *Virology* 169:90-99.

Hanna, Sheri L, Theodore C. Pierson, Melissa D. Sanchez, Asim A. Ahmed, Mariam M. Murtadha, and Robert W. Doms (2005) "N-Linked Glycosylation of West Nile Virus Envelope Proteins Influences Particle Assembly and Infectivity" *J Virol.* 79:13262-13274.

Hasegawa, H., M. Yoshida, T. Shiosaka, S. Fujita, and Y. Kobayashi (1992) "Mutations in the envelope protein of Japanese encephalitis virus affect entry into cultured cells and virulence in mice" *Virology* 191:158-165.

Heinz, F., and C. Kunz (1977) "Characterization of tick-borne encephalitis virus and immunogenicity of its surface components in mice" *Acta Virol* 21:308-316.

Heinz, F. X. (1986) "Epitope mapping of flavivirus glycoproteins" *Adv Virus Res* 31:103-168.

Heinz, F. X., R. Berger, W. Tuma, and C. Kunz (1983) "A topological and functional model of epitopes on the structural glycoprotein of tick-borne encephalitis virus defined by monoclonal antibodies" *Virology* 126:525-537.

Heinz, F. X., and C. Kunz (1982) "Molecular epidemiology of tick-borne encephalitis virus: peptide mapping of large non-structural proteins of European isolates and comparison with other flaviviruses" *J Gen Virol* 62 (Pt 2):271-285.

Heinz, F. X., C. W. Mandl, H. Holzmann, C. Kunz, B. A. Harris, F. Rey, and S. C. Harrison (1991) "The flavivirus envelope protein E: isolation of a soluble form from tick-borne encephalitis virus and its crystallization" *J Virol* 65:5579-5583.

Heinz, F. X., and J. T. Roehrig (1990) Flaviviruses, p. 289-305, Immunochemistry of viruses, vol. II. Elsevier, Amsterdam-New York-Oxford.

Herrera-Estrella, L. et al. (1983) "Expression of chimaeric genes transferred into plant cells using a Ti-plasmid-derived vector" *Nature* 303:209-213.

Herrera-Estrella, L. et al. (1984) "Light-inducible and chloroplast-associated expression of a chimaeric gene introduced into *Nicotiana tabacum* using a Ti plasmid vector" *Nature* 310:115-120.

Higgins, D. G. et al. (1996) "Using CLUSTAL for multiple sequence alignments" *Methods Enzymol.* 266:383-402.

Holliger, P. et al. (1993) "'Diabodies': small bivalent and bispecific antibody fragments" *Proc. Natl. Acad. Sci. USA* 90:6444-6448.

Holzmann, H., K. Stiasny, M. Ecker, C. Kunz, and F. X. Heinz (1997) "Characterization of monoclonal antibody-escape mutants of tick-borne encephalitis virus with reduced neuroinvasiveness in mice" *J Gen Virol* 78 (Pt 1):31-37.

Holzmann, H., G. Utter, E. Norrby, C. W. Mandl, C. Kunz, and F. X. Heinz (1993) "Assessment of the antigenic structure of tick-borne encephalitis virus by the use of synthetic peptides" *J Gen Virol* 74 (Pt 9):2031-2035.

Jan, L. R., C. S. Yang, L. S. Henchal, H. Sumiyoshi, P. L. Summers, D. R. Dubois, and C. J. Lai (1993) "Increased immunogenicity and protective efficacy in outbred and inbred mice by strategic carboxyl-terminal truncation of Japanese encephalitis virus envelope glycoprotein" *Am J Trop Med Hyg* 48:412-423.

Jefferson, R. A. (1987) "Assaying chimeric genes in plants: the GUS fusion system" *Plant Mol Biol Rep* 5:387-405.

Jiang, W. R., A. Lowe, S. Higgs, H. Reid, and E. A. Gould (1993) "Single amino acid codon changes detected in louping ill virus antibody-resistant mutants with reduced neurovirulence" *J Gen Virol* 74 (Pt 5):931-935.

Johnston, S. A., Tang, D. C. (1994) "Gene gun transfection of animal cells and genetic immunization" *Methods Cell. Biol.* 43(A):353-365.

Jones, C. et al. (1995) "Current Trends in Molecular Recognition and Bioseparation" *J. of Chromatography A.* 707:3-22.

Jorgensen, R. A. et al. (1987) T-DNA is organized predominantly in inverted repeat structures in plants transformed with *Agrobacterium tumefaciens* C58 derivatives" *Mol. Gen. Genet.* 207:471-477.

Kanai R, Kar K, Anthony K, Gould L H, Ledizet M, Fikrig E, Koski R A, Modis Y. (2006) "Crystal structure of West Nile virus envelope glycoprotein reveals viral surface epitopes". *J Virol*. 80(22):11000-11008.

Keller, G. H., M. M. Manak (1987) *DNA Probes*, Stockton Press, New York, N.Y., pp. 169-170.

Kohler, G. et al. (1975) "Continuous Cultures of Fused Cells Secreting Antibody of Predefined Specificity" *Nature* 256 (5517):495-497.

Kolaskar, A. S., and U. Kulkarni-Kale (1999) "Prediction of three-dimensional structure and mapping of conformational epitopes of envelope glycoprotein of Japanese encephalitis virus" *Virology* 261:31-42.

Konishi, E., S. Pincus, E. Paoletti, R. E. Shope, T. Burrage, and P. W. Mason (1992) "Mice immunized with a subviral particle containing the Japanese encephalitis virus prM/M and E proteins are protected from lethal JEV infection" *Virology* 188:714-720.

Kuhn, R. J., W. Zhang, M. G. Rossmann, S. V. Pletnev, J. Corver, E. Lenches, C. T. Jones, S. Mukhopadhyay, P. R. Chipman, E. G. Strauss, T. S. Baker, and J. H. Strauss (2002) "Structure of dengue virus: implications for flavivirus organization, maturation, and fusion" *Cell* 108:717-725.

Kusterbeck, A. W. et al. (1990a) "A Continuous Flow Immunoassay for Rapid and Sensitive Detection of Small Molecules" *Journal of Immunological Methods* 135(1-2): 191-197.

Kusterbeck, A. W. et al. (1990) "Antibody-Based Biosensor for Continuous Monitoring" In *Biosensor Technology*, R. P. Buck et al., eds., Marcel Dekker, N.Y. pp. 345-350.

Lee, E., and M. Lobigs (2000) "Substitutions at the putative receptor-binding site of an encephalitic flavivirus alter virulence and host cell tropism and reveal a role for glycosaminoglycans in entry" *J Virol* 74:8867-8875.

Letchworth, G. J. and J. A. Appleton (1984) *Methods for Production of Monoclonal Antibodies*. USDA Handbook #630.

Ligler, F. S. et al. (1992) "Drug Detection Using the Flow Immunosensor" In *Biosensor Design and Application*, J. Findley et al., eds., American Chemical Society Press, pp. 73-80.

Lin, B., C. R. Parrish, J. M. Murray, and P. J. Wright (1994) "Localization of a neutralizing epitope on the envelope protein of dengue virus type 2" *Virology* 202:885-890.

Lu, L. et al. (1993) "High efficiency retroviral mediated gene transduction into single isolated immature and replatable CD34 (3+) hematopoietic stem/progenitor cells from human umbilical cord blood" *J. Exp. Med.* 178(6):2089-2096.

Mandl, C. W., F. Guirakhoo, H. Holzmann, F. X. Heinz, and C. Kunz (1989) "Antigenic structure of the flavivirus envelope protein E at the molecular level, using tick-borne encephalitis virus as a model" *J Virol* 63:564-571.

Maniatis, J.-M. et al. (1982) *Molecular Cloning. A Laboratory Manual*, Cold Spring Harbor Laboratory, New York.

Marcotte, W. R. et al. (1988) "Regulation of a wheat promoter by abscisic acid in rice protoplasts" *Nature* 335:454-457.

Margolin, W. (2000) "Green Fluorescent Protein as a Reporter for Macromolecular Localization in Bacterial Cells" *Methods* 20:62-72.

Marks, J. D. et al. (1991) "By-Passing Immunization: Human Antibodies from V-Gene Libraries Displayed on Phage" *J. Mol. Biol.* 222(3):581-597.

Mason, P. W., J. M. Dalrymple, M. K. Gentry, J. M. McCown, C. H. Hoke, D. S. Burke, M. J. Fournier, and T. L. Mason (1989) "Molecular characterization of a neutralizing domain of the Japanese encephalitis virus structural glycoprotein" *J Gen Virol* 70 (Pt 8):2037-2049.

Mason, P. W., S. Pincus, M. J. Fournier, T. L. Mason, R. E. Shope, and E. Paoletti (1991) "Japanese encephalitis virus-vaccinia recombinants produce particulate forms of the structural membrane proteins and induce high levels of protection against lethal JEV infection" *Virology* 180:294-305.

Melton, D. A. et al. (1984) "Efficient In Vitro Synthesis of Biologically Active RNA and RNA Hybridization Probes From Plasmids Containing a Bacteriophage SP6 Promoter" *Nuc. Acids Res.* 12:7035-7036.

Men, R. H., M. Bray, and C. J. Lai (1991) "Carboxy-terminally truncated dengue virus envelope glycoproteins expressed on the cell surface and secreted extracellularly exhibit increased immunogenicity in mice" *J Virol* 65:1400-1407.

Modis, Y., Ogata, S., Clements, D., Harrison, S. C. (2004) "Structure of the dengue virus envelope protein after membrane fusion" *Nature* 427:313-319.

Morrison, S. L. et al. (1984) "Chimeric Human Antibody Molecules: Mouse Antigen-Binding Domains with Human Constant Region Domains" *Proc. Natl. Acad. Sci. USA* 81:6851-6855.

Mukhopadhyay, S., B. S. Kim, P. R. Chipman, M. G. Rossmann, and R. J. Kuhn (2003) "Structure of West Nile virus" *Science* 302:248.

Murai et al. (1982) "T-DNA of pTi-15955 from *Agrobacterium tumefaciens* is transcribed into a minimum of seven polyadenylated RNAs in a sunflower crown gall tumor" *Nucleic Acids Res.* 10(5):1679-1689.

Murray, E. E. et al. (1989) "Codon usage in plant genes" *Nucleic Acids Res.* 17(2):477-498.

Norris, S. R. et al. (1993) "The intron of *Arabidopsis thaliana* polyubiquitin genes is conserved in location and is a quantitative determinant of chimeric gene expression" *Plant Mol. Biol.* 21(5):895-906.

Nowak, T., and G. Wengler (1987) "Analysis of disulfides present in the membrane proteins of the West Nile flavivirus" *Virology* 156:127-137.

Ogert, R. A. et al. (1992) "Detection of Cocaine Using the Flow Immunosensor" *Analytical Letters* 25:1999-2019.

Pearson, W. R. et al. (1988) "Improved Tools for Biological Sequence Comparison" *Proc. Natl. Acad. Sci. USA* 85(8): 2444-2448.

Pietu, G. et al. (1996) "Novel gene transcripts preferentially expressed in human muscles revealed by quantitative hybridization of a high density cDNA array" *Genome Research* 6(6):492-503.

Pincus, S., P. W. Mason, E. Konishi, B. A. Fonseca, R. E. Shope, C. M. Rice, and E. Paoletti (1992) "Recombinant vaccinia virus producing the prM and E proteins of yellow fever virus protects mice from lethal yellow fever encephalitis" *Virology* 187:290-297.

Pluckthun, A. (1994) In *The Pharmacology of Monoclonal Antibodies*, Vol. 113:269-315, Rosenburg and Moore eds. Springer-Verlag, New York.

Potrykus, I. et al. (1985) "Direct gene transfer to cells of a graminaceous monocot" *Mol. Gen. Genet.* 199:183-188.

Puig, O. et al. (2001) "The Tandem Affinity Purification (TAP) Method: A General Procedure of Protein Complex Purification" *Methods* 24:218-29.

Rey, F. A., F. X. Heinz, C. Mandl, C. Kunz, and S. C. Harrison (1995) "The envelope glycoprotein from tick-borne encephalitis virus at 2 A resolution" *Nature* 375:291-298.

Roehrig, J. T., J. H. Mathews, and D. W. Trent (1983) "Identification of epitopes on the E glycoprotein of Saint Louis encephalitis virus using monoclonal antibodies" *Virology* 128:118-126.

Roehrig, J. T. (1986) The use of monoclonal antibodies in studies of the structural proteins of togaviruses and flaviviruses, p. 251-278. In S. Schlesinger and M. J. Schlesinger (ed.), The Togaviridae and Flaviviridae. Plenum Press, New York.

Roehrig, J. T., A. R. Hunt, A. J. Johnson, and R. A. Hawkes (1989) "Synthetic peptides derived from the deduced amino acid sequence of the E-glycoprotein of Murray Valley encephalitis virus elicit antiviral antibody" *Virology* 171:49-60.

Rogers, S. G. et al. (1987) "Improved Vector for plant transformation: expression cassette vectors and new selectable markers" *Meth. in Enzymol.* 153:253-277.

Sambrook, J. et al. (1989) Molecular Cloning, A Laboratory Manual, Second Edition, Cold Spring Harbor Press, N.Y., pp. 9.47-9.57.

Sanchez, M. D., T. C. Pierson, D. McAllister, S. L. Hanna, B. A. Puffer, L. E. Valentine, M. M. Murtadha, J. A. Hoxie, and R. W. Doms (2005) "Characterization of neutralizing antibodies to West Nile virus" *Virology* 336:70-82.

Sassenfeld, H. M. (1990) "Engineering Proteins for Purification" *TibTech* 8:88-93.

Schena, M. et al. (1995) "Quantitative Monitoring of Gene Expression Patterns With a Complementary DNA Microarray" *Science* 270:467-470.

Schena, M. et al (1996a) "Parallel human genome analysis: microarray-based expression monitoring of 1000 genes" *Proc. Natl. Acad. Sci. U.S.A.* 93(20):10614-10619.

Schena, M. (1996b) "Genome analysis with gene expression microarrays" *BioEssays* 18(5):427-431.

Schlesinger, J. J., J. R. Putnak, and K. H. Eckels (1992) "New approaches to flavivirus vaccine development" *Biotechnology* 20:289-307.

Sheibani, N. (1999) "Prokaryotic Gene Fusion Expression Systems and Their Use in Structural and Functional Studies of Proteins" *Prep. Biochem. & Biotechnol.* 29(1):77-90.

Skerra, A. et al. (1999) "Applications of a Peptide Ligand for Streptavidin: the *Strep*-tag" *Biomolecular Engineering* 16:79-86.

Smith, C. (1998) "Cookbook for Eukaryotic Protein Expression: Yeast, Insect, and Plant Expression Systems" *The* Scientist 12(22):20.

Smith, G. L. and B. Moss (1984) "Vaccinia Virus expression Vectors: Construction, Properties, and applications" *Bio Techniques November/December:*306-312.

Smyth, G. K. et al. (2000) "Eukaryotic Expression and Purification of Recombinant Extracellular Matrix Proteins Carrying the Strep II Tag" *Methods in Molecular Biology* 139:49-57.

Spielmann, A. et al. (1986) "T-DNA structure in transgenic tobacco plants with multiple independent integration sites" *Mol. Gen. Genet.* 205:34-41.

Stiasny, K., S. L. Allison, A. Marchler-Bauer, C. Kunz, and F. X. Heinz (1996) "Structural requirements for low-pH-induced rearrangements in the envelope glycoprotein of tick-borne encephalitis virus" *J Virol* 70:8142-8147.

Suggs, S. V. et al. (1981) *ICN-UCLA Symp. Dev. Biol. Using Purified Genes*, D. D. Brown [ed.], Academic Press, New York, 23:683-693.

Sun C.-W. et al. (1997) "Independent modulation of *Iarabidopsis thaliana* polyubiquitin mRNAs in different organs and in response to environmental changes" *Plant J.* 11(5): 1017-1027.

Sutter, G. et al. (1994) "A recombinant vector derived from the host range-restricted and highly attenuated MVA strain of vaccinia virus stimulates protective immunity in mice to influenza virus" *Vaccine* 12(11):1032-1040.

Sutter, G., Moss, B. (1992) "Nonreplicating Vaccinia Vector Efficiently Expresses Recombinant Genes" *Proc. Nat'l. Acad. Sci. U.S.A.* 89:10847-10851.

Thompson, J. et al. (1994) "Clustal-W: *improving the sensitivity of progressive multiple sequence alignment through sequence weighting*, position specific gap penalties and weight matrix choice" *Nucleic Acids Res.* 22(2):4673-4680.

Unger, T. F. (1997) "Show Me the Money: Prokaryotic Expression Vectors and Purification Systems" *The Scientist* 11(17):20.

Villa-Kamaroff, L. et al. (1978) "A bacterial clone synthesizing proinsulin" *Proc. Natl. Acad. Sci. U.S.A.* 75(8):3727-3731.

Wagner, M. J. et al. (1981) "Nucleotide sequence of the thymidine kinase gene of herpes simplex virus type 1" *Proc. Natl. Acad. Sci. U.S.A.* 78(3):1441-1445.

Wagner, E. et al. (1992) "Coupling of Adenovirus to Transferrin-Polylysine/DNA Complexes Greatly Enhances Receptor-Mediated Gene Delivery and Expression of Transfected Genes" *Proc. Natl. Acad. Sci. USA* 89(13): 6099-6103.

Wei, C. F. et al. (1983) “Isolation and comparison of two molecular species of the BAL 31 nuclease from *Alteromonas espejiana* with distinct kinetic properties” *J. Biol. Chem.* 258:13506-13512.

Wengler, G., and G. Wengler (1989) “An analysis of the antibody response against West Nile virus E protein purified by SDS-PAGE indicates that this protein does not contain sequential epitopes for efficient induction of neutralizing antibodies” *J Gen Virol* 70 (Pt 4):987-992.

Winkler, G., F. X. Heinz, and C. Kunz (1987) “Characterization of a disulphide bridge-stabilized antigenic domain of tick-borne encephalitis virus structural glycoprotein” *J Gen Virol* 68 (Pt 8):2239-2244.

Wong, T. K., Neumann, E. (1982) Electric field mediated gene transfer” *Biochim. Biophys. Res. Commun.,* 107(2):584-587.

Yamamoto, T. et al. (1980) “Identification of a functional promoter in the long terminal repeat of Rous sarcoma virus” *Cell* 22(3):787-797.

Zapata, G. et al. (1995) “Engineering linear F(ab')$_2$ fragments for efficient production in *Escherichia coli* and enhanced antiproliferative activity” *Protein Eng.* 8(10):1057-1062.

Zatloukal, K. et al. (1992) “Transferrinfection: a highly efficient way to express gene constructs in eukaryotic cells” *Ann. N.Y. Acad. Sci.* 660:136-153.

---

We claim:

1. An isolated polynucleotide comprising:

a) a sequence encoding a polypeptide comprising SEQ ID NO: 11 optionally wherein said polynucleotide sequence has a G+C content of at least 40% and less than 50%;

b) a genetic construct comprising a polynucleotide sequence as set forth in (a); or c) a vector comprising a polynucleotide or genetic construct as set forth in (a) or (b).

2. The isolated polynucleotide according to claim 1, wherein said polynucleotide comprises SEQ ID NO: 4 or 10.

3. The isolated polynucleotide according to claim 2, wherein said polynucleotide comprises SEQ ID NO: 4.

4. The isolated polynucleotide according to claim 2, wherein said polynucleotide comprises SEQ ID NO: 10.

5. A transgenic plant, plant cell, or plant part comprising a polynucleotide as set forth in claim 1.

6. A method of making polypeptide comprising:

a) transforming a cell with a polynucleotide encoding SEQ ID NO: 11;

b) culturing said transformed cell under conditions that allow for the proliferation of said transformed plant cell and the accumulation of said polypeptide; and c) recovering or purifying said at least one polypeptide from said cell.

7. The method according to claim 6, wherein the cell is selected from the group consisting of a lower plant cell, a monocot plant cell, and a dicot plant cell, a prokaryotic cell and a mammalian cell line.

8. The method according to claim 7, wherein the cell is a tobacco cell line.

9. The method according to claim 8, wherein said tobacco cell line is NT-1.

10. A method of making polypeptide comprising:

a) transforming a cell with a polynucleotide comprising SEQ ID NO: 4 or 10;

b) culturing said transformed cell under conditions that allow for the proliferation of said transformed plant cell and the accumulation of said polypeptide; and c) recovering or purifying said at least one polypeptide from said cell, wherein said cell is a tobacco cell line.

11. The method according to claim 10, wherein said tobacco cell line is NT-1.

* * * * *

UNITED STATES PATENT AND TRADEMARK OFFICE

CERTIFICATE OF CORRECTION

PATENT NO. : 7,888,069 B2
APPLICATION NO. : 11/962924
DATED : February 15, 2011
INVENTOR(S) : Kelley Smith et al.

It is certified that error appears in the above-identified patent and that said Letters Patent is hereby corrected as shown below:

Column 2,
Line 51, "Roebrig et al., 1989" should read --Roehrig et al., 1989--.

Column 6,
Line 41, "kDA ER targeting" should read --15kDA ER targeting--.

Column 12,
Line 14, "SEQ TD NO:" should read --SEQ ID NO:--.

Column 16,
Line 53, "Antibodies. Principals" should read --Antibodies: Principals--.

Column 17,
Line 48, "$V_H$ and $V_T$" should read --$V_H$ and $V_L$--.

Column 21,
Line 1, "9) kNase" should read --9) RNase--.
Line 31, "($^{32}P$, $^{35}S$, $^{3}H$, $^{121}I$)" should read --($^{32}P$, $^{35}S$, $^{3}H$, $^{125}I$)--.

Column 36,
Line 24, "cassaya vein" should read --cassava vein--.

Column 38,
Line 38, "the AMAS 4OCS" should read --the ΔMAS 4OCS--.
Line 67, "ctt age atg" should read --ctt agc atg--.

Column 40,
Line 20, "atg egg ctg" should read --atg egg ctg--.
Line 53, "ccg etc gag egg atc" should read --ccg ctc gag cgg atc--.

Signed and Sealed this
Thirteenth Day of September, 2011

David J. Kappos
*Director of the United States Patent and Trademark Office*

Column 47,
Line 39, "(PM2): harvested" should read --(PM2): Harvested--.

Column 50,
Line 20, "was revaccinatedu at" should read --was revaccinated at--.

Column 72,
Line 66, "18 1 and 679 Y + 17" should read
--18 1 and 677 Y + 17--.

Column 123,
Line 27, "Brinster, R.I." should read --Brinster, R.L.--.

Column 126,
Line 31, "Molecular Cloning. A Laboratory" should read --Molecular Cloning: A Laboratory--.

SEQUENCE LISTING

```
<160> NUMBER OF SEQ ID NOS: 15

<210> SEQ ID NO 1
<211> LENGTH: 2004
<212> TYPE: DNA
<213> ORGANISM: West Nile virus
<220> FEATURE:
<221> NAME/KEY: CDS
<222> LOCATION: (1)..(2004)

<400> SEQUENCE: 1

gtt acc ctc tct aac ttc caa ggg aag gtg atg atg acg gta aat gct       48
Val Thr Leu Ser Asn Phe Gln Gly Lys Val Met Met Thr Val Asn Ala
1               5                   10                  15

act gac gtc aca gat gtc atc acg att cca aca gct gct gga aag aac       96
Thr Asp Val Thr Asp Val Ile Thr Ile Pro Thr Ala Ala Gly Lys Asn
            20                  25                  30

cta tgc att gtc aga gca atg gat gtg gga tac atg tgc gat gat act      144
Leu Cys Ile Val Arg Ala Met Asp Val Gly Tyr Met Cys Asp Asp Thr
        35                  40                  45

atc act tat gaa tgc cca gtg ctg tcg gct ggt aat gat cca gaa gac      192
Ile Thr Tyr Glu Cys Pro Val Leu Ser Ala Gly Asn Asp Pro Glu Asp
    50                  55                  60

atc gac tgt tgg tgc aca aag tca gca gtc tac gtc agg tat gga aga      240
Ile Asp Cys Trp Cys Thr Lys Ser Ala Val Tyr Val Arg Tyr Gly Arg
65                  70                  75                  80

tgc acc aag aca cgc cac tca aga cgc agt cgg agg tca ctg aca gtg      288
Cys Thr Lys Thr Arg His Ser Arg Arg Ser Arg Arg Ser Leu Thr Val
                85                  90                  95

cag aca cac gga gaa agc act cta gcg aac aag aag ggg gct tgg atg      336
Gln Thr His Gly Glu Ser Thr Leu Ala Asn Lys Lys Gly Ala Trp Met
            100                 105                 110

gac agc acc aag gcc aca agg tat ttg gta aaa aca gaa tca tgg atc      384
Asp Ser Thr Lys Ala Thr Arg Tyr Leu Val Lys Thr Glu Ser Trp Ile
        115                 120                 125

ttg agg aac cct gga tat gcc ctg gtg gca gcc gtc att ggt tgg atg      432
Leu Arg Asn Pro Gly Tyr Ala Leu Val Ala Ala Val Ile Gly Trp Met
    130                 135                 140

ctt ggg agc aac acc atg cag aga gtt gtg ttt gtc gtg cta ttg ctt      480
Leu Gly Ser Asn Thr Met Gln Arg Val Val Phe Val Val Leu Leu Leu
145                 150                 155                 160

ttg gtg gcc cca gct tac agc ttc aac tgc ctt gga atg agc aac aga      528
Leu Val Ala Pro Ala Tyr Ser Phe Asn Cys Leu Gly Met Ser Asn Arg
                165                 170                 175

gac ttc ttg gaa gga gtg tct gga gca aca tgg gtg gat ttg gtt ctc      576
Asp Phe Leu Glu Gly Val Ser Gly Ala Thr Trp Val Asp Leu Val Leu
            180                 185                 190
```

-continued

```
gaa ggc gac agc tgc gtg act atc atg tct aag gac aag cct acc atc      624
Glu Gly Asp Ser Cys Val Thr Ile Met Ser Lys Asp Lys Pro Thr Ile
        195                 200                 205

gat gtg aag atg atg aat atg gag gcg gcc aac ctg gca gag gtc cgc      672
Asp Val Lys Met Met Asn Met Glu Ala Ala Asn Leu Ala Glu Val Arg
    210                 215                 220

agt tat tgc tat ttg gct acc gtc agc gat ctc tcc acc aaa gct gcg      720
Ser Tyr Cys Tyr Leu Ala Thr Val Ser Asp Leu Ser Thr Lys Ala Ala
225                 230                 235                 240

tgc ccg acc atg gga gaa gct cac aat gac aaa cgt gct gac cca gct      768
Cys Pro Thr Met Gly Glu Ala His Asn Asp Lys Arg Ala Asp Pro Ala
                245                 250                 255

ttt gtg tgc aga caa gga gtg gtg gac agg ggc tgg ggc aac ggc tgc      816
Phe Val Cys Arg Gln Gly Val Val Asp Arg Gly Trp Gly Asn Gly Cys
            260                 265                 270

gga cta ttt ggc aaa gga agc att gac aca tgc gcc aaa ttt gcc tgc      864
Gly Leu Phe Gly Lys Gly Ser Ile Asp Thr Cys Ala Lys Phe Ala Cys
        275                 280                 285

tct acc aag gca ata gga aga acc atc ttg aaa gag aat atc aag tac      912
Ser Thr Lys Ala Ile Gly Arg Thr Ile Leu Lys Glu Asn Ile Lys Tyr
    290                 295                 300

gaa gtg gcc att ttt gtc cat gga cca act act gtg gag tcg cac gga      960
Glu Val Ala Ile Phe Val His Gly Pro Thr Thr Val Glu Ser His Gly
305                 310                 315                 320

aac tac tcc aca cag gtt gga gcc act cag gca ggg aga ttc agc atc     1008
Asn Tyr Ser Thr Gln Val Gly Ala Thr Gln Ala Gly Arg Phe Ser Ile
                325                 330                 335

act cct gcg gcg cct tca tac aca cta aag ctt gga gaa tat gga gag     1056
Thr Pro Ala Ala Pro Ser Tyr Thr Leu Lys Leu Gly Glu Tyr Gly Glu
            340                 345                 350

gtg aca gtg gac tgt gaa cca cgg tca ggg att gac acc aat gca tac     1104
Val Thr Val Asp Cys Glu Pro Arg Ser Gly Ile Asp Thr Asn Ala Tyr
        355                 360                 365

tac gtg atg act gtt gga aca aag acg ttc ttg gtc cat cgt gag tgg     1152
Tyr Val Met Thr Val Gly Thr Lys Thr Phe Leu Val His Arg Glu Trp
    370                 375                 380

ttc atg gac ctc aac ctc cct tgg agc agt gct gga agt act gtg tgg     1200
Phe Met Asp Leu Asn Leu Pro Trp Ser Ser Ala Gly Ser Thr Val Trp
385                 390                 395                 400

agg aac aga gag acg tta atg gag ttt gag gaa cca cac gcc acg aag     1248
Arg Asn Arg Glu Thr Leu Met Glu Phe Glu Glu Pro His Ala Thr Lys
                405                 410                 415

cag tct gtg ata gca ttg ggc tca caa gag gga gct ctg cat caa gct     1296
Gln Ser Val Ile Ala Leu Gly Ser Gln Glu Gly Ala Leu His Gln Ala
            420                 425                 430

ttg gct gga gcc att cct gtg gaa ttt tca agc aac act gtc aag ttg     1344
Leu Ala Gly Ala Ile Pro Val Glu Phe Ser Ser Asn Thr Val Lys Leu
        435                 440                 445

acg tcg ggt cat ttg aag tgt aga gtg aag atg gaa aaa ttg cag ttg     1392
Thr Ser Gly His Leu Lys Cys Arg Val Lys Met Glu Lys Leu Gln Leu
    450                 455                 460

aag gga aca acc tat ggc gtc tgt tca aag gct ttc aag ttt ctt ggg     1440
Lys Gly Thr Thr Tyr Gly Val Cys Ser Lys Ala Phe Lys Phe Leu Gly
465                 470                 475                 480

act ccc gca gac aca ggt cac ggc act gtg gtg ttg gaa ttg cag tac     1488
Thr Pro Ala Asp Thr Gly His Gly Thr Val Val Leu Glu Leu Gln Tyr
                485                 490                 495

act ggc acg gat gga cct tgc aaa gtt cct atc tcg tca gtg gct tca     1536
Thr Gly Thr Asp Gly Pro Cys Lys Val Pro Ile Ser Ser Val Ala Ser
```

-continued

```
            500                 505                 510

ttg aac gac cta acg cca gtg ggc aga ttg gtc act gtc aac cct ttt      1584
Leu Asn Asp Leu Thr Pro Val Gly Arg Leu Val Thr Val Asn Pro Phe
        515                 520                 525

gtt tca gtg gcc acg gcc aac gct aag gtc ctg att gaa ttg gaa cca      1632
Val Ser Val Ala Thr Ala Asn Ala Lys Val Leu Ile Glu Leu Glu Pro
    530                 535                 540

ccc ttt gga gac tca tac ata gtg gtg ggc aga gga gaa caa cag atc      1680
Pro Phe Gly Asp Ser Tyr Ile Val Val Gly Arg Gly Glu Gln Gln Ile
545                 550                 555                 560

aat cac cat tgg cac aag tct gga agc agc att ggc aaa gcc ttt aca      1728
Asn His His Trp His Lys Ser Gly Ser Ser Ile Gly Lys Ala Phe Thr
                565                 570                 575

acc acc ctc aaa gga gcg cag aga cta gcc gct cta gga gac aca gct      1776
Thr Thr Leu Lys Gly Ala Gln Arg Leu Ala Ala Leu Gly Asp Thr Ala
            580                 585                 590

tgg gac ttt gga tca gtt gga ggg gtg ttc acc tca gtt ggg aag gct      1824
Trp Asp Phe Gly Ser Val Gly Gly Val Phe Thr Ser Val Gly Lys Ala
        595                 600                 605

gtc cat caa gtg ttc gga gga gca ttc cgc tca ctg ttc gga ggc atg      1872
Val His Gln Val Phe Gly Gly Ala Phe Arg Ser Leu Phe Gly Gly Met
    610                 615                 620

tcc tgg ata acg caa gga ttg ctg ggg gct ctc ctg ttg tgg atg ggc      1920
Ser Trp Ile Thr Gln Gly Leu Leu Gly Ala Leu Leu Leu Trp Met Gly
625                 630                 635                 640

atc aat gct cgt gat agg tcc ata gct ctc acg ttt ctc gca gtt gga      1968
Ile Asn Ala Arg Asp Arg Ser Ile Ala Leu Thr Phe Leu Ala Val Gly
                645                 650                 655

gga gtt ctg ctc ttc ctc tcc gtg aac gtg cac gct                      2004
Gly Val Leu Leu Phe Leu Ser Val Asn Val His Ala
            660                 665


<210> SEQ ID NO 2
<211> LENGTH: 668
<212> TYPE: PRT
<213> ORGANISM: West Nile virus

<400> SEQUENCE: 2

Val Thr Leu Ser Asn Phe Gln Gly Lys Val Met Met Thr Val Asn Ala
1               5                   10                  15

Thr Asp Val Thr Asp Val Ile Thr Ile Pro Thr Ala Ala Gly Lys Asn
            20                  25                  30

Leu Cys Ile Val Arg Ala Met Asp Val Gly Tyr Met Cys Asp Asp Thr
        35                  40                  45

Ile Thr Tyr Glu Cys Pro Val Leu Ser Ala Gly Asn Asp Pro Glu Asp
    50                  55                  60

Ile Asp Cys Trp Cys Thr Lys Ser Ala Val Tyr Val Arg Tyr Gly Arg
65                  70                  75                  80

Cys Thr Lys Thr Arg His Ser Arg Arg Ser Arg Arg Ser Leu Thr Val
                85                  90                  95

Gln Thr His Gly Glu Ser Thr Leu Ala Asn Lys Lys Gly Ala Trp Met
            100                 105                 110

Asp Ser Thr Lys Ala Thr Arg Tyr Leu Val Lys Thr Glu Ser Trp Ile
        115                 120                 125

Leu Arg Asn Pro Gly Tyr Ala Leu Val Ala Ala Val Ile Gly Trp Met
    130                 135                 140

Leu Gly Ser Asn Thr Met Gln Arg Val Val Phe Val Val Leu Leu Leu
145                 150                 155                 160
```

-continued

```
Leu Val Ala Pro Ala Tyr Ser Phe Asn Cys Leu Gly Met Ser Asn Arg
                165                 170                 175

Asp Phe Leu Glu Gly Val Ser Gly Ala Thr Trp Val Asp Leu Val Leu
            180                 185                 190

Glu Gly Asp Ser Cys Val Thr Ile Met Ser Lys Asp Lys Pro Thr Ile
        195                 200                 205

Asp Val Lys Met Met Asn Met Glu Ala Ala Asn Leu Ala Glu Val Arg
    210                 215                 220

Ser Tyr Cys Tyr Leu Ala Thr Val Ser Asp Leu Ser Thr Lys Ala Ala
225                 230                 235                 240

Cys Pro Thr Met Gly Glu Ala His Asn Asp Lys Arg Ala Asp Pro Ala
                245                 250                 255

Phe Val Cys Arg Gln Gly Val Val Asp Arg Gly Trp Gly Asn Gly Cys
            260                 265                 270

Gly Leu Phe Gly Lys Gly Ser Ile Asp Thr Cys Ala Lys Phe Ala Cys
        275                 280                 285

Ser Thr Lys Ala Ile Gly Arg Thr Ile Leu Lys Glu Asn Ile Lys Tyr
    290                 295                 300

Glu Val Ala Ile Phe Val His Gly Pro Thr Thr Val Glu Ser His Gly
305                 310                 315                 320

Asn Tyr Ser Thr Gln Val Gly Ala Thr Gln Ala Gly Arg Phe Ser Ile
                325                 330                 335

Thr Pro Ala Ala Pro Ser Tyr Thr Leu Lys Leu Gly Glu Tyr Gly Glu
            340                 345                 350

Val Thr Val Asp Cys Glu Pro Arg Ser Gly Ile Asp Thr Asn Ala Tyr
        355                 360                 365

Tyr Val Met Thr Val Gly Thr Lys Thr Phe Leu Val His Arg Glu Trp
    370                 375                 380

Phe Met Asp Leu Asn Leu Pro Trp Ser Ser Ala Gly Ser Thr Val Trp
385                 390                 395                 400

Arg Asn Arg Glu Thr Leu Met Glu Phe Glu Glu Pro His Ala Thr Lys
                405                 410                 415

Gln Ser Val Ile Ala Leu Gly Ser Gln Glu Gly Ala Leu His Gln Ala
            420                 425                 430

Leu Ala Gly Ala Ile Pro Val Glu Phe Ser Ser Asn Thr Val Lys Leu
        435                 440                 445

Thr Ser Gly His Leu Lys Cys Arg Val Lys Met Glu Lys Leu Gln Leu
    450                 455                 460

Lys Gly Thr Thr Tyr Gly Val Cys Ser Lys Ala Phe Lys Phe Leu Gly
465                 470                 475                 480

Thr Pro Ala Asp Thr Gly His Gly Thr Val Val Leu Glu Leu Gln Tyr
                485                 490                 495

Thr Gly Thr Asp Gly Pro Cys Lys Val Pro Ile Ser Ser Val Ala Ser
            500                 505                 510

Leu Asn Asp Leu Thr Pro Val Gly Arg Leu Val Thr Val Asn Pro Phe
        515                 520                 525

Val Ser Val Ala Thr Ala Asn Ala Lys Val Leu Ile Glu Leu Glu Pro
    530                 535                 540

Pro Phe Gly Asp Ser Tyr Ile Val Val Gly Arg Gly Glu Gln Gln Ile
545                 550                 555                 560

Asn His His Trp His Lys Ser Gly Ser Ser Ile Gly Lys Ala Phe Thr
                565                 570                 575
```

-continued

```
Thr Thr Leu Lys Gly Ala Gln Arg Leu Ala Ala Leu Gly Asp Thr Ala
            580                 585                 590

Trp Asp Phe Gly Ser Val Gly Gly Val Phe Thr Ser Val Gly Lys Ala
        595                 600                 605

Val His Gln Val Phe Gly Gly Ala Phe Arg Ser Leu Phe Gly Gly Met
    610                 615                 620

Ser Trp Ile Thr Gln Gly Leu Leu Gly Ala Leu Leu Leu Trp Met Gly
625                 630                 635                 640

Ile Asn Ala Arg Asp Arg Ser Ile Ala Leu Thr Phe Leu Ala Val Gly
                645                 650                 655

Gly Val Leu Leu Phe Leu Ser Val Asn Val His Ala
            660                 665


<210> SEQ ID NO 3
<211> LENGTH: 2004
<212> TYPE: DNA
<213> ORGANISM: West Nile virus

<400> SEQUENCE: 3

gtgactctga gcaactttca aggaaaggtc atgatgactg tcaatgcaac tgatgtcact      60

gatgtgataa caatcccaac agcagctggg aagaatcttt gcattgtcag agctatggat     120

gtgggctaca tgtgtgatga cacaatcact tatgagtgtc cagtactttc tgctggaaat     180

gatcctgaag acattgattg ttggtgcacc aaatcagctg tctatgttcg ttatgggagg     240

tgcacaaaga ccagacactc acgaagaagt cgaaggtccc tgacagtgca aactcatgga     300

gagtcaactt tggccaacaa gaaaggcgca tggatggatt ctaccaaagc aacaagatat     360

cttgtcaaaa ctgagtcatg gattcttagg aatcctggat atgctttagt tgcagctgtc     420

attggatgga tgcttgggtc caataccatg cagagagttg tcttcgtagt tctgttgtta     480

cttgtagctc cagcttactc attcaactgt cttggaatga gcaataggga tttccttgaa     540

ggtgtttccg gtgcaacatg ggttgatctt gtcttagaag gagattcatg tgtgacaatc     600

atgtccaaag acaagccaac cattgatgtc aagatgatga acatggaagc tgccaatctt     660

gcagaagtta ggtcttactg ctatctggca acagtgagtg atttgtcaac aaaagctgcc     720

tgtcccacaa tgggagaggc tcacaatgac aaacgtgctg atcctgcatt tgtatgcaga     780

caaggagttg tagacagagg ttggggaaat ggttgtggtc tctttggcaa aggcagcatt     840

gacacttgtg caaagtttgc ttgcagcacc aaagcaattg gtcgaaccat attgaaagag     900

aacattaagt atgaagttgc catctttgtt catggtccaa caactgtgga atctcatggc     960

aattacagca cacaagttgg tgccacccaa gctgggaggt tttcaatcac tcctgctgct    1020

ccaagttaca ctctgaaatt gggtgaatat ggtgaagtaa cagttgattg tgaacctagg    1080

tctggcattg acaccaatgc ttactatgta atgactgtgg gaacaaagac attcttagtt    1140

cacagagaat ggttcatgga tttgaatctc ccttggagtt ctgctggaag cactgtttgg    1200

aggaatcgtg aaacattgat ggagtttgag gaaccacatg caacaaaaca gtcagtaata    1260

gcattgggca gtcaagaggg agcattacat caagccttgg ctggggcaat tcctgttgag    1320

tttagttcca acactgtgaa actgacaagt ggtcatctga aatgcagagt aaagatggag    1380

aagttacagt tgaaaggaac cacttatggt gtttgttcca aagccttcaa gtttcttgga    1440

actcctgctg acactggtca tgggactgtg gttttggaat tgcagtacac tggcactgat    1500

ggtccatgca aggttcccat aagcagtgtt gcttcactca atgatctcac tccagtaggc    1560

agacttgtga cagtcaaccc ctttgtttct gttgcaactg ccaatgcaaa ggtgctcata    1620
```

-continued

```
gaattggagc ctccatttgg tgattcttac attgttgtag gcagaggaga gcaacagatc   1680

aaccatcact ggcacaaatc tggttcttca attggcaaag ccttcacaac cactctcaaa   1740

ggggcacaga gacttgctgc tttaggagac actgcatggg atttcggatc tgttggaggt   1800

gttttcacct ctgtgggaaa ggctgtgcat caagtttttg gtggggcttt tcgatccttg   1860

tttggtggaa tgtcttggat aactcaaggt cttttagggg ctctgctttt gtggatgggc   1920

atcaatgcaa gggacagatc aattgcctta accttccttg cagttggagg tgttcttctc   1980

tttctctctg taaatgttca tgct                                          2004


<210> SEQ ID NO 4
<211> LENGTH: 2004
<212> TYPE: DNA
<213> ORGANISM: West Nile virus
<220> FEATURE:
<221> NAME/KEY: CDS
<222> LOCATION: (1)..(2004)

<400> SEQUENCE: 4

gtg act ctg agc aac ttt caa gga aag gtc atg atg act gtc aat gca       48
Val Thr Leu Ser Asn Phe Gln Gly Lys Val Met Met Thr Val Asn Ala
1               5                   10                  15

act gat gtc act gat gtg ata aca atc cca aca gca gct ggg aag aat       96
Thr Asp Val Thr Asp Val Ile Thr Ile Pro Thr Ala Ala Gly Lys Asn
            20                  25                  30

ctt tgc att gtc aga gct atg gat gtg ggc tac atg tgt gat gac aca      144
Leu Cys Ile Val Arg Ala Met Asp Val Gly Tyr Met Cys Asp Asp Thr
        35                  40                  45

atc act tat gag tgt cca gta ctt tct gct gga aat gat cct gaa gac      192
Ile Thr Tyr Glu Cys Pro Val Leu Ser Ala Gly Asn Asp Pro Glu Asp
    50                  55                  60

att gat tgt tgg tgc acc aaa tca gct gtc tat gtt cgt tat ggg agg      240
Ile Asp Cys Trp Cys Thr Lys Ser Ala Val Tyr Val Arg Tyr Gly Arg
65                  70                  75                  80

tgc aca aag acc aga cac tca cga aga agt cga agg tcc ctg aca gtg      288
Cys Thr Lys Thr Arg His Ser Arg Arg Ser Arg Arg Ser Leu Thr Val
                85                  90                  95

caa act cat gga gag tca act ttg gcc aac aag aaa ggc gca tgg atg      336
Gln Thr His Gly Glu Ser Thr Leu Ala Asn Lys Lys Gly Ala Trp Met
            100                 105                 110

gat tct acc aaa gca aca aga tat ctt gtc aaa act gag tca tgg att      384
Asp Ser Thr Lys Ala Thr Arg Tyr Leu Val Lys Thr Glu Ser Trp Ile
        115                 120                 125

ctt agg aat cct gga tat gct tta gtt gca gct gtc att gga tgg atg      432
Leu Arg Asn Pro Gly Tyr Ala Leu Val Ala Ala Val Ile Gly Trp Met
    130                 135                 140

ctt ggg tcc aat acc atg cag aga gtt gtc ttc gta gtt ctg ttg tta      480
Leu Gly Ser Asn Thr Met Gln Arg Val Val Phe Val Val Leu Leu Leu
145                 150                 155                 160

ctt gta gct cca gct tac tca ttc aac tgt ctt gga atg agc aat agg      528
Leu Val Ala Pro Ala Tyr Ser Phe Asn Cys Leu Gly Met Ser Asn Arg
                165                 170                 175

gat ttc ctt gaa ggt gtt tcc ggt gca aca tgg gtt gat ctt gtc tta      576
Asp Phe Leu Glu Gly Val Ser Gly Ala Thr Trp Val Asp Leu Val Leu
            180                 185                 190

gaa gga gat tca tgt gtg aca atc atg tcc aaa gac aag cca acc att      624
Glu Gly Asp Ser Cys Val Thr Ile Met Ser Lys Asp Lys Pro Thr Ile
        195                 200                 205

gat gtc aag atg atg aac atg gaa gct gcc aat ctt gca gaa gtt agg      672
```

-continued

```
Asp Val Lys Met Met Asn Met Glu Ala Ala Asn Leu Ala Glu Val Arg
    210                 215                 220

tct tac tgc tat ctg gca aca gtg agt gat ttg tca aca aaa gct gcc      720
Ser Tyr Cys Tyr Leu Ala Thr Val Ser Asp Leu Ser Thr Lys Ala Ala
225                 230                 235                 240

tgt ccc aca atg gga gag gct cac aat gac aaa cgt gct gat cct gca      768
Cys Pro Thr Met Gly Glu Ala His Asn Asp Lys Arg Ala Asp Pro Ala
                245                 250                 255

ttt gta tgc aga caa gga gtt gta gac aga ggt tgg gga aat ggt tgt      816
Phe Val Cys Arg Gln Gly Val Val Asp Arg Gly Trp Gly Asn Gly Cys
            260                 265                 270

ggt ctc ttt ggc aaa ggc agc att gac act tgt gca aag ttt gct tgc      864
Gly Leu Phe Gly Lys Gly Ser Ile Asp Thr Cys Ala Lys Phe Ala Cys
        275                 280                 285

agc acc aaa gca att ggt cga acc ata ttg aaa gag aac att aag tat      912
Ser Thr Lys Ala Ile Gly Arg Thr Ile Leu Lys Glu Asn Ile Lys Tyr
    290                 295                 300

gaa gtt gcc atc ttt gtt cat ggt cca aca act gtg gaa tct cat ggc      960
Glu Val Ala Ile Phe Val His Gly Pro Thr Thr Val Glu Ser His Gly
305                 310                 315                 320

aat tac cca aca caa gtt ggt gcc acc caa gct ggg agg ttt tca atc     1008
Asn Tyr Pro Thr Gln Val Gly Ala Thr Gln Ala Gly Arg Phe Ser Ile
                325                 330                 335

act cct gct gct cca agt tac act ctg aaa ttg ggt gaa tat ggt gaa     1056
Thr Pro Ala Ala Pro Ser Tyr Thr Leu Lys Leu Gly Glu Tyr Gly Glu
            340                 345                 350

gta aca gtt gat tgt gaa cct agg tct ggc att gac acc aat gct tac     1104
Val Thr Val Asp Cys Glu Pro Arg Ser Gly Ile Asp Thr Asn Ala Tyr
        355                 360                 365

tat gta atg act gtg gga aca aag aca ttc tta gtt cac aga gaa tgg     1152
Tyr Val Met Thr Val Gly Thr Lys Thr Phe Leu Val His Arg Glu Trp
    370                 375                 380

ttc atg gat ttg aat ctc cct tgg agt tct gct gga agc act gtt tgg     1200
Phe Met Asp Leu Asn Leu Pro Trp Ser Ser Ala Gly Ser Thr Val Trp
385                 390                 395                 400

agg aat cgt gaa aca ttg atg gag ttt gag gaa cca cat gca aca aaa     1248
Arg Asn Arg Glu Thr Leu Met Glu Phe Glu Glu Pro His Ala Thr Lys
                405                 410                 415

cag tca gta ata gca ttg ggc agt caa gag gga gca tta cat caa gcc     1296
Gln Ser Val Ile Ala Leu Gly Ser Gln Glu Gly Ala Leu His Gln Ala
            420                 425                 430

ttg gct ggg gca att cct gtt gag ttt agt tcc aac act gtg aaa ctg     1344
Leu Ala Gly Ala Ile Pro Val Glu Phe Ser Ser Asn Thr Val Lys Leu
        435                 440                 445

aca agt ggt cat ctg aaa tgc aga gta aag atg gag aag tta cag ttg     1392
Thr Ser Gly His Leu Lys Cys Arg Val Lys Met Glu Lys Leu Gln Leu
    450                 455                 460

aaa gga acc act tat ggt gtt tgt tcc aaa gcc ttc aag ttt ctt gga     1440
Lys Gly Thr Thr Tyr Gly Val Cys Ser Lys Ala Phe Lys Phe Leu Gly
465                 470                 475                 480

act cct gct gac act ggt cat ggg act gtg gtt ttg gaa ttg cag tac     1488
Thr Pro Ala Asp Thr Gly His Gly Thr Val Val Leu Glu Leu Gln Tyr
                485                 490                 495

act ggc act gat ggt cca tgc aag gtt ccc ata agc agt gtt gct tca     1536
Thr Gly Thr Asp Gly Pro Cys Lys Val Pro Ile Ser Ser Val Ala Ser
            500                 505                 510

ctc aat gat ctc act cca gta ggc aga ctt gtg aca gtc aac ccc ttt     1584
Leu Asn Asp Leu Thr Pro Val Gly Arg Leu Val Thr Val Asn Pro Phe
        515                 520                 525
```

-continued

```
gtt tct gtt gca act gcc aat gca aag gtg ctc ata gaa ttg gag cct      1632
Val Ser Val Ala Thr Ala Asn Ala Lys Val Leu Ile Glu Leu Glu Pro
    530                 535                 540

cca ttt ggt gat tct tac att gtt gta ggc aga gga gag caa cag atc      1680
Pro Phe Gly Asp Ser Tyr Ile Val Val Gly Arg Gly Glu Gln Gln Ile
545                 550                 555                 560

aac cat cac tgg cac aaa tct ggt tct tca att ggc aaa gcc ttc aca      1728
Asn His His Trp His Lys Ser Gly Ser Ser Ile Gly Lys Ala Phe Thr
                565                 570                 575

acc act ctc aaa ggg gca cag aga ctt gct gct tta gga gac act gca      1776
Thr Thr Leu Lys Gly Ala Gln Arg Leu Ala Ala Leu Gly Asp Thr Ala
            580                 585                 590

tgg gat ttc gga tct gtt gga ggt gtt ttc acc tct gtg gga aag gct      1824
Trp Asp Phe Gly Ser Val Gly Gly Val Phe Thr Ser Val Gly Lys Ala
        595                 600                 605

gtg cat caa gtt ttt ggt ggg gct ttt cga tcc ttg ttt ggt gga atg      1872
Val His Gln Val Phe Gly Gly Ala Phe Arg Ser Leu Phe Gly Gly Met
    610                 615                 620

tct tgg ata act caa ggt ctt tta ggg gct ctg ctt ttg tgg atg ggc      1920
Ser Trp Ile Thr Gln Gly Leu Leu Gly Ala Leu Leu Leu Trp Met Gly
625                 630                 635                 640

atc aat gca agg gac aga tca att gcc tta acc ttc ctt gca gtt gga      1968
Ile Asn Ala Arg Asp Arg Ser Ile Ala Leu Thr Phe Leu Ala Val Gly
                645                 650                 655

ggt gtt ctt ctc ttt ctc tct gta aat gtt cat gct                      2004
Gly Val Leu Leu Phe Leu Ser Val Asn Val His Ala
            660                 665


<210> SEQ ID NO 5
<211> LENGTH: 668
<212> TYPE: PRT
<213> ORGANISM: West Nile virus

<400> SEQUENCE: 5

Val Thr Leu Ser Asn Phe Gln Gly Lys Val Met Met Thr Val Asn Ala
1               5                   10                  15

Thr Asp Val Thr Asp Val Ile Thr Ile Pro Thr Ala Ala Gly Lys Asn
            20                  25                  30

Leu Cys Ile Val Arg Ala Met Asp Val Gly Tyr Met Cys Asp Asp Thr
        35                  40                  45

Ile Thr Tyr Glu Cys Pro Val Leu Ser Ala Gly Asn Asp Pro Glu Asp
    50                  55                  60

Ile Asp Cys Trp Cys Thr Lys Ser Ala Val Tyr Val Arg Tyr Gly Arg
65                  70                  75                  80

Cys Thr Lys Thr Arg His Ser Arg Arg Ser Arg Arg Ser Leu Thr Val
                85                  90                  95

Gln Thr His Gly Glu Ser Thr Leu Ala Asn Lys Lys Gly Ala Trp Met
            100                 105                 110

Asp Ser Thr Lys Ala Thr Arg Tyr Leu Val Lys Thr Glu Ser Trp Ile
        115                 120                 125

Leu Arg Asn Pro Gly Tyr Ala Leu Val Ala Ala Val Ile Gly Trp Met
    130                 135                 140

Leu Gly Ser Asn Thr Met Gln Arg Val Val Phe Val Val Leu Leu Leu
145                 150                 155                 160

Leu Val Ala Pro Ala Tyr Ser Phe Asn Cys Leu Gly Met Ser Asn Arg
                165                 170                 175

Asp Phe Leu Glu Gly Val Ser Gly Ala Thr Trp Val Asp Leu Val Leu
            180                 185                 190
```

-continued

```
Glu Gly Asp Ser Cys Val Thr Ile Met Ser Lys Asp Lys Pro Thr Ile
        195                 200                 205

Asp Val Lys Met Met Asn Met Glu Ala Ala Asn Leu Ala Glu Val Arg
    210                 215                 220

Ser Tyr Cys Tyr Leu Ala Thr Val Ser Asp Leu Ser Thr Lys Ala Ala
225                 230                 235                 240

Cys Pro Thr Met Gly Glu Ala His Asn Asp Lys Arg Ala Asp Pro Ala
                245                 250                 255

Phe Val Cys Arg Gln Gly Val Val Asp Arg Gly Trp Gly Asn Gly Cys
            260                 265                 270

Gly Leu Phe Gly Lys Gly Ser Ile Asp Thr Cys Ala Lys Phe Ala Cys
        275                 280                 285

Ser Thr Lys Ala Ile Gly Arg Thr Ile Leu Lys Glu Asn Ile Lys Tyr
    290                 295                 300

Glu Val Ala Ile Phe Val His Gly Pro Thr Thr Val Glu Ser His Gly
305                 310                 315                 320

Asn Tyr Pro Thr Gln Val Gly Ala Thr Gln Ala Gly Arg Phe Ser Ile
                325                 330                 335

Thr Pro Ala Ala Pro Ser Tyr Thr Leu Lys Leu Gly Glu Tyr Gly Glu
            340                 345                 350

Val Thr Val Asp Cys Glu Pro Arg Ser Gly Ile Asp Thr Asn Ala Tyr
        355                 360                 365

Tyr Val Met Thr Val Gly Thr Lys Thr Phe Leu Val His Arg Glu Trp
    370                 375                 380

Phe Met Asp Leu Asn Leu Pro Trp Ser Ser Ala Gly Ser Thr Val Trp
385                 390                 395                 400

Arg Asn Arg Glu Thr Leu Met Glu Phe Glu Glu Pro His Ala Thr Lys
                405                 410                 415

Gln Ser Val Ile Ala Leu Gly Ser Gln Glu Gly Ala Leu His Gln Ala
            420                 425                 430

Leu Ala Gly Ala Ile Pro Val Glu Phe Ser Ser Asn Thr Val Lys Leu
        435                 440                 445

Thr Ser Gly His Leu Lys Cys Arg Val Lys Met Glu Lys Leu Gln Leu
    450                 455                 460

Lys Gly Thr Thr Tyr Gly Val Cys Ser Lys Ala Phe Lys Phe Leu Gly
465                 470                 475                 480

Thr Pro Ala Asp Thr Gly His Gly Thr Val Val Leu Glu Leu Gln Tyr
                485                 490                 495

Thr Gly Thr Asp Gly Pro Cys Lys Val Pro Ile Ser Ser Val Ala Ser
            500                 505                 510

Leu Asn Asp Leu Thr Pro Val Gly Arg Leu Val Thr Val Asn Pro Phe
        515                 520                 525

Val Ser Val Ala Thr Ala Asn Ala Lys Val Leu Ile Glu Leu Glu Pro
    530                 535                 540

Pro Phe Gly Asp Ser Tyr Ile Val Val Gly Arg Gly Glu Gln Gln Ile
545                 550                 555                 560

Asn His His Trp His Lys Ser Gly Ser Ser Ile Gly Lys Ala Phe Thr
                565                 570                 575

Thr Thr Leu Lys Gly Ala Gln Arg Leu Ala Ala Leu Gly Asp Thr Ala
            580                 585                 590

Trp Asp Phe Gly Ser Val Gly Gly Val Phe Thr Ser Val Gly Lys Ala
        595                 600                 605
```

-continued

```
Val His Gln Val Phe Gly Gly Ala Phe Arg Ser Leu Phe Gly Gly Met
    610                 615                 620

Ser Trp Ile Thr Gln Gly Leu Leu Gly Ala Leu Leu Leu Trp Met Gly
625                 630                 635                 640

Ile Asn Ala Arg Asp Arg Ser Ile Ala Leu Thr Phe Leu Ala Val Gly
                645                 650                 655

Gly Val Leu Leu Phe Leu Ser Val Asn Val His Ala
            660                 665
```

<210> SEQ ID NO 6
<211> LENGTH: 1728
<212> TYPE: DNA
<213> ORGANISM: West Nile virus

<400> SEQUENCE: 6

```
tccctgacag tgcaaactca tggagagtca actttggcca acaagaaagg cgcatggatg     60

gattctacca aagcaacaag atatcttgtc aaaactgagt catggattct taggaatcct    120

ggatatgctt tagttgcagc tgtcattgga tggatgcttg ggtccaatac catgcagaga    180

gttgtcttcg tagttctgtt gttacttgta gctccagctt actcattcaa ctgtcttgga    240

atgagcaata gggatttcct tgaaggtgtt tccggtgcaa catgggttga tcttgtctta    300

gaaggagatt catgtgtgac aatcatgtcc aaagacaagc caaccattga tgtcaagatg    360

atgaacatgg aagctgccaa tcttgcagaa gttaggtctt actgctatct ggcaacagtg    420

agtgatttgt caacaaaagc tgcctgtccc acaatgggag aggctcacaa tgacaaacgt    480

gctgatcctg catttgtatg cagacaagga gttgtagaca gaggttgggg aaatggttgt    540

ggtctctttg gcaaaggcag cattgacact tgtgcaaagt ttgcttgcag caccaaagca    600

attggtcgaa ccatattgaa agagaacatt aagtatgaag ttgccatctt tgttcatggt    660

ccaacaactg tggaatctca tggcaattac agcacacaag ttggtgccac ccaagctggg    720

aggttttcaa tcactcctgc tgctccaagt tacactctga aattgggtga atatggtgaa    780

gtaacagttg attgtgaacc taggtctggc attgacacca atgcttacta tgtaatgact    840

gtgggaacaa agacattctt agttcacaga gaatggttca tggatttgaa tctcccttgg    900

agttctgctg gaagcactgt ttggaggaat cgtgaaacat tgatggagtt tgaggaacca    960

catgcaacaa aacagtcagt aatagcattg ggcagtcaag agggagcatt acatcaagcc   1020

ttggctgggg caattcctgt tgagtttagt tccaacactg tgaaactgac aagtggtcat   1080

ctgaaatgca gagtaaagat ggagaagtta cagttgaaag gaaccactta tggtgtttgt   1140

tccaaagcct tcaagtttct tggaactcct gctgacactg gtcatgggac tgtggttttg   1200

gaattgcagt acactggcac tgatggtcca tgcaaggttc ccataagcag tgttgcttca   1260

ctcaatgatc tcactccagt aggcagactt gtgacagtca accccttgt ttctgttgca    1320

actgccaatg caaaggtgct catagaattg gagcctccat ttggtgattc ttacattgtt   1380

gtaggcagag gagagcaaca gatcaaccat cactggcaca aatctggttc ttcaattggc   1440

aaagccttca caaccactct caaaggggca cagagacttg ctgctttagg agacactgca   1500

tgggatttcg gatctgttgg aggtgttttc acctctgtgg gaaaggctgt gcatcaagtt   1560

tttggtgggg cttttcgatc cttgtttggt ggaatgtctt ggataactca aggtctttta   1620

ggggctctgc ttttgtggat gggcatcaat gcaagggaca gatcaattgc cttaaccttc   1680

cttgcagttg gaggtgttct tctctttctc tctgtaaatg ttcatgct                1728
```

-continued

<210> SEQ ID NO 7
<211> LENGTH: 1728
<212> TYPE: DNA
<213> ORGANISM: West Nile virus

<400> SEQUENCE: 7

```
agcttaactg tccagacaca cggtgaatcc acacttgcta acaagaaagg tgcttggatg     60

gacagcacta aagcaactag atacttggtc aagacagaat cttggatctt acgtaatcct    120

ggttacgcac ttgtagccgc agtcataggt tggatgttgg gcagtaacac tatgcaacgt    180

gtagtgtttg ttgtacttct tctcttggtt gcacctgcat attccttcaa ttgcttgggg    240

atgtccaaca gagatttcct ggaaggagta agtggagcaa cttgggtcga tttggttctt    300

gagggtgatt cttgtgtcac cattatgagt aaagacaaac ccacaataga tgtgaaaatg    360

atgaatatgg aggccgctaa cttggcagaa gtccgtagct attgttactt agctactgtt    420

tcagaccttt ctactaaagc cgcttgccca actatgggtg aagcacacaa tgataagagg    480

gcagaccctg cttttgtttg tcgtcaaggt gtagttgata ggggatgggg aaatggctgt    540

ggactgtttg ggaagggttc tatagatact tgcgctaagt tcgcatgttc aacaaaagct    600

ataggacgaa caattctcaa ggaaaacatc aagtatgagg tcgcaatctt cgtacatgga    660

cccactacag tcgaaagcca cgggaactat tccactcaag taggagcaac acaagctgga    720

agattcagca ttacaccagc cgctccttca tacacattga aacttggtga gtacggtgag    780

gtcactgttg attgcgagcc aagaagtgga atagatacaa atgcctatta cgttatgaca    840

gttggcacta agacttttct tgttcatagg gagtggttca tggacttgaa tctgccctgg    900

tccagtgctg gctctacagt ttggagaaac agagaaactc tcatggaatt tgaagagcct    960

catgctacta agcaatcagt tattgctctt gggtcccaag aaggtgctct ccatcaggct   1020

ttagctggtg ctattccagt tgagttttcc agcaatactg ttaagttgac ttctggccat   1080

ttgaagtgta gggtgaagat ggagaaactc caacttaaag ggacaaccta tggagtttgc   1140

tctaaggctt tcaagttctt gggcacacca gcagataccg gacatggaac agttgtactt   1200

gaacttcagt atactgggac cgatggacct tgtaaagtgc caatttcttc agttgcctct   1260

ctcaatgact taactcctgt tgggaggtta gttaccgtga atccatttgt gagtgtagct   1320

accgcaaatg ctaaagttct cattgagctt gaaccacctt ttggcgattc ctacatagtg   1380

gttggaaggg gtgaacagca aatcaatcac cattggcata agagtggctc ttcaatcgga   1440

aaggccttta ccacaaccct gaaaggtgct caacgtttag ccgcactcgg tgataccgct   1500

tgggactttg gttcagtggg tggtgtgttt acatcagttg gcaaagcagt gcatcaggtg   1560

tttggaggag cctttagaag tcttttcgga gggatgtcat ggattaccca aggtttgctt   1620

ggagccttgt tactttggat ggggatcaac gctagagatc gatctattgc actgactttt   1680

ctggctgtgg gtggcgtgtt gctgttctta tcagtgaatg tacacgct                1728
```

<210> SEQ ID NO 8
<211> LENGTH: 2106
<212> TYPE: DNA
<213> ORGANISM: West Nile virus
<220> FEATURE:
<221> NAME/KEY: CDS
<222> LOCATION: (1)..(2082)

<400> SEQUENCE: 8

```
atg gct aag atg gtc att gtg ctt gtt gtg tgc ttg gct ctc tct gct       48
Met Ala Lys Met Val Ile Val Leu Val Val Cys Leu Ala Leu Ser Ala
1               5                   10                  15
```

-continued

```
gcc tca gct tct gcc tct gtg act ctg agc aac ttt caa gga aag gtc       96
Ala Ser Ala Ser Ala Ser Val Thr Leu Ser Asn Phe Gln Gly Lys Val
            20                  25                  30

atg atg act gtc aat gca act gat gtc act gat gtg ata aca atc cca      144
Met Met Thr Val Asn Ala Thr Asp Val Thr Asp Val Ile Thr Ile Pro
        35                  40                  45

aca gca gct ggg aag aat ctt tgc att gtc aga gct atg gat gtg ggc      192
Thr Ala Ala Gly Lys Asn Leu Cys Ile Val Arg Ala Met Asp Val Gly
    50                  55                  60

tac atg tgt gat gac aca atc act tat gag tgt cca gta ctt tct gct      240
Tyr Met Cys Asp Asp Thr Ile Thr Tyr Glu Cys Pro Val Leu Ser Ala
65                  70                  75                  80

gga aat gat cct gaa gac att gat tgt tgg tgc acc aaa tca gct gtc      288
Gly Asn Asp Pro Glu Asp Ile Asp Cys Trp Cys Thr Lys Ser Ala Val
                85                  90                  95

tat gtt cgt tat ggg agg tgc aca aag acc aga cac tca cga aga agt      336
Tyr Val Arg Tyr Gly Arg Cys Thr Lys Thr Arg His Ser Arg Arg Ser
            100                 105                 110

cga agg tcc ctg aca gtg caa act cat gga gag tca act ttg gcc aac      384
Arg Arg Ser Leu Thr Val Gln Thr His Gly Glu Ser Thr Leu Ala Asn
        115                 120                 125

aag aaa ggc gca tgg atg gat tct acc aaa gca aca aga tat ctt gtc      432
Lys Lys Gly Ala Trp Met Asp Ser Thr Lys Ala Thr Arg Tyr Leu Val
    130                 135                 140

aaa act gag tca tgg att ctt agg aat cct gga tat gct tta gtt gca      480
Lys Thr Glu Ser Trp Ile Leu Arg Asn Pro Gly Tyr Ala Leu Val Ala
145                 150                 155                 160

gct gtc att gga tgg atg ctt ggg tcc aat acc atg cag aga gtt gtc      528
Ala Val Ile Gly Trp Met Leu Gly Ser Asn Thr Met Gln Arg Val Val
                165                 170                 175

ttc gta gtt ctg ttg tta ctt gta gct cca gct tac tca ttc aac tgt      576
Phe Val Val Leu Leu Leu Leu Val Ala Pro Ala Tyr Ser Phe Asn Cys
            180                 185                 190

ctt gga atg agc aat agg gat ttc ctt gaa ggt gtt tcc ggt gca aca      624
Leu Gly Met Ser Asn Arg Asp Phe Leu Glu Gly Val Ser Gly Ala Thr
        195                 200                 205

tgg gtt gat ctt gtc tta gaa gga gat tca tgt gtg aca atc atg tcc      672
Trp Val Asp Leu Val Leu Glu Gly Asp Ser Cys Val Thr Ile Met Ser
    210                 215                 220

aaa gac aag cca acc att gat gtc aag atg atg aac atg gaa gct gcc      720
Lys Asp Lys Pro Thr Ile Asp Val Lys Met Met Asn Met Glu Ala Ala
225                 230                 235                 240

aat ctt gca gaa gtt agg tct tac tgc tat ctg gca aca gtg agt gat      768
Asn Leu Ala Glu Val Arg Ser Tyr Cys Tyr Leu Ala Thr Val Ser Asp
                245                 250                 255

ttg tca aca aaa gct gcc tgt ccc aca atg gga gag gct cac aat gac      816
Leu Ser Thr Lys Ala Ala Cys Pro Thr Met Gly Glu Ala His Asn Asp
            260                 265                 270

aaa cgt gct gat cct gca ttt gta tgc aga caa gga gtt gta gac aga      864
Lys Arg Ala Asp Pro Ala Phe Val Cys Arg Gln Gly Val Val Asp Arg
        275                 280                 285

ggt tgg gga aat ggt tgt ggt ctc ttt ggc aaa ggc agc att gac act      912
Gly Trp Gly Asn Gly Cys Gly Leu Phe Gly Lys Gly Ser Ile Asp Thr
    290                 295                 300

tgt gca aag ttt gct tgc agc acc aaa gca att ggt cga acc ata ttg      960
Cys Ala Lys Phe Ala Cys Ser Thr Lys Ala Ile Gly Arg Thr Ile Leu
305                 310                 315                 320

aaa gag aac att aag tat gaa gtt gcc atc ttt gtt cat ggt cca aca     1008
Lys Glu Asn Ile Lys Tyr Glu Val Ala Ile Phe Val His Gly Pro Thr
```

-continued

```
                325                 330                 335

act gtg gaa tct cat ggc aat tac agc aca caa gtt ggt gcc acc caa      1056
Thr Val Glu Ser His Gly Asn Tyr Ser Thr Gln Val Gly Ala Thr Gln
            340                 345                 350

gct ggg agg ttt tca atc act cct gct gct cca agt tac act ctg aaa      1104
Ala Gly Arg Phe Ser Ile Thr Pro Ala Ala Pro Ser Tyr Thr Leu Lys
        355                 360                 365

ttg ggt gaa tat ggt gaa gta aca gtt gat tgt gaa cct agg tct ggc      1152
Leu Gly Glu Tyr Gly Glu Val Thr Val Asp Cys Glu Pro Arg Ser Gly
    370                 375                 380

att gac acc aat gct tac tat gta atg act gtg gga aca aag aca ttc      1200
Ile Asp Thr Asn Ala Tyr Tyr Val Met Thr Val Gly Thr Lys Thr Phe
385                 390                 395                 400

tta gtt cac aga gaa tgg ttc atg gat ttg aat ctc cct tgg agt tct      1248
Leu Val His Arg Glu Trp Phe Met Asp Leu Asn Leu Pro Trp Ser Ser
                405                 410                 415

gct gga agc act gtt tgg agg aat cgt gaa aca ttg atg gag ttt gag      1296
Ala Gly Ser Thr Val Trp Arg Asn Arg Glu Thr Leu Met Glu Phe Glu
            420                 425                 430

gaa cca cat gca aca aaa cag tca gta ata gca ttg ggc agt caa gag      1344
Glu Pro His Ala Thr Lys Gln Ser Val Ile Ala Leu Gly Ser Gln Glu
        435                 440                 445

gga gca tta cat caa gcc ttg gct ggg gca att cct gtt gag ttt agt      1392
Gly Ala Leu His Gln Ala Leu Ala Gly Ala Ile Pro Val Glu Phe Ser
    450                 455                 460

tcc aac act gtg aaa ctg aca agt ggt cat ctg aaa tgc aga gta aag      1440
Ser Asn Thr Val Lys Leu Thr Ser Gly His Leu Lys Cys Arg Val Lys
465                 470                 475                 480

atg gag aag tta cag ttg aaa gga acc act tat ggt gtt tgt tcc aaa      1488
Met Glu Lys Leu Gln Leu Lys Gly Thr Thr Tyr Gly Val Cys Ser Lys
                485                 490                 495

gcc ttc aag ttt ctt gga act cct gct gac act ggt cat ggg act gtg      1536
Ala Phe Lys Phe Leu Gly Thr Pro Ala Asp Thr Gly His Gly Thr Val
            500                 505                 510

gtt ttg gaa ttg cag tac act ggc act gat ggt cca tgc aag gtt ccc      1584
Val Leu Glu Leu Gln Tyr Thr Gly Thr Asp Gly Pro Cys Lys Val Pro
        515                 520                 525

ata agc agt gtt gct tca ctc aat gat ctc act cca gta ggc aga ctt      1632
Ile Ser Ser Val Ala Ser Leu Asn Asp Leu Thr Pro Val Gly Arg Leu
    530                 535                 540

gtg aca gtc aac ccc ttt gtt tct gtt gca act gcc aat gca aag gtg      1680
Val Thr Val Asn Pro Phe Val Ser Val Ala Thr Ala Asn Ala Lys Val
545                 550                 555                 560

ctc ata gaa ttg gag cct cca ttt ggt gat tct tac att gtt gta ggc      1728
Leu Ile Glu Leu Glu Pro Pro Phe Gly Asp Ser Tyr Ile Val Val Gly
                565                 570                 575

aga gga gag caa cag atc aac cat cac tgg cac aaa tct ggt tct tca      1776
Arg Gly Glu Gln Gln Ile Asn His His Trp His Lys Ser Gly Ser Ser
            580                 585                 590

att ggc aaa gcc ttc aca acc act ctc aaa ggg gca cag aga ctt gct      1824
Ile Gly Lys Ala Phe Thr Thr Thr Leu Lys Gly Ala Gln Arg Leu Ala
        595                 600                 605

gct tta gga gac act gca tgg gat ttc gga tct gtt gga ggt gtt ttc      1872
Ala Leu Gly Asp Thr Ala Trp Asp Phe Gly Ser Val Gly Gly Val Phe
    610                 615                 620

acc tct gtg gga aag gct gtg cat caa gtt ttt ggt ggg gct ttt cga      1920
Thr Ser Val Gly Lys Ala Val His Gln Val Phe Gly Gly Ala Phe Arg
625                 630                 635                 640

tcc ttg ttt ggt gga atg tct tgg ata act caa ggt ctt tta ggg gct      1968
```

-continued

```
Ser Leu Phe Gly Gly Met Ser Trp Ile Thr Gln Gly Leu Leu Gly Ala
                645                 650                 655

ctg ctt ttg tgg atg ggc atc aat gca agg gac aga tca att gcc tta      2016
Leu Leu Leu Trp Met Gly Ile Asn Ala Arg Asp Arg Ser Ile Ala Leu
            660                 665                 670

acc ttc ctt gca gtt gga ggt gtt ctt ctc ttt ctc tct gta aat gtt      2064
Thr Phe Leu Ala Val Gly Gly Val Leu Leu Phe Leu Ser Val Asn Val
        675                 680                 685

cat gct aag gat gaa ctg tgagtagtta gcttaatcac ctag                  2106
His Ala Lys Asp Glu Leu
    690


<210> SEQ ID NO 9
<211> LENGTH: 694
<212> TYPE: PRT
<213> ORGANISM: West Nile virus

<400> SEQUENCE: 9

Met Ala Lys Met Val Ile Val Leu Val Val Cys Leu Ala Leu Ser Ala
1               5                   10                  15

Ala Ser Ala Ser Ala Ser Val Thr Leu Ser Asn Phe Gln Gly Lys Val
            20                  25                  30

Met Met Thr Val Asn Ala Thr Asp Val Thr Asp Val Ile Thr Ile Pro
        35                  40                  45

Thr Ala Ala Gly Lys Asn Leu Cys Ile Val Arg Ala Met Asp Val Gly
    50                  55                  60

Tyr Met Cys Asp Asp Thr Ile Thr Tyr Glu Cys Pro Val Leu Ser Ala
65                  70                  75                  80

Gly Asn Asp Pro Glu Asp Ile Asp Cys Trp Cys Thr Lys Ser Ala Val
                85                  90                  95

Tyr Val Arg Tyr Gly Arg Cys Thr Lys Thr Arg His Ser Arg Arg Ser
            100                 105                 110

Arg Arg Ser Leu Thr Val Gln Thr His Gly Glu Ser Thr Leu Ala Asn
        115                 120                 125

Lys Lys Gly Ala Trp Met Asp Ser Thr Lys Ala Thr Arg Tyr Leu Val
    130                 135                 140

Lys Thr Glu Ser Trp Ile Leu Arg Asn Pro Gly Tyr Ala Leu Val Ala
145                 150                 155                 160

Ala Val Ile Gly Trp Met Leu Gly Ser Asn Thr Met Gln Arg Val Val
                165                 170                 175

Phe Val Val Leu Leu Leu Leu Val Ala Pro Ala Tyr Ser Phe Asn Cys
            180                 185                 190

Leu Gly Met Ser Asn Arg Asp Phe Leu Glu Gly Val Ser Gly Ala Thr
        195                 200                 205

Trp Val Asp Leu Val Leu Glu Gly Asp Ser Cys Val Thr Ile Met Ser
    210                 215                 220

Lys Asp Lys Pro Thr Ile Asp Val Lys Met Met Asn Met Glu Ala Ala
225                 230                 235                 240

Asn Leu Ala Glu Val Arg Ser Tyr Cys Tyr Leu Ala Thr Val Ser Asp
                245                 250                 255

Leu Ser Thr Lys Ala Ala Cys Pro Thr Met Gly Glu Ala His Asn Asp
            260                 265                 270

Lys Arg Ala Asp Pro Ala Phe Val Cys Arg Gln Gly Val Val Asp Arg
        275                 280                 285

Gly Trp Gly Asn Gly Cys Gly Leu Phe Gly Lys Gly Ser Ile Asp Thr
    290                 295                 300
```

-continued

```
Cys Ala Lys Phe Ala Cys Ser Thr Lys Ala Ile Gly Arg Thr Ile Leu
305                 310                 315                 320

Lys Glu Asn Ile Lys Tyr Glu Val Ala Ile Phe Val His Gly Pro Thr
                325                 330                 335

Thr Val Glu Ser His Gly Asn Tyr Ser Thr Gln Val Gly Ala Thr Gln
            340                 345                 350

Ala Gly Arg Phe Ser Ile Thr Pro Ala Ala Pro Ser Tyr Thr Leu Lys
        355                 360                 365

Leu Gly Glu Tyr Gly Glu Val Thr Val Asp Cys Glu Pro Arg Ser Gly
    370                 375                 380

Ile Asp Thr Asn Ala Tyr Tyr Val Met Thr Val Gly Thr Lys Thr Phe
385                 390                 395                 400

Leu Val His Arg Glu Trp Phe Met Asp Leu Asn Leu Pro Trp Ser Ser
                405                 410                 415

Ala Gly Ser Thr Val Trp Arg Asn Arg Glu Thr Leu Met Glu Phe Glu
            420                 425                 430

Glu Pro His Ala Thr Lys Gln Ser Val Ile Ala Leu Gly Ser Gln Glu
        435                 440                 445

Gly Ala Leu His Gln Ala Leu Ala Gly Ala Ile Pro Val Glu Phe Ser
    450                 455                 460

Ser Asn Thr Val Lys Leu Thr Ser Gly His Leu Lys Cys Arg Val Lys
465                 470                 475                 480

Met Glu Lys Leu Gln Leu Lys Gly Thr Thr Tyr Gly Val Cys Ser Lys
                485                 490                 495

Ala Phe Lys Phe Leu Gly Thr Pro Ala Asp Thr Gly His Gly Thr Val
            500                 505                 510

Val Leu Glu Leu Gln Tyr Thr Gly Thr Asp Gly Pro Cys Lys Val Pro
        515                 520                 525

Ile Ser Ser Val Ala Ser Leu Asn Asp Leu Thr Pro Val Gly Arg Leu
    530                 535                 540

Val Thr Val Asn Pro Phe Val Ser Val Ala Thr Ala Asn Ala Lys Val
545                 550                 555                 560

Leu Ile Glu Leu Glu Pro Pro Phe Gly Asp Ser Tyr Ile Val Val Gly
                565                 570                 575

Arg Gly Glu Gln Gln Ile Asn His His Trp His Lys Ser Gly Ser Ser
            580                 585                 590

Ile Gly Lys Ala Phe Thr Thr Thr Leu Lys Gly Ala Gln Arg Leu Ala
        595                 600                 605

Ala Leu Gly Asp Thr Ala Trp Asp Phe Gly Ser Val Gly Gly Val Phe
    610                 615                 620

Thr Ser Val Gly Lys Ala Val His Gln Val Phe Gly Gly Ala Phe Arg
625                 630                 635                 640

Ser Leu Phe Gly Gly Met Ser Trp Ile Thr Gln Gly Leu Leu Gly Ala
                645                 650                 655

Leu Leu Leu Trp Met Gly Ile Asn Ala Arg Asp Arg Ser Ile Ala Leu
            660                 665                 670

Thr Phe Leu Ala Val Gly Gly Val Leu Leu Phe Leu Ser Val Asn Val
        675                 680                 685

His Ala Lys Asp Glu Leu
    690
```

<210> SEQ ID NO 10
<211> LENGTH: 2106

-continued

```
<212> TYPE: DNA
<213> ORGANISM: West Nile virus
<220> FEATURE:
<221> NAME/KEY: CDS
<222> LOCATION: (1)..(2082)

<400> SEQUENCE: 10

atg gct aag atg gtc att gtg ctt gtt gtg tgc ttg gct ctc tct gct       48
Met Ala Lys Met Val Ile Val Leu Val Val Cys Leu Ala Leu Ser Ala
1               5                   10                  15

gcc tca gct tct gcc tct gtg act ctg agc aac ttt caa gga aag gtc       96
Ala Ser Ala Ser Ala Ser Val Thr Leu Ser Asn Phe Gln Gly Lys Val
            20                  25                  30

atg atg act gtc aat gca act gat gtc act gat gtg ata aca atc cca      144
Met Met Thr Val Asn Ala Thr Asp Val Thr Asp Val Ile Thr Ile Pro
        35                  40                  45

aca gca gct ggg aag aat ctt tgc att gtc aga gct atg gat gtg ggc      192
Thr Ala Ala Gly Lys Asn Leu Cys Ile Val Arg Ala Met Asp Val Gly
    50                  55                  60

tac atg tgt gat gac aca atc act tat gag tgt cca gta ctt tct gct      240
Tyr Met Cys Asp Asp Thr Ile Thr Tyr Glu Cys Pro Val Leu Ser Ala
65                  70                  75                  80

gga aat gat cct gaa gac att gat tgt tgg tgc acc aaa tca gct gtc      288
Gly Asn Asp Pro Glu Asp Ile Asp Cys Trp Cys Thr Lys Ser Ala Val
                85                  90                  95

tat gtt cgt tat ggg agg tgc aca aag acc aga cac tca cga aga agt      336
Tyr Val Arg Tyr Gly Arg Cys Thr Lys Thr Arg His Ser Arg Arg Ser
            100                 105                 110

cga agg tcc ctg aca gtg caa act cat gga gag tca act ttg gcc aac      384
Arg Arg Ser Leu Thr Val Gln Thr His Gly Glu Ser Thr Leu Ala Asn
        115                 120                 125

aag aaa ggc gca tgg atg gat tct acc aaa gca aca aga tat ctt gtc      432
Lys Lys Gly Ala Trp Met Asp Ser Thr Lys Ala Thr Arg Tyr Leu Val
    130                 135                 140

aaa act gag tca tgg att ctt agg aat cct gga tat gct tta gtt gca      480
Lys Thr Glu Ser Trp Ile Leu Arg Asn Pro Gly Tyr Ala Leu Val Ala
145                 150                 155                 160

gct gtc att gga tgg atg ctt ggg tcc aat acc atg cag aga gtt gtc      528
Ala Val Ile Gly Trp Met Leu Gly Ser Asn Thr Met Gln Arg Val Val
                165                 170                 175

ttc gta gtt ctg ttg tta ctt gta gct cca gct tac tca ttc aac tgt      576
Phe Val Val Leu Leu Leu Leu Val Ala Pro Ala Tyr Ser Phe Asn Cys
            180                 185                 190

ctt gga atg agc aat agg gat ttc ctt gaa ggt gtt tcc ggt gca aca      624
Leu Gly Met Ser Asn Arg Asp Phe Leu Glu Gly Val Ser Gly Ala Thr
        195                 200                 205

tgg gtt gat ctt gtc tta gaa gga gat tca tgt gtg aca atc atg tcc      672
Trp Val Asp Leu Val Leu Glu Gly Asp Ser Cys Val Thr Ile Met Ser
    210                 215                 220

aaa gac aag cca acc att gat gtc aag atg atg aac atg gaa gct gcc      720
Lys Asp Lys Pro Thr Ile Asp Val Lys Met Met Asn Met Glu Ala Ala
225                 230                 235                 240

aat ctt gca gaa gtt agg tct tac tgc tat ctg gca aca gtg agt gat      768
Asn Leu Ala Glu Val Arg Ser Tyr Cys Tyr Leu Ala Thr Val Ser Asp
                245                 250                 255

ttg tca aca aaa gct gcc tgt ccc aca atg gga gag gct cac aat gac      816
Leu Ser Thr Lys Ala Ala Cys Pro Thr Met Gly Glu Ala His Asn Asp
            260                 265                 270

aaa cgt gct gat cct gca ttt gta tgc aga caa gga gtt gta gac aga      864
Lys Arg Ala Asp Pro Ala Phe Val Cys Arg Gln Gly Val Val Asp Arg
        275                 280                 285
```

-continued

```
ggt tgg gga aat ggt tgt ggt ctc ttt ggc aaa ggc agc att gac act      912
Gly Trp Gly Asn Gly Cys Gly Leu Phe Gly Lys Gly Ser Ile Asp Thr
    290                 295                 300

tgt gca aag ttt gct tgc agc acc aaa gca att ggt cga acc ata ttg      960
Cys Ala Lys Phe Ala Cys Ser Thr Lys Ala Ile Gly Arg Thr Ile Leu
305                 310                 315                 320

aaa gag aac att aag tat gaa gtt gcc atc ttt gtt cat ggt cca aca     1008
Lys Glu Asn Ile Lys Tyr Glu Val Ala Ile Phe Val His Gly Pro Thr
                325                 330                 335

act gtg gaa tct cat ggc aat tac cca aca caa gtt ggt gcc acc caa     1056
Thr Val Glu Ser His Gly Asn Tyr Pro Thr Gln Val Gly Ala Thr Gln
            340                 345                 350

gct ggg agg ttt tca atc act cct gct gct cca agt tac act ctg aaa     1104
Ala Gly Arg Phe Ser Ile Thr Pro Ala Ala Pro Ser Tyr Thr Leu Lys
        355                 360                 365

ttg ggt gaa tat ggt gaa gta aca gtt gat tgt gaa cct agg tct ggc     1152
Leu Gly Glu Tyr Gly Glu Val Thr Val Asp Cys Glu Pro Arg Ser Gly
    370                 375                 380

att gac acc aat gct tac tat gta atg act gtg gga aca aag aca ttc     1200
Ile Asp Thr Asn Ala Tyr Tyr Val Met Thr Val Gly Thr Lys Thr Phe
385                 390                 395                 400

tta gtt cac aga gaa tgg ttc atg gat ttg aat ctc cct tgg agt tct     1248
Leu Val His Arg Glu Trp Phe Met Asp Leu Asn Leu Pro Trp Ser Ser
                405                 410                 415

gct gga agc act gtt tgg agg aat cgt gaa aca ttg atg gag ttt gag     1296
Ala Gly Ser Thr Val Trp Arg Asn Arg Glu Thr Leu Met Glu Phe Glu
            420                 425                 430

gaa cca cat gca aca aaa cag tca gta ata gca ttg ggc agt caa gag     1344
Glu Pro His Ala Thr Lys Gln Ser Val Ile Ala Leu Gly Ser Gln Glu
        435                 440                 445

gga gca tta cat caa gcc ttg gct ggg gca att cct gtt gag ttt agt     1392
Gly Ala Leu His Gln Ala Leu Ala Gly Ala Ile Pro Val Glu Phe Ser
    450                 455                 460

tcc aac act gtg aaa ctg aca agt ggt cat ctg aaa tgc aga gta aag     1440
Ser Asn Thr Val Lys Leu Thr Ser Gly His Leu Lys Cys Arg Val Lys
465                 470                 475                 480

atg gag aag tta cag ttg aaa gga acc act tat ggt gtt tgt tcc aaa     1488
Met Glu Lys Leu Gln Leu Lys Gly Thr Thr Tyr Gly Val Cys Ser Lys
                485                 490                 495

gcc ttc aag ttt ctt gga act cct gct gac act ggt cat ggg act gtg     1536
Ala Phe Lys Phe Leu Gly Thr Pro Ala Asp Thr Gly His Gly Thr Val
            500                 505                 510

gtt ttg gaa ttg cag tac act ggc act gat ggt cca tgc aag gtt ccc     1584
Val Leu Glu Leu Gln Tyr Thr Gly Thr Asp Gly Pro Cys Lys Val Pro
        515                 520                 525

ata agc agt gtt gct tca ctc aat gat ctc act cca gta ggc aga ctt     1632
Ile Ser Ser Val Ala Ser Leu Asn Asp Leu Thr Pro Val Gly Arg Leu
    530                 535                 540

gtg aca gtc aac ccc ttt gtt tct gtt gca act gcc aat gca aag gtg     1680
Val Thr Val Asn Pro Phe Val Ser Val Ala Thr Ala Asn Ala Lys Val
545                 550                 555                 560

ctc ata gaa ttg gag cct cca ttt ggt gat tct tac att gtt gta ggc     1728
Leu Ile Glu Leu Glu Pro Pro Phe Gly Asp Ser Tyr Ile Val Val Gly
                565                 570                 575

aga gga gag caa cag atc aac cat cac tgg cac aaa tct ggt tct tca     1776
Arg Gly Glu Gln Gln Ile Asn His His Trp His Lys Ser Gly Ser Ser
            580                 585                 590

att ggc aaa gcc ttc aca acc act ctc aaa ggg gca cag aga ctt gct     1824
Ile Gly Lys Ala Phe Thr Thr Thr Leu Lys Gly Ala Gln Arg Leu Ala
```

-continued

```
        595                 600                 605

gct tta gga gac act gca tgg gat ttc gga tct gtt gga ggt gtt ttc      1872
Ala Leu Gly Asp Thr Ala Trp Asp Phe Gly Ser Val Gly Gly Val Phe
    610                 615                 620

acc tct gtg gga aag gct gtg cat caa gtt ttt ggt ggg gct ttt cga      1920
Thr Ser Val Gly Lys Ala Val His Gln Val Phe Gly Gly Ala Phe Arg
625                 630                 635                 640

tcc ttg ttt ggt gga atg tct tgg ata act caa ggt ctt tta ggg gct      1968
Ser Leu Phe Gly Gly Met Ser Trp Ile Thr Gln Gly Leu Leu Gly Ala
                645                 650                 655

ctg ctt ttg tgg atg ggc atc aat gca agg gac aga tca att gcc tta      2016
Leu Leu Leu Trp Met Gly Ile Asn Ala Arg Asp Arg Ser Ile Ala Leu
            660                 665                 670

acc ttc ctt gca gtt gga ggt gtt ctt ctc ttt ctc tct gta aat gtt      2064
Thr Phe Leu Ala Val Gly Gly Val Leu Leu Phe Leu Ser Val Asn Val
        675                 680                 685

cat gct aag gat gaa ctg tgagtagtta gcttaatcac ctag                  2106
His Ala Lys Asp Glu Leu
    690


<210> SEQ ID NO 11
<211> LENGTH: 694
<212> TYPE: PRT
<213> ORGANISM: West Nile virus

<400> SEQUENCE: 11

Met Ala Lys Met Val Ile Val Leu Val Val Cys Leu Ala Leu Ser Ala
1               5                   10                  15

Ala Ser Ala Ser Ala Ser Val Thr Leu Ser Asn Phe Gln Gly Lys Val
            20                  25                  30

Met Met Thr Val Asn Ala Thr Asp Val Thr Asp Val Ile Thr Ile Pro
        35                  40                  45

Thr Ala Ala Gly Lys Asn Leu Cys Ile Val Arg Ala Met Asp Val Gly
    50                  55                  60

Tyr Met Cys Asp Asp Thr Ile Thr Tyr Glu Cys Pro Val Leu Ser Ala
65                  70                  75                  80

Gly Asn Asp Pro Glu Asp Ile Asp Cys Trp Cys Thr Lys Ser Ala Val
                85                  90                  95

Tyr Val Arg Tyr Gly Arg Cys Thr Lys Thr Arg His Ser Arg Arg Ser
            100                 105                 110

Arg Arg Ser Leu Thr Val Gln Thr His Gly Glu Ser Thr Leu Ala Asn
        115                 120                 125

Lys Lys Gly Ala Trp Met Asp Ser Thr Lys Ala Thr Arg Tyr Leu Val
    130                 135                 140

Lys Thr Glu Ser Trp Ile Leu Arg Asn Pro Gly Tyr Ala Leu Val Ala
145                 150                 155                 160

Ala Val Ile Gly Trp Met Leu Gly Ser Asn Thr Met Gln Arg Val Val
                165                 170                 175

Phe Val Val Leu Leu Leu Leu Val Ala Pro Ala Tyr Ser Phe Asn Cys
            180                 185                 190

Leu Gly Met Ser Asn Arg Asp Phe Leu Glu Gly Val Ser Gly Ala Thr
        195                 200                 205

Trp Val Asp Leu Val Leu Glu Gly Asp Ser Cys Val Thr Ile Met Ser
    210                 215                 220

Lys Asp Lys Pro Thr Ile Asp Val Lys Met Met Asn Met Glu Ala Ala
225                 230                 235                 240
```

-continued

```
Asn Leu Ala Glu Val Arg Ser Tyr Cys Tyr Leu Ala Thr Val Ser Asp
                245                 250                 255

Leu Ser Thr Lys Ala Ala Cys Pro Thr Met Gly Glu Ala His Asn Asp
            260                 265                 270

Lys Arg Ala Asp Pro Ala Phe Val Cys Arg Gln Gly Val Val Asp Arg
        275                 280                 285

Gly Trp Gly Asn Gly Cys Gly Leu Phe Gly Lys Gly Ser Ile Asp Thr
    290                 295                 300

Cys Ala Lys Phe Ala Cys Ser Thr Lys Ala Ile Gly Arg Thr Ile Leu
305                 310                 315                 320

Lys Glu Asn Ile Lys Tyr Glu Val Ala Ile Phe Val His Gly Pro Thr
                325                 330                 335

Thr Val Glu Ser His Gly Asn Tyr Pro Thr Gln Val Gly Ala Thr Gln
            340                 345                 350

Ala Gly Arg Phe Ser Ile Thr Pro Ala Ala Pro Ser Tyr Thr Leu Lys
        355                 360                 365

Leu Gly Glu Tyr Gly Glu Val Thr Val Asp Cys Glu Pro Arg Ser Gly
    370                 375                 380

Ile Asp Thr Asn Ala Tyr Tyr Val Met Thr Val Gly Thr Lys Thr Phe
385                 390                 395                 400

Leu Val His Arg Glu Trp Phe Met Asp Leu Asn Leu Pro Trp Ser Ser
                405                 410                 415

Ala Gly Ser Thr Val Trp Arg Asn Arg Glu Thr Leu Met Glu Phe Glu
            420                 425                 430

Glu Pro His Ala Thr Lys Gln Ser Val Ile Ala Leu Gly Ser Gln Glu
        435                 440                 445

Gly Ala Leu His Gln Ala Leu Ala Gly Ala Ile Pro Val Glu Phe Ser
    450                 455                 460

Ser Asn Thr Val Lys Leu Thr Ser Gly His Leu Lys Cys Arg Val Lys
465                 470                 475                 480

Met Glu Lys Leu Gln Leu Lys Gly Thr Thr Tyr Gly Val Cys Ser Lys
                485                 490                 495

Ala Phe Lys Phe Leu Gly Thr Pro Ala Asp Thr Gly His Gly Thr Val
            500                 505                 510

Val Leu Glu Leu Gln Tyr Thr Gly Thr Asp Gly Pro Cys Lys Val Pro
        515                 520                 525

Ile Ser Ser Val Ala Ser Leu Asn Asp Leu Thr Pro Val Gly Arg Leu
    530                 535                 540

Val Thr Val Asn Pro Phe Val Ser Val Ala Thr Ala Asn Ala Lys Val
545                 550                 555                 560

Leu Ile Glu Leu Glu Pro Pro Phe Gly Asp Ser Tyr Ile Val Val Gly
                565                 570                 575

Arg Gly Glu Gln Gln Ile Asn His His Trp His Lys Ser Gly Ser Ser
            580                 585                 590

Ile Gly Lys Ala Phe Thr Thr Thr Leu Lys Gly Ala Gln Arg Leu Ala
        595                 600                 605

Ala Leu Gly Asp Thr Ala Trp Asp Phe Gly Ser Val Gly Gly Val Phe
    610                 615                 620

Thr Ser Val Gly Lys Ala Val His Gln Val Phe Gly Gly Ala Phe Arg
625                 630                 635                 640

Ser Leu Phe Gly Gly Met Ser Trp Ile Thr Gln Gly Leu Leu Gly Ala
                645                 650                 655

Leu Leu Leu Trp Met Gly Ile Asn Ala Arg Asp Arg Ser Ile Ala Leu
```

-continued

```
            660                 665                 670

Thr Phe Leu Ala Val Gly Gly Val Leu Leu Phe Leu Ser Val Asn Val
        675                 680                 685

His Ala Lys Asp Glu Leu
    690


<210> SEQ ID NO 12
<211> LENGTH: 1830
<212> TYPE: DNA
<213> ORGANISM: West Nile virus
<220> FEATURE:
<221> NAME/KEY: CDS
<222> LOCATION: (1)..(1806)

<400> SEQUENCE: 12

atg gct aag atg gtc att gtg ctt gtt gtg tgc ttg gct ctc tct gct       48
Met Ala Lys Met Val Ile Val Leu Val Val Cys Leu Ala Leu Ser Ala
1               5                   10                  15

gcc tca gct tct gcc tct tcc ctg aca gtg caa act cat gga gag tca       96
Ala Ser Ala Ser Ala Ser Ser Leu Thr Val Gln Thr His Gly Glu Ser
            20                  25                  30

act ttg gcc aac aag aaa ggc gca tgg atg gat tct acc aaa gca aca      144
Thr Leu Ala Asn Lys Lys Gly Ala Trp Met Asp Ser Thr Lys Ala Thr
        35                  40                  45

aga tat ctt gtc aaa act gag tca tgg att ctt agg aat cct gga tat      192
Arg Tyr Leu Val Lys Thr Glu Ser Trp Ile Leu Arg Asn Pro Gly Tyr
    50                  55                  60

gct tta gtt gca gct gtc att gga tgg atg ctt ggg tcc aat acc atg      240
Ala Leu Val Ala Ala Val Ile Gly Trp Met Leu Gly Ser Asn Thr Met
65                  70                  75                  80

cag aga gtt gtc ttc gta gtt ctg ttg tta ctt gta gct cca gct tac      288
Gln Arg Val Val Phe Val Val Leu Leu Leu Leu Val Ala Pro Ala Tyr
                85                  90                  95

tca ttc aac tgt ctt gga atg agc aat agg gat ttc ctt gaa ggt gtt      336
Ser Phe Asn Cys Leu Gly Met Ser Asn Arg Asp Phe Leu Glu Gly Val
            100                 105                 110

tcc ggt gca aca tgg gtt gat ctt gtc tta gaa gga gat tca tgt gtg      384
Ser Gly Ala Thr Trp Val Asp Leu Val Leu Glu Gly Asp Ser Cys Val
        115                 120                 125

aca atc atg tcc aaa gac aag cca acc att gat gtc aag atg atg aac      432
Thr Ile Met Ser Lys Asp Lys Pro Thr Ile Asp Val Lys Met Met Asn
    130                 135                 140

atg gaa gct gcc aat ctt gca gaa gtt agg tct tac tgc tat ctg gca      480
Met Glu Ala Ala Asn Leu Ala Glu Val Arg Ser Tyr Cys Tyr Leu Ala
145                 150                 155                 160

aca gtg agt gat ttg tca aca aaa gct gcc tgt ccc aca atg gga gag      528
Thr Val Ser Asp Leu Ser Thr Lys Ala Ala Cys Pro Thr Met Gly Glu
                165                 170                 175

gct cac aat gac aaa cgt gct gat cct gca ttt gta tgc aga caa gga      576
Ala His Asn Asp Lys Arg Ala Asp Pro Ala Phe Val Cys Arg Gln Gly
            180                 185                 190

gtt gta gac aga ggt tgg gga aat ggt tgt ggt ctc ttt ggc aaa ggc      624
Val Val Asp Arg Gly Trp Gly Asn Gly Cys Gly Leu Phe Gly Lys Gly
        195                 200                 205

agc att gac act tgt gca aag ttt gct tgc agc acc aaa gca att ggt      672
Ser Ile Asp Thr Cys Ala Lys Phe Ala Cys Ser Thr Lys Ala Ile Gly
    210                 215                 220

cga acc ata ttg aaa gag aac att aag tat gaa gtt gcc atc ttt gtt      720
Arg Thr Ile Leu Lys Glu Asn Ile Lys Tyr Glu Val Ala Ile Phe Val
225                 230                 235                 240
```

-continued

```
cat ggt cca aca act gtg gaa tct cat ggc aat tac agc aca caa gtt      768
His Gly Pro Thr Thr Val Glu Ser His Gly Asn Tyr Ser Thr Gln Val
                245                 250                 255

ggt gcc acc caa gct ggg agg ttt tca atc act cct gct gct cca agt      816
Gly Ala Thr Gln Ala Gly Arg Phe Ser Ile Thr Pro Ala Ala Pro Ser
                260                 265                 270

tac act ctg aaa ttg ggt gaa tat ggt gaa gta aca gtt gat tgt gaa      864
Tyr Thr Leu Lys Leu Gly Glu Tyr Gly Glu Val Thr Val Asp Cys Glu
        275                 280                 285

cct agg tct ggc att gac acc aat gct tac tat gta atg act gtg gga      912
Pro Arg Ser Gly Ile Asp Thr Asn Ala Tyr Tyr Val Met Thr Val Gly
    290                 295                 300

aca aag aca ttc tta gtt cac aga gaa tgg ttc atg gat ttg aat ctc      960
Thr Lys Thr Phe Leu Val His Arg Glu Trp Phe Met Asp Leu Asn Leu
305                 310                 315                 320

cct tgg agt tct gct gga agc act gtt tgg agg aat cgt gaa aca ttg     1008
Pro Trp Ser Ser Ala Gly Ser Thr Val Trp Arg Asn Arg Glu Thr Leu
                325                 330                 335

atg gag ttt gag gaa cca cat gca aca aaa cag tca gta ata gca ttg     1056
Met Glu Phe Glu Glu Pro His Ala Thr Lys Gln Ser Val Ile Ala Leu
                340                 345                 350

ggc agt caa gag gga gca tta cat caa gcc ttg gct ggg gca att cct     1104
Gly Ser Gln Glu Gly Ala Leu His Gln Ala Leu Ala Gly Ala Ile Pro
        355                 360                 365

gtt gag ttt agt tcc aac act gtg aaa ctg aca agt ggt cat ctg aaa     1152
Val Glu Phe Ser Ser Asn Thr Val Lys Leu Thr Ser Gly His Leu Lys
    370                 375                 380

tgc aga gta aag atg gag aag tta cag ttg aaa gga acc act tat ggt     1200
Cys Arg Val Lys Met Glu Lys Leu Gln Leu Lys Gly Thr Thr Tyr Gly
385                 390                 395                 400

gtt tgt tcc aaa gcc ttc aag ttt ctt gga act cct gct gac act ggt     1248
Val Cys Ser Lys Ala Phe Lys Phe Leu Gly Thr Pro Ala Asp Thr Gly
                405                 410                 415

cat ggg act gtg gtt ttg gaa ttg cag tac act ggc act gat ggt cca     1296
His Gly Thr Val Val Leu Glu Leu Gln Tyr Thr Gly Thr Asp Gly Pro
                420                 425                 430

tgc aag gtt ccc ata agc agt gtt gct tca ctc aat gat ctc act cca     1344
Cys Lys Val Pro Ile Ser Ser Val Ala Ser Leu Asn Asp Leu Thr Pro
        435                 440                 445

gta ggc aga ctt gtg aca gtc aac ccc ttt gtt tct gtt gca act gcc     1392
Val Gly Arg Leu Val Thr Val Asn Pro Phe Val Ser Val Ala Thr Ala
    450                 455                 460

aat gca aag gtg ctc ata gaa ttg gag cct cca ttt ggt gat tct tac     1440
Asn Ala Lys Val Leu Ile Glu Leu Glu Pro Pro Phe Gly Asp Ser Tyr
465                 470                 475                 480

att gtt gta ggc aga gga gag caa cag atc aac cat cac tgg cac aaa     1488
Ile Val Val Gly Arg Gly Glu Gln Gln Ile Asn His His Trp His Lys
                485                 490                 495

tct ggt tct tca att ggc aaa gcc ttc aca acc act ctc aaa ggg gca     1536
Ser Gly Ser Ser Ile Gly Lys Ala Phe Thr Thr Thr Leu Lys Gly Ala
                500                 505                 510

cag aga ctt gct gct tta gga gac act gca tgg gat ttc gga tct gtt     1584
Gln Arg Leu Ala Ala Leu Gly Asp Thr Ala Trp Asp Phe Gly Ser Val
        515                 520                 525

gga ggt gtt ttc acc tct gtg gga aag gct gtg cat caa gtt ttt ggt     1632
Gly Gly Val Phe Thr Ser Val Gly Lys Ala Val His Gln Val Phe Gly
    530                 535                 540

ggg gct ttt cga tcc ttg ttt ggt gga atg tct tgg ata act caa ggt     1680
Gly Ala Phe Arg Ser Leu Phe Gly Gly Met Ser Trp Ile Thr Gln Gly
545                 550                 555                 560
```

-continued

```
ctt tta ggg gct ctg ctt ttg tgg atg ggc atc aat gca agg gac aga      1728
Leu Leu Gly Ala Leu Leu Leu Trp Met Gly Ile Asn Ala Arg Asp Arg
                565                 570                 575

tca att gcc tta acc ttc ctt gca gtt gga ggt gtt ctt ctc ttt ctc      1776
Ser Ile Ala Leu Thr Phe Leu Ala Val Gly Gly Val Leu Leu Phe Leu
            580                 585                 590

tct gta aat gtt cat gct aag gat gaa ctg tgagtagtta gcttaatcac        1826
Ser Val Asn Val His Ala Lys Asp Glu Leu
        595                 600

ctag                                                                 1830


<210> SEQ ID NO 13
<211> LENGTH: 602
<212> TYPE: PRT
<213> ORGANISM: West Nile virus

<400> SEQUENCE: 13

Met Ala Lys Met Val Ile Val Leu Val Val Cys Leu Ala Leu Ser Ala
1               5                   10                  15

Ala Ser Ala Ser Ala Ser Ser Leu Thr Val Gln Thr His Gly Glu Ser
            20                  25                  30

Thr Leu Ala Asn Lys Lys Gly Ala Trp Met Asp Ser Thr Lys Ala Thr
        35                  40                  45

Arg Tyr Leu Val Lys Thr Glu Ser Trp Ile Leu Arg Asn Pro Gly Tyr
    50                  55                  60

Ala Leu Val Ala Ala Val Ile Gly Trp Met Leu Gly Ser Asn Thr Met
65                  70                  75                  80

Gln Arg Val Val Phe Val Val Leu Leu Leu Leu Val Ala Pro Ala Tyr
                85                  90                  95

Ser Phe Asn Cys Leu Gly Met Ser Asn Arg Asp Phe Leu Glu Gly Val
            100                 105                 110

Ser Gly Ala Thr Trp Val Asp Leu Val Leu Glu Gly Asp Ser Cys Val
        115                 120                 125

Thr Ile Met Ser Lys Asp Lys Pro Thr Ile Asp Val Lys Met Met Asn
    130                 135                 140

Met Glu Ala Ala Asn Leu Ala Glu Val Arg Ser Tyr Cys Tyr Leu Ala
145                 150                 155                 160

Thr Val Ser Asp Leu Ser Thr Lys Ala Ala Cys Pro Thr Met Gly Glu
                165                 170                 175

Ala His Asn Asp Lys Arg Ala Asp Pro Ala Phe Val Cys Arg Gln Gly
            180                 185                 190

Val Val Asp Arg Gly Trp Gly Asn Gly Cys Gly Leu Phe Gly Lys Gly
        195                 200                 205

Ser Ile Asp Thr Cys Ala Lys Phe Ala Cys Ser Thr Lys Ala Ile Gly
    210                 215                 220

Arg Thr Ile Leu Lys Glu Asn Ile Lys Tyr Glu Val Ala Ile Phe Val
225                 230                 235                 240

His Gly Pro Thr Thr Val Glu Ser His Gly Asn Tyr Ser Thr Gln Val
                245                 250                 255

Gly Ala Thr Gln Ala Gly Arg Phe Ser Ile Thr Pro Ala Ala Pro Ser
            260                 265                 270

Tyr Thr Leu Lys Leu Gly Glu Tyr Gly Glu Val Thr Val Asp Cys Glu
        275                 280                 285

Pro Arg Ser Gly Ile Asp Thr Asn Ala Tyr Tyr Val Met Thr Val Gly
    290                 295                 300
```

-continued

```
Thr Lys Thr Phe Leu Val His Arg Glu Trp Phe Met Asp Leu Asn Leu
305                 310                 315                 320

Pro Trp Ser Ser Ala Gly Ser Thr Val Trp Arg Asn Arg Glu Thr Leu
                325                 330                 335

Met Glu Phe Glu Glu Pro His Ala Thr Lys Gln Ser Val Ile Ala Leu
            340                 345                 350

Gly Ser Gln Glu Gly Ala Leu His Gln Ala Leu Ala Gly Ala Ile Pro
        355                 360                 365

Val Glu Phe Ser Ser Asn Thr Val Lys Leu Thr Ser Gly His Leu Lys
    370                 375                 380

Cys Arg Val Lys Met Glu Lys Leu Gln Leu Lys Gly Thr Thr Tyr Gly
385                 390                 395                 400

Val Cys Ser Lys Ala Phe Lys Phe Leu Gly Thr Pro Ala Asp Thr Gly
                405                 410                 415

His Gly Thr Val Val Leu Glu Leu Gln Tyr Thr Gly Thr Asp Gly Pro
            420                 425                 430

Cys Lys Val Pro Ile Ser Ser Val Ala Ser Leu Asn Asp Leu Thr Pro
        435                 440                 445

Val Gly Arg Leu Val Thr Val Asn Pro Phe Val Ser Val Ala Thr Ala
    450                 455                 460

Asn Ala Lys Val Leu Ile Glu Leu Glu Pro Pro Phe Gly Asp Ser Tyr
465                 470                 475                 480

Ile Val Val Gly Arg Gly Glu Gln Gln Ile Asn His His Trp His Lys
                485                 490                 495

Ser Gly Ser Ser Ile Gly Lys Ala Phe Thr Thr Thr Leu Lys Gly Ala
            500                 505                 510

Gln Arg Leu Ala Ala Leu Gly Asp Thr Ala Trp Asp Phe Gly Ser Val
        515                 520                 525

Gly Gly Val Phe Thr Ser Val Gly Lys Ala Val His Gln Val Phe Gly
    530                 535                 540

Gly Ala Phe Arg Ser Leu Phe Gly Gly Met Ser Trp Ile Thr Gln Gly
545                 550                 555                 560

Leu Leu Gly Ala Leu Leu Leu Trp Met Gly Ile Asn Ala Arg Asp Arg
                565                 570                 575

Ser Ile Ala Leu Thr Phe Leu Ala Val Gly Gly Val Leu Leu Phe Leu
            580                 585                 590

Ser Val Asn Val His Ala Lys Asp Glu Leu
        595                 600


<210> SEQ ID NO 14
<211> LENGTH: 1832
<212> TYPE: DNA
<213> ORGANISM: West Nile virus
<220> FEATURE:
<221> NAME/KEY: CDS
<222> LOCATION: (6)..(1808)

<400> SEQUENCE: 14

aaaca atg gct aag atg gtc att gtt ctt gtt gtg tgt ttg gca ctc tct      50
      Met Ala Lys Met Val Ile Val Leu Val Val Cys Leu Ala Leu Ser
      1               5                   10                  15

gct gca tca gct tct gcc agc tta act gtc cag aca cac ggt gaa tcc        98
Ala Ala Ser Ala Ser Ala Ser Leu Thr Val Gln Thr His Gly Glu Ser
                20                  25                  30

aca ctt gct aac aag aaa ggt gct tgg atg gac agc act aaa gca act       146
Thr Leu Ala Asn Lys Lys Gly Ala Trp Met Asp Ser Thr Lys Ala Thr
```

-continued

```
            35                  40                  45

aga tac ttg gtc aag aca gaa tct tgg atc tta cgt aat cct ggt tac      194
Arg Tyr Leu Val Lys Thr Glu Ser Trp Ile Leu Arg Asn Pro Gly Tyr
        50                  55                  60

gca ctt gta gcc gca gtc ata ggt tgg atg ttg ggc agt aac act atg      242
Ala Leu Val Ala Ala Val Ile Gly Trp Met Leu Gly Ser Asn Thr Met
    65                  70                  75

caa cgt gta gtg ttt gtt gta ctt ctt ctc ttg gtt gca cct gca tat      290
Gln Arg Val Val Phe Val Val Leu Leu Leu Leu Val Ala Pro Ala Tyr
80                  85                  90                  95

tcc ttc aat tgc ttg ggg atg tcc aac aga gat ttc ctg gaa gga gta      338
Ser Phe Asn Cys Leu Gly Met Ser Asn Arg Asp Phe Leu Glu Gly Val
                100                 105                 110

agt gga gca act tgg gtc gat ttg gtt ctt gag ggt gat tct tgt gtc      386
Ser Gly Ala Thr Trp Val Asp Leu Val Leu Glu Gly Asp Ser Cys Val
            115                 120                 125

acc att atg agt aaa gac aaa ccc aca ata gat gtg aaa atg atg aat      434
Thr Ile Met Ser Lys Asp Lys Pro Thr Ile Asp Val Lys Met Met Asn
        130                 135                 140

atg gag gcc gct aac ttg gca gaa gtc cgt agc tat tgt tac tta gct      482
Met Glu Ala Ala Asn Leu Ala Glu Val Arg Ser Tyr Cys Tyr Leu Ala
    145                 150                 155

act gtt tca gac ctt tct act aaa gcc gct tgc cca act atg ggt gaa      530
Thr Val Ser Asp Leu Ser Thr Lys Ala Ala Cys Pro Thr Met Gly Glu
160                 165                 170                 175

gca cac aat gat aag agg gca gac cct gct ttt gtt tgt cgt caa ggt      578
Ala His Asn Asp Lys Arg Ala Asp Pro Ala Phe Val Cys Arg Gln Gly
                180                 185                 190

gta gtt gat agg gga tgg gga aat ggc tgt gga ctg ttt ggg aag ggt      626
Val Val Asp Arg Gly Trp Gly Asn Gly Cys Gly Leu Phe Gly Lys Gly
            195                 200                 205

tct ata gat act tgc gct aag ttc gca tgt tca aca aaa gct ata gga      674
Ser Ile Asp Thr Cys Ala Lys Phe Ala Cys Ser Thr Lys Ala Ile Gly
        210                 215                 220

cga aca att ctc aag gaa aac atc aag tat gag gtc gca atc ttc gta      722
Arg Thr Ile Leu Lys Glu Asn Ile Lys Tyr Glu Val Ala Ile Phe Val
    225                 230                 235

cat gga ccc act aca gtc gaa agc cac ggg aac tat tcc act caa gta      770
His Gly Pro Thr Thr Val Glu Ser His Gly Asn Tyr Ser Thr Gln Val
240                 245                 250                 255

gga gca aca caa gct gga aga ttc agc att aca cca gcc gct cct tca      818
Gly Ala Thr Gln Ala Gly Arg Phe Ser Ile Thr Pro Ala Ala Pro Ser
                260                 265                 270

tac aca ttg aaa ctt ggt gag tac ggt gag gtc act gtt gat tgc gag      866
Tyr Thr Leu Lys Leu Gly Glu Tyr Gly Glu Val Thr Val Asp Cys Glu
            275                 280                 285

cca aga agt gga ata gat aca aat gcc tat tac gtt atg aca gtt ggc      914
Pro Arg Ser Gly Ile Asp Thr Asn Ala Tyr Tyr Val Met Thr Val Gly
        290                 295                 300

act aag act ttt ctt gtt cat agg gag tgg ttc atg gac ttg aat ctg      962
Thr Lys Thr Phe Leu Val His Arg Glu Trp Phe Met Asp Leu Asn Leu
    305                 310                 315

ccc tgg tcc agt gct ggc tct aca gtt tgg aga aac aga gaa act ctc     1010
Pro Trp Ser Ser Ala Gly Ser Thr Val Trp Arg Asn Arg Glu Thr Leu
320                 325                 330                 335

atg gaa ttt gaa gag cct cat gct act aag caa tca gtt att gct ctt     1058
Met Glu Phe Glu Glu Pro His Ala Thr Lys Gln Ser Val Ile Ala Leu
                340                 345                 350

ggg tcc caa gaa ggt gct ctc cat cag gct tta gct ggt gct att cca     1106
```

-continued

```
Gly Ser Gln Glu Gly Ala Leu His Gln Ala Leu Ala Gly Ala Ile Pro
            355                 360                 365

gtt gag ttt tcc agc aat act gtt aag ttg act tct ggc cat ttg aag      1154
Val Glu Phe Ser Ser Asn Thr Val Lys Leu Thr Ser Gly His Leu Lys
        370                 375                 380

tgt agg gtg aag atg gag aaa ctc caa ctt aaa ggg aca acc tat gga      1202
Cys Arg Val Lys Met Glu Lys Leu Gln Leu Lys Gly Thr Thr Tyr Gly
    385                 390                 395

gtt tgc tct aag gct ttc aag ttc ttg ggc aca cca gca gat acc gga      1250
Val Cys Ser Lys Ala Phe Lys Phe Leu Gly Thr Pro Ala Asp Thr Gly
400                 405                 410                 415

cat gga aca gtt gta ctt gaa ctt cag tat act ggg acc gat gga cct      1298
His Gly Thr Val Val Leu Glu Leu Gln Tyr Thr Gly Thr Asp Gly Pro
                420                 425                 430

tgt aaa gtg cca att tct tca gtt gcc tct ctc aat gac tta act cct      1346
Cys Lys Val Pro Ile Ser Ser Val Ala Ser Leu Asn Asp Leu Thr Pro
            435                 440                 445

gtt ggg agg tta gtt acc gtg aat cca ttt gtg agt gta gct acc gca      1394
Val Gly Arg Leu Val Thr Val Asn Pro Phe Val Ser Val Ala Thr Ala
        450                 455                 460

aat gct aaa gtt ctc att gag ctt gaa cca cct ttt ggc gat tcc tac      1442
Asn Ala Lys Val Leu Ile Glu Leu Glu Pro Pro Phe Gly Asp Ser Tyr
    465                 470                 475

ata gtg gtt gga agg ggt gaa cag caa atc aat cac cat tgg cat aag      1490
Ile Val Val Gly Arg Gly Glu Gln Gln Ile Asn His His Trp His Lys
480                 485                 490                 495

agt ggc tct tca atc gga aag gcc ttt acc aca acc ctg aaa ggt gct      1538
Ser Gly Ser Ser Ile Gly Lys Ala Phe Thr Thr Thr Leu Lys Gly Ala
                500                 505                 510

caa cgt tta gcc gca ctc ggt gat acc gct tgg gac ttt ggt tca gtg      1586
Gln Arg Leu Ala Ala Leu Gly Asp Thr Ala Trp Asp Phe Gly Ser Val
            515                 520                 525

ggt ggt gtg ttt aca tca gtt ggc aaa gca gtg cat cag gtg ttt gga      1634
Gly Gly Val Phe Thr Ser Val Gly Lys Ala Val His Gln Val Phe Gly
        530                 535                 540

gga gcc ttt aga agt ctt ttc gga ggg atg tca tgg att acc caa ggt      1682
Gly Ala Phe Arg Ser Leu Phe Gly Gly Met Ser Trp Ile Thr Gln Gly
    545                 550                 555

ttg ctt gga gcc ttg tta ctt tgg atg ggg atc aac gct aga gat cga      1730
Leu Leu Gly Ala Leu Leu Leu Trp Met Gly Ile Asn Ala Arg Asp Arg
560                 565                 570                 575

tct att gca ctg act ttt ctg gct gtg ggt ggc gtg ttg ctg ttc tta      1778
Ser Ile Ala Leu Thr Phe Leu Ala Val Gly Gly Val Leu Leu Phe Leu
                580                 585                 590

tca gtg aat gta cac gct aag gat gaa ctg tgagtagtta gcttaatcac        1828
Ser Val Asn Val His Ala Lys Asp Glu Leu
            595                 600

ctag                                                                 1832


<210> SEQ ID NO 15
<211> LENGTH: 601
<212> TYPE: PRT
<213> ORGANISM: West Nile virus

<400> SEQUENCE: 15

Met Ala Lys Met Val Ile Val Leu Val Val Cys Leu Ala Leu Ser Ala
1               5                   10                  15

Ala Ser Ala Ser Ala Ser Leu Thr Val Gln Thr His Gly Glu Ser Thr
            20                  25                  30
```

-continued

```
Leu Ala Asn Lys Lys Gly Ala Trp Met Asp Ser Thr Lys Ala Thr Arg
        35                  40                  45

Tyr Leu Val Lys Thr Glu Ser Trp Ile Leu Arg Asn Pro Gly Tyr Ala
    50                  55                  60

Leu Val Ala Ala Val Ile Gly Trp Met Leu Gly Ser Asn Thr Met Gln
65                  70                  75                  80

Arg Val Val Phe Val Val Leu Leu Leu Leu Val Ala Pro Ala Tyr Ser
                85                  90                  95

Phe Asn Cys Leu Gly Met Ser Asn Arg Asp Phe Leu Glu Gly Val Ser
            100                 105                 110

Gly Ala Thr Trp Val Asp Leu Val Leu Glu Gly Asp Ser Cys Val Thr
        115                 120                 125

Ile Met Ser Lys Asp Lys Pro Thr Ile Asp Val Lys Met Met Asn Met
    130                 135                 140

Glu Ala Ala Asn Leu Ala Glu Val Arg Ser Tyr Cys Tyr Leu Ala Thr
145                 150                 155                 160

Val Ser Asp Leu Ser Thr Lys Ala Ala Cys Pro Thr Met Gly Glu Ala
                165                 170                 175

His Asn Asp Lys Arg Ala Asp Pro Ala Phe Val Cys Arg Gln Gly Val
            180                 185                 190

Val Asp Arg Gly Trp Gly Asn Gly Cys Gly Leu Phe Gly Lys Gly Ser
        195                 200                 205

Ile Asp Thr Cys Ala Lys Phe Ala Cys Ser Thr Lys Ala Ile Gly Arg
    210                 215                 220

Thr Ile Leu Lys Glu Asn Ile Lys Tyr Glu Val Ala Ile Phe Val His
225                 230                 235                 240

Gly Pro Thr Thr Val Glu Ser His Gly Asn Tyr Ser Thr Gln Val Gly
                245                 250                 255

Ala Thr Gln Ala Gly Arg Phe Ser Ile Thr Pro Ala Ala Pro Ser Tyr
            260                 265                 270

Thr Leu Lys Leu Gly Glu Tyr Gly Glu Val Thr Val Asp Cys Glu Pro
        275                 280                 285

Arg Ser Gly Ile Asp Thr Asn Ala Tyr Tyr Val Met Thr Val Gly Thr
    290                 295                 300

Lys Thr Phe Leu Val His Arg Glu Trp Phe Met Asp Leu Asn Leu Pro
305                 310                 315                 320

Trp Ser Ser Ala Gly Ser Thr Val Trp Arg Asn Arg Glu Thr Leu Met
                325                 330                 335

Glu Phe Glu Glu Pro His Ala Thr Lys Gln Ser Val Ile Ala Leu Gly
            340                 345                 350

Ser Gln Glu Gly Ala Leu His Gln Ala Leu Ala Gly Ala Ile Pro Val
        355                 360                 365

Glu Phe Ser Ser Asn Thr Val Lys Leu Thr Ser Gly His Leu Lys Cys
    370                 375                 380

Arg Val Lys Met Glu Lys Leu Gln Leu Lys Gly Thr Thr Tyr Gly Val
385                 390                 395                 400

Cys Ser Lys Ala Phe Lys Phe Leu Gly Thr Pro Ala Asp Thr Gly His
                405                 410                 415

Gly Thr Val Val Leu Glu Leu Gln Tyr Thr Gly Thr Asp Gly Pro Cys
            420                 425                 430

Lys Val Pro Ile Ser Ser Val Ala Ser Leu Asn Asp Leu Thr Pro Val
        435                 440                 445

Gly Arg Leu Val Thr Val Asn Pro Phe Val Ser Val Ala Thr Ala Asn
```

-continued

```
    450                 455                 460

Ala Lys Val Leu Ile Glu Leu Glu Pro Pro Phe Gly Asp Ser Tyr Ile
465                 470                 475                 480

Val Val Gly Arg Gly Glu Gln Gln Ile Asn His His Trp His Lys Ser
                485                 490                 495

Gly Ser Ser Ile Gly Lys Ala Phe Thr Thr Thr Leu Lys Gly Ala Gln
            500                 505                 510

Arg Leu Ala Ala Leu Gly Asp Thr Ala Trp Asp Phe Gly Ser Val Gly
        515                 520                 525

Gly Val Phe Thr Ser Val Gly Lys Ala Val His Gln Val Phe Gly Gly
    530                 535                 540

Ala Phe Arg Ser Leu Phe Gly Gly Met Ser Trp Ile Thr Gln Gly Leu
545                 550                 555                 560

Leu Gly Ala Leu Leu Leu Trp Met Gly Ile Asn Ala Arg Asp Arg Ser
                565                 570                 575

Ile Ala Leu Thr Phe Leu Ala Val Gly Gly Val Leu Leu Phe Leu Ser
            580                 585                 590

Val Asn Val His Ala Lys Asp Glu Leu
        595                 600
```